United States Patent
Baloglu et al.

(10) Patent No.: US 11,945,794 B2
(45) Date of Patent: *Apr. 2, 2024

(54) NUCLEAR TRANSPORT MODULATORS AND USES THEREOF

(71) Applicant: Karyopharm Therapeutics Inc., Newton, MA (US)

(72) Inventors: Erkan Baloglu, Stoneham, MA (US); Sharon Shacham, Newton, MA (US); Dilara McCauley, Arlington, MA (US); Trinayan Kashyap, Framingham, MA (US); William Senapedis, Millis, MA (US); Yosef Landesman, Brookline, MA (US); Gali Golan, Mesilat Zion (IL); Ori Kalid, Pardes Hanna (IL); Sharon Shechter, Andover, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/409,150

(22) Filed: Aug. 23, 2021

(65) Prior Publication Data
US 2022/0177445 A1  Jun. 9, 2022

Related U.S. Application Data

(63) Continuation of application No. 16/519,955, filed on Jul. 23, 2019, now Pat. No. 11,124,493, which is a continuation of application No. 15/651,856, filed on Jul. 17, 2017, now Pat. No. 10,407,405, which is a continuation of application No. 14/900,469, filed as (Continued)

(51) Int. Cl.
| | | |
|---|---|---|
| C07D 249/08 | (2006.01) |
| A61K 31/4196 | (2006.01) |
| A61K 31/422 | (2006.01) |
| A61K 31/426 | (2006.01) |
| A61K 31/4439 | (2006.01) |
| A61K 31/4709 | (2006.01) |
| A61K 31/501 | (2006.01) |
| A61K 31/506 | (2006.01) |
| A61P 3/04 | (2006.01) |
| A61P 11/00 | (2006.01) |
| A61P 17/02 | (2006.01) |
| A61P 25/00 | (2006.01) |
| A61P 25/28 | (2006.01) |
| A61P 27/02 | (2006.01) |
| A61P 29/00 | (2006.01) |
| A61P 31/12 | (2006.01) |
| A61P 35/00 | (2006.01) |
| A61P 37/00 | (2006.01) |
| C07D 401/06 | (2006.01) |
| C07D 403/06 | (2006.01) |
| C07D 405/06 | (2006.01) |

(Continued)

(52) U.S. Cl.
CPC ........ *C07D 401/06* (2013.01); *C07D 249/08* (2013.01); *C07D 403/06* (2013.01); *C07D 405/06* (2013.01); *C07D 413/06* (2013.01); *C07D 417/06* (2013.01)

(58) Field of Classification Search
CPC .. C07D 249/08; C07D 401/06; C07D 403/06; C07D 405/06; C07D 413/06; C07D 417/06; A61K 31/4196; A61K 31/422; A61K 31/426; A61K 31/4439; A61K 31/4709; A61K 31/501; A61K 31/506; A61P 3/04; A61P 11/00; A61P 17/02; A61P 25/00; A61P 25/28; A61P 27/02; A61P 29/00; A61P 31/12; A61P 35/00; A61P 37/00

See application file for complete search history.

(56) References Cited

U.S. PATENT DOCUMENTS

| 5,153,201 A | 10/1992 | Aono et al. |
| 5,817,677 A | 10/1998 | Linz et al. |

(Continued)

FOREIGN PATENT DOCUMENTS

| CN | 101309912 A | 11/2008 |
| CN | 101466687 A | 6/2009 |

(Continued)

OTHER PUBLICATIONS

Balbach et al., "Pharmaceutical evaluation of early development candidates: 'The 100 mg-approach'," International Journal of Pharmaceutics, 275:1-12 (2004).

(Continued)

*Primary Examiner* — Brenda L Coleman
(74) *Attorney, Agent, or Firm* — FOLEY HOAG LLP

(57) ABSTRACT

The present invention relates to compounds of formula I:

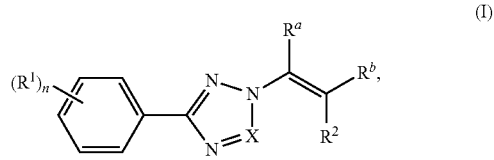

and pharmaceutically acceptable salts thereof, pharmaceutical compositions comprising the compounds of formula I or their pharmaceutically acceptable salts, and methods of using said compounds, salts and compositions in the treatment of various disorders associated with CRM1 activity.

18 Claims, 8 Drawing Sheets

Related U.S. Application Data application No. PCT/US2014/043479 on Jun. 20, 2014, now Pat. No. 9,738,624.

(60) Provisional application No. 61/838,172, filed on Jun. 21, 2013.

(51) Int. Cl.
  *C07D 413/06* (2006.01)
  *C07D 417/06* (2006.01)

(56) References Cited

U.S. PATENT DOCUMENTS

| | | | |
|---|---|---|---|
| 6,462,049 B1 | 10/2002 | Ogura et al. | |
| 7,342,115 B2 | 3/2008 | Hutchison et al. | |
| 7,667,041 B2 | 2/2010 | Kimura et al. | |
| 7,795,457 B2 | 9/2010 | Fu et al. | |
| 7,858,621 B2 | 12/2010 | Kim et al. | |
| 7,902,367 B2 | 3/2011 | Nomura et al. | |
| 8,273,738 B2 | 9/2012 | Osakada et al. | |
| 8,299,102 B2 | 10/2012 | Strobel et al. | |
| 8,304,438 B2 | 11/2012 | Strobel et al. | |
| 8,513,230 B2 | 8/2013 | Shacham et al. | |
| 8,598,168 B2 | 12/2013 | Moradei et al. | |
| 8,999,996 B2 | 4/2015 | Sandanayaka et al. | |
| 9,079,865 B2 | 7/2015 | Sandanayaka et al. | |
| 9,096,543 B2 | 8/2015 | Sandanayaka et al. | |
| 9,206,158 B2 | 12/2015 | Sandanayaka et al. | |
| 9,266,843 B2 | 2/2016 | Sandanayaka et al. | |
| 9,303,000 B2 | 4/2016 | Sandanayaka et al. | |
| 9,428,490 B2 | 8/2016 | Sandanayaka et al. | |
| 9,550,757 B2 | 1/2017 | Shacham et al. | |
| 9,585,874 B2 | 3/2017 | Sandanayaka et al. | |
| 9,714,226 B2 | 7/2017 | Sandanayaka et al. | |
| 9,738,624 B2 * | 8/2017 | Baloglu | A61P 31/12 |
| 9,828,373 B2 | 11/2017 | Liu et al. | |
| 9,861,614 B2 | 1/2018 | Sandanayaka et al. | |
| 10,058,535 B2 | 8/2018 | Sandanayaka et al. | |
| 10,173,987 B2 | 1/2019 | Sandanayaka et al. | |
| 10,202,366 B2 | 2/2019 | Rashal et al. | |
| 10,335,393 B2 | 7/2019 | Sandanayaka et al. | |
| 10,407,405 B2 * | 9/2019 | Baloglu | C07D 403/06 |
| 10,519,139 B2 | 12/2019 | Austad et al. | |
| 10,526,295 B2 | 1/2020 | Baloglu | |
| 10,544,108 B2 | 1/2020 | Sandanayaka et al. | |
| 10,709,706 B2 | 7/2020 | Baloglu | |
| 11,034,660 B2 | 6/2021 | Sandanayaka et al. | |
| 11,078,190 B2 | 8/2021 | Austad et al. | |
| 11,124,493 B2 * | 9/2021 | Baloglu | A61P 11/00 |
| 11,746,102 B2 | 9/2023 | Austad et al. | |
| 11,753,401 B2 | 9/2023 | Austad et al. | |
| 11,787,771 B2 | 10/2023 | Sandanayaka et al. | |
| 11,807,629 B2 | 11/2023 | Austad et al. | |
| 2003/0018025 A1 | 1/2003 | Thurkauf et al. | |
| 2004/0092598 A1 | 5/2004 | Watkins et al. | |
| 2006/0004069 A1 | 1/2006 | Momose et al. | |
| 2009/0221586 A1 | 9/2009 | Okada et al. | |
| 2009/0298896 A1 | 12/2009 | Sakuma et al. | |
| 2010/0016272 A1 | 1/2010 | Strobel et al. | |
| 2010/0056569 A1 | 3/2010 | Nan et al. | |
| 2011/0009374 A1 | 1/2011 | Keller | |
| 2011/0275607 A1 | 11/2011 | Shacham et al. | |
| 2012/0258986 A1 | 10/2012 | Sandanayaka et al. | |
| 2013/0317031 A1 | 11/2013 | Sandanayaka et al. | |
| 2014/0155370 A1 | 6/2014 | Shacham et al. | |
| 2014/0235653 A1 | 8/2014 | Sandanayaka et al. | |
| 2014/0364408 A1 | 12/2014 | Sandanayaka et al. | |
| 2015/0018332 A1 | 1/2015 | Sandanayaka et al. | |
| 2015/0111893 A1 | 4/2015 | Sandanayaka et al. | |
| 2015/0274698 A1 | 10/2015 | Sandanayaka et al. | |
| 2016/0145246 A1 | 5/2016 | Sandanayaka et al. | |
| 2016/0152596 A1 | 6/2016 | Baloglu et al. | |
| 2016/0258931 A1 | 9/2016 | Silva et al. | |
| 2016/0304500 A1 | 10/2016 | Rashal et al. | |
| 2017/0137430 A1 | 5/2017 | Sandanayaka et al. | |
| 2017/0319551 A1 | 11/2017 | Sandanayaka et al. | |
| 2018/0155317 A1 | 6/2018 | Baloglu et al. | |
| 2019/0016690 A1 | 1/2019 | Baloglu | |
| 2019/0023693 A1 | 1/2019 | Chennuru et al. | |
| 2019/0160063 A1 | 5/2019 | Baloglu | |
| 2020/0087313 A1 | 3/2020 | Sandanayaka et al. | |
| 2020/0199099 A1 | 6/2020 | Baloglu et al. | |
| 2020/0283419 A1 | 9/2020 | Austad et al. | |
| 2020/0339521 A1 | 10/2020 | Sandanayaka et al. | |
| 2022/0056038 A1 | 2/2022 | Sandanayaka et al. | |
| 2022/0073478 A1 | 3/2022 | Sandanayaka et al. | |
| 2022/0135545 A1 | 5/2022 | Austad et al. | |
| 2022/0177445 A1 | 6/2022 | Baloglu et al. | |
| 2023/0024251 A1 | 1/2023 | Morant | |
| 2023/0242516 A1 | 8/2023 | Austad et al. | |

FOREIGN PATENT DOCUMENTS

| | | |
|---|---|---|
| CN | 103002742 A | 3/2013 |
| CN | 103874690 B | 7/2016 |
| EP | 0069513 A2 | 1/1983 |
| EP | 1939180 A1 | 7/2008 |
| EP | 1992618 A1 | 11/2008 |
| EP | 2003118 A1 | 12/2008 |
| EP | 2 090 570 A1 | 8/2009 |
| EP | 2736887 A1 | 6/2014 |
| EP | 3808742 A1 | 4/2021 |
| JP | S5841875 A | 3/1983 |
| JP | S62103065 A | 5/1987 |
| JP | H04211089 A | 8/1992 |
| JP | H07118237 A | 5/1995 |
| JP | H11263764 A | 9/1999 |
| JP | 2003342262 A | 12/2003 |
| JP | 2004509941 A | 4/2004 |
| JP | 2004168768 A | 6/2004 |
| JP | 2005508905 A | 4/2005 |
| JP | 2005255683 A | 9/2005 |
| JP | 2006504761 A | 2/2006 |
| JP | 2007210929 A | 8/2007 |
| JP | 2009203238 A | 9/2009 |
| JP | 2009536615 A | 10/2009 |
| JP | 2009544696 A | 12/2009 |
| JP | 2010513341 A | 4/2010 |
| JP | 2010519337 A | 6/2010 |
| JP | 2015516434 A | 6/2015 |
| JP | 2018012715 A | 1/2018 |
| KR | 20050062645 A | 6/2005 |
| WO | WO-1996/16040 A1 | 5/1996 |
| WO | WO-1997/15567 A1 | 5/1997 |
| WO | WO-1997/37996 A1 | 10/1997 |
| WO | WO-1997/48696 A1 | 12/1997 |
| WO | WO-1998/25893 A1 | 6/1998 |
| WO | WO-1999/50264 A1 | 10/1999 |
| WO | WO-2001/62756 A1 | 8/2001 |
| WO | WO-2002/26696 A1 | 4/2002 |
| WO | WO-2003/024448 A2 | 3/2003 |
| WO | WO-2004/039365 A1 | 5/2004 |
| WO | WO-2004/039764 A1 | 5/2004 |
| WO | WO-2004/043925 A2 | 5/2004 |
| WO | WO-2004/043951 A1 | 5/2004 |
| WO | WO-2004/076418 A1 | 9/2004 |
| WO | WO-2005/115990 A1 | 12/2005 |
| WO | WO-2006/016637 A1 | 2/2006 |
| WO | WO-2006/019020 A1 | 2/2006 |
| WO | WO-2006/088246 A1 | 8/2006 |
| WO | WO-2007/102580 A1 | 9/2007 |
| WO | WO-2007/147336 A1 | 12/2007 |
| WO | WO-2008/029825 A1 | 3/2008 |
| WO | WO-2008/074413 A2 | 6/2008 |
| WO | WO-2008/152097 A1 | 12/2008 |
| WO | WO-2010/017545 A2 | 2/2010 |
| WO | WO-2011/069039 A1 | 6/2011 |
| WO | WO-2011/109799 A1 | 9/2011 |
| WO | WO-2012/099807 A1 | 7/2012 |
| WO | WO-2013/019548 A1 | 2/2013 |
| WO | WO-2013/019561 A1 | 2/2013 |
| WO | WO-2013/020024 A2 | 2/2013 |
| WO | WO-2013/170068 A2 | 11/2013 |
| WO | WO-2014/144772 A1 | 9/2014 |

(56) References Cited

FOREIGN PATENT DOCUMENTS

| | | |
|---|---|---|
| WO | WO-2014/152263 A1 | 9/2014 |
| WO | WO-2014/205389 A1 | 12/2014 |
| WO | WO-2014/205393 A1 | 12/2014 |
| WO | WO-2016/025904 A1 | 2/2016 |
| WO | WO-2017/117529 A1 | 7/2017 |
| WO | WO-2017/117535 A1 | 7/2017 |
| WO | WO-2017/118940 A1 | 7/2017 |
| WO | WO-2018/098472 A1 | 5/2018 |
| WO | WO-2018/129227 A1 | 7/2018 |
| WO | WO-2022/087218 A1 | 4/2022 |

OTHER PUBLICATIONS

Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (Jan. 1, 1998).
Brekhov, Y. et al., "Cyanomethyltetrazoles II reactions of the methylene Fragment", Zhurnal organicheskoi Khimii, 28(9): 1921-1925 (1992).
Brittain, "Drugs in Pharmaceutical Sciences, v. 192. Polymorphism in Pharmaceutical Solids," CRC Press (2009).
Bryn, "Pharmaceutical Solids: A Strategic Approach To Regulatory Considerations," Pharma Res 12(7):945-954 (1995).
Buckler, R.T. et al., "Synthesis and Antiinflammatory Activity of Some 1,2,3- and 1,2,4-Triazolepropionic Acids", Journal of Medicinal Chemistry, 21(12): 1254-1260 (1978).
Burdeska et al., "Anil-Synthese. 23. Mitteilung. Ueber die Herstellung von Styryl- und Stilbenyl-Derivaten des Pyrimidins // Anil synthesis. Part 23. Preparation of styryl and stilbenyl derivatives of pyrimidines," Helv Chim Acta, 64(1): 113-152 (1981).
Cai, X., et al., "Inhibition of Thr-55 phosphorylation restores p53 nuclear localization and sensitizes cancer cells to DNA damage", Proc Nat Acad Sci, 105(44):16958-16963 (2008).
Cancer [online], [retrieved on Jul. 6, 2007] Retrieved from the Internet, URL: http://www.nlm.nih.gov/medlineplus/cancer.html (Year: 2007).
Cantu et al., "Using the Selective Inhibitor of Nuclear Export (SINE) Compound KPT-350 to Reduce Cortical Circuit Hyperexcitability and Interneuron Cell Loss in the Controlled Cortical Impact (CCI) Model of Traumatic Brain Injury (TBI) (111.001)," Neurology, 86(16 Supplement):IT1.001 (2016).
CHEMCATS RN# 1035122-02-1; Publicly available on Jul. 12, 2009.
CHEMCATS RN# 1134927-58-4; Publicly available on Apr. 15, 2009.
CHEMCATS RN# 930886-49-0; Publicly available on Apr. 29, 2007.
Chemical Abstract Registry Nos. 1181485-58-4; 1100108-00-6 (2009).
Cheng et al., "XPO1 (CRM1) Inhibition Represses STAT3 Activation to Drive a Surviving-Dependent Oncogenic Switch in Triple-Negative Breast Cancer," Mol Cancer Ther 13(3):675-686 (2014).
Ciara, M.R., "Crystalline polymorphism of organic compounds". In: Weber, E., et al. Design of Organic Solids. Topics in Current Chemistry, vol. 198. pp. 163-208 (1998).
Cooper et al., "Synthesis of Some 1,2,4-Triazoles and 1,2,4-Triazolines by Reaction of Oxamidrazone Condensation Products with Acetic Anhydride," Journal of Chemical Society Perkin Transactions 1, 15: 1433-1437 (1975).
Cronshaw, J.M. et al., "The nuclear pore complex: disease associations and functional correlations", TRENDS Endocrin Metab. 15:34-39 (2004).
Daelemans, D. et al., "A synthetic HIV-1 Rev inhibitor interfering with the CRM1-mediated nuclear export", PNAS, 99(22):14440-14445 (2002).
Database PubChem Compound, Database Accession No. 33777540 (May 29, 2009), 3 pages.
Database PubChem Compound, Database Accession No. 33777561 (May 29, 2009), 3 pages.
Database PubChem Compound, Database Accession No. 33777585 (May 29, 2009), 3 pages.
Database PubChem Compound, Database Accession No. 66525271 (Oct. 24, 2012), 3 pages.
Database PubChem Compound, Database Accession No. 66525276 (Oct. 24. 2012), 3 pages.
Database PubChem Compound, Database Accession No. 72062355 (2007), 11 pages.
Database PubChem Compound, Database Accession No. 940775133 (Jul. 7, 2017), 1 page.
Davis, J.R. et al., "Controlling protein compartmentalization to overcome disease" Pharmaceut Res., 24:17-27 (2007).
Dorwald, "Side Reactions in Organic Synthesis: A Guide to Successful Synthesis Design," Wiley-VCH Verlag Gmbh & Co. KGaA, Weinheim (2005).
Etchin et al., "KPT-330 inhibitor of CRM1 (XPO1)-mediated nuclear export has selective anti-leukaemic activity in preclinical models of T-cell acute lymphoblastic leukaemia and acute myeloid leukaemia," British Journal of Haematology, 161:117-127 (2013).
Extended European Search Report for EP Application No. 17189480.1 dated May 16, 2018.
Extended European Search Report for EP Application No. 22176543.1 dated Oct. 12, 2022.
Extended European Search Report for EP Application No. 23162715.9 dated Aug. 9, 2023.
Extended European Search Report for EP Application No. EP 18202641 dated Feb. 15, 2019.
Extended European Search Report issued by the European Patent Office in corresponding European Application No. 18164757.0 dated Aug. 8, 2018.
Extended Search Report for EP Application No. 11751491.9, "Nuclear Transport Modulators And Uses Thereof", Date of Completion of the Search: Dec. 17, 2013.
Extended Search Report for EP Application No. 12736172.3, "Olefin Containing Nuclear Transport Modulators And Uses Thereof", Date of Completion of the Search: May 8, 2014, 3 pages.
Falini, B. et al., "Both carboxy-terminus NES motif and mutated tryptophan(s) are crucial for aberrant nuclear export of nucleophosmin leukemic mutants in NPMc+ AML", Blood, 107(11):4514-4523 (2013).
Final Rejection for U.S. Appl. No. 13/931,372, "Nuclear Transport Modulators and Uses Thereof," dated Oct. 16, 2015.
Final Rejection for U.S. Appl. No. 14/747,394, "Nuclear Transport Modulators and Uses Thereof," dated Feb. 1, 2017.
Freundt, E.C. et al., "Molecular Determinants for Subcellular Localization of the Severe Acute Respiratory Syndrome Coronavirus Open Reading Frame 3b Protein", Journal of Virology, 83(13):6631-6640 (Jul. 2009).
Ghildyal, R. et al., "The Respiratory Syncytial Virus Matrix Protein Possesses a Crm1-Mediated Nuclear Export Mechanism", Journal of Virology, 83(11):5353-5362 (2009).
Ghosh, C.C. et al., "Analysis of nucleocytoplasmic shuttling of NF kappa B proteins in human leukocytes", Methods Mol. Biol. 457:279-92 (2008).
Golub, T.R. et al., "Molecular Classification of Cancer: Class Discovery and Class Prediction by Gene Expression Monitoring", Science, 286: 531-537 (1999).
Gravina et al., "XPO1/CRM1-Selective inhibitors of nuclear export (SINE) reduce tumor spreading and improve overall survival in preclinical models of prostate cancer (PCa)," Journal of Hematology & Oncology, 7(46):1-17 (2014).
Gupta, N. et al., "Retinal tau pathology in human glaucomas" Can J Ophthalmol. 43(1):53-60 (2008).
Haines et al., "Selective Inhibitors of Nuclear Export Avert Progression in Preclinical Models of Inflammatory Demyelination," Nature Neuroscience, 18(4): 511-520 (2015).
Hilliard et al., "The anti-inflammatory prostaglandin 15-Deoxy-Δ12,14 PGJ2 inhibits CRM1-dependent nuclear protein export," Journal of Biological Chemistry, 1-12 (2010).
Hoffman et al., "Synthesis of Vinyl-Functionalized Oxazoles by Olefin Cross-Metathesis", J. Org. Chem. 73: 2400-2403 (2008).

(56) References Cited

OTHER PUBLICATIONS

Hoshino, I. et al., "Combined effects of p53 gene therapy and leptomycin B in human esophageal squamous cell carcinoma", Oncology, 75:113-119 (2008).
Huff, J., "HIV Protease: A Novel Chemotherapeutic Target for AIDS", Journal of Medicinal Chemistry, 34(8): 2305-2314 (1991).
International Preliminary Report on Patentability for International Application No. PCT/US2011/027328, "Nuclear Transport Modulators and Uses Thereof" dated Sep. 11, 2012.
International Preliminary Report on Patentability for International Application No. PCT/US2012/021406, "Olefin Containing Nuclear Transport Modulators and Uses Thereof" dated Jul. 17, 2013.
International Preliminary Report on Patentability for International Application No. PCT/US2014/029322 dated Sep. 15, 2015.
International Preliminary Report on Patentability for International Application No. PCT/US2014/043479, dated Dec. 22, 2015.
International Preliminary Report on Patentability for International Application No. PCT/US2014/043484, dated Dec. 22, 2015.
International Preliminary Report on Patentability for International Application No. PCT/US2015/045395 dated Feb. 21, 2017.
International Preliminary Report on Patentability for International Application No. PCT/US2016/069492 dated Jul. 3, 2018.
International Preliminary Report on Patentability for International Application No. PCT/US2016/069508 dated Jul. 3, 2018.
International Preliminary Report on Patentability for International Application No. PCT/US2017/063439 dated May 28, 2019.
International Preliminary Report on Patentability for International Application No. PCT/US2012/048319, "Hydrazide Containing Nuclear Transport Modulators And Uses Thereof"; dated Feb. 4, 2014.
International Preliminary Report on Patentability for International Application No. PCT/US2012/048368, "Nuclear Transport "Modulators And Uses Thereof; dated Feb. 4, 2014.
International Preliminary Report on Patentability for International Application No. PCT/US2013/040404, "Nuclear Transport Modulators And Uses Thereof"; dated Nov. 11, 2014.
International Search Report and The Written Opinion of the International Searching Authority for International Application No. PCT/US2012/021406, "Olefin-Containing Nuclear Transport Modulators And Uses Thereof" dated Apr. 30, 2012.
International Search Report and The Written Opinion of the International Searching Authority for International Application No. PCT/US2012/049470, "Maleimide Compounds and Methods of Treatment," dated Feb. 13, 2013.
International Search Report and The Written Opinion of the International Searching Authority for International Application No. PCT/US2013/040404, "Nuclear Transport Modulators And Uses Thereof"; dated Nov. 18, 2013.
International Search Report and the Written Opinion of the International Searching Authority, or the Declaration for International Application No. PCT/US2014/027136 "Exo Olefin-Containing Nuclear Transport Modulators And Uses Thereof"; dated Jul. 11, 2014.
International Search Report and the Written Opinion of the International Searching Authority, or the Declaration for International Application No. PCT/US2014/029322 "Methods Of Promoting Wound Healing Using CRM1 Inhibitors"; dated May 28, 2014.
International Search Report and the Written Opinion of the International Searching Authority, or the Declaration for International Application No. PCT/US2014/043479 "Nuclear Transport Modulators And Uses Thereof"; dated Sep. 17, 2014.
International Search Report and the Written Opinion of the International Searching Authority, or the Declaration for International Application No. PCT/US2014/043484 "Nuclear Transport Modulators And Uses Thereof"; dated Sep. 2, 2014.
International Search Report and Written Opinion for International Application No. PCT/US2015/045395 dated Jan. 12, 2016.
International Search Report and Written Opinion for International Application No. PCT/US2016/069492 dated Feb. 16, 2017.
International Search Report and Written Opinion for International Application No. PCT/US2016/069508 dated May 23, 2017.
International Search Report and Written Opinion for International Application No. PCT/US2017/063439 dated Feb. 2, 2018.
International Search Report and Written Opinion for International Application No. PCT/US2021/055974 dated Jan. 4, 2022.
International Search Report for International Application No. PCT/US2011/027328, "Nuclear Transport Modulators And Uses Thereof" dated Apr. 29, 2011.
International Search Report for International Application No. PCT/US2012/048319, "Hydrazide Containing Nuclear Transport Modulators And Uses Thereof" dated Nov. 9, 2012.
International Search Report for International Application No. PCT/US2012/048368, "Nuclear Transport Modulators And Uses Thereof" dated Sep. 21, 2012.
Jiang et al., "Palladium-Catalyzed Alkenylation of 1,2,3-Trizoles with Terminal Conjugated Alkenes by Direct C—H Bond Functionalization," Eur J Org Chem, 7:1227-30 (2010).
Karyagin, A. Yu., "Reagents for addressed modification of biopolymers," Russian Chemical Bulletin, 2000, 49(3):540-5.
Karyopharm Therapeutics, "Karyopharm Presents Data Demonstrating the Potential of Nuclear Export Protein Exportin 1 (XPO1) Inhibition in the Treatment of Traumatic Brain Injury," Apr. 20, 2016, Retrieved from the Internet: http://investors.karyopharm.com/static-files/577eb861-4183-463a-9a5b-d0f1def1629d [retrieved on Jan. 25, 2018].
Kau, T.R. et al., "A chemical genetic screen identifies inhibitors of regulated nuclear export of a Forkhead transcription factor in PTEN-deficient tumor cells", Cancer Cell, pp. 463-476 (2003).
Kaur et al., "Tyrphostin Induced Growth Inhibition: Correlation with Effect on p210bcr-abl Autokinase Activity in K562 Chronic Myelogenous Leukemia," Anti-Cancer Drugs, 5(2): 213-222 (1994).
Lain, S. et al., "Accumulating active p53 in the nucleus by inhibition of nuclear export: a novel strategy to promote the p53 tumor suppressor function", Exp Cell Res. 253: 315-324 (1999).
Lain, S. et al., "An inhibitor of nuclear export activates the p53 response and induces the localization of HDM2 and p53 to U1A-positive nuclear bodies associated with the PODs", Exp Cell Res. 248:457-472 (1999).
Lala, P.K. et al., "Role of nitric oxide in tumor progression: Lessons from experimental tumors", Cancer and Metastasis Reviews, 17: 91-106 (1998).
Lapalombella, R. et al., "Selective Inhibitors of nuclear exports show that CRM1/XPO1 is a target in chronic lymphocytic leukemia", Blood, 120(23): 4621-4634 (Nov. 29, 2012).
Li, A. et al., "Upregulation of CRM1 Relates to Neuronal Apoptosis after Traumatic Brain Injury in Adult Rats", J Mol Neurosci, 51(1):208-218 (2013).
Maekawa et al., "Efficient Formation of a Triazole Ring Via Novel Ring-Opening Reaction of (z)-2-Methyl-4-arylmethylene-5(4H)-Oxazolones with Hydrazides," Heterocycles, 75(12): 2959-2971 (2008).
Maga et al., "Pharmacophore modeling and molecular docking led to the discovery of inhibitors of human immunodeficiency virus-1 replication targeting the human cellular aspartic acid-glutamic acid-alanine-aspartic acid box polypeptide 3," J Med Chem, 51(21):6635-8 (2008).
Marelli et al., "Tumor targeting via integrin ligands," Frontiers in Oncology, 3(222):1-12 (2013).
Miskolci et al., "TNFα release from peripheral blood leukocytes depends on a CRM1-mediated nuclear export," Biochemical and Biophysical Research Communications, 351:354-360 (2006).
Modzelewska-Banachiewicz, B. et al., "Synthesis and biological activity of (Z) and (E) isomers of 3-(3,4-diaryl-1,2,4-triazole-5-yl)prop-2-enoic acid" Monatsh Chem. 140:439-444 (2009).
Modzelewska-Banachiewicz, B. et al., "Synthesis and biological activity of new derivatives of 3-(3,4-diaryl-1,2,4-triazole-5-yl)propenoic acid" European Journal of Medicinal Chemistry, 39:873-877 (2004).
Monecke, T. et al., "Crystal Structure of the Nuclear Export Receptor CRM1 in Complex with Snurportin1 and RanGTP", Science, 324:1087-1091 (2009).
Morales et al., "Mechanical Particle-Size Reduction Techniques, Formulating Poorly Water Soluble Dugs," AAPS Advances in Pharmaceutical Sciences Series, 133-170 (2012).

(56) References Cited

OTHER PUBLICATIONS

Morissette et al., "High-throughput crystallization: polymorphs, salts, co-crystals and solvates of pharmaceutical solids," Adv Drug Deliv Rev, 56(3):275-300 (2004).
Muller, P.A.J. et al., "Nuclear-Cytosolic Transport of COMMD1 Regulates NF-κB and HIF-1 Activity", Traffic, 10:514-527 (2009).
Mutka et al., "Identification of Nuclear Export Inhibitors with Potent Anticancer Activity in Vivo," Cancer Research, 69(2): 510-517 (2009).
Mutka, S. et al., "Nuclear export inhibitors (NEIs) as novel cancer therapeutics", 98th AACr Ann. Mtg., 2 pgs (Apr. 14-18, 2007) (Poster).
Nagase, The Practice of Medicinal Chemistry, Chapter 13. Conversion of Molecules Based on Equivalent Substitution, vol. 1, Technomics Inc., 1998, 253.
Nair, V., "Thermally induced skeletal rearrangement in a triazepine," J Heterocyclic Chem, 12(1):183-4 (1975).
Nakahara, J. et al., "Abnormal expression of TIP30 and arrested nucleocytoplasmic transport within oligodendrocyte precursor cells in multiple sclerosis", Journal of Clinical Investigation, 119(1):169-181 (2009).
Nautiyal et al., "Distinct functions for RIP140 in development, inflammation, and metabolism," Trends in Endocrinology and Metabolism, 24(9):451-459 (2013).
Non-Final Office Action dated Jul. 3, 2014 for U.S. Appl. No. 14/219,638 "Hydrazide Containing Nuclear Transport Modulators And Uses Thereof".
Non-Final Office Action dated Sep. 21, 2012 for U.S. Appl. No. 13/041,377 "Nuclear Transport Modulators and Uses Thereof".
Non-Final Rejection for U.S. Appl. No. 14/235,342, "Nuclear Transport Modulators and Uses Thereof," dated Aug. 28, 2015.
Non-Final Rejection for U.S. Appl. No. 14/777,302, "Methods of Promoting Wound Healing Using CRM1 Inhibitors," dated Mar. 9, 2017.
Non-Final Rejection for U.S. Appl. No. 14/900,469, "Nuclear Transport Modulators and Uses Thereof," dated Nov. 14, 2016.
Non-Final Rejection for U.S. Appl. No. 14/940,310, "Hydrazide Containing Nuclear Transport Modulators and Uses Thereof," dated Aug. 11, 2016.
Non-Final Rejection for U.S. Appl. No. 15/217,514 "Nuclear Transport Modulators and Uses Thereof" dated Mar. 9, 2018.
Non-Final Rejection for U.S. Appl. No. 15/413,889, "Nuclear Transport Modulators and Uses Thereof," dated Sep. 14, 2017.
Non-Final Rejection for U.S. Appl. No. 15/629,307, "Hydrazide Containing Nuclear Transport Modulators and Uses Thereof," dated Feb. 14, 2018.
Noske, A., et al., "Expression of the Nuclear Export Protein Chromosomal Region Maintenance/Exportin 1/Xpo1 Is a Prognostic Factor in Human Ovarian Cancer", Cancer, 112(8):1733-1743 (2008).
Notice of Allowance for U.S. Appl. No. 16/203,181 dated Oct. 3, 2019.
Notice of Allowance for U.S. Appl. No. 13/891,044 "Nuclear Transport Modulators and Uses Thereof", dated Apr. 7, 2015.
Notice of Allowance for U.S. Appl. No. 13/931,372 "Nuclear Transport Modulators and Uses Thereof", dated Sep. 7, 2016.
Notice of Allowance for U.S. Appl. No. 14/235,342 "Nuclear Transport Modulators and Uses Thereof", dated Apr. 25, 2016.
Notice of Allowance for U.S. Appl. No. 14/735,853 "Nuclear Transport Modulators and Uses Thereof", dated Aug. 4, 2015.
Notice of Allowance for U.S. Appl. No. 14/747,394 "Nuclear Transport Modulators and Uses Thereof", dated Aug. 30, 2017.
Notice of Allowance for U.S. Appl. No. 14/900,469 "Nuclear Transport Modulators and Uses Thereof", dated Apr. 18, 2017.
Notice of Allowance for U.S. Appl. No. 14/940,310 "Hydrazide Containing Nuclear Transport Modulators and Uses Thereof", dated Mar. 14, 2017.
Notice of Allowance for U.S. Appl. No. 14/989,377 "Nuclear Transport Modulators and Uses Thereof", dated Oct. 28, 2016.
Notice of Allowance for U.S. Appl. No. 15/413,889 "Nuclear Transport Modulators and Uses Thereof", dated Apr. 10, 2018.
Notice of Allowance for U.S. Appl. No. 15/629,307, Hydrazide Containing Nuclear Transport Modulators and Uses Thereof dated Aug. 29, 2008.
Notice of Allowance for U.S. Appl. No. 15/651,856, "Nuclear Transport Modulators and Uses Thereof" dated Apr. 24, 2019.
Notice of Allowance for U.S. Appl. No. 16/037,798 "Nuclear Transport Modulators and Uses Thereof," dated Nov. 8, 2019.
Notice of Allowance for U.S. Appl. No. 17/365,656 dated Jun. 16, 2023.
Notice of Allowance for U.S. Appl. No. 18/131,273 dated Jul. 11, 2023.
Notice of Allowance for U.S. Appl. No. 18/132,241 dated Jul. 6, 2023.
Orsted et al., "Basic principles of wound healing," Wound Care Canada, 9(2): 4-12 (2011).
Patani, G.A., et al., "Bioisosterism: A Rational Approach in Drug Design", Chem Rev, 96:3147-3176 (1996).
Procopiou et al., "Inhibitors of Cholesterol Biosynthesis. 2. 3,5-Dihydroxy-7-(N-pyrrolyl)-6-heptenoates, a Novel Series of HMG-CoA Reductase Inhibitors," J Med Chem, 36(23): 3658-3662 (1993).
Quan, M.L. et al., "Design and Synthesis of Isoxazoline Derivatives as Factor Xa Inhibitors", J. Med. Chem. 42: 2760-2773 (1999).
Rawlinson, S.M. et al., "CRM1-mediated Nuclear Export of Dengue Virus RNA Polymerase NS5 Modulates Interleukin-8 Induction and Virus Production", Journal of Biological Chemistry, 284(23):15589-15597 (2009).
Registry(STN) [online] Nov. 25, 1993, CAS Registration No. 151446-45-6.
Registry(STN)[online], Jan. 23, 2008, CAS registered No. 1000508-38-2, 1 page.
Requirement for Restriction/Election for U.S. Appl. No. 13/041,377 "Nuclear Transport Modulators and Uses Thereof", dated Jul. 5, 2012.
Requirement for Restriction/Election for U.S. Appl. No. 13/350,864 "Olefin Containing Nuclear Transport Modulators and Uses Thereof", dated Dec. 19, 2013.
Requirement for Restriction/Election for U.S. Appl. No. 13/931,372 "Nuclear Transport Modulators and Uses Thereof", dated May 22, 2014.
Requirement for Restriction/Election for U.S. Appl. No. 14/235,342 "Nuclear Transport Modulators and Uses Thereof", dated Jun. 9, 2015.
Requirement for Restriction/Election for U.S. Appl. No. 14/777,302 "Methods of Promoting Wound Healing Using CRM1 Inhibitors", dated Sep. 22, 2016.
Requirement for Restriction/Election for U.S. Appl. No. 15/217,514 "Nuclear Transport Modulators and Uses Thereof", dated Aug. 8, 2017.
Sakamoto et al., "Studies on Pyrimidine Derivatives. XXV. Reaction of Pyrimidinyl Aldehydes and Ketones with Wittig Reagents," Chem Pharm Bull, 30(2): 610-614 (1982).
Sanchez, V. et al., "Nuclear Export of the Human Cytomegalovirus Tegument Protein pp65 Requires Cyclin-Dependent Kinase Activity and the Crm1 Exporter", Journal of Virology, 81(21):11730-11736 (2007).
Shaoyong, Ke. et al., "Research Advance of Acylhydrazine Derivatives with Biological Activities", Chinese Journal of Organic Chemistry 30(12):1820-1830 (2010).
Shasheva, "Reactions of Hydroxyphenyl-Substituted 1,2,4-Triazoles with Electrophilic Reagents", Russian Journal of General Chemistry, 79(10): 2234-2243 (2009).
Singhal et al., "Drug Polymorphism and Dosage Form Design: A practical perspective," Advanced Drug Delivery Reviews, 56:335-347 (2004).
Sorokin, A.V. et al., "Nucleocytoplasmic Transport of Proteins", Biochemistry Moscow, 72(13):1439-1457 (2007).
Storey et al., "Solid State Characterization of Pharmaceuticals," Blackwell Publishing, (2011).
Sun Q., et al., "Nuclear export inhibition through covalent conjugation and hydrolysis of Leptomycin B by CRM1", Proc Nat Acad Sci, 110(4): 1303-1308 (2013).

(56) References Cited

OTHER PUBLICATIONS

Tai et al., "CRM1 inhibition induces tumor cell cytotoxicity and impairs osteoclastogenesis in multiple myeloma: molecular mechanisms and therapeutic implications," Leukemia, 28:155-165 (2014).
Tamir et al., "KPT-350, a Selective Inhibitor of Nuclear Export (SINE) Compound, Shows Efficacy in the Mouse Pilocapine Model of Temporal Lobe Epilepsy," Journal of Neurological Sciences, 381: 87-88 (2017).
Terry, L.J. et al., "Crossing the Nuclear Envelope: Hierarchical Regulation of Nucleocytoplasmic Transport", Science, 318:1412-1416 (2007).
Van der Watt, P.J. et al., "The Karyopherin proteins, Crm1 and Karyopherin β1, are overexpressed in cervical cancer and are critical for cancer cell survival and proliferation", Int. J. Cancer, 124:1829-1840 (2009).
Van Neck et al., "Inhibition of the CRM1-mediated nucleocytoplasmic transport by N-azolylacrylates: Structure-activity relationship and mechanism of action", Bioorganic & Medicinal Chemistry 16:9487-9497 (2008).
Walsh, Jr., M.D., et al., Exportin 1 Inhibition Attenuates Nuclear Factor-κB-Dependent Gene Expression, Shock, 29(2):160-166 (2008).
Wang et al., "Mathematical modeling in cancer drug discovery," Drug Discovery Today, 19(2):145-150 (2014).
Williams, P., et al., "Characterization of a CRM1-Dependent Nuclear Export Signal in the C Terminus of Herpes Simplex Virus Type 1 Tegument Protein UL47", Journal of Virology, 82(21):10946-10952 (2008).
Written Opinion of the International Searching Authority for International Application No. PCT/US2011/027328, "Nuclear Transport Modulators And Uses Thereof" dated Apr. 29, 2011, 8 pages.
Written Opinion of the International Searching Authority for International Application No. PCT/US2012/048319, "Hydrazide Containing Nuclear Transport Modulators And Uses Thereof" dated Nov. 9, 2012, 9 pages.
Written Opinion of the International Searching Authority for International Application No. PCT/US2012/048368, "Nuclear Transport Modulators And Uses Thereof" dated Sep. 21, 2012, 11 pages.
Wu et al., Application of temperature cycling for crystal quality control during crystallization, CrystEngComm, 18(13): 2222-2238 (2016).
Yao, Y., et al., "The expression of CRM1 is associated with prognosis in human osteosarcoma", Oncology Reports, 21:229-235 (2009).
Yonemochi, "Physicochemical Properties for Amorphous Pharmaceuticals and their Stability," Cryobiol and Cryotechnol 51(1):25-30 (2005).
Zheng et al., "KPT-330 inhibitor of XPO1-mediated nuclear export has anti-proliferative activity in hepatocellular carcinoma," Cancer Chemother Pharmacol, 74:487-495 (2014).
Zimmerman, T.L. et al., "Nuclear Export of Retinoid X Receptor a in Response to Interleukin-1β-mediated Cell Signaling Roles for JNK and Ser260", The Journal of Biological Chemistry, 281(22):15434-15440 (2006).
Final Rejection for U.S. Appl. No. 14/777,302 , "Methods of Promoting Wound Healing Using CRMI Inhibitors," dated Nov. 15, 2017.

* cited by examiner

NUCLEAR TRANSPORT MODULATORS AND USES THEREOF

RELATED APPLICATION

This application is a a continuation of U.S. application Ser. No. 16/519,955, filed Jul. 23, 2019, which is a continuation of U.S. application Ser. No. 15/651,856 (Now U.S. Pat. No. 10,407,405), filed Jul. 17, 2017, which is a continuation of U.S. application Ser. No. 14/900,469 (now U.S. Pat. No. 9,738,624), filed Dec. 21, 2015, filed Jun. 20, 2014, which is the U.S. National Stage of International Application No. PCT/US2014/043479, filed on Jun. 20, 2014, published in English, which claims the benefit of U.S. Provisional Application No. 61/838,172, filed on Jun. 21, 2013. The entire teachings of the above application(s) are incorporated herein by reference.

BACKGROUND OF THE INVENTION

Cells from most major human solid and hematologic malignancies exhibit abnormal cellular localization of a variety of oncogenic proteins, tumor suppressor proteins, and cell cycle regulators (Cronshaw et al, 2004, Falini et al 2006). For example, certain p53 mutations lead to localization in the cytoplasm rather than in the nucleus. This results in the loss of normal growth regulation, despite intact tumor suppressor function. In other tumors, wild-type p53 is sequestered in the cytoplasm or rapidly degraded, again leading to loss of its suppressor function. Restoration of appropriate nuclear localization of functional p53 protein can normalize some properties of neoplastic cells (Cai et al, 2008; Hoshino et al 2008; Lain et al 1999a; Lain et al 1999b; Smart et al 1999), can restore sensitivity of cancer cells to DNA damaging agents (Cai et al, 2008), and can lead to regression of established tumors (Sharpless & DePinho 2007, Xue et al, 2007). Similar data have been obtained for other tumor suppressor proteins such as forkhead (Turner and Sullivan 2008) and c-Abl (Vignari and Wang 2001). In addition, abnormal localization of several tumor suppressor and growth regulatory proteins may be involved in the pathogenesis of autoimmune diseases (Davis 2007, Nakahara 2009). CRM1 inhibition may provide particularly interesting utility in familial cancer syndromes (e.g., Li-Fraumeni Syndrome due to loss of one p53 allele, BRCA1 or 2 cancer syndromes), where specific tumor suppressor proteins (TSP) are deleted or dysfunctional and where increasing TSP levels by systemic (or local) administration of CRM1 inhibitors could help restore normal tumor suppressor function.

Specific proteins and RNAs are carried into and out of the nucleus by specialized transport molecules, which are classified as importins if they transport molecules into the nucleus, and exportins if they transport molecules out of the nucleus (Terry et al, 2007; Sorokin et al 2007). Proteins that are transported into or out of the nucleus contain nuclear import/localization (NLS) or export (NES) sequences that allow them to interact with the relevant transporters. Chromosomal Region Maintenance 1 (Crm1), which is also called exportin-1 or Xpo1, is a major exportin.

Overexpression of Crm1 has been reported in several tumors, including human ovarian cancer (Noske et al, 2008), cervical cancer (van der Watt et al, 2009), pancreatic cancer (Huang et al, 2009), hepatocellular carcinoma (Pascale et al, 2005) and osteosarcoma (Yao et al, 2009) and is independently correlated with poor clinical outcomes in these tumor types.

Inhibition of Crm1 blocks the exodus of tumor suppressor proteins and/or growth regulators such as p53, c-Abl, p21, p27, pRB, BRCA1, IkB, ICp27, E2F4, KLF5, YAP1, ZAP, KLF5, HDAC4, HDAC5 or forkhead proteins (e.g. FOXO3a) from the nucleus that are associated with gene expression, cell proliferation, angiogenesis and epigenetics. Crm1 inhibitors have been shown to induce apoptosis in cancer cells even in the presence of activating oncogenic or growth stimulating signals, while sparing normal (untransformed) cells. Most studies of Crm1 inhibition have utilized the natural product Crm1 inhibitor Leptomycin B (LMB). LMB itself is highly toxic to neoplastic cells, but poorly tolerated with marked gastrointestinal toxicity in animals (Roberts et al, 1986) and humans (Newlands et al, 1996). Derivatization of LMB to improve drug-like properties leads to compounds that retain antitumor activity and are better tolerated in animal tumor models (Yang et al, 2007, Yang et al, 2008, Mutka et al, 2009). Therefore, nuclear export inhibitors could have beneficial effects in neoplastic and other proliferative disorders. To date, however, small-molecule, drug-like Crm1 inhibitors for use in vitro and in vivo are uncommon.

In addition to tumor suppressor proteins, Crm1 also exports several key proteins that are involved in many inflammatory processes. These include IkB, NF-kB, Cox-2, RXRα, Commd1, HIF1, HMGB1, FOXO, FOXP and others. The nuclear factor kappa B (NF-kB/rel) family of transcriptional activators, named for the discovery that it drives immunoglobulin kappa gene expression, regulate the mRNA expression of variety of genes involved in inflammation, proliferation, immunity and cell survival. Under basal conditions, a protein inhibitor of NF-kB, called IkB, binds to NF-kB in the nucleus and the complex IkB-NF-kB renders the NF-kB transcriptional function inactive. In response to inflammatory stimuli, IkB dissociates from the IkB-NF-kB complex, which releases NF-kB and unmasks its potent transcriptional activity. Many signals that activate NF-kB do so by targeting IkB for proteolysis (Phosphorylation of IkB renders it "marked" for ubiquitination and then proteolysis). The nuclear IkBa-NF-kB complex can be exported to the cytoplasm by Crm1 where it dissociates and NF-kB can be reactivated. Ubiquitinated IkB may also dissociate from the NF-kB complex, restoring NF-kB transcriptional activity. Inhibition of Crm1 induced export in human neutrophils and macrophage like cells (U937) by LMB not only results in accumulation of transcriptionally inactive, nuclear IkBa-NF-kB complex but also prevents the initial activation of NF-kB even upon cell stimulation (Ghosh 2008, Huang 2000). In a different study, treatment with LMB inhibited IL-1β induced NF-kB DNA binding (the first step in NF-kB transcriptional activation), IL-8 expression and intercellular adhesion molecule expression in pulmonary microvascular endothelial cells (Walsh 2008). COMMD1 is another nuclear inhibitor of both NF-kB and hypoxia-inducible factor 1 (HIF1) transcriptional activity. Blocking the nuclear export of COMMD1 by inhibiting Crm1 results in increased inhibition of NF-kB and HIF1 transcriptional activity (Muller 2009).

Crm1 also mediates Retinoid X receptor α (RXRα) transport. RXRα is highly expressed in the liver and plays a central role in regulating bile acid, cholesterol, fatty acid, steroid and xenobiotic metabolism and homeostasis. During liver inflammation, nuclear RXRα levels are significantly reduced, mainly due to inflammation-mediated nuclear export of RXRα by Crm1. Lep B is able to prevent IL-1β induced cytoplasmic increase in RXRα levels in human liver derived cells (Zimmerman 2006).

The role of Crm1-mediated nuclear export in NF-kB, HIF-1 and RXRα signalling suggests that blocking nuclear export can be potentially beneficial in many inflammatory processes across multiple tissues and organs including the vasculature (vasculitis, arteritis, polymyalgia rheumatic, atherosclerosis), dermatologic (see above), rheumatologic (rheumatoid and related arthritis, psoriatic arthritis, spondyloarthropathies, crystal arthropathies, systemic lupus erythematosus, mixed connective tissue disease, myositis syndromes, dermatomyositis, inclusion body myositis, undifferentiated connective tissue disease, Sjogren's syndrome, scleroderma and overlap syndromes, etc.).

CRM1 Inhibition affects gene expression by inhibiting/activating a series of transcription factors like ICp27, E2F4, KLF5, YAP1, ZAP Crm1 inhibition has potential therapeutic effects across many dermatologic syndromes including inflammatory dermatoses (atopy, allergic dermatitis, chemical dermatitis, psoriasis), sun-damage (Ultraviolet/UV damage), and infections. CRM1 inhibition, best studied with LMB, showed minimal effects on normal keratinocytes, and exerted anti-inflammatory activity on keratinocytes subjected to UV, TNFa, or other inflammatory stimuli (Kobayashi & Shinkai 2005, Kannan & Jaiswal 2006). Crm1 inhibition also upregulates NRF2 (nuclear factor erythroid-related factor 2) activity, which protects keratinocytes (Schafer et al, 2010, Kannan & Jaiswal 2006) and other cell types (Wang et al, 2009) from oxidative damage. LMB induces apoptosis in keratinocytes infected with oncogenic human papillomavirus (HPV) strains such as HPV16, but not in uninfected keratinocytes (Jolly et al, 2009).

Crm1 also mediates the transport of key neuroprotectant proteins that may be useful in neurodegenerative diseases including Parkinson's Disease (PD), Alzheimer's Disease, and Amyotrophic Lateral Sclerosis. For example, (1) forcing nuclear retention of key neuroprotective regulators such as NRF2 (Wang 2009), FOXA2 (Kittappa et al, 2007), parking in neuronal cells and/or by (2) inhibiting NFκB transcriptional activity by sequestering IκB to the nucleus in glial cells, Crm1 inhibition could slow or prevent neuronal cell death found in these disorders. There is also evidence linking abnormal glial cell proliferation to abnormalities in CRM1 levels or CR1 function (Shen 2008).

Intact nuclear export, primarily mediated through CRM1, is also required for the intact maturation of many viruses. Viruses where nuclear export, and/or CRM1 itself, has been implicated in their lifecycle include human immunodeficiency virus (HIV), adenovirus, simian retrovirus type 1, Borna disease virus, influenza (usual strains as well as H1N1 and avian H5N1 strains), hepatitis B (HBV) and C (HCV) viruses, human papillomavirus (HPV), respiratory syncytial virus (RSV), Dungee, Severe Acute Respiratory Syndrome coronavirus, yellow fever virus, West Nile Virus, herpes simplex virus (HSV), cytomegalovirus (CMV), and Merkel cell polyomavirus (MCV). (Bhuvanakantham 2010, Cohen 2010, Whittaker 1998). It is anticipated that additional viral infections reliant on intact nuclear export will be uncovered in the near future.

The HIV-1 Rev protein, which traffics through nucleolus and shuttles between the nucleus and cytoplasm, facilitates export of unspliced and singly spliced HIV transcripts containing Rev Response Elements (RRE) RNA by the CRM1 export pathway. Inhibition of Rev-mediated RNA transport using CRM1 inhibitors such as LepB or PKF050-638 can arrest the HIV-1 transcriptional process, inhibit the production of new HIV-1 virions, and thereby reduce HIV-1 levels (Pollard 1998, Daelemans 2002).

Dengue virus (DENV) is the causative agent of the common arthropod-borne viral disease, dengue fever (DF), and its more severe and potentially deadly dengue hemorrhagic fever (DHF). DHF appears to be the result of an over exuberant inflammatory response to DENV. NS5 is the largest and most conserved protein of DENV. CRM1 regulates the transport of NS5 from the nucleus to the cytoplasm, where most of the NS5 functions are mediated. Inhibition of CRM1 mediated export of NS5 results in altered kinetics of virus production and reduces induction of the inflammatory chemokine interleukin-8 (IL-8), presenting a new avenue for the treatment of diseases caused by DENV and other medically important flaviviruses including Hepatitis C virus (Rawlinson 2009).

Other virus-encoded RNA-binding proteins that use CRM1 to exit the nucleus include the HSV type 1 tegument protein (VP13/14, or hUL47), human CMV protein pp65, the SARS Coronavirus ORF 3b Protein, and the RSV matrix (M) protein (Williams 2008, Sanchez 2007, Freundt 2009, Ghildyal 2009).

Interestingly, many of these viruses are associated with specific types of human cancer including hepatocellular carcinoma (HCC) due to chronic HBV or HCV infection, cervical cancer due to HPV, and Merkel cell carcinoma associated with MCV. CRM1 inhibitors could therefore have beneficial effects on both the viral infectious process as well as on the process of neoplastic transformation due to these viruses.

CRM1 controls the nuclear localization and therefore activity of multiple DNA metabolizing enzymes including histone deacetylases (HDAC), histone acetyltransferases (HAT), and histone methyltransferases (HMT). Suppression of cardiomyocyte hypertrophy with irreversible CRM1 inhibitors has been demonstrated and is believed to be linked to nuclear retention (and activation) of HDAC 5, an enzyme known to suppress a hypertrophic genetic program (Monovich et al, 2009). Thus, CRM1 inhibition may have beneficial effects in hypertrophic syndromes, including certain forms of congestive heart failure and hypertrophic cardiomyopathies.

CRM1 has also been linked to other disorders. Leber's disorder, a hereditary disorder characterized by degeneration of retinal ganglion cells and visual loss, is associated with inaction of the CRM1 switch (Gupta N 2008). There is also evidence linking neurodegenerative disorders to abnormalities in nuclear transport.

In view of the above, the discovery of compounds that modulate nuclear transport is desirable.

SUMMARY OF THE INVENTION

The present invention relates to compounds, and pharmaceutically acceptable salts thereof, useful as nuclear transport modulators; pharmaceutically acceptable compositions comprising compounds of the present invention or their pharmaceutically acceptable salts; and methods of using said compounds, salts and compositions in the treatment of various disorders.

The compounds of the invention have general formula I:

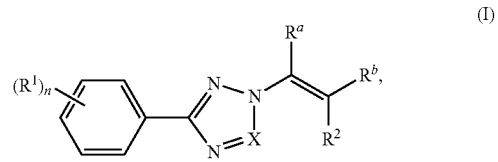

wherein each variable is as defined and described herein.

Compounds of the present invention and pharmaceutically acceptable salts and compositions thereof are useful for treating a variety of diseases, disorders or conditions associated with abnormal cellular responses triggered by improper nuclear transport. Therefore, one embodiment of the invention is use of a compound of the invention, or a pharmaceutically acceptable salt thereof, for treating a variety of diseases, disorders or conditions associated with abnormal cellular responses triggered by improper nuclear transport. Another embodiment of the invention is a method for treating a variety of diseases, disorders or conditions associated with CRM1 activity in a subject in need thereof, the method comprising administering to the subject in need thereof a therapeutically effective amount of a compound the invention, or a pharmaceutically acceptable salt or composition thereof. Such diseases, disorders, or conditions include those described herein.

Compounds of the invention, and pharmaceutically acceptable salts thereof, are also useful in the manufacture of a medicament for the treatment of a variety of diseases, disorders or conditions associated with abnormal cellular responses triggered by improper nuclear transport. Such diseases, disorders, or conditions include those described herein.

Compounds provided by this invention are also useful for the study of nuclear transport modulation in biological and pathological phenomena; the study of intracellular signal transduction pathways mediated by, for example, kinases; and the comparative evaluation of new nuclear transport modulators.

BRIEF DESCRIPTION OF THE FIGURES

The foregoing will be apparent from the following more particular description of example embodiments of the invention.

DETAILED DESCRIPTION OF THE INVENTION

Compounds of the Invention

Figure 1:
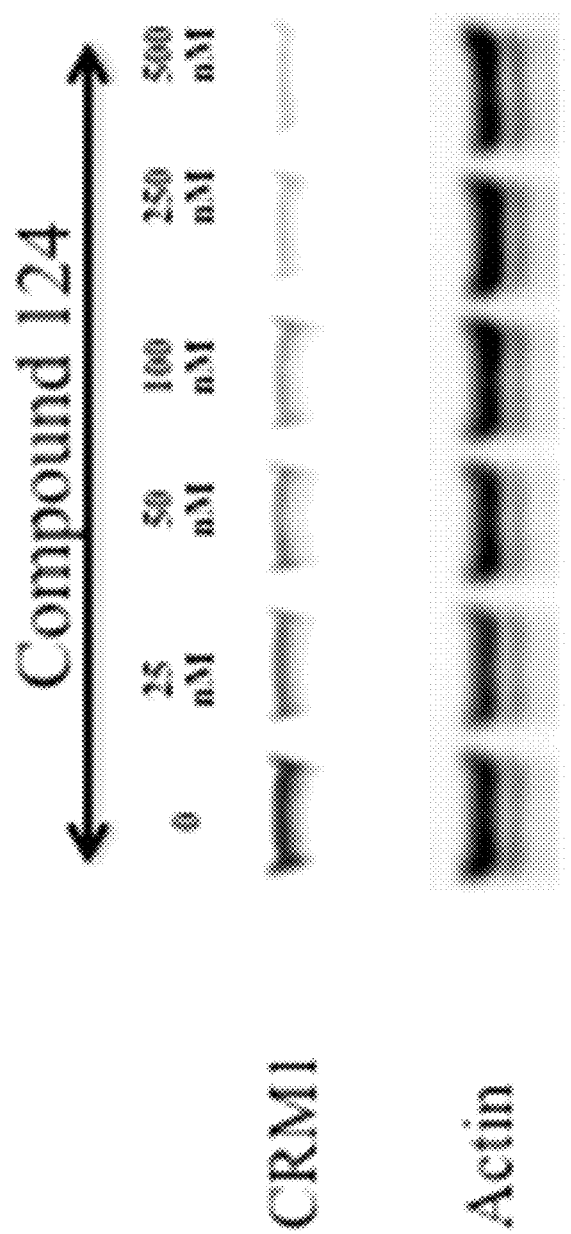
FIG. 1 is an image of a Western blot, and shows that treatment of HT1080 cells with Compound 124 results in a dose-dependent degradation of CRM1.

A first embodiment of the invention is a compound of structural formula I:

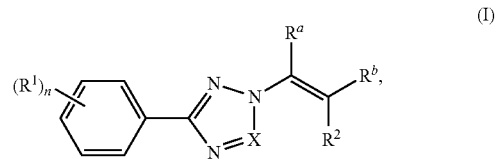

or a pharmaceutically acceptable salt thereof, wherein:

X is —C(H)— or —N—;

each $R^1$ is independently selected from halo; haloalkyl; —$(CH_2)_{1-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}$-carbocyclyl, which may be substituted with $R°$; —$(CH_2)_{0-4}$-aryl, which may be substituted with $R°$; —$(CH_2)_{0-4}$-heterocyclyl, which may be substituted with $R°$; —$(CH_2)_{0-4}$-heteroaryl, which may be substituted with $R°$; —CH=CH-carbocyclyl, which may be substituted with $R°$; —CH=CH-aryl, which may be substituted with $R°$; —CH=CH-heterocyclyl, which may be substituted with $R°$; —CH=CH-heteroaryl, which may be substituted with $R°$; —$NO_2$; —CN; —$N_3$; —$(CH_2)_{0-4}N(R°)_2$; —$(CH_2)_{0-4}N(R°)C(O)R°$; —$(CH_2)_{0-4}N(R°)C(S)R°$; —$(CH_2)_{0-4}N(R°)C(O)NR°_2$; —$(CH_2)_{0-4}N(R°)C(S)NR°_2$; —$(CH_2)_{0-4}N(R°)C(O)OR°$; —$(CH_2)_{0-4}N(R°)N(R°)C(O)R°$; —$(CH_2)_{0-4}N(R°)N(R°)C(O)NR°_2$; —$(CH_2)_{0-4}N(R°)N(R°)C(O)OR°$; —$(CH_2)_{0-4}C(O)R°$; —$(CH_2)_{0-4}C(S)R°$; —$(CH_2)_{0-4}C(O)OR°$; —$(CH_2)_{0-4}C(O)SR°$; —$(CH_2)_{0-4}OC(O)R°$; —$(CH_2)_{0-4}OC(O)(CH_2)_{0-4}SR°$; —$(CH_2)_{0-4}SC(S)SR°$; —$(CH_2)_{0-4}SC(O)R°$; —$(CH_2)_{0-4}C(O)NR°_2$; —$(CH_2)_{0-4}C(S)NR°_2$; —$(CH_2)_{0-4}C(S)SR°$; —$(CH_2)_{0-4}OC(O)NR°_2$; —$(CH_2)_{0-4}C(O)N(OR°)R°$; —$(CH_2)_{0-4}C(O)C(O)R°$; —$(CH_2)_{0-4}C(O)CH_2C(O)R°$; —$(CH_2)_{0-4}C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$(CH_2)_{0-4}S(O)_2NR°_2$; —$(CH_2)_{0-4}S(O)R°$; —$(CH_2)_{0-4}N(R°)S(O)_2NR°_2$; —$(CH_2)_{0-4}N(R°)S(O)_2R°$; —$(CH_2)_{0-4}N(OR°)R°$; —$(CH_2)_{0-4}C(NH)NR°_2$; —$(CH_2)_{0-4}P(O)_2R°$; —$(CH_2)_{0-4}P(O)R°_2$; —$(CH_2)_{0-4}OP(O)R°_2$; —$(CH_2)_{0-4}OP(O)(OR°)_2$; —$(CH_2)_{0-4}ON(R°)_2$; and —$(CH_2)_{0-4}C(O)O—N(R°)_2$, wherein:

each $R°$ is independently hydrogen, $C_{1-6}$ aliphatic, —$CH_2$-carbocyclyl, —$CH_2$-aryl, —$CH_2$-heterocyclyl, —$CH_2$-heteroaryl, —$O(CH_2)_{0-1}$-carbocyclyl, —$O(CH_2)_{0-1}$-aryl, —$O(CH_2)_{0-1}$-heterocyclyl, —$O(CH_2)_{0-1}$-heteroaryl, carbocyclyl, aryl, heterocyclyl or heteroaryl, or two independent occurrences of $R°$, taken together with their intervening atom(s), form a 3-12-membered carbocyclyl, aryl, heterocyclyl or heteroaryl; and each $R°$ and each ring formed from two independent occurrences of $R°$, taken together with their intervening atom(s), are optionally and independently substituted with one or more substituents selected from the group consisting of halo, CN, OH, unsubstituted $C_1$-$C_3$ alkyl, halo-$C_1$-$C_3$ alkyl, —$NH_2$, —$NO_2$, —NH(unsubstituted $C_1$-$C_3$ alkyl), —N(unsubstituted $C_1$-$C_3$ alkyl)$_2$, —O—$C_1$-$C_3$ alkyl, —C(O)OH, —C(O)O-(unsubstituted $C_1$-$C_3$ alkyl), —C(O)-(unsubstituted $C_1$-$C_3$ alkyl), —O-(unsubstituted $C_1$-$C_3$ alkyl), and —S-(unsubstituted $C_1$-$C_3$ alkyl);

$R^2$ is selected from optionally substituted heteroaryl and optionally substituted aryl; one of $R^a$ and $R^b$ is hydrogen, and the other is selected from —C(O)—N($R^5$)($R^6$), —CN, —C(O)—O—$R^3$, —C(S)—O—$R^3$, —C(S)—N($R^5$)($R^6$), —C(O)—N($R^7$)—N($R^5$)($R^6$), —C(S)—N($R^7$)—N($R^5$)($R^6$), —C(O)—N($R^7$)—N($R^7$)—C(O)—$R^4$, —C(S)—N($R^7$)—N($R^7$)—C(O)—$R^4$, —C(O)—N($R^7$)—N($R^7$)—C(S)—$R^4$, —C(S)—N($R^7$)—N($R^7$)—C(S)—$R^4$, —C(O)—N($R^7$)—N($R^7$)—S(O)$_{1\text{-}2}$—$R^4$ and —C(S)—N($R^7$)—N($R^7$)—S(O)$_{1\text{-}2}$—$R^4$, wherein:

$R^3$ is selected from hydrogen, $C_1$-$C_4$ alkyl, $C_2$-$C_4$ alkenyl, $C_2$-$C_4$ alkynyl, carbocyclyl, aryl, heterocyclyl and heteroaryl;

$R^4$ is selected from —N(H)($C_3$-$C_6$ cycloalkyl), —N($C_1$-$C_4$ alkyl)($C_3$-$C_6$ cycloalkyl), —$C_1$-$C_6$ alkyl, —($C_0$-$C_4$ alkylene)-carbocyclyl, —($C_0$-$C_4$ alkylene)-heterocyclyl, —($C_0$-$C_4$ alkylene)-aryl, and —($C_0$-$C_4$ alkylene)-heteroaryl;

$R^5$ and $R^6$ are each independently selected from hydrogen, $C_1$-$C_4$ alkyl, $C_2$-$C_4$ alkenyl, $C_2$-$C_4$ alkynyl, carbocyclyl, aryl, heterocyclyl and heteroaryl; or $R^5$ and $R^6$ are taken together with the nitrogen atom to which they are commonly attached to form a heterocyclyl or heteroaryl;

each $R^7$ is independently hydrogen or $C_1$-$C_4$ alkyl; and n is 0, 1, 2, 3, 4 or 5; wherein:

unless otherwise designated, each alkyl, alkenyl, alkynyl, alkylene, carbocyclyl, aryl, cycloalkyl, heterocyclyl and heteroaryl is optionally and independently substituted.

In a first aspect of the first embodiment, one of $R^a$ and $R^b$ is hydrogen, and the other is selected from —C(O)—O—$R^3$, —C(O)—N($R^5$)($R^6$), —C(O)—N($R^7$)—N($R^5$)($R^6$), —C(O)—N($R^7$)—N($R^7$)—C(O)—$R^4$ and —C(O)—N($R^7$)—N($R^7$)—S(O)$_{1\text{-}2}$—$R^4$. The values for the remaining variables are as described in the first embodiment.

In a second aspect of the first embodiment, one of $R^a$ and $R^b$ is hydrogen, and the other is selected from —C(O)—OH, —C(O)—$NH_2$, —C(O)—N($R^7$)—N($R^5$)($R^6$), —C(O)—N($R^7$)—N($R^7$)—C(O)—$R^4$ and —C(O)—N($R^7$)—N($R^7$)—S(O)$_{1\text{-}2}$—$R^4$. The values for the remaining variables are as described in the first embodiment, or first aspect thereof.

In a third aspect of the first embodiment, one of $R^a$ and $R^b$ is hydrogen, and the other is —C(O)—OH; or —C(O)—$NH_2$; or —C(O)—NH—NH($R^6$), and $R^6$ is an optionally substituted heteroaryl; or —C(O)—NH—NH—C(O)—$R^4$ or —C(O)—NH—NH—S(O)$_{1\text{-}2}$—$R^4$, and $R^4$ is selected from optionally substituted —N(H)($C_3$-$C_6$ cycloalkyl), —N($C_1$-$C_4$ alkyl)($C_3$-$C_6$ cycloalkyl), —$C_1$-$C_6$ alkyl, —($C_0$-$C_4$ alkylene)-heterocyclyl and —($C_0$-$C_4$ alkylene)-heteroaryl. The values for the remaining variables are as described in the first embodiment, or first or second aspect thereof.

In a fourth aspect of the first embodiment, one of $R^a$ and $R^b$ is hydrogen and the other is —C(O)$NH_2$. The values for the remaining variables are as described in the first embodiment, or first through third aspects thereof.

In a fifth aspect of the first embodiment, $R^a$ is hydrogen. The values for the remaining variables are as described in the first embodiment, or first through fourth aspects thereof.

In a sixth aspect of the first embodiment, $R^2$ is an optionally substituted $C_5$-$C_{15}$ heteroaryl. The values for the remaining variables are as described in the first embodiment, or first through fifth aspects thereof.

In a seventh aspect of the first embodiment, $R^2$ is an optionally substituted 5-6-membered heteroaryl having 1, 2 or 3 heteroatoms independently selected from the group consisting of nitrogen, oxygen and sulfur. The values for the remaining variables are as described in the first embodiment, or first through sixth aspects thereof.

In an eighth aspect of the first embodiment, $R^2$ is an optionally substituted 5-membered heteroaryl having 1, 2 or 3 heteroatoms independently selected from the group consisting of nitrogen, oxygen and sulfur. The values for the remaining variables are as described in the first embodiment, or first through seventh aspects thereof.

In a ninth aspect of the first embodiment, $R^2$ is an optionally substituted pyrrolyl, furanyl, thiophenyl, pyrazolyl, imidazolyl, thiazolyl, isothiazolyl, oxazolyl, isoxazolyl, triazolyl, thiadiazolyl, or oxadiazolyl. The values for the remaining variables are as described in the first embodiment, or first through eighth aspects thereof.

In a tenth aspect of the first embodiment, $R^2$ is an optionally substituted 6-membered heteroaryl having 1, 2 or 3 heteroatoms independently selected from the group consisting of nitrogen, oxygen and sulfur. The values for the remaining variables are as described in the first embodiment, or first through ninth aspects thereof.

In an eleventh aspect of the first embodiment, $R^2$ is an optionally substituted pyridinyl, pyrimidinyl, pyrazinyl, pyridazinyl or triazinyl. The values for the remaining variables are as described in the first embodiment, or first through tenth aspects thereof.

In a twelfth aspect of the first embodiment, $R^2$ is optionally substituted with halogen, $C_1$-$C_4$ alkyl, $C_1$-$C_4$ alkoxy, $C_1$-$C_4$ thioalkoxy, hydroxyl, amino, $C_1$-$C_4$ alkylamino, $C_1$-$C_4$ dialkylamino, sulfhydryl or cyano. The values for the remaining variables are as described in the first embodiment, or first through eleventh aspects thereof.

In a thirteenth aspect of the first embodiment, $R^2$ is optionally substituted with halogen, $C_1$-$C_4$ alkyl or $C_1$-$C_4$ alkoxy. The values for the remaining variables are as described in the first embodiment, or first through twelfth aspects thereof.

In a fourteenth aspect of the first embodiment, X is —C(H)—. The values for the remaining variables are as described in the first embodiment, or first through thirteenth aspects thereof.

In a fifteenth aspect of the first embodiment, n is 0, 1 or 2. The values for the remaining variables are as described in the first embodiment, or first through fourteenth aspects thereof.

In a sixteenth aspect of the first embodiment, each $R^1$ is independently selected from —$CF_3$, —CN, halo, —OH, $C_1$-$C_3$ alkyl, $C_3$-$C_6$ cycloalkyl, $C_3$-$C_{12}$ heterocycloalkyl, halo-$C_1$-$C_3$ alkyl, —$NH_2$, —$NO_2$, —NH($C_1$-$C_3$ alkyl), —N($C_1$-$C_3$ alkyl)($C_1$-$C_3$ alkyl), —C(O)OH, —C(O)O—($C_1$-$C_6$ alkyl), —C(O)—($C_1$-$C_3$ alkyl), —O—($C_1$-$C_3$ alkyl), —O—($C_1$-$C_3$ haloalkyl), and —S—($C_1$-$C_3$ alkyl), or is absent. The values for the remaining variables are as described in the first embodiment, or first through fifteenth aspects thereof.

In a seventeenth aspect of the first embodiment, each $R^1$ is independently selected from halo, —$C_1$-$C_4$ alkyl, —$C_1$-$C_4$ haloalkyl and —O—$C_1$-$C_4$ alkyl, or is absent. The values for the remaining variables are as described in the first embodiment, or first through sixteenth aspects thereof.

In an eighteenth aspect of the first embodiment, one of $R^a$ and $R^b$ is hydrogen, and the other is —C(O)OH; or —C(O)NH$_2$; or —C(O)—NH—NH($R^6$), and $R^6$ is an optionally substituted $C_5$-$C_6$ heteroaryl; or —C(O)—NH—NH—C(O)—$R^4$ or —C(O)—NH—NH—S(O)$_{1-2}$—$R^4$, and $R^4$ is selected from optionally substituted —N(H)($C_3$-$C_6$ cycloalkyl), —N($C_1$-$C_4$ alkyl)($C_3$-$C_6$ cycloalkyl), —$C_1$-$C_6$ alkyl, —($C_0$-$C_4$ alkylene)-($C_3$-$C_7$)heterocyclyl and —($C_0$-$C_4$ alkylene)-($C_5$-$C_6$)heteroaryl. The values for the remaining variables are as described in the first embodiment, or first through seventeenth aspects thereof.

In a nineteenth aspect of the first embodiment, each $R^7$ is hydrogen. The values for the remaining variables are as described in the first embodiment, or first through eighteenth aspects thereof.

In a twentieth aspect of the first embodiment, $R^5$ is selected from hydrogen and $C_1$-$C_4$ alkyl; and $R^6$ is selected from $C_1$-$C_4$ alkyl, carbocyclyl, aryl, heterocyclyl and heteroaryl. The values for the remaining variables are as described in the first embodiment, or first through nineteenth aspects thereof.

In a twenty-first aspect of the first embodiment, $R^5$ and $R^6$ are taken together with the nitrogen atom to which they are commonly attached to form a heterocyclyl or heteroaryl. The values for the remaining variables are as described in the first embodiment, or first through twentieth aspects thereof.

In a twenty-second aspect of the first embodiment, $R^3$ is selected from optionally substituted $C_1$-$C_4$ alkyl, carbocyclyl, aryl, heterocyclyl and heteroaryl. The values for the remaining variables are as described in the first embodiment, or first through twenty-first aspects thereof.

In a twenty-third aspect of the first embodiment, $R^4$ is selected from —N($R^8$)($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl, wherein $R^8$ is hydrogen or —$C_1$-$C_4$ alkyl; any alkyl or alkylene portion of $R^4$ is optionally and independently substituted with one or more substituents selected from the group consisting of oxo and —N($R^9$)$_2$, wherein each $R^9$ is independently selected from hydrogen and $C_1$-$C_4$ alkyl; any heterocyclyl portion of $R^4$ comprises at least one nitrogen atom in a ring, and is optionally substituted with one or more substituents selected from the group consisting of $C_1$-$C_4$ alkyl and oxo; and any heteroaryl portion of $R^4$ comprises at least one nitrogen atom in a ring and is optionally substituted with one or more $C_1$-$C_4$ alkyl. The values for the remaining variables are as described in the first embodiment, or first through twenty-second aspects thereof.

In a twenty-fourth aspect of the first embodiment, $R^2$ is optionally substituted with 1, 2 or 3 substituents independently selected from halogen, $C_1$-$C_4$ alkyl, halo-$C_1$-$C_4$ alkyl, $C_1$-$C_4$ alkoxy, $C_1$-$C_4$ thioalkoxy, hydroxyl, amino, $C_1$-$C_4$ alkylamino, $C_1$-$C_4$ dialkylamino, sulfhydryl, cyano, $C_6$ aryl and $C_5$-$C_6$ heteroaryl. Values for the variables are as described in the first embodiment, or first through twenty-third aspects thereof.

In a twenty-fifth aspect of the first embodiment, $R^2$ is optionally substituted with 1, 2 or 3 substituents independently selected from fluoro, chloro, $C_1$-$C_4$ alkyl, —CF$_3$, amino and cyano. Values for the variables are as described in the first embodiment, or first through twenty-fourth aspects thereof.

A second embodiment of the invention is a compound of structural formula II:

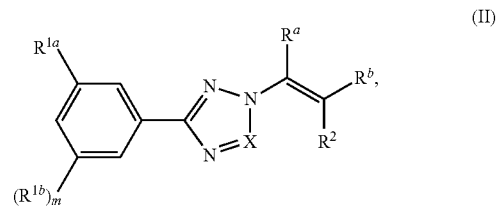

or a pharmaceutically acceptable salt thereof, wherein:
$R^{1a}$ and $R^{1b}$ are each independently selected from halo; haloalkyl; —(CH$_2$)$_{1-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$-carbocyclyl, which may be substituted with R°; —(CH$_2$)$_{0-4}$-aryl, which may be substituted with R°; —(CH$_2$)$_{0-4}$-heterocyclyl, which may be substituted with R°; —(CH$_2$)$_{0-4}$-heteroaryl, which may be substituted with R°; —CH=CH-carbocyclyl, which may be substituted with R°; —CH=CH-aryl, which may be substituted with R°; —CH=CH-heterocyclyl, which may be substituted with R°; —CH=CH-heteroaryl, which may be substituted with R°; —NO$_2$; —CN; —N$_3$; —(CH$_2$)$_{0-4}$N(R°)$_2$; —(CH$_2$)$_{0-4}$N(R°)C(O)R°; —(CH$_2$)$_{0-4}$N(R°)C(S)R°; —(CH$_2$)$_{0-4}$N(R°)C(O)NR°$_2$; —(CH$_2$)$_{0-4}$N(R°)C(S)NR°$_2$; —(CH$_2$)$_{0-4}$N(R°)C(O)OR°; —(CH$_2$)$_{0-4}$N(R°)N(R°)C(O)R°; —(CH$_2$)$_{0-4}$N(R°)N(R°)C(O)NR°$_2$; —(CH$_2$)$_{0-4}$N(R°)N(R°)C(O)OR°; —(CH$_2$)$_{0-4}$C(O)R°; —(CH$_2$)$_{0-4}$C(S)R°; —(CH$_2$)$_{0-4}$C(O)OR°; —(CH$_2$)$_{0-4}$C(O)SR°; —(CH$_2$)$_{0-4}$OC(O)R°; —(CH$_2$)$_{0-4}$OC(O)(CH$_2$)$_{0-4}$SR°, —(CH$_2$)$_{0-4}$SC(S)SR°; —(CH$_2$)$_{0-4}$SC(O)R°; —(CH$_2$)$_{0-4}$C(O)NR°$_2$; —(CH$_2$)$_{0-4}$C(S)NR°$_2$; —(CH$_2$)$_{0-4}$C(S)SR°; —(CH$_2$)$_{0-4}$OC(O)NR°$_2$; —(CH$_2$)$_{0-4}$C(O)N(OR°)R°; —(CH$_2$)$_{0-4}$C(O)C(O)R°; —(CH$_2$)$_{0-4}$C(O)CH$_2$C(O)R°; —(CH$_2$)$_{0-4}$C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —(CH$_2$)$_{0-4}$S(O)$_2$NR°$_2$; —(CH$_2$)$_{0-4}$S(O)R°; —(CH$_2$)$_{0-4}$N(R°)S(O)$_2$NR°$_2$; —(CH$_2$)$_{0-4}$N(R°)S(O)$_2$R°; —(CH$_2$)$_{0-4}$N(OR°)R°; —(CH$_2$)$_{0-4}$C(NH)NR°$_2$; —(CH$_2$)$_{0-4}$P(O)$_2$R°; —(CH$_2$)$_{0-4}$P(O)R°$_2$; —(CH$_2$)$_{0-4}$OP(O)R°$_2$; —(CH$_2$)$_{0-4}$OP(O)(OR°)$_2$; —(CH$_2$)$_{0-4}$ON(R°)$_2$; and —(CH$_2$)$_{0-4}$C(O)O—N(R°)$_2$, wherein:
each R° is independently hydrogen, $C_{1-6}$ aliphatic, —CH$_2$-carbocyclyl, —CH$_2$-aryl, —CH$_2$-heterocyclyl, —CH$_2$-heteroaryl, —O(CH$_2$)$_{0-1}$-carbocyclyl, —O(CH$_2$)$_{0-1}$-aryl, —O(CH$_2$)$_{0-1}$-heterocyclyl, —O(CH$_2$)$_{0-1}$-heteroaryl, carbocyclyl, aryl, heterocyclyl or heteroaryl, or two independent occurrences of R°, taken together with their intervening atom(s), form a 3-12-membered carbocyclyl, aryl, heterocyclyl or heteroaryl; and
each R° and each ring formed from two independent occurrences of R°, taken together with their intervening atom(s), are optionally and independently substituted with one or more substituents selected from the group consisting of halo, CN, OH, unsubstituted $C_1$-$C_3$ alkyl, halo-$C_1$-$C_3$ alkyl, —NH$_2$, —NO$_2$, —NH(unsubstituted $C_1$-$C_3$ alkyl), —N(unsubstituted $C_1$-$C_3$ alkyl)$_2$, —O—$C_1$-$C_3$ alkyl, —C(O)OH, —C(O)O-(unsubstituted $C_1$-$C_3$ alkyl), —C(O)-(unsubstituted $C_1$-$C_3$ alkyl), —O-(unsubstituted $C_1$-$C_3$ alkyl), and —S-(unsubstituted $C_1$-$C_3$ alkyl); and m is 0 or 1.

The values for the remaining variables are as described in the first embodiment, or any aspect thereof.

In a first aspect of the second embodiment, m is 1. The values for the remaining variables are as described in the first embodiment, or any aspect thereof, or the second embodiment.

In a second aspect of the second embodiment, $R^{1a}$ is halo or —$C_1$-$C_4$ haloalkyl. The values for the remaining variables are as described in the first embodiment, or any aspect thereof, or the second embodiment, or first aspect thereof.

In a third aspect of the second embodiment, $R^{1a}$ is —$C_1$-$C_4$ haloalkyl. The values for the remaining variables are as described in the first embodiment, or any aspect thereof, or the second embodiment, or first or second aspect thereof.

In a fourth aspect of the second embodiment, $R^{1b}$ is —$C_1$-$C_4$ haloalkyl or —O—$C_1$-$C_4$ alkyl. The values for the remaining variables are as described in the first embodiment, or any aspect thereof, or the second embodiment, or first through third aspects thereof.

In a fifth aspect of the second embodiment, $R^{1b}$ is —$C_1$-$C_4$ haloalkyl. The values for the remaining variables are as described in the first embodiment, or any aspect thereof, or the second embodiment, or first through fourth aspects thereof.

In a sixth aspect of the second embodiment, $R^{1a}$ is —$CF_3$ and $R^{1b}$ is —$CF_3$. The values for the remaining variables are as described in the first embodiment, or any aspect thereof, or the second embodiment, or first through fifth aspects thereof.

A third embodiment of the invention is a compound of structural formula III:

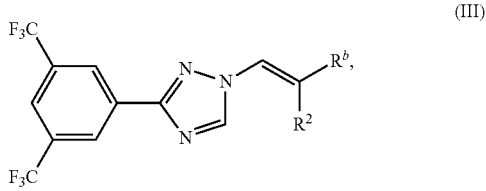

(III)

or a pharmaceutically acceptable salt thereof, wherein:
$R^b$ is selected from —C(O)OH, —C(O)$NH_2$, —C(O)—N($R^7$)—N($R^5$)($R^6$), —C(O)—N($R^7$)—N($R^7$)—C(O)—$R^4$ and —C(O)—N($R^7$)—N($R^7$)—S(O)$_{1-2}$—$R^4$; wherein:
  $R^4$ is selected from —N(H)($C_3$-$C_6$ cycloalkyl), —N($C_1$-$C_4$ alkyl)($C_3$-$C_6$ cycloalkyl), —$C_1$-$C_6$ alkyl, —($C_0$-$C_4$ alkylene)-carbocyclyl, —($C_0$-$C_4$ alkylene)-heterocyclyl, —($C_0$-$C_4$ alkylene)-aryl, and —($C_0$-$C_4$ alkylene)-heteroaryl;
  $R^5$ and $R^6$ are each independently selected from hydrogen, $C_1$-$C_4$ alkyl, $C_2$-$C_4$ alkenyl, $C_2$-$C_4$ alkynyl, carbocyclyl, aryl, heterocyclyl and heteroaryl; or
  $R^5$ and $R^6$ are taken together with the nitrogen atom to which they are commonly attached to form a heterocyclyl or heteroaryl; and each $R^7$ is independently hydrogen or $C_1$-$C_4$ alkyl; and
$R^2$ is an optionally substituted $C_5$-$C_{15}$ heteroaryl, wherein:
  unless otherwise designated, each alkyl, alkenyl, alkynyl, alkylene, carbocyclyl, aryl, cycloalkyl, heterocyclyl and heteroaryl is optionally and independently substituted.

Alternative values for the variables in structural formula III are as described in the first embodiment, or any aspect thereof.

In a first aspect of the third embodiment, $R^b$ is —C(O)OH; or —C(O)$NH_2$; or —C(O)—NH—NH($R^6$), and $R^6$ is an optionally substituted heteroaryl; or —C(O)—NH—NH—C(O)—$R^4$ or —C(O)—NH—NH—S(O)$_{1-2}$—$R^4$, and $R^4$ is selected from optionally substituted —N(H)($C_3$-$C_6$ cycloalkyl), —N($C_1$-$C_4$ alkyl)($C_3$-$C_6$ cycloalkyl), —$C_1$-$C_6$ alkyl, —($C_0$-$C_4$ alkylene)-heterocyclyl and —($C_0$-$C_4$ alkylene)-heteroaryl. The values for the remaining variables are as described in the first embodiment, or any aspect thereof, or the third embodiment.

In a second aspect of the third embodiment, $R^b$ is —C(O)$NH_2$. The values for the remaining variables are as described in the first embodiment, or any aspect thereof, or the third embodiment, or first aspect thereof.

In a third aspect of the third embodiment, $R^2$ is an optionally substituted 5-6-membered heteroaryl having 1, 2 or 3 heteroatoms independently selected from the group consisting of nitrogen, oxygen and sulfur. The values for the remaining variables are as described in the first embodiment, or any aspect thereof, or the third embodiment, or first or second aspect thereof.

In a fourth aspect of the third embodiment, $R^2$ is an optionally substituted 5-membered heteroaryl having 1, 2 or 3 heteroatoms independently selected from the group consisting of nitrogen, oxygen and sulfur. The values for the remaining variables are as described in the first embodiment, or any aspect thereof, or the third embodiment, or first through third aspects thereof.

In a fifth aspect of the third embodiment, $R^2$ is an optionally substituted pyrrolyl, furanyl, thiophenyl, pyrazolyl, imidazolyl, thiazolyl, isothiazolyl, oxazolyl, isoxazolyl, triazolyl, thiadiazolyl, or oxadiazolyl. The values for the remaining variables are as described in the first embodiment, or any aspect thereof, or the third embodiment, or first through fourth aspects thereof.

In a sixth aspect of the third embodiment, $R^2$ is an optionally substituted 6-membered heteroaryl having 1, 2 or 3 heteroatoms independently selected from the group consisting of nitrogen, oxygen and sulfur. The values for the remaining variables are as described in the first embodiment, or any aspect thereof, or the third embodiment, or first through fifth aspects thereof.

In a seventh aspect of the third embodiment, $R^2$ is an optionally substituted pyridinyl, pyrimidinyl, pyrazinyl, pyridazinyl or triazinyl. The values for the remaining variables are as described in the first embodiment, or any aspect thereof, or the third embodiment, or first through sixth aspects thereof.

In an eighth aspect of the third embodiment, $R^2$ is optionally substituted with halogen, $C_1$-$C_4$ alkyl, $C_1$-$C_4$ alkoxy, $C_1$-$C_4$ thioalkoxy, hydroxyl, amino, $C_1$-$C_4$ alkylamino, $C_1$-$C_4$ dialkylamino, sulfhydryl or cyano. The values for the remaining variables are as described in the first embodiment, or any aspect thereof, or the third embodiment, or first through seventh aspects thereof.

In a ninth aspect of the third embodiment, $R^2$ is optionally substituted with halogen, $C_1$-$C_4$ alkyl or $C_1$-$C_4$ alkoxy. The values for the remaining variables are as described in the first embodiment, or any aspect thereof, or the third embodiment, or first through eighth aspects thereof.

In a tenth aspect of the third embodiment, $R^b$ is —C(O)OH; or —C(O)NH$_2$; or —C(O)—NH—NH($R^6$), and $R^6$ is an optionally substituted $C_5$-$C_6$ heteroaryl; or —C(O)—NH—NH—C(O)—$R^4$ or —C(O)—NH—NH—S(O)$_{1-2}$—$R^4$, and $R^4$ is selected from optionally substituted —N(H)($C_3$-$C_6$ cycloalkyl), —N($C_1$-$C_4$ alkyl)($C_3$-$C_6$ cycloalkyl), —$C_1$-$C_6$ alkyl, —($C_0$-$C_4$ alkylene)-($C_3$-$C_7$)heterocyclyl and —($C_0$-$C_4$ alkylene)-($C_5$-$C_6$)heteroaryl. The values for the remaining variables are as described in the first embodiment, or any aspect thereof, or the third embodiment, or first through ninth aspects thereof.

In an eleventh aspect of the third embodiment, $R^2$ is optionally substituted with 1, 2 or 3 substituents independently selected from halogen, $C_1$-$C_4$ alkyl, halo-$C_1$-$C_4$ alkyl, $C_1$-$C_4$ alkoxy, $C_1$-$C_4$ thioalkoxy, hydroxyl, amino, $C_1$-$C_4$ alkylamino, $C_1$-$C_4$ dialkylamino, sulfhydryl, cyano, $C_6$ aryl and $C_5$-$C_6$ heteroaryl. Values for the variables are as described in the first embodiment, or any aspect thereof, or the third embodiment, or the first through tenth aspects thereof.

In a twelfth aspect of the third embodiment, $R^2$ is optionally substituted with 1, 2 or 3 substituents independently selected from fluoro, chloro, $C_1$-$C_4$ alkyl, —CF$_3$, amino and cyano. Values for the variables are as described in the first embodiment, or any aspect thereof, or the third embodiment, or the first through eleventh aspects thereof.

A fourth embodiment of the invention is a compound represented by structural formula IV:

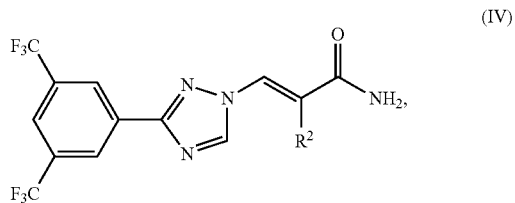

(IV)

or a pharmaceutically acceptable salt thereof, wherein $R^2$ is selected from optionally substituted heteroaryl and optionally substituted aryl.

In a first aspect of the fourth embodiment, $R^2$ is optionally substituted $C_5$-$C_{15}$ heteroaryl.

In a second aspect of the fourth embodiment, $R^2$ is an optionally substituted 5-6 membered heteroaryl having 1, 2 or 3 heteroatoms independently selected from the group consisting of nitrogen, oxygen and sulfur.

In a third aspect of the fourth embodiment, $R^2$ is an optionally substituted 5-membered heteroaryl having 1, 2 or 3 heteroatoms independently selected from the group consisting of nitrogen, oxygen and sulfur.

In a fourth aspect of the fourth embodiment, $R^2$ is an optionally substituted pyrrolyl, furanyl, thiophenyl, pyrazolyl, imidazolyl, thiazolyl, isothiazolyl, oxazolyl, isoxazolyl, triazolyl, thiadiazolyl, or oxadiazolyl.

In a fifth aspect of the fourth embodiment, $R^2$ is an optionally substituted 6-membered heteroaryl having 1, 2 or 3 heteroatoms independently selected from the group consisting of nitrogen, oxygen and sulfur.

In a sixth aspect of the fourth embodiment, $R^2$ is an optionally substituted pyridinyl, pyrimidinyl, pyrazinyl, pyridazinyl or triazinyl.

In a seventh aspect of the fourth embodiment, $R^2$ is optionally substituted with 1, 2 or 3 substituents independently selected from halogen, $C_1$-$C_4$ alkyl, halo-$C_1$-$C_4$ alkyl, $C_1$-$C_4$ alkoxy, $C_1$-$C_4$ thioalkoxy, hydroxyl, amino, $C_1$-$C_4$ alkylamino, $C_1$-$C_4$ dialkylamino, sulfhydryl, cyano, $C_6$ aryl and $C_5$-$C_6$ heteroaryl. Values and alternative values for $R^2$ are as described in the first through third embodiments, or any aspect thereof, or the fourth embodiment, or the first through sixth aspects thereof.

In an eighth aspect of the fourth embodiment, $R^2$ is optionally substituted with 1, 2 or 3 substituents independently selected from fluoro, chloro, $C_1$-$C_4$ alkyl, —CF$_3$, amino and cyano. Values and alternative values for $R^2$ are as described in the first through third embodiments, or any aspect thereof, or the fourth embodiment, or the first through seventh aspects thereof.

Exemplary compounds are set forth in Table A and Table 1.

TABLE A

| Structure | E isomer | Z isomer |
|---|---|---|

TABLE A-continued
| Structure | E isomer | Z isomer |
|---|---|---|
| 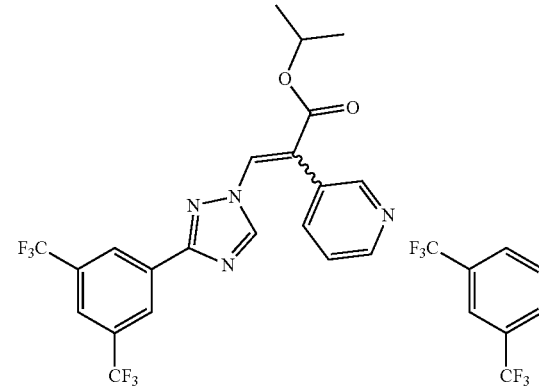 | 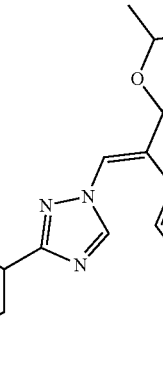 | 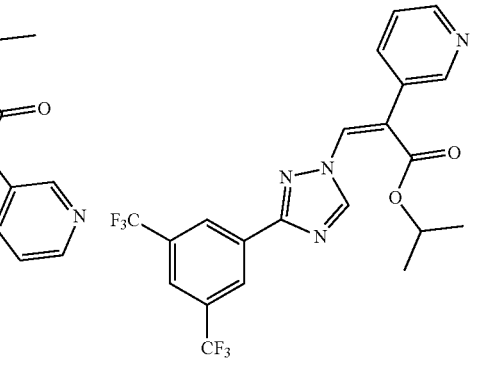 |
| 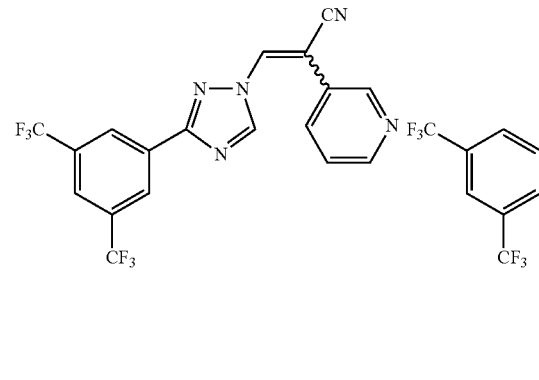 | 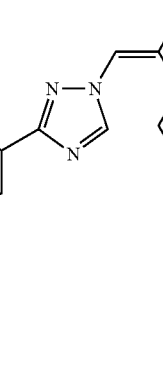 | 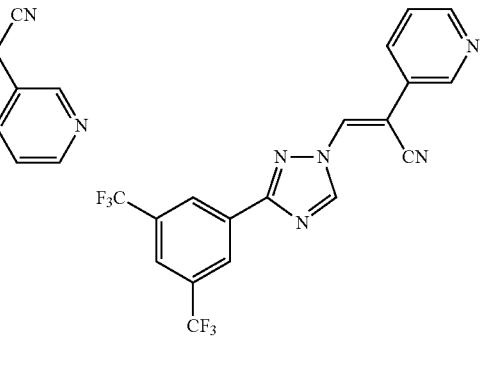 |
| 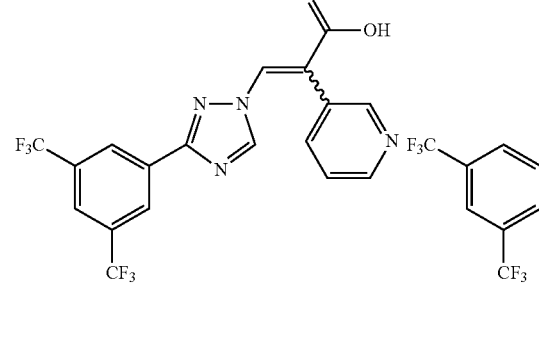 | 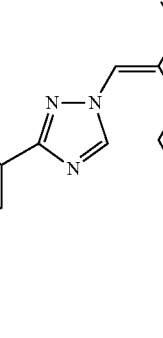 | 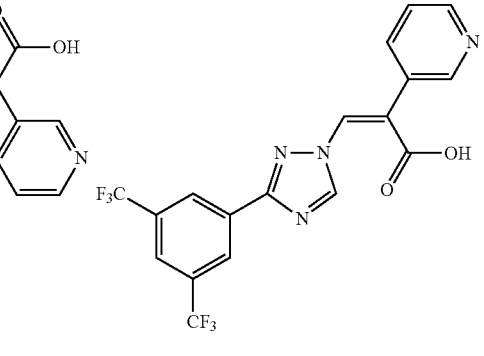 |
| 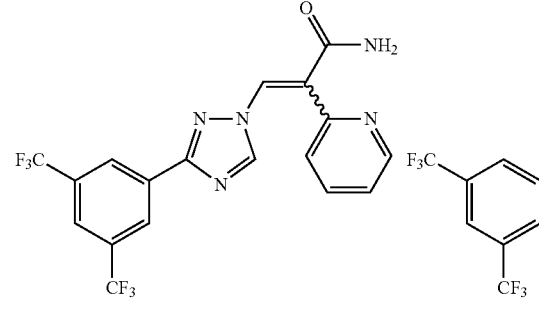 | 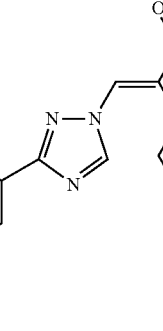 | 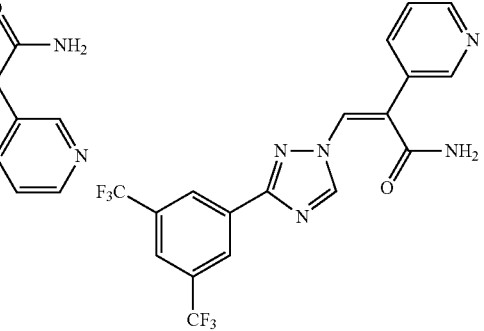 |

TABLE A-continued

| Structure | E isomer | Z isomer |
|---|---|---|

TABLE A-continued

| Structure | E isomer | Z isomer |
|---|---|---|

TABLE A-continued

| Structure | E isomer | Z isomer |
| --- | --- | --- |

TABLE A-continued

| Structure | E isomer | Z isomer |
|---|---|---|

TABLE A-continued

| Structure | E isomer | Z isomer |
|---|---|---|

TABLE A-continued

| Structure | E isomer | Z isomer |
|---|---|---|

TABLE A-continued
| Structure | E isomer | Z isomer |
|---|---|---|
| 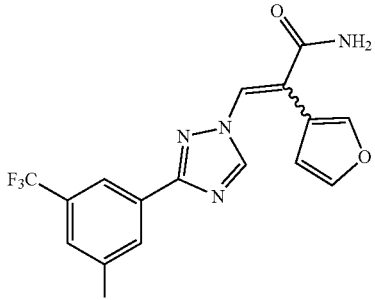 | 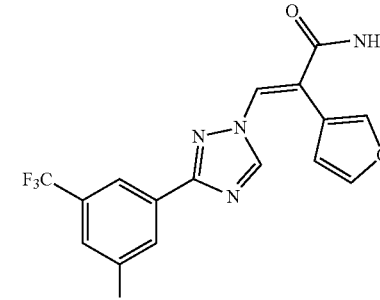 | 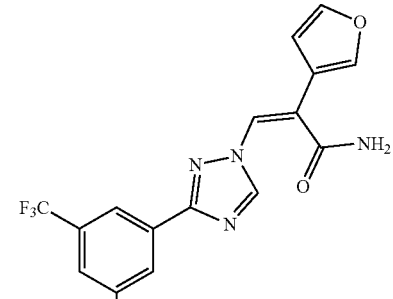 |
| 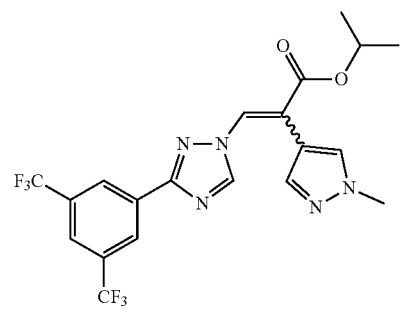 | 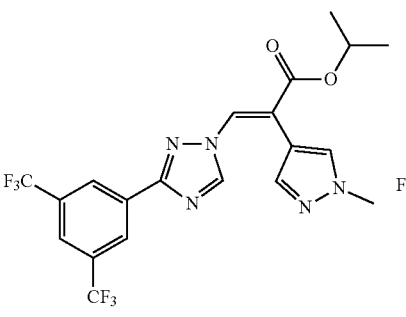 | 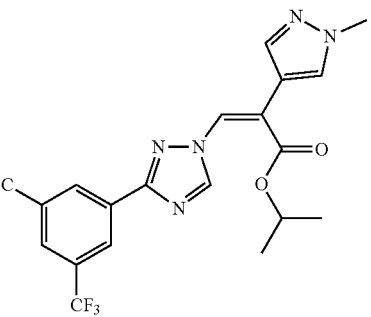 |
| 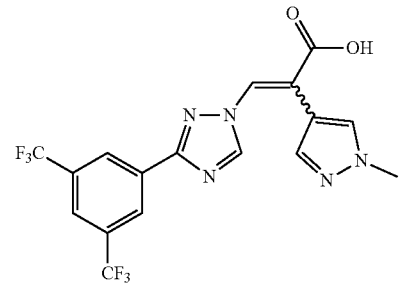 | 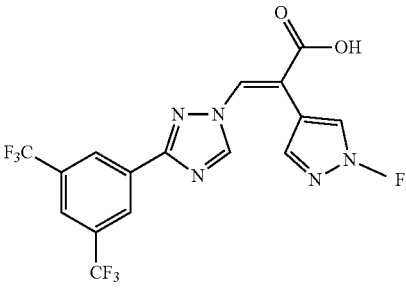 | 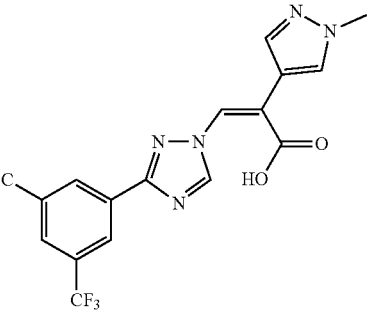 |
| 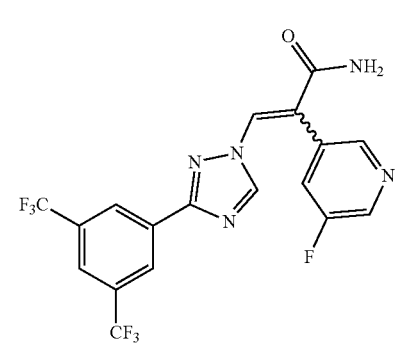 [SMILES: NC(=O)C(=Cn1cnc(-c2cc(C(F)(F)F)cc(C(F)(F)F)c2)n1)c1cncc(F)c1] | 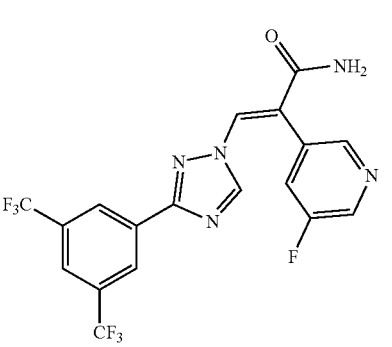 [SMILES: NC(=O)/C(=C/n1cnc(-c2cc(C(F)(F)F)cc(C(F)(F)F)c2)n1)c1cncc(F)c1] | 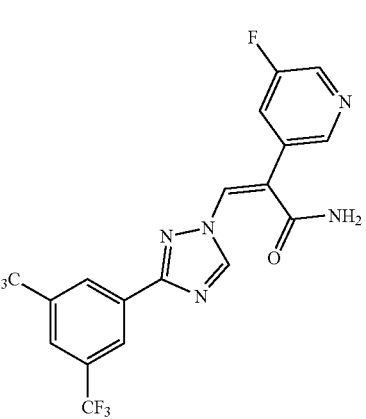 |

TABLE A-continued

| Structure | E isomer | Z isomer |
| --- | --- | --- |

TABLE A-continued

| Structure | E isomer | Z isomer |
|---|---|---|

TABLE A-continued

TABLE A-continued
| Structure | E isomer | Z isomer |
|---|---|---|
| 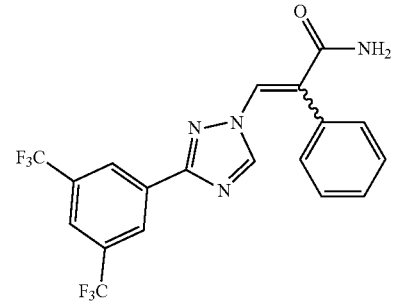 [SMILES: NC(=O)C(=Cn1cnc(-c2cc(C(F)(F)F)cc(C(F)(F)F)c2)n1)c1ccccc1] | 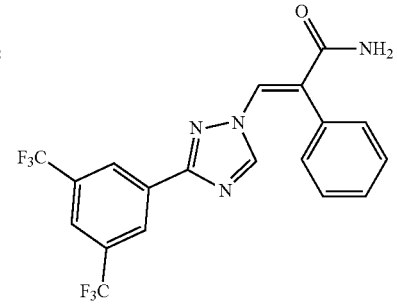 [SMILES: NC(=O)/C(=C/n1cnc(-c2cc(C(F)(F)F)cc(C(F)(F)F)c2)n1)c1ccccc1] | 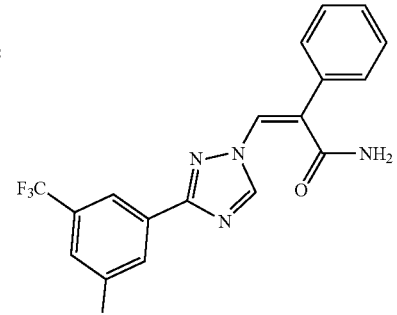 |
| 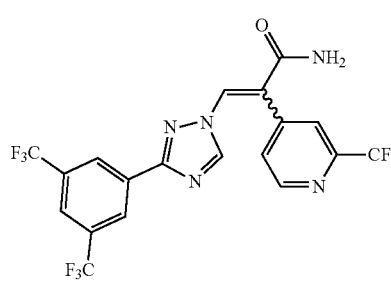 [SMILES: N#Cc1cncc(C(=Cn2cnc(-c3cc(C(F)(F)F)cc(C(F)(F)F)c3)n2)C(N)=O)c1] | 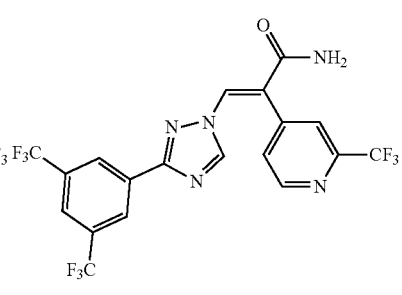 | 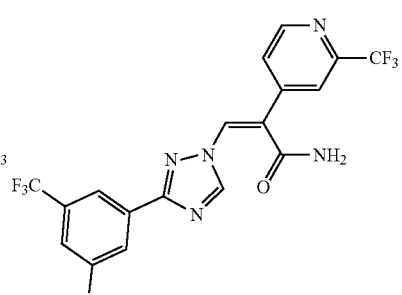 |
| 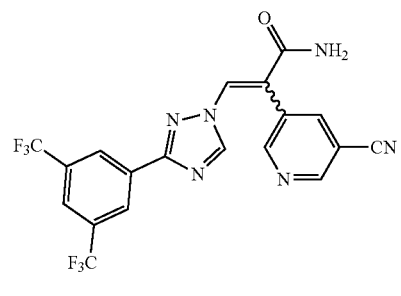 | 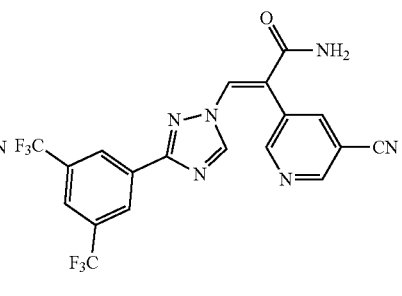 | 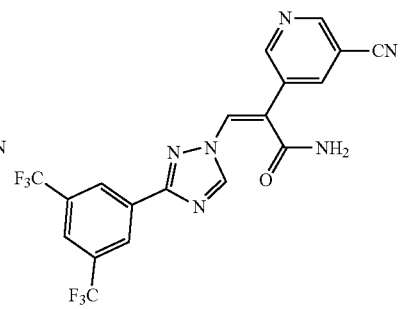 |
| 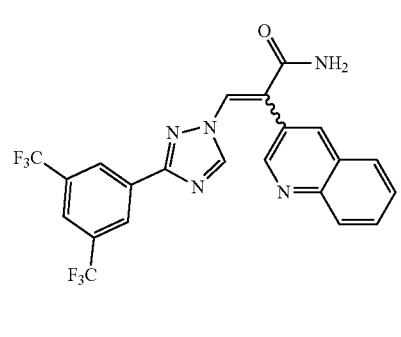 | 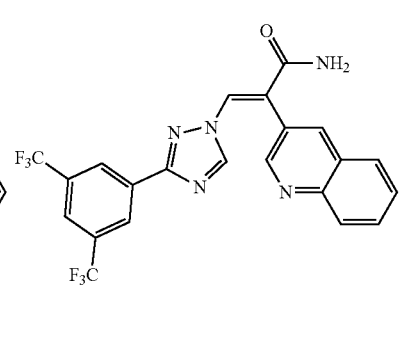 | 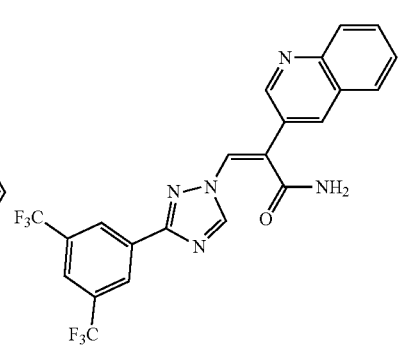 |

TABLE A-continued
| Structure | E isomer | Z isomer |
|---|---|---|
| 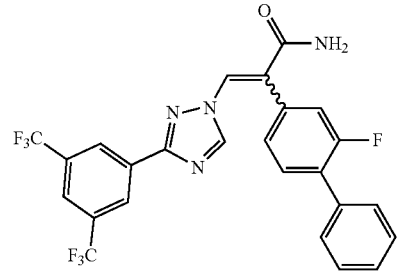 [SMILES: NC(=O)C(=Cn1cnc(-c2cc(C(F)(F)F)cc(C(F)(F)F)c2)n1)c1ccc(-c2ccccc2)c(F)c1] | 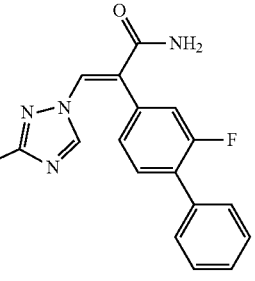 | 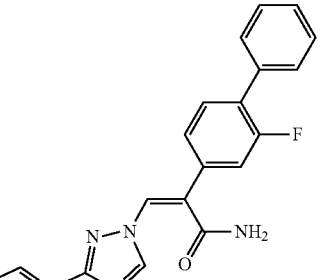 |
| 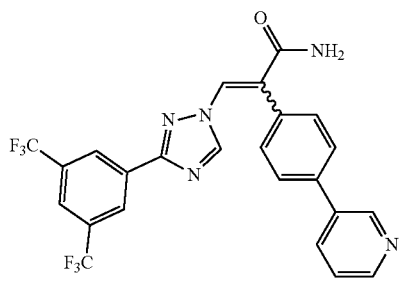 [SMILES: NC(=O)C(=Cn1cnc(-c2cc(C(F)(F)F)cc(C(F)(F)F)c2)n1)c1ccc(-c2cccnc2)cc1] | 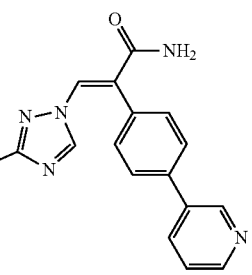 | 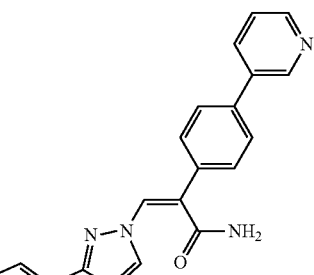 |
| 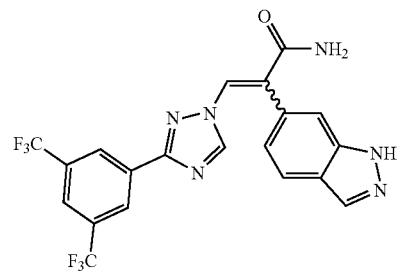 [SMILES: NC(=O)C(=Cn1cnc(-c2cc(C(F)(F)F)cc(C(F)(F)F)c2)n1)c1ccc2cn[nH]c2c1] | 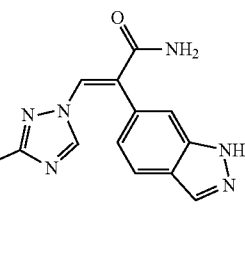 | 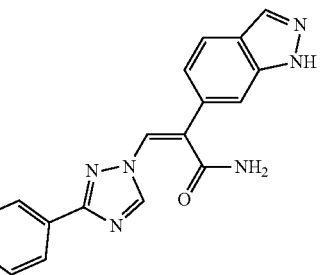 |
| 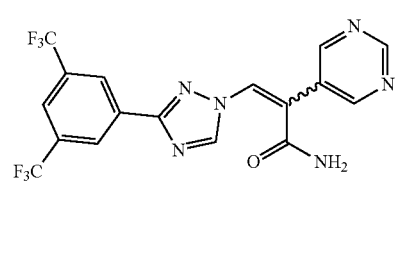 [SMILES: NC(=O)/C(=C\n1cnc(-c2cc(C(F)(F)F)cc(C(F)(F)F)c2)n1)c1cncnc1] | 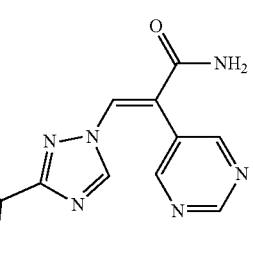 | 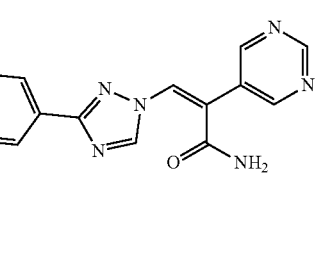 |

TABLE A-continued

| Structure | E isomer | Z isomer |
|---|---|---|
| (structure) | (structure) | (structure) |
| (structure) | (structure) | (structure) |
| (structure) | (structure) | (structure) |
| (structure) | (structure) | (structure) |

Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

The term "aliphatic" or "aliphatic group," as used herein, denotes a monovalent hydrocarbon radical that is straight-chain (i.e., unbranched), branched, or cyclic (including fused, bridged, and spiro-fused polycyclic). An aliphatic group can be saturated or can contain one or more units of unsaturation, but is not aromatic. Unless otherwise specified, aliphatic groups contain 1-12 carbon atoms. However, in some embodiments, an aliphatic group contains 1-6 or 2-8 carbon atoms. In some embodiments, aliphatic groups contain 1-4 carbon atoms and, in yet other embodiments, aliphatic groups contain 1-3 carbon atoms. Suitable aliphatic groups include, but are not limited to, linear or branched, alkyl, alkenyl, and alkynyl groups, and hybrids thereof, such as (cycloalkyl)alkyl, (cycloalkenyl)alkyl or (cycloalkyl)alkenyl.

The term "alkyl," as used herein, unless otherwise indicated, means straight or branched saturated monovalent hydrocarbon radicals, typically $C_1$-$C_{12}$, preferably $C_1$-$C_6$. As such, "$C_1$-$C_6$ alkyl" means a straight or branched saturated monovalent hydrocarbon radical having from one to six carbon atoms (e.g., 1, 2, 3, 4, 5 or 6). Examples of alkyl groups include, but are not limited to, methyl, ethyl, propyl, isopropyl, and t-butyl.

The term "alkoxy," as used herein, means an "alkyl-O—" group, wherein alkyl is defined above. Examples of alkoxy include methoxy and ethoxy.

As used herein, the term "alkenyl" means a saturated straight chain or branched non-cyclic hydrocarbon having from 2 to 12 carbon atoms and having at least one carbon-carbon double bond. Alkenyl groups may be optionally substituted with one or more substituents. The term "alkenyl" encompasses radicals having carbon-carbon double bonds in the "cis" and "trans" or, alternatively, the "E" and "Z" configurations. If an alkenyl group includes more than one carbon-carbon double bond, each carbon-carbon double bond is independently a cis or trans double bond, or a mixture thereof.

As used herein, the term "alkynyl" means a saturated straight chain or branched non-cyclic hydrocarbon having from 2 to 12 carbon atoms and having at least one carbon-carbon triple bond. Alkynyl groups may be optionally substituted with one or more substituents.

As used herein, the term "alkylene" refers to an alkyl group having from 2 to 12 carbon atoms and two points of attachment to the rest of the compound. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be optionally substituted with one or more substituents.

The term "amino," as used herein, refers to a chemical moiety having the formula —$N(R)_2$, wherein each R is independently selected from hydrogen and $C_1$-$C_4$ alkyl.

The term "aryl," alone or in combination, as used herein, means a carbocyclic aromatic system containing one or more rings, which may be attached together in a pendent manner or may be fused. In particular embodiments, aryl is one, two or three rings. In one aspect, the aryl has six to twelve ring atoms. The term "aryl" encompasses aromatic radicals such as phenyl, naphthyl, tetrahydronaphthyl, indanyl, biphenyl, phenanthryl, anthryl and acenaphthyl. An aryl group can be optionally substituted as defined and described herein.

The terms "cycloaliphatic," "carbocyclyl," "carbocyclo," and "carbocyclic," used alone or as part of a larger moiety, refer to a saturated or partially unsaturated cyclic aliphatic monocyclic or bicyclic ring system, as described herein, having from 3 to 12 members, wherein the aliphatic ring system is optionally substituted as defined and described herein. Cycloaliphatic groups include, without limitation, cycloalkyl, for example, cyclopropyl, cyclobutyl, cyclopentyl, cyclohexyl and cycloheptyl and cycloalkenyl, for example cyclopentenyl, cyclohexenyl, cycloheptenyl, cyclooctenyl and cyclooctadienyl. The terms "cycloaliphatic," "carbocyclyl," "carbocyclo," and "carbocyclic" also include aliphatic rings that are fused to one or more aromatic or nonaromatic rings, such as decahydronaphthyl, tetrahydronaphthyl, decalin, or bicyclo[2.2.2]octane.

The term "cycloalkyl", as used herein, means saturated cyclic hydrocarbons, i.e. compounds where all ring atoms are carbons. Examples of cycloalkyl include, but are not limited to, cyclopropyl, cyclobutyl, cyclopentyl, cyclohexyl, and cycloheptyl. In some embodiments, cycloalkyl can optionally be substituted with one or more substituents selected from —OH, —SH, halogen, amino, nitro, cyano, $C_1$-$C_{12}$ alkyl, $C_2$-$C_{12}$ alkenyl or $C_2$-$C_{12}$ alkynyl group, $C_1$-$C_{12}$ alkoxy, $C_1$-$C_{12}$ haloalkyl, and $C_1$-$C_{12}$ haloalkoxy.

The term "halo" or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The term "haloalkyl", as used herein, includes an alkyl substituted with one or more F, Cl, Br, or I, wherein alkyl is defined above.

The term "heteroaryl", as used herein, refers to an aromatic group containing one or more heteroatoms (e.g., one or more heteroatoms independently selected from O, S and N). A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. In one aspect, heteroaryl has five to fifteen ring atoms and, preferably, 5 or 6 ring atoms. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. The foregoing heteroaryl groups may be C-attached or N-attached (where such is possible). For instance, a group derived from pyrrole may be pyrrol-1-yl (N-attached) or pyrrol-3-yl (C-attached).

"Heterocyclyl" means a cyclic 3-12 membered saturated or unsaturated aliphatic ring containing 1, 2, 3, 4 or 5 heteroatoms (e.g., one or more heteroatoms independently selected from O, S and N). When one heteroatom is S, it can be optionally mono- or di-oxygenated (i.e. —S(O)— or —S(O)₂—). The heterocyclyl can be monocyclic or polycyclic, in which case the rings can be attached together in a pendent manner or can be fused or spiro. In one aspect, a heterocyclyl is a three- to seven-membered ring system. Exemplary heterocyclyls include, for example, and without being limited thereto, piperidinyl, piperazinyl, pyrrolidinyl, tetrahydrofuranyl and the like.

"Hydroxyl" means —OH.

"Oxo" means =O.

"Thioalkoxy" means —S-alkyl, wherein alkyl is defined as above.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstituted.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted group" are independently halogen; —(CH₂)₀₋₄R°; —(CH₂)₀₋₄OR°; —O(CH₂)₀₋₄R°, —O—(CH₂)₀₋₄C(O)OR°; —(CH₂)₀₋₄CH(OR°)₂; —(CH₂)₀₋₄SR°; —(CH₂)₀₋₄Ph, which may be substituted with R°; —(CH₂)₀₋₄O(CH₂)₀₋₁Ph which may be substituted with R°; —CH=CHPh, which may be substituted with R°; —(CH₂)₀₋₄O(CH₂)₀₋₁-pyridyl which may be substituted with R°; —NO₂; —CN; —N₃; —(CH₂)₀₋₄N(R°)₂; —(CH₂)₀₋₄N(R°)C(O)R°; —N(R°)C(S)R°; —(CH₂)₀₋₄N(R°)C(O)NR°₂; —N(R°)C(S)NR°₂; —(CH₂)₀₋₄N(R°)C(O)OR°; —N(R°)N(R°)C(O)R°; —N(R°)N(R°)C(O)NR°₂; —N(R°)N(R°)C(O)OR°; —(CH₂)₀₋₄C(O)R°; —C(S)R°; —(CH₂)₀₋₄C(O)OR°; —(CH₂)₀₋₄C(O)SR°; —(CH₂)₀₋₄C(O)OSiR°₃; —(CH₂)₀₋₄OC(O)R°; —OC(O)(CH₂)₀₋₄SR—, SC(S)SR°; —(CH₂)₀₋₄SC(O)R°; —(CH₂)₀₋₄C(O)NR°₂; —C(S)NR°₂; —C(S)SR°; —SC(S)SR°, —(CH₂)₀₋₄OC(O)NR°₂; —C(O)N(OR°)R°; —C(O)C(O)R°; —C(O)CH₂C(O)R°; —C(NOR°)R°; —(CH₂)₀₋₄SSR°; —(CH₂)₀₋₄S(O)₂R°; —(CH₂)₀₋₄S(O)₂OR°; —(CH₂)₀₋₄OS(O)₂R°; —S(O)₂NR°₂; —(CH₂)₀₋₄S(O)R°; —N(R°)S(O)₂NR°₂; —N(R°)S(O)₂R°; —N(OR°)R°; —C(NH)NR°₂; —P(O)₂R°; —P(O)R°₂; —OP(O)R°₂; —OP(O)(OR°)₂; SiR°₃; —(C₁₋₄ straight or branched alkylene)O—N(R°)₂; or —(C₁₋₄ straight or branched alkylene)C(O)O—N(R°)₂, wherein each R° may be substituted as defined below and is independently hydrogen, C₁₋₆ aliphatic, —CH₂Ph, —O(CH₂)₀₋₁Ph, —CH₂-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH₂)₀₋₂R●, -(haloR●), —(CH₂)₀₋₂OH, —(CH₂)₀₋₂OR●, —(CH₂)₀₋₂CH(OR●)₂; —O(haloR●), —CN, —N₃, —(CH₂)₀₋₂C(O)R●, —(CH₂)₀₋₂C(O)OH, —(CH₂)₀₋₂C(O)OR●, —(CH₂)₀₋₂SR●, —(CH₂)₀₋₂SH, —(CH₂)₀₋₂NH₂, —(CH₂)₀₋₂NHR●, —(CH₂)₀₋₂NR●₂, —NO₂, —SiR●₃, —OSiR●₃, —C(O)SR●, —(C₁₋₄ straight or branched alkylene)C(O)OR●, or —SSR● wherein each R● is unsubstituted or where preceded by "halo" is substituted only with one or more halogens, and is independently selected from C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted group" include the following: =O, =S, =NNR*₂, =NNHC(O)R*, =NNHC(O)OR*, =NNHS(O)₂R*, =NR*, =NOR*, —O(C(R*₂))₂₋₃O—, and —S(C(R*₂))₂₋₃S—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*₂)₂₋₃O—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R●, -(haloR●), —OH, —OR●, —O(haloR●), —CN, —C(O)OH, —C(O)OR●, —NH₂, —NHR●, —NR●₂, and —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R†, —NR†₂, —C(O)R†, —C(O)OR†, —C(O)C(O)R†, —C(O)CH₂C(O)R†, S(O)₂R†, —S(O)₂NR†₂, —C(S)NR†₂, —C(NH)NR†₂, and —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R†, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of $R^†$ are independently halogen, —R●, -(halonR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Preferred substituents on heteroaryl can be selected from the group consisting of —OH, —SH, nitro, halogen, amino, cyano, $C_1$-$C_{12}$ alkyl, $C_2$-$C_{12}$ alkenyl, $C_2$-$C_{12}$ alkynyl, $C_1$-$C_{12}$ alkoxy, $C_1$-$C_{12}$ haloalkyl, $C_1$-$C_{12}$ haloalkoxy and $C_1$-$C_{12}$ thioalkoxy. Preferred substituents on alkyl, alkylene and heterocyclyl include the preferred substituents on heteroaryl and oxo. In one embodiment, the substituent on an alkyl, alkylene, heterocyclyl or heteroaryl is an amino group having the formula —N(R)$_2$, wherein each R is independently selected from hydrogen and $C_1$-$C_4$ alkyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid (2,2,2-trifluoroacetic acid), oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, trifluoroacetate (2,2,2-trifluoroacetate), undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereoisomers as well as enantiomeric, diastereomeric, and geometric (or conformational) mixtures of the present compounds are within the scope of the invention. Unless otherwise stated, all tautomeric forms of the compounds of the invention are within the scope of the invention.

Unless specifically indicated (by a chemical name or other indicator designating double bond geometry, for example), each structural formula used herein is meant to include compounds having a carbon-carbon double bond (e.g., an exocyclic double bond) with a configuration that is cis (or Z), trans (or E), or a mixture of cis and trans. For example, formula I:

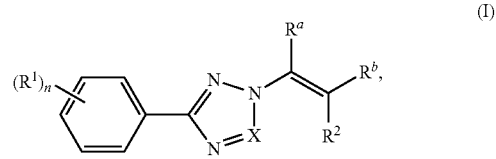

is meant to denote both:

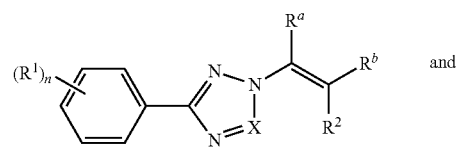 and

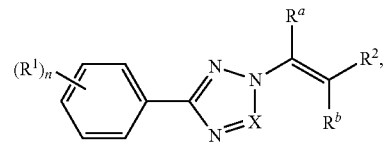

and mixtures thereof. Similarly, the following structural formulas:

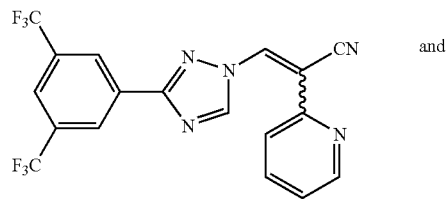 and

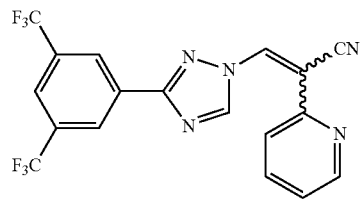

are meant to denote both

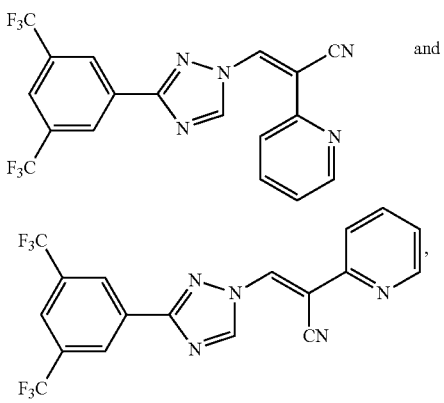

and mixtures thereof.

As used herein, "exocyclic double bond" refers to the carbon-carbon double bond in a compound of formula I indicated with an arrow in the following structure:

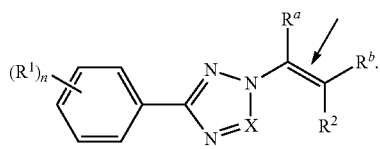

In some embodiments described herein, the exocyclic double bond is in a cis configuration. In other embodiments, the exocyclic double bond is in a trans configuration.

The configuration of the exocyclic double bond in Compounds 7, 104, 124 and 153 has been established by x-ray crystallography. The Exemplification reflects whether the exocyclic double bond in Compounds 7, 104, 125 and 153 exists in a cis or trans configuration by indicating the configuration of the exocyclic double bond in the chemical name associated with Compounds 7, 104, 124 and 153.

Compound 7 and Compound 104 serve as intermediates in the synthesis of other compounds described in the Exemplification (e.g., Compounds 115, 123, 124, etc.). Although not wishing to be bound by any particular theory, it is believed (and supported by x-ray crystallography) that the reactions used to transform Compound 7 or Compound 104, for example, into subsequent compounds (such as Compounds 115, 123 and 124, for example) proceed in a stereospecific fashion. As such, it is possible to assign a configuration to the exocyclic double bonds in many of the compounds described in the Exemplification. Where possible, the Exemplification reflects whether the exocyclic double bond in a particular compound exists in a cis or trans configuration by indicating the configuration of the exocyclic double bond in the chemical name associated with the compound.

As used herein, "cis" or "cis configuration" refers to a carbon-carbon double bond, typically an exocyclic double bond, that is predominantly cis. In some embodiments, greater than about 85% of compound molecules in a mixture of the compound have a carbon-carbon double bond (e.g., an exocyclic double bond) that is cis. In some embodiments, greater than about 90%, greater than about 95%, greater than about 98%, greater than about 99%, greater than about 99.5% or greater than about 99.8% of compound molecules in a mixture of the compound have a carbon-carbon double bond (e.g., an exocyclic double bond) that is cis.

As used herein, "trans" or "trans configuration" refers to a carbon-carbon double bond, typically an exocyclic double bond, that is predominantly trans. In some embodiments, greater than about 85% of compound molecules in a mixture of the compound have a carbon-carbon double bond (e.g., an exocyclic double bond) that is cis. In some embodiments, greater than about 90%, greater than about 95%, greater than about 98%, greater than about 99%, greater than about 99.5% or greater than about 99.8% of compound molecules in a mixture of the compound have a carbon-carbon double bond (e.g., an exocyclic double bond) that is cis.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "pharmaceutically acceptable salt" means either an acid addition salt or a basic addition salt which is compatible with the treatment of patients.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, trifluoroacetic acid (2,2,2-trifluoroacetic acid), glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. Other non-pharmaceutically acceptable salts, e.g., oxalates may be used, for example, in the isolation of compounds described herein for laboratory use, or for subsequent conversion to a pharmaceutically acceptable acid addition salt.

A "pharmaceutically acceptable basic addition salt" is any non-toxic organic or inorganic base addition salt of the acid compounds described herein or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Acid addition salts of the compounds described herein are most suitably formed from pharmaceutically acceptable acids, and include, for example, those formed with inorganic acids, e.g., hydrochloric, sulphuric or phosphoric acids and organic acids, e.g., succinic, maleic, acetic, trifluoroacetic or fumaric acid. Other non-pharmaceutically acceptable salts, e.g., oxalates may be used for example in the isolation of compounds described herein for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

As used herein, "promoting wound healing" means treating a subject with a wound and achieving healing, either partially or fully, of the wound. Promoting wound healing can mean, e.g., one or more of the following: promoting epidermal closure; promoting migration of the dermis; promoting dermal closure in the dermis; reducing wound healing complications, e.g., hyperplasia of the epidermis and adhesions; reducing wound dehiscence; and promoting proper scab formation.

The term "therapeutically effective amount" means an amount of the compound which is effective in treating or lessening the severity of one or more symptoms of a disorder or condition. In the case of wound healing, a therapeutically effective amount is an amount that promotes healing of a wound.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of being administered to a subject. One example of such a carrier is pharmaceutically acceptable oil typically used for parenteral administration. Pharmaceutically acceptable carriers are well known in the art.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CRM1, in a biological sample or in a patient. In certain embodiments, a composition of this invention is formulated for administration to a patient in need of such composition. The term "patient", as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral" as used herein includes subcutaneous, intravenous, intramuscular, intraocular, intravitreal, intra-articular, intra-synovial, intrasternal, intrathecal, intra-hepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In some embodiments, pharmaceutically acceptable compositions of this invention are formulated for intra-peritoneal administration.

The amount of compounds of the present invention that may be combined with the carrier materials to produce a composition in a single dosage form will vary depending upon the host treated, the particular mode of administration. In one embodiment, provided compositions should be formulated so that a dosage of between 0.01-100 mg/kg body weight/day of the inhibitor can be administered to a patient receiving these compositions. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this invention will be administered from about 1 to about 6 times per day.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms Uses of Compounds and Pharmaceutically Acceptable Compositions Compounds and compositions described herein are generally useful for the inhibition of CRM1 and are therefore useful for treating one or more disorders associated with activity of CRM1. Thus, in certain embodiments, the present invention provides a method for treating a CRM1-mediated disorder comprising the step of administering to a patient in need thereof a compound of the present invention, or pharmaceutically acceptable composition thereof. The compounds and compositions described herein can also be administered to cells in culture, e.g. in vitro or ex vivo, or to a subject, e.g., in vivo, to treat, prevent, and/or diagnose a variety of disorders, including those described herein below.

The activity of a compound utilized in this invention as an inhibitor of CRM1 may be assayed in vitro, in vivo or in a cell line. Detailed conditions for assaying a compound utilized in this invention as an inhibitor of CRM1 are set forth in the Examples below.

As used herein, the term "CRM1-mediated" disorder or condition, as used herein, means any disease or other deleterious condition in which CRM1 is known to play a role. Accordingly, another embodiment of the present invention relates to treating or lessening the severity of one or more diseases in which CRM1 is known to play a role. In some embodiments, the present invention provides methods of treating a disease associated with expression or activity of p53, p73, p21, pRB, p27, IκB, NFκB, c-Abl, FOXO proteins, COX-2, or an HDAC (histone deacetylases) in a subject comprising administering to the patient a therapeutically effective amount of a compound described herein. In another embodiment, the present invention relates to a method of treating or lessening the severity of a disease or condition selected from a proliferative disorder (e.g., cancer), an inflammatory disorder, an autoimmune disorder, a viral infection, an ophthalmological disorder or a neurodegenerative disorder wherein said method comprises administering to a patient in need thereof a compound or composition according to the present invention. In a more specific embodiment, the present invention relates to a method of treating or lessening the severity of cancer. Specific examples of the above disorders are set forth in detail below.

Cancers treatable by the compounds of this invention include, but are not limited to, hematologic malignancies (leukemias, lymphomas, myelomas including multiple myeloma, myelodysplastic and myeloproliferative syndromes) and solid tumors (carcinomas such as prostate, breast, lung, colon, pancreatic, renal, ovarian as well as soft tissue and osteosarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple.

Inflammatory disorders treatable by the compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by the compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by a compound of Formula I include, but are not limited to, Parkinson's, Alzheimer's, and Huntington's, and Amyotrophic lateral sclerosis (ALS/Lou Gehrig's Disease).

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Compounds and compositions described herein may also be used to treat disorders related to food intake such as obesity and hyperphagia.

In another embodiment, a compound or composition described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

In some embodiments, the disorder or condition associated with CRM1 activity is muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodonitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present invention provides a use of a compound described herein for the manufacture of a medicament for the treatment of a disease associated with expression or activity of p53, p73, p21, pRB, p27, IκB, NFκB, c-Abl, FOXO proteins, COX-2 or an HDAC in a subject. In some embodiments, the present invention provides a use of a compound described herein in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthalmologic disorders.

In some embodiments, the present invention provides a method for inhibiting CRM1 in a biological sample comprising contacting the biological sample with, or administering to the patient, a pharmaceutically acceptable salt of a compound of the invention, or pharmaceutically acceptable composition thereof.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor.

Further exemplary cancers include diffuse large B-cell lymphoma (DLBCL) and mantle cell lymphoma (MCL). Yet further exemplary cancers include endocervical cancer, B-cell ALL, T-cell ALL, B- or T-cell lymphoma, mast cell cancer, glioblastoma, neuroblastoma, follicular lymphoma and Richter's syndrome.

Exemplary sarcomas include fibrosarcoma, alveolar soft part sarcoma (ASPS), liposarcoma, leiomyosarcoma, chondrosarcoma, synovial sarcoma, chordoma, spindle cell sarcoma, histiocytoma, rhabdomyosarcoma, Ewing's sarcoma, neuroectodermal sarcoma, phyllodes/osteogenic sarcoma and chondroblastic osteosarcoma.

Metastases of the aforementioned cancers can also be treated or prevented in accordance with the methods described herein.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

Cancer Combination Therapies

In some embodiments, a compound described herein is administered together with an additional cancer treatment. Exemplary additional cancer treatments include, for example: chemotherapy, targeted therapies such as antibody therapies, kinase inhibitors, immunotherapy, and hormonal therapy, epigenetic therapy, proteosome inhibitors, and anti-angiogenic therapies. Examples of each of these treatments are provided below. As used herein, the term "combination," "combined," and related terms refer to the simultaneous or sequential administration of therapeutic agents in accordance with this invention. For example, a compound of the present invention can be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustin, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including 06-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

The compounds and methods described herein may be used to treat or prevent a disease or disorder associated with inflammation, particularly in humans and other mammals. A compound described herein may be administered prior to the onset of, at, or after the initiation of inflammation. When used prophylactically, the compounds are preferably provided in advance of any inflammatory response or symptom. Administration of the compounds can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a compound or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a compound or method described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the compounds described herein can be used to treat multiple sclerosis.

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isofluipredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a compound described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection, particularly in humans and other mammals. A compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral influenza A strains include H1N1, H3N2, H5N1, H7N3, H7N9. A compound described herein can also be used to treat or prevent influenza B.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

Ophthalmology

Compounds and methods described herein may be used to treat or prevent an ophthamology disorder. Exemplary ophthamology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using the compounds and methods described herein include proliferative vitreoretinopathy and chronic retinal detachment.

Inflammatory eye diseases are also treatable using the compounds and methods described herein.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a therapeutically effective amount of a compound (e.g., a CRM1 inhibitor), or pharmaceutically acceptable salt or composition thereof. The method need not achieve complete healing or closure of the wound; it is sufficient for the method to promote any degree of wound closure. In this respect, the method can be employed alone or as an adjunct to other methods for healing wounded tissue.

The compounds and compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a dog, a cat, a horse, a pig, or a rodent, such as a mouse.

In some embodiments, the compounds and compositions described herein useful for wound healing are administered topically, for example, proximate to the wound site, or systemically.

More specifically, a therapeutically effective amount of a compound or composition described herein can be administered (optionally in combination with other agents) to the wound site by coating the wound or applying a bandage, packing material, stitches, etc., that are coated or treated with the compound or composition described herein. As such, the compounds and compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the compound or composition described herein. Topical delivery systems may be used to administer topical formulations of the compounds and compositions described herein.

Alternatively, the compounds and compositions described herein can be administered at or near the wound site by, for example, injection of a solution, injection of an extended release formulation, or introduction of a biodegradable implant comprising the compound or composition described herein.

The compounds and compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and, thus, initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds. Other examples of chronic wounds include chronic ulcers, diabetic wounds, wounds caused by diabetic neuropathy, venous insufficiencies, and arterial insufficiencies, and pressure wounds and cold and warm burns. Yet other examples of chronic wounds include chronic ulcers, diabetic wounds, wounds caused by diabetic neuropathy, venous insufficiencies, arterial insufficiencies, and pressure wounds.

Acute wounds include, but are not limited to, post-surgical wounds, lacerations, hemorrhoids and fissures.

In a particular embodiment, the compounds and compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

The compounds and compositions described herein can also be used for diabetic wound healing, gastrointestinal wound healing, or healing of an adhesion due, for example, to an operation.

The compounds and compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. The compounds and compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer. Examples of internal wounds include, but are not limited to, fistulas and internal wounds associated with cosmetic surgery, internal indications, Crohn's disease, ulcerative colitis, internal surgical sutures and skeletal fixation. Other examples of internal wounds include, but are not limited to, fistulas and internal wounds associated with cosmetic surgery, internal indications, internal surgical sutures and skeletal fixation.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In preferred embodiments, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation. In more preferred embodiments, the wound is selected from the group consisting of an incised wound, an open wound, a surgical or post surgical wound, a diabetic lesion, a pressure sore, a bedsore, and a condition or wound related to diabetes or poor circulation.

In some embodiments, the wound is selected from the group consisting of a non-radiation burn wound, an incised wound, an open wound, a surgical or post surgical wound, a diabetic lesion, a thermal burn, a chemical burn, a pressure sore, a bedsore, and a condition related to diabetes or poor circulation. In some embodiments, the wound is selected from the group consisting of an incised wound, an open wound, a surgical or post surgical wound, a diabetic lesion, a pressure sore, a bedsore, and a condition related to diabetes or poor circulation.

The present disclosure also relates to methods and compositions of reducing scar formation during wound healing in a subject. The compounds and compositions described herein can be administered directly to the wound or to cells proximate the wound at an amount effective to reduce scar formation in and/or around the wound. Thus, in some embodiments, a method of reducing scar formation during wound healing in a subject is provided, the method comprising administering to the subject a therapeutically effective amount of a compound described herein (e.g., a CRM1 inhibitor), or a pharmaceutically acceptable salt thereof.

The wound can include any injury to any portion of the body of a subject. According to embodiments, methods are provided to ameliorate, reduce, or decrease the formation of scars in a subject that has suffered a burn injury. According to preferred embodiments, methods are provided to treat, reduce the occurrence of, or reduce the probability of developing hypertrophic scars in a subject that has suffered an acute or chronic wound or injury.

Other Disorders

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Combination Radiation Therapy

Compounds and compositions described herein are useful as radiosensitizers. Therefore, compounds and compositions described herein can be administered in combination with radiation therapy. Radiation therapy is the medical use of high-energy radiation (e.g., x-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}$Co, $^{137}$Cs, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intercavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. *Cancer Res.,* 2001; 61:2008-2014 and Goldenber, D. M. *J. Nucl. Med.,* 2002; 43(5):693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57(5): 749-63, the contents of which are incorporated by reference herein.

In addition to targeted delivery, bracytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin- 114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both a and n-particle emitters have been investigated. Alpha particles are particularly good cytotoxic agents because they dissipate a large amount of energy within one or two cell diameters. The n-particle emitters have relatively long penetration range (2-12 mm in the tissue) depending on the energy level. The long-range penetration is particularly important for solid tumors that have heterogeneous blood flow and/or receptor expression. The n-particle emitters yield a more homogeneous dose distribution even when they are heterogeneously distributed within the target tissue.

In a particular embodiment, therapeutically effective amounts of the compounds and compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine 5th ed., Edited by R. C. Bast et al., July 2000, BC Decker.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations
aq. Aqueous
DMF N,N-Dimethylformamide
DMSO Dimethylsulfoxide
eq. equivalent(s)
Et Ethyl
EtOAc Ethyl acetate
g gram
h hour(s)
HPLC High performance liquid chromatography
LCMS Liquid Chromatography Mass Spectrometry
Me methyl
mg milligram(s)
min minute
mL milliliters
NMM N-methyl morpholine
NMR Nuclear magnetic resonance
Ph phenyl
THF Tetrahydrofuran
$t_R$ Retention time Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallization, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

Example 1. Synthetic Procedures

Synthesis of 3-(3-(3, 5-bis (trifluoromethyl) phenyl)-1H-1,2,4-triazol-1-yl)-2-(pyridin-2-yl) acrylonitrile (100)

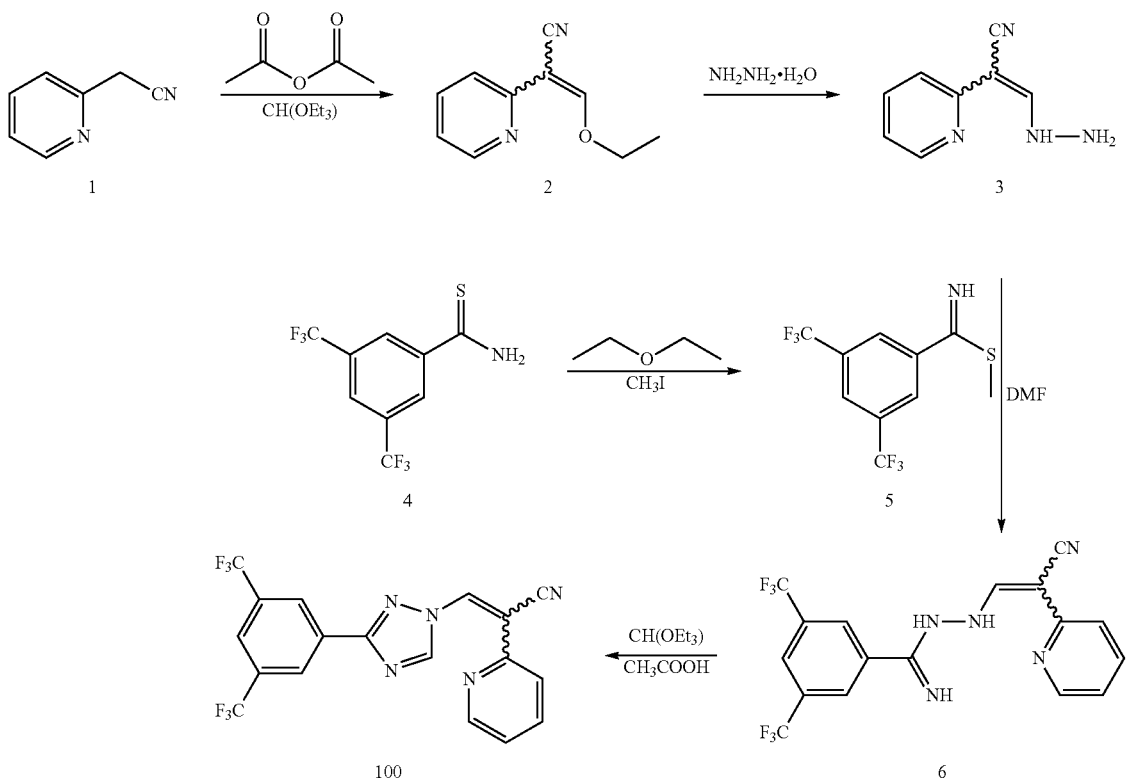

Synthesis of 3-ethoxy-2-(pyridin-2-yl) acrylonitrile (2)

2-Pyridyl acetonitrile (1) (1.00 g, 8.46 mmol) and triethyl orthoformate (1.25 g, 8.46 mmol) were added to acetic anhydride (1.73 g, 16.93 mmol) at room temperature. The resulting reaction mixture was heated at 100° C. for 3 h, cooled to room temperature, diluted with water (500 mL), and extracted with ethyl acetate (100 mL×3). The combined organic layers were washed with brine, dried over anhydrous Na$_2$SO$_4$, and concentrated under reduced pressure to give 800 mg of crude 3-ethoxy-2-(pyridin-2-yl) acrylonitrile (2), which was used without further purification in the following step. Yield (34%), LCMS: m/z 175.20 [M+H]$^+$, t$_R$=1.52 min.

Synthesis of 3-hydrazinyl-2-(pyridin-2-yl) acrylonitrile (3)

3-Ethoxy-2-(pyridin-2-yl) acrylonitrile (2) (800 mg, 4.59 mmol) and hydrazine hydrate (230 mg, 4.59 mmol) were added to water (8 mL) at room temperature. The reaction mixture was heated at 80° C. for 1 h, cooled to room temperature, diluted with water (500 mL) and extracted with ethyl acetate (3×100 mL). The combined organic layers were washed with brine, dried over anhydrous $Na_2SO_4$, and concentrated under reduced pressure to give 435 mg of crude 3-hydrazinyl-2-(pyridin-2-yl) acrylonitrile (3), which was used without further purification in the following step. Yield (42%), LCMS: m/z 161.18 [M+H]$^+$, $t_R$=0.24 min.

Synthesis of methyl 3, 5-bis(trifluoromethyl)benzimidothioate (5)

3,5-Bis (trifluoromethyl) benzothioamide (4) (15.0 g, 54.91 mmol) and methyl iodide (38.97 g, 274.53 mmol, 17.1 mL) were added to diethyl ether (120 mL) at 0° C. The reaction mixture was stirred at room temperature for 12 h. The solid product was filtered and dried to give methyl 3,5-bis (trifluoromethyl) benzimidothioate (5). Yield (8 g, 51%), $^1$H NMR (400 MHz, DMSO-d$_6$) δ 8.51 (s, 1H), 8.44 (s, 2H), 2.72 (s, 3H).

Synthesis of methyl-N'-(2-cyano-2-(pyridin-2-yl) vinyl)-3,5-bis(trifluoromethyl) benzimidohydrazide (6)

Methyl 3, 5-bis (trifluoromethyl) benzimidothioate (5) (300 mg, 1.04 mmol) and 3-hydrazinyl-2-(pyridin-2-yl) acrylonitrile (3) (184 mg, 1.15 mmol) were added to dimethylformamide (1.5 mL) at room temperature. After stirring at room temperature for 1 h, the reaction mixture was diluted with water (500 mL) and extracted with ethyl acetate (3×100 mL). The combined organic layers were washed with brine, dried over anhydrous $Na_2SO_4$ and concentrated under reduced pressure to give 400 mg of crude N-(2-cyano-2-(pyridin-2-yl)vinyl)-3,5-bis(trifluoromethyl) benzimidohydrazide (6) which was used without further purification in the following step. Yield (96%).

Synthesis of 3-(3-(3,5-bis(trifluoromethyl)phenyl)-1H-1,2,4-triazol-1-yl)-2-(pyridin-2-yl)acrylonitrile (100)

N-(2-cyano-2-(pyridin-2-yl) vinyl)-3,5-bis (trifluoromethyl) benzimidohydrazide (6) (400 mg, 1.00 mmol) and triethyl orthoformate (148 mg, 1.00 mmol) was added to acetic acid (2 mL) at room temperature. The reaction mixture was heated at 100° C. for 30 min. After cooling to room temperature, the reaction mixture was diluted with water (500 mL) and extracted with ethyl acetate (2×50 mL). The combined organic layers were washed with brine, dried over anhydrous $Na_2SO_4$, concentrated under reduced pressure and purified by silica gel chromatography to afford 3-(3-(3, 5-bis (trifluoromethyl) phenyl)-1H-1,2,4-triazol-1-yl)-2-(pyridin-2-yl) acrylonitrile (100). Yield (100 mg, 24%). $^1$H NMR (400 MHz, DMSO-d$_6$) δ 10.11 (s, 1H), 9.05-9.01 (m, 3H), 8.68-8.67 (m, 1H), 8.47-8.45 (m, 2H), 8.05-8.00 (m, 1H), 7.36-7.33 (m, 1H). LCMS: m/z 410.29 [M+H]$^+$, $t_R$=2.71 min.

Synthesis of (E)-isopropyl 3-(3-(3,5-bis(trifluoromethyl)phenyl)-1H-1,2,4-triazol-1-yl)-2-(pyridin-3-yl) acrylate (101)

General Procedure 1: Suzuki Cross-Coupling

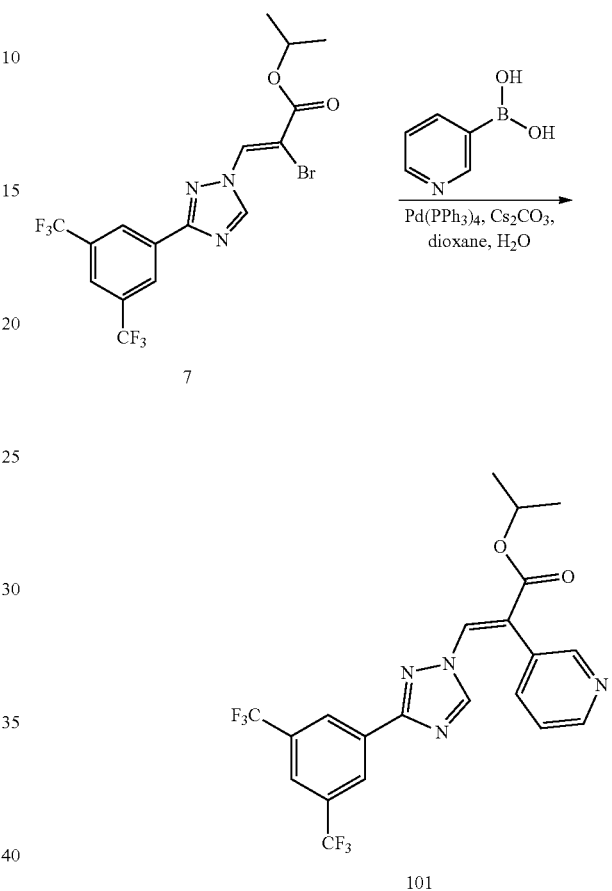

(Z)-Isopropyl 3-(3-(3,5-bis(trifluoromethyl)phenyl)-1H-1,2,4-triazol-1-yl)-2-bromoacrylate (7) (1.0 g, 2.0 mmol), pyridine 3-boronic acid (0.39 g, 3.20 mmol) and a solution of cesium carbonate (1.38 g, 4.0 mmol) in water (5 mL) were added to dioxane (20 mL) at room temperature, degassed and purged with $N_2$. Tetrakis(triphenylphosphine) palladium (0) (0.23 g, 0.2 mmol) was added to the reaction mixture and the resulting mixture was degassed, and purged with $N_2$. The reaction mixture was stirred at 50° C. for 12 h. The reaction mixture was diluted with water (150 mL) and extracted with ethyl acetate (3×50 mL). The combined organic layers were washed with brine, dried over anhydrous $Na_2SO_4$ and concentrated under reduced pressure. The crude product was purified by silica gel chromatography using (10% EtOAc in hexane) to give (E)-isopropyl 3-(3-(3, 5-bis (trifluoromethyl) phenyl)-1H-1, 2, 4-triazol-1-yl)-2-(pyridin-3-yl) acrylate (101). Yield (0.399 g, 40%), $^1$H NMR (400 MHz, DMSO-d$_6$) δ 9.16 (s, 1H), 8.58 (s, 2H), 8.48 (s, 1H), 8.23 (s, 1H), 8.06 (s, 2H), 7.74 (d, J=7.2 Hz, 1H), 7.48-7.45 (m, 1H), 5.12-5.06 (m, 1H), 1.28-1.26 (m, 6H). LCMS: m/z 471.37 [M+H]$^+$, $t_R$=2.73 min.

Syntheses of (E)-3-(3-(3,5-bis(trifluoromethyl)phenyl)-1H-1,2,4-triazol-1-yl)-2-(pyridin-3-yl)acrylonitrile (102), (E)-3-(3-(3,5-bis(trifluoromethyl)phenyl)-1H-1,2,4-triazol-1-yl)-2-(pyridin-3-yl)acrylic acid (103) and (E)-3-(3-(3,5-bis(trifluoromethyl)phenyl)-1H-1,2,4-triazol-1-yl)-2-(pyridin-3-yl)acrylamide (104)

the crude product was purified by silica gel chromatography (6% MeOH in CH$_2$Cl$_2$) to give (E)-3-(3-(3,5-bis(trifluoromethyl)phenyl)-1H-1,2,4-triazol-1-yl)-2-(pyridin-3-yl)acrylic acid (103). Yield (0.42 g, 42%), $^1$H NMR (400 MHz, DMSO-d$_6$) δ 13.33 (s, 1H), 9.12 (s, 1H), 8.59-8.56 (m, 2H), 8.46 (s, 1H), 8.23 (s, 1H), 8.07 (s, 2H), 7.74-7.70 (m, 1H), 7.47-7.43 (m, 1H). LCMS: m/z 429.29 [M+H]$^+$, t$_R$=2.17 min.

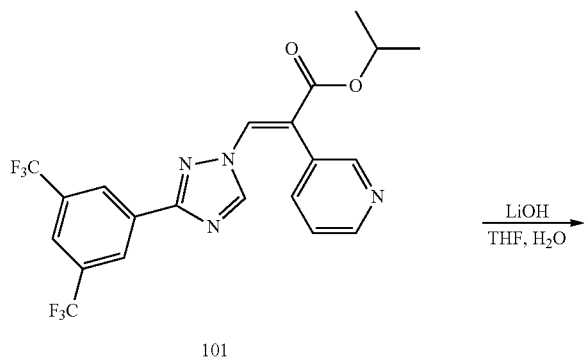

101

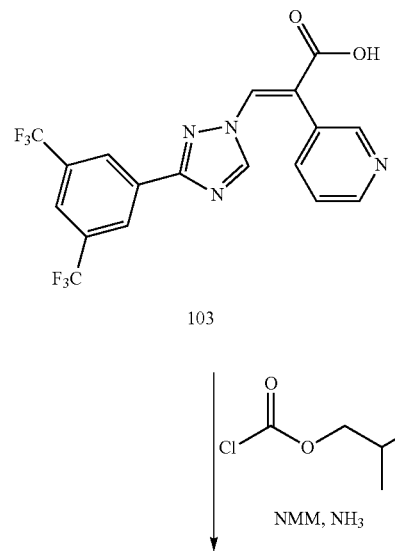

103

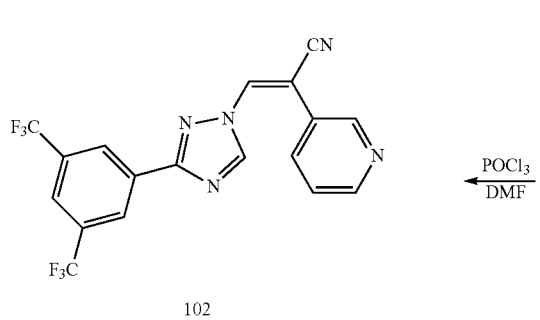

102

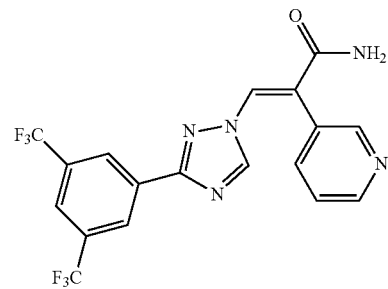

104

Synthesis of (E)-3-(3-(3,5-bis(trifluoromethyl)phenyl)-1H-1,2,4-triazol-1-yl)-2-(pyridin-3-yl)acrylic acid (103)

General Procedure 2: Ester Hydrolysis

Isopropyl (E)-3-(3-(3,5-bis (trifluoromethyl) phenyl)-1H-1,2,4-triazol-1-yl)-2-(pyridin-3-yl) acrylate (101) (1.1 g, 2.3 mmol) was dissolved in a solution of THF:H$_2$O (1:1) (11 mL) and LiOH·H$_2$O (0.29 g, 7.0 mmol) at 0° C. The reaction mixture was stirred at room temperature for 4 h. The reaction mixture was transferred into iced water and neutralized using 3M HCl solution (10 mL) and extracted with ethyl acetate (50 mL×3). The combined organic layers were washed with brine and dried over anhydrous Na$_2$SO$_4$. The organic layer was concentrated under reduced pressure and Synthesis of (E)-3-(3-(3,5-bis(trifluoromethyl)phenyl)-1H-1,2,4-triazol-1-yl)-2-(pyridin-3-yl)acrylamide (104)

General Procedure 3: Conversion of Carboxylic Acid to Primary Amide (E)-3-(3-(3,5-Bis(trifluoromethyl)phenyl)-1H-1,2,4-triazol-1-yl-2-(pyridin-3-yl) acrylic acid (103) (1 g, 2.3 mmol) was dissolved in THF (10 mL) and cooled to 0° C. To the solution was added isobutyl chloroformate (0.49 g, 3.64 mmol), N-methyl morpholine (0.33 g, 3.26 mmol). The reaction mixture was stirred at room temperature for 30 min. The reaction mixture was filtered and ammonia gas was purged through the filtrate for 15 min at 0° C. The reaction mixture was transferred into ice water and compound was extracted with ethyl acetate (3×50 mL). The combined organic layers were washed with brine and dried over anhydrous $Na_2SO_4$. The organic layer was concentrated under reduced pressure and the crude product was purified by silica gel chromatography to give 0.370 g of (E)-3-(3-(3,5-bis(trifluoromethyl) phenyl)-1H-1,2,4-triazol-1-yl)-2-(pyridin-3-yl) acrylamide (104). Yield (0.370 g, 37%), $^1$H NMR (400 MHz, DMSO-$d_6$) δ 8.99 (s, 1H), 8.61-8.59 (m, 1H), 8.45 (s, 1H), 8.30 (s, 1H), 8.22 (s, 1H), 8.09 (s, 2H), 7.71-7.69 (m, 1H), 7.61 (s, 1H), 7.48-7.45 (m, 1H), 7.23 (s, 1H). LCMS: m/z 428.30 $[M+H]^+$, $t_R$=2.31 min.

Synthesis of (E)-3-(3-(3,5-bis(trifluoromethyl)phenyl)-1H-1,2,4-triazol-1-yl)-2-(pyridin-3-yl)acrylonitrile (102)

General Procedure 4: Conversion of Primary Amide to Nitrile (E)-3-(3-(3,5-Bis(trifluoromethyl)phenyl)-1H-1,2,4-triazol-1-yl)-2-(pyridin-3-yl)acrylamide (104) (260 mg, 0.60 mmol) was dissolved in dimethylformamide (5 mL) and cooled to 0° C. to which was added phosphorus oxychloride (110 mg, 1.21 mmol). The reaction mixture was stirred at 0° C. for 1 h, transferred into iced water and extracted with ethyl acetate (3×50 mL). The combined organic layers were washed with brine, dried over anhydrous $Na_2SO_4$, concentrated under reduced pressure. The crude product was purified by silica gel chromatography to give (E)-3-(3-(3,5-bis(trifluoromethyl)phenyl)-1H-1,2,4-triazol-1-yl)-2-(pyridin-3-yl)acrylonitrile (102). Yield (0.08 g, 32%), $^1$H NMR (400 MHz, DMSO-$d_6$) δ 9.04 (s, 1H), 8.73 (s, 1H), 8.68-8.67 (m, 1H), 8.59 (s, 1H), 8.28 (s, 1H), 8.13 (s, 2H), 8.00-7.97 (m, 1H), 7.55-7.52 (m, 1H). LCMS: m/z 410.0 $[M+H]^+$, $t_R$=2.37 min.

Syntheses of (E)-3-(3-(3,5-bis(trifluoromethyl)phenyl)-1H-1,2,4-triazol-1-yl)-2-(pyridin-4-yl)acrylonitrile (105), isopropyl (E)-3-(3-(3,5-bis(trifluoromethyl)phenyl)-1H-1,2,4-triazol-1-yl)-2-(pyridin-4-yl) acrylate (106), (E)-3-(3-(3,5-bis(trifluoromethyl) phenyl)-1H-1,2,4-triazol-1-yl)-2-(pyridin-4-yl) acrylic acid (107), and (E)-3-(3-(3,5-bis (trifluoromethyl)phenyl)-1H-1,2,4-triazol-1-yl)-2-(pyridin-4-yl)acrylamide (108)

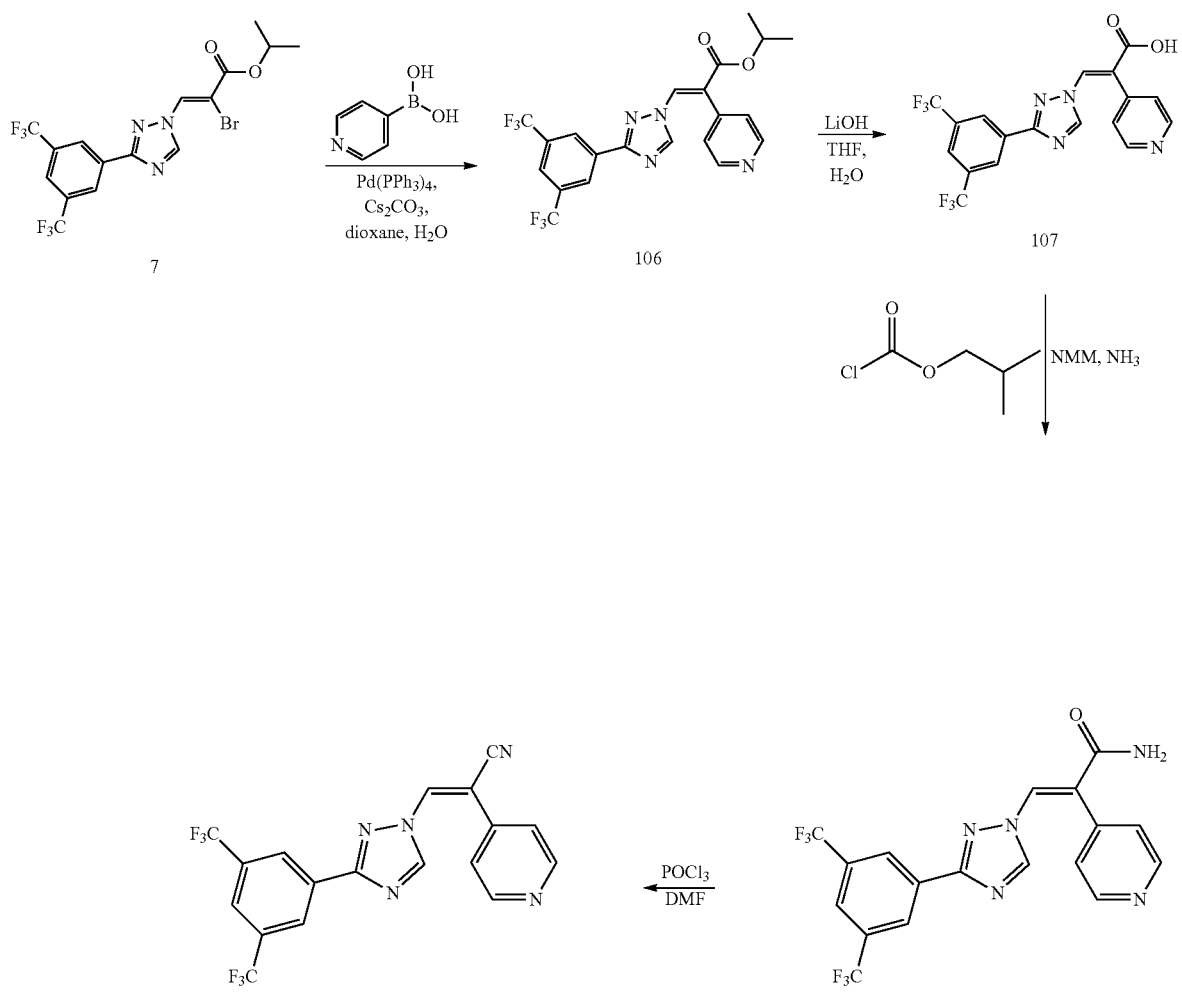

Synthesis of isopropyl (E)-3-(3-(3,5-bis(trifluoromethyl)phenyl)-1H-1,2,4-triazol-1-yl)-2-(pyridin-4-yl)acrylate (106)

Isopropyl (E)-3-(3-(3,5-bis(trifluoromethyl)phenyl)-1H-1,2,4-triazol-1-yl)-2-(pyridin-4-yl)acrylate (106) was synthesized using General Procedure 1. Yield (9%), $^1$H NMR (400 MHz, DMSO-d$_6$) δ 9.13 (s, 1H), 8.63-8.61 (m, 2H), 8.54 (s, 1H), 8.24 (s, 1H), 8.06 (s, 2H), 7.34-7.32 (m, 2H), 5.10-5.06 (m, 1H), 1.27-1.25 (m, 6H). LCMS: m/z 471.5 [M+H]$^+$, t$_R$=2.73 min.

Synthesis of (E)-3-(3-(3,5-bis(trifluoromethyl)phenyl)-1H-1,2,4-triazol-1-yl)-2-(pyridin-4-yl)acrylic acid (107)

(E)-3-(3-(3,5-Bis(trifluoromethyl)phenyl)-1H-1,2,4-triazol-1-yl)-2-(pyridin-4-yl)acrylic acid (107) was synthesized using General Procedure 2. Yield (52%), $^1$H NMR (400 MHz, DMSO-d$_6$) δ 13.38 (s, 1H), 9.12-9.08 (m, 1H), 8.24-8.23 (m, 2H), 8.09 (s, 2H), 7.63 (s, 1H), 7.31-7.29 (m, 2H), 7.18 (s, 1H). LCMS: m/z 428.16 [M+H]$^+$, t$_R$=2.10 min.

Synthesis of (E)-3-(3-(3,5-bis(trifluoromethyl)phenyl)-1H-1,2,4-triazol-1-yl)-2-(pyridin-4-yl)acrylonitrile (105)

(E)-3-(3-(3,5-Bis(trifluoromethyl)phenyl)-1H-1,2,4-triazol-1-yl)-2-(pyridin-4-yl)acrylonitrile (105) was synthesized using General Procedure 4. Yield (58%), $^1$H NMR (400 MHz, DMSO-d$_6$) δ 9.16 (s, 1H), 9.04 (s, 1H), 8.77-8.75 (m, 2H), 8.61 (s, 2H), 8.38 (s, 1H), 7.72-7.70 (m, 2H). LCMS: m/z 410.1 [M+H]$^+$, t$_R$=2.64 min.

Synthesis of isopropyl (Z)-3-(3-(3,5-bis(trifluoromethyl)phenyl)-1H-1,2,4-triazol-1-yl)-2-(thiazol-2-yl)acrylate (109), (Z)-3-(3-(3,5-bis(trifluoromethyl)phenyl)-1H-1,2,4-triazol-1-yl)-2-(thiazol-2-yl)acrylonitrile (110) and (Z)-3-(3-(3,5-bis(trifluoromethyl)phenyl)-1H-1,2,4-triazol-1-yl)-2-(thiazol-2-yl)acrylamide (111)

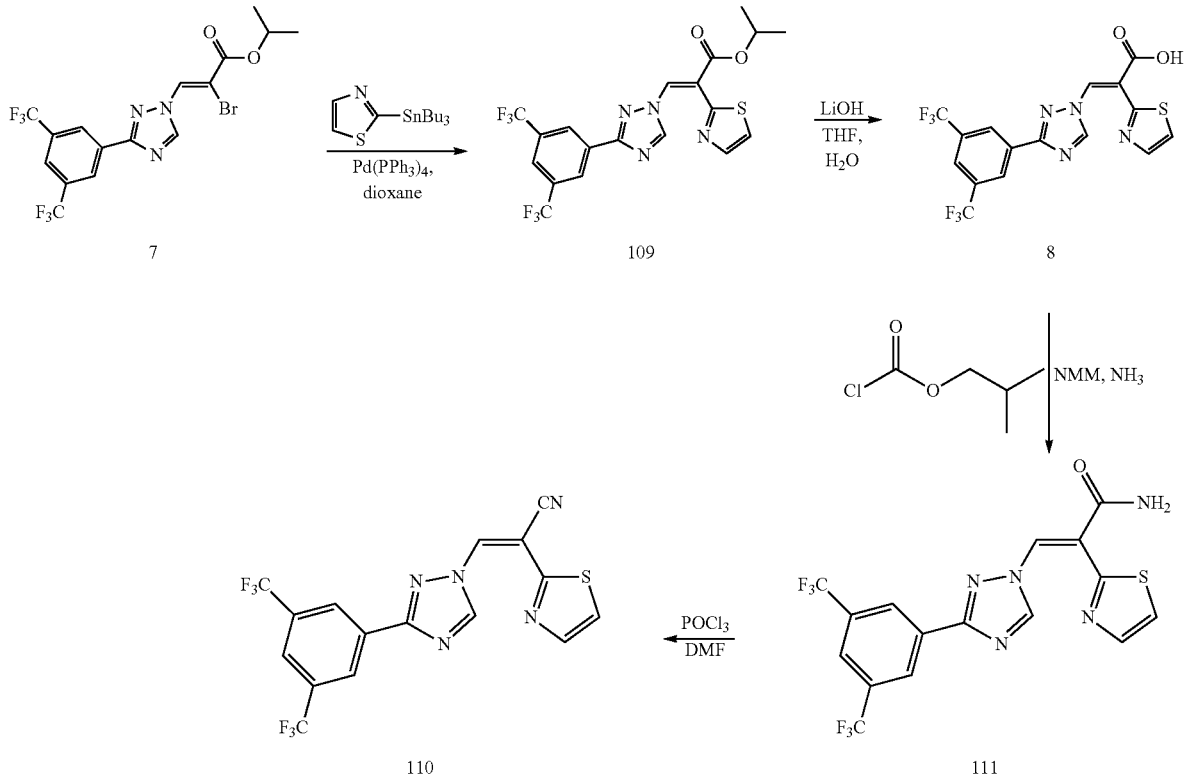

8.63-8.53 (m, 3H), 8.25-8.22 (m, 1H), 8.10-8.06 (m, 2H), 7.35-7.31 (m, 2H). LCMS: m/z 429.11 [M+H]$^+$, t$_R$=2.01 min.

Synthesis of (E)-3-(3-(3,5-bis(trifluoromethyl)phenyl)-1H-1,2,4-triazol-1-yl)-2-(pyridin-4-yl)acrylamide (108)

(E)-3-(3-(3,5-Bis(trifluoromethyl)phenyl)-1H-1,2,4-triazol-1-yl)-2-(pyridin-4-yl)acrylamide (108) was synthesized using General Procedure 3. Yield (33%), $^1$H NMR (400 MHz, DMSO-d$_6$) δ 8.95 (s, 1H), 8.66-8.62 (m, 2H),

Synthesis of isopropyl (Z)-3-(3-(3,5-bis(trifluoromethyl)phenyl)-1H-1,2,4-triazol-1-yl)-2-(thiazol-2-yl)acrylate (109)

Isopropyl (Z)-3-(3-(3,5-bis(trifluoromethyl)phenyl)-1H-1,2,4-triazol-1-yl)-2-(thiazol-2-yl)acrylate (109) was synthesized using General Procedure 5, which is described in detail for the synthesis of (E)-3-(3-(3,5-bis(trifluoromethyl)phenyl)-1H-1,2,4-triazol-1-yl)-N,N-dimethyl-2-(pyridin-4-yl)acrylamide (113). Yield (54%). $^1$H NMR (400 MHz, DMSO-d$_6$) δ 9.27 (s, 1H), 9.12 (s, 1H), 8.59 (s, 1H), 8.27 (s, 1H), 8.22 (s, 2H), 7.88 (s, 1H), 5.13-5.01 (m, 1H), 1.25 (d, J=6 Hz, 6H). LCMS: m/z 477.18 [M+H]⁺, $t_R$=2.94 min.

Synthesis of (Z)-3-(3-(3,5-bis(trifluoromethyl)phenyl)-1H-1,2,4-triazol-1-yl)-2-(thiazol-2-yl)acrylic acid (8)

(Z)-3-(3-(3,5-Bis(trifluoromethyl)phenyl)-1H-1,2,4-triazol-1-yl)-2-(thiazol-2-yl)acrylic acid (8) was synthesized using General Procedure 2 and the crude product was used in the next step without purification.

Synthesis of (Z)-3-(3-(3,5-bis(trifluoromethyl)phenyl)-1H-1,2,4-triazol-1-yl)-2-(thiazol-2-yl)acrylamide (111)

(Z)-3-(3-(3,5-Bis(trifluoromethyl)phenyl)-1H-1,2,4-triazol-1-yl)-2-(thiazol-2-yl)acrylamide (111) was synthesized using General Procedure 3. Yield (55%). ¹H NMR (400 MHz, DMSO-d₆) δ 9.26 (s, 1H), 9.97 (s, 1H), 8.26-8.22 (m, 4H), 7.87 (s, 1H), 7.70 (s, 1H), 7.50 (s, 1H). LCMS: m/z 434.21 [M+H]⁺, $t_R$=2.28 min.

Synthesis of (Z)-3-(3-(3,5-bis(trifluoromethyl)phenyl)-1H-1,2,4-triazol-1-yl)-2-(thiazol-2-yl)acrylonitrile (110)

(Z)-3-(3-(3,5-Bis(trifluoromethyl)phenyl)-1H-1,2,4-triazol-1-yl)-2-(thiazol-2-yl) acrylonitrile (110) was synthesized using General Procedure 4. Yield (30%). ¹H NMR (400 MHz, DMSO-d₆) δ 9.36 (s, 1H), 9.36 (s, 1H), 9.09 (s, 1H), 8.53 (s, 1H), 8.42 (s, 2H), 8.35 (s, 1H), 8.30 (s, 1H). LCMS: m/z 416.01 [M+H]⁺, $t_R$: 2.69 min.

Synthesis of (E)-(3-(3-(3,5-bis(trifluoromethyl)phenyl)-1H-1,2,4-triazol-1-yl)-N,N-dimethyl-2-(pyridin-3-yl)acrylamide (112)

(E)-3-(3-(3,5-Bis(trifluoromethyl)phenyl)-1H-1,2,4-triazol-1-yl)-2-(pyridin-3-yl)acrylic acid (103) (0.15 g, 0.35 mmol) was dissolved in THF (5 mL) at room temperature. The reaction mixture was cooled to 0° C. and isobutyl chloroformate (0.067 mL, 0.525 mmol) was added dropwise. 4-methyl morpholine (0.04 mL, 0.52 mmol) was then added. The reaction mixture was allowed to warm to room temperature and stirred for 30 min. The reaction mixture was filtered and the filtrate was cooled to 0° C. Dimethylamine (2N in THF, 2 mL) was added dropwise to the reaction mixture. The reaction mixture was stirred at 0° C. for 15 min, warmed to room temperature, transferred into iced water, and extracted with ethyl acetate (3×30 mL). The combined organic layers were washed with brine, dried over anhydrous Na₂SO₄, and concentrated under reduced pressure to give the crude product, which was purified by silica gel chromatography (0-5% MeOH:CH₂Cl₂) to obtain (E)-3-(3-(3,5-bis(trifluoromethyl) phenyl)-1H-1,2,4-triazol-1-yl)-N,N-dimethyl-2-(pyridin-3-yl)acrylamide (112). (Yield: 0.040 g, 25%). ¹H NMR (400 MHz, DMSO-d₆) δ 8.82 (s, 1H), 8.57 (s, 1H), 8.56 (s, 1H), 8.23 (s, 1H), 8.21 (s, 2H), 7.80 (d, J=11.6 Hz, 1H), 7.68 (s, 1H), 7.45-7.42 (m, 1H), 2.97 (s, 3H), 2.88 (s, 3H). LCMS: m/z 456.61 [M+H]⁻, $t_R$=2.30 min.

Synthesis of (E)-(3-(3-(3,5-bis(trifluoromethyl)phenyl)-1H-1,2,4-triazol-1-yl)-N,N-dimethyl-2-(pyridin-4-yl)acrylamide (113)

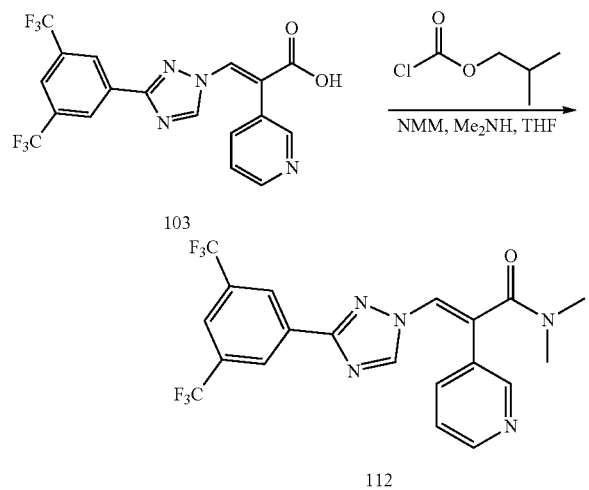

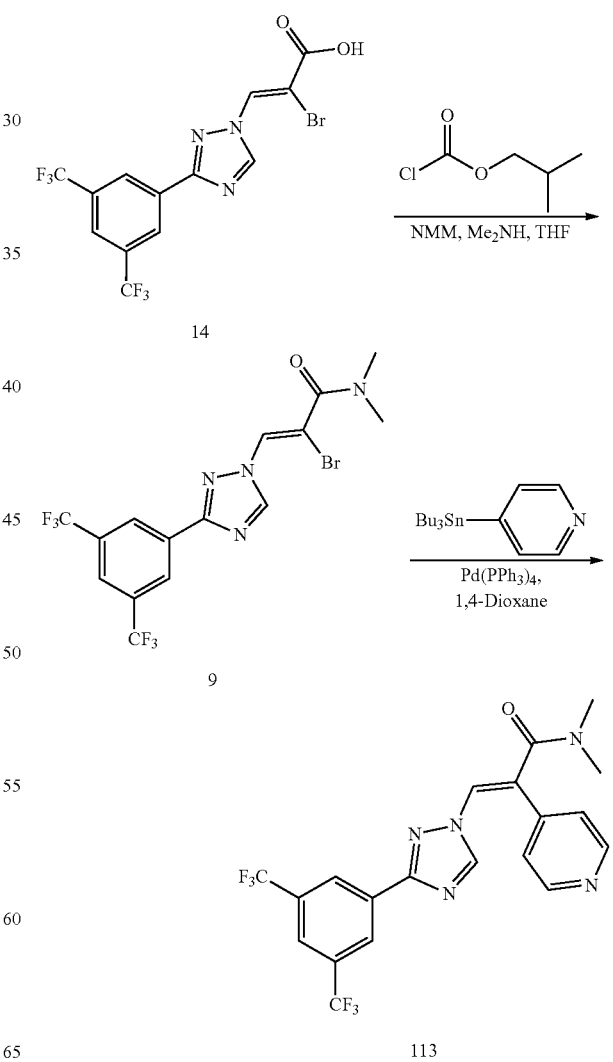

Synthesis of (Z)-3-(3-(3,5-bis(trifluoromethyl)phenyl)-1H-1,2,4-triazol-1-yl)-2-bromo-N,N-dimethylacrylamide (9)

(Z)-3-(3-(3,5-Bis(trifluoromethyl)phenyl)-1H-1,2,4-triazol-1-yl)-2-bromoacrylic acid (7) (0.5 g, 1.16 mmol) was dissolved in THF (10 mL) at room temperature. The reaction mixture was cooled to 0° C. and isobutyl chloroformate (0.22 mL, 1.74 mmol) was added drop wise. N-methyl morpholine (0.19 mL, 1.74 mmol) was then added to the reaction mixture and stirred for 5 min. The reaction mixture was allowed to warm to room temperature, stirred for 30 min and filtered. The filtrate was cooled to 0° C. and dimethylamine (2N in THF, 2 mL) was added dropwise and stirred for 15 min. The reaction mixture was allowed to warm to room temperature, transferred into iced water and extracted with ethyl acetate (3×50 mL). The combined organic layers were washed with brine, dried over anhydrous $Na_2SO_4$ and concentrated under reduced pressure to give the crude product, which was purified by silica gel chromatography (0-5% $MeOH:CH_2Cl_2$) to obtain (Z)-3-(3-(3,5-bis(trifluoromethyl)phenyl)-1H-1,2,4-triazol-1-yl)-2-bromo-N,N-dimethyl acrylamide (9). (Yield: 0.2 g, 37%). $^1$H NMR (400 MHz, DMSO $d_6$) δ 9.41 (s, 1H), 8.70 (s, 1H), 8.57 (s, 2H), 8.32 (s, 1H), 2.97 (s, 3H), 2.88 (s, 3H). LCMS: m/z 457.17 [M+H]$^-$, $t_R$=2.55 min.

Synthesis of (E)-(3-(3-(3,5-bis(trifluoromethyl)phenyl)-1H-1,2,4-triazol-1-yl)-N,N-dimethyl-2-(pyridin-4-yl)acrylamide (113)

General Procedure 5: Stille Coupling (Z)-3-(3-(3,5-Bis(trifluoromethyl)phenyl)-1H-1,2,4-triazol-1-yl)-2-bromo-N,N-dimethylacrylamide (9) (0.2 g, 0.437 mmol) was dissolved in dry 1,4-dioxane (10 mL) at room temperature and degassed using $N_2$ for 30 min. 4-(tributylstannyl)pyridine (0.19 g, 0.524 mmol) and tetrakis (triphenylphosphine) palladium (0) (0.05 g, 0.0437 mmol) were added and the reaction mixture was heated at 90° C. for 2 h and then cooled to room temperature. The reaction mixture was transferred into iced water and extracted with ethyl acetate (3×25 mL). The combined organic layers were washed with brine, dried over anhydrous $Na_2SO_4$ and concentrated under reduced pressure to give crude compound which was purified by column silica gel chromatography using (0-5% $MeOH:CH_2Cl_2$) to obtain (E)-(3-(3-(3,5-bis(trifluoromethyl)phenyl)-1H-1,2,4-triazol-1-yl)-N,N-dimethyl-2-(pyridin-4-yl)acrylamide (113). (Yield: 0.05 g, 25%). $^1$H NMR (400 MHz, DMSO-$d_6$) δ 9.02 (s, 1H), 8.67 (d, J=5.6 Hz, 2H), 8.52 (s, 2H), 8.33 (s, 1H), 8.21 (s, 1H), 7.49 (d, J=6 Hz, 2H), 3.10 (s, 3H), 2.85 (s, 3H). LCMS: m/z 456.31 [M+H]$^+$, $t_R$=2.20 min.

Synthesis of (E)-3-(3-(3,5-bis(trifluoromethyl)phenyl)-1H-1,2,4-triazol-1-yl)-2-(1-methyl-1H-pyrazol-4-yl)acrylamide (114)

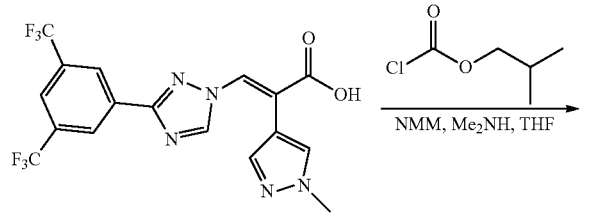

131

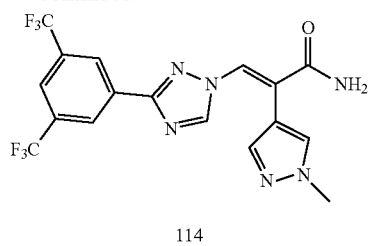

114

(E)-3-(3-(3,5-Bis(trifluoromethyl)phenyl)-1H-1,2,4-triazol-1-yl)-2-(1-methyl-1H-pyrazol-4-yl) acrylamide (114) was synthesized using General procedure 3. (Yield: 0.01 g, 33%). $^1$H NMR (400 MHz, DMSO-$d_6$) δ 8.79 (s, 1H), 8.45 (s, 2H), 8.28 (s, 1H), 7.84 (s, 1H), 7.75 (s, 1H), 7.57 (s, 1H), 7.48 (s, 1H), 7.27 (s, 1H), 3.84 (s, 3H). LCMS: m/z 431.21 [M+H]$^+$, $t_R$=2.22 min.

Synthesis of isopropyl (E)-3-(3-(3,5-bis(trifluoromethyl)phenyl)-1H-1,2,4-triazol-1-yl)-2-(pyrimidin-5-yl)acrylate (115)

General Procedure 6: Suzuki Coupling—Method 2

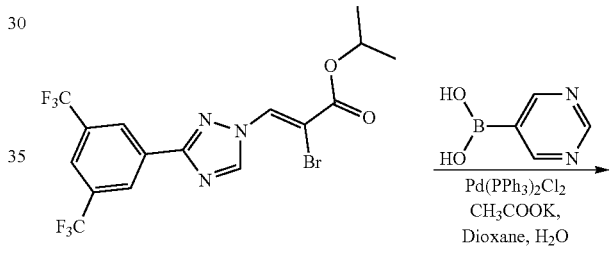

7

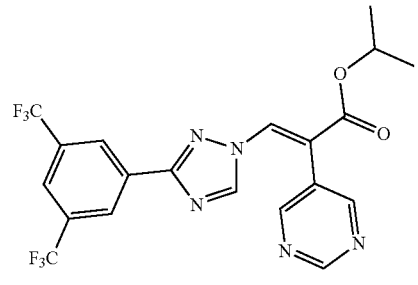

115

Isopropyl-(E)-3-(3-(3,5-bis(trifluoromethyl)phenyl)-1H-1,2,4-triazol-1-yl)-2-bromoacrylate (7) (0.7 g, 1.48 mmol), pyrimidine 5-boronic acid (0.22 g, 1.77 mmol) and a solution of potassium acetate (0.43 g, 4.4 mmol) in water (3.0 mL) were added in dioxane (15 mL) at room temperature, degassed and purged with N₂. Bis(triphenylphosphine) palladium (II) dichloride (0.1 g, 0.14 mmol) was added and the reaction mixture was degassed, and purged with N₂. The reaction mixture was stirred at 100° C. for 12 h, diluted with water (150 mL) and extracted with ethyl acetate (3×50 mL). The combined organic layers were washed with brine, dried over anhydrous Na₂SO₄ and concentrated under reduced pressure. The crude product was purified by silica gel chromatography (30% EtOAc in hexane) to give isopropyl-(E)-3-(3-(3,5-bis(trifluoromethyl)phenyl)-1H-1,2,4-triazol-1-yl)-2-(pyrimidin-5-yl)acrylate (115) (Yield: 0.2 g, 20%). ¹H NMR (400 MHz, DMSO-d₆) δ 9.26 (s, 1H), 9.20 (s, 1H), 8.79 (s, 2H), 8.68 (s, 1H), 8.26 (s, 1H), 8.07 (s, 2H), 5.13-5.07 (m, 1H), 1.27 (d, J=6 Hz, 6H). LCMS: m/z 472.22 [M+H]⁺, $t_R$=2.73 min.

Synthesis of isopropyl (E)-3-(3-(3,5-bis (trifluoromethyl) phenyl)-1H-1, 2, 4-triazol-1-yl)-2-(3,5-dimethylisoxazol-4-yl) acrylate (116)

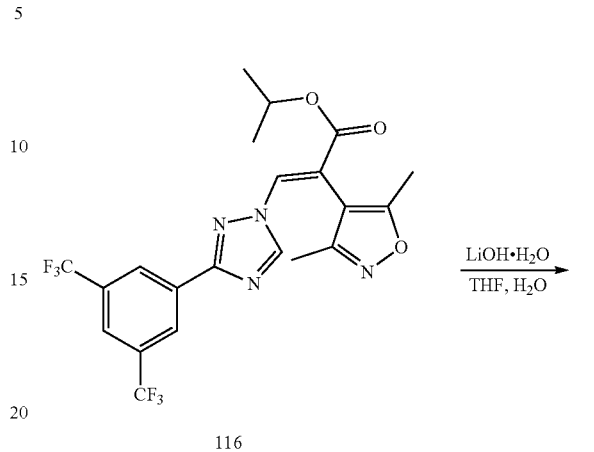

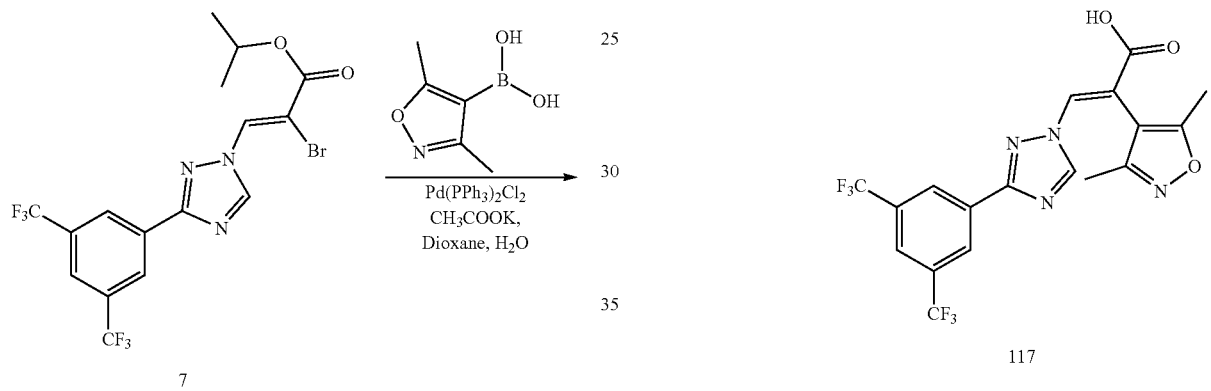

Isopropyl (E)-3-(3-(3,5-bis (trifluoromethyl) phenyl)-1H-1, 2, 4-triazol-1-yl)-2-(3, 5-dimethylisoxazol-4-yl) acrylate (116) was synthesized using General Procedure 6. (Yield: 0.2 g, 20%). ¹H NMR (400 MHz, DMSO-d₆) δ 9.21 (s, 1H), 8.63 (s, 1H), 8.29 (s, 3H), 5.10-5.07 (m, 1H), 2.16 (s, 3H), 1.98 (s, 3H), 1.27 (d, J=6 Hz, 6H). LCMS: m/z 489.22 [M+H]⁺, $t_R$=2.95 min.

Synthesis of (E)-3-(3-(3,5-bis(trifluoromethyl)phenyl)-1H-1,2,4-triazol-1-yl)-2-(3,5-dimethyl isoxazol-4-yl) acrylic acid (117)

(E)-3-(3-(3,5-Bis (trifluoromethyl phenyl)-1H-1, 2, 4-triazol-1-yl)-2-(3, 5-dimethyl isoxazol-4-yl) acrylic acid (117) was synthesized using General Procedure 2. (Yield: 0.1 g, 50%). ¹H NMR (400 MHz, DMSO-d₆) δ 13.37 (s, 1H), 9.17 (s, 1H), 8.63 (s, 1H), 8.29 (s, 3H), 2.15 (s, 3H), 1.98 (s, 3H). LCMS: m/z 447.23 [M+H]⁺, $t_R$=2.46 min.

Synthesis of (E)-3-(3-(3,5-bis(trifluoromethyl)phenyl)-1H-1,2,4-triazol-1-yl)-2-(3,5-dimethyl isoxazol-4-yl) acrylamide (118)

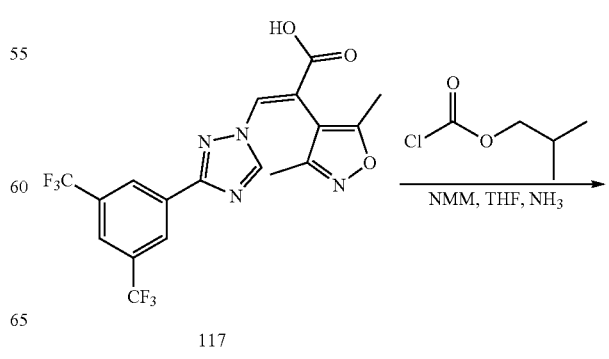

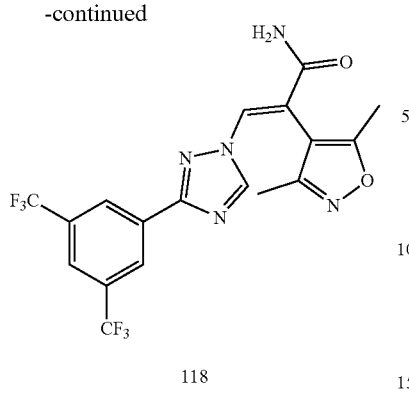

118

(E)-3-(3-(3, 5-Bis (trifluoromethyl) phenyl)-1H-1, 2, 4-triazol-1-yl)-2-(3, 5-dimethyl isoxazol-4-yl) acrylamide (118) was synthesized using General Procedure 3. (Yield: 0.015 g, 15%). $^1$H NMR (400 MHz, DMSO-$d_6$) δ 9.09 (s, 1H), 8.39 (s, 1H), 8.30 (s, 2H), 8.27 (s, 1H), 7.53 (s, 1H), 7.37 (s, 1H) 2.33 (s, 3H), 2.17 (s, 3H). LCMS: m/z 490.27 [M+45]$^+$, $t_R$=2.37 min Synthesis of isopropyl (E)-3-(3-(3,5-bis(trifluoromethyl)phenyl)-1H-1,2,4-triazol-1-yl)-2-(5-fluoropyridin-3-yl)acrylate (119)

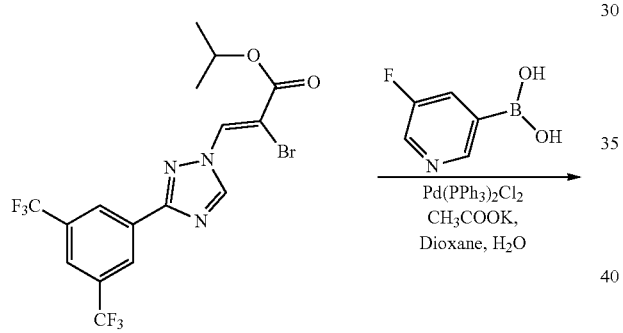

119

Isopropyl (E)-3-(3-(3,5-bis(trifluoromethyl)phenyl)-1H-1,2,4-triazol-1-yl)-2-(5-fluoropyridin-3-yl)acrylate (119) was synthesized using General Procedure 6. (Yield: 0.2 g, 19%). $^1$H NMR (400 MHz, DMSO-$d_6$) δ 9.21 (s, 1H), 8.63 (s, 1H), 8.60 (s, 1H), 8.37 (s, 1H), 8.25 (s, 1H), 8.07 (s, 2H), 7.83-7.80 (m, 1H) 5.10-5.07 (m, 1H), 1.27 (d, J=6 Hz, 6H). LCMS: m/z 489.32 [M+H]$^+$, $t_R$=2.91 min.

Synthesis of isopropyl (E)-3-(3-(3,5-bis (trifluoromethyl)phenyl)-1H-1,2,4-triazol-1-yl)-2-(6-methoxypyridin-3-yl) acrylate (120)

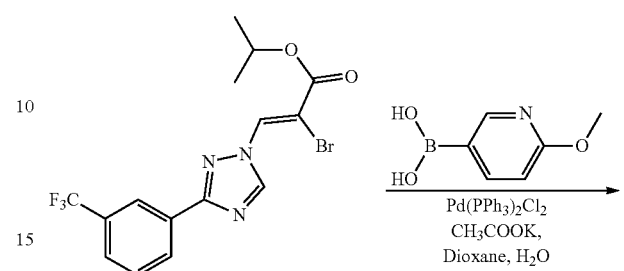

7

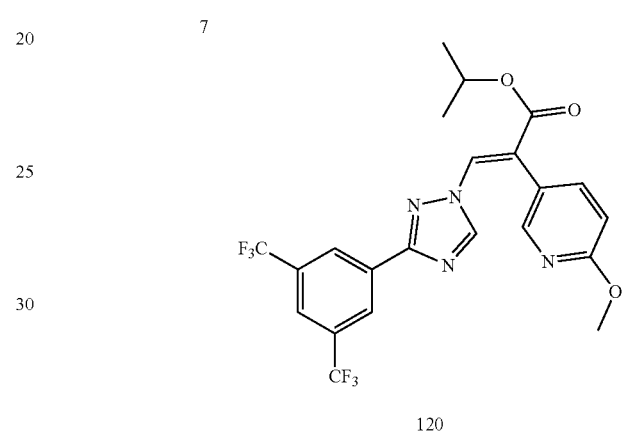

120

Isopropyl (E)-3-(3-(3,5-bis (trifluoromethyl) phenyl)-1H-1, 2, 4-triazol-1-yl)-2-(6-methoxypyridin-3-yl) acrylate (120) was synthesized using General Procedure 6. (Yield: 0.14 g, 20%). $^1$H NMR (400 MHz, DMSO-$d_6$) δ 9.12 (s, 1H), 8.51 (s, 1H), 8.23 (s, 1H), 8.14 (s, 2H), 8.07 (s, 1H), 7.62 (dd, $J_1$, $J_2$=2.4 Hz, 1H), 6.87 (d, J=8.4 Hz, 1H), 5.09-5.06 (m, 1H). 3.89 (s, 3H), 1.27 (d, J=6 Hz, 6H). LCMS: m/z 501.33 [M+H]$^+$, $t_R$=3.06 min.

Synthesis of (E)-3-(3-(3,5-bis(trifluoromethyl)phenyl)-1H-1,2,4-triazol-1-yl)-2-(6-methoxypyridin-3-yl) acrylic acid (121)

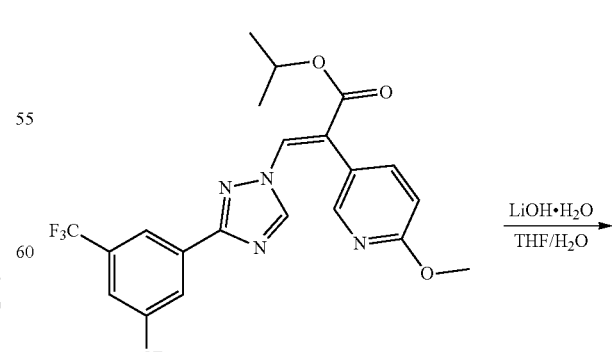

120

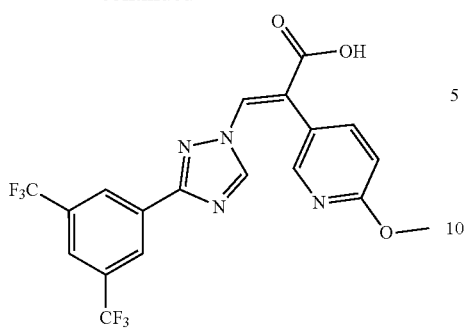

121

(E)-3-(3-(3, 5-Bis (trifluoromethyl) phenyl)-1H-1, 2, 4-triazol-1-yl)-2-(6-methoxypyridin-3-yl) acrylic acid (121) was synthesized using General Procedure 2. (Yield: 0.1 g, 71%). $^1$H NMR (400 MHz, DMSO-$d_6$) δ 13.25 (s, 1H), 9.09 (s, 1H), 8.52 (s, 1H), 8.23 (s, 1H), 8.14 (s, 2H), 8.06 (s, 1H), 7.60 (dd, $J_1$, $J_2$=2.4 Hz, 1H), 6.86 (dd, $J_1$, $J_2$=0.8 Hz, 1H), 3.89 (s, 3H). LCMS: m/z 459.21 [M+H]$^+$, $t_R$=2.53 min.

Synthesis of isopropyl (E)-3-(3-(3,5-bis (trifluoromethyl) phenyl)-1H-1, 2, 4-triazol-1-yl)-2-(furan-3-yl) acrylate (122)

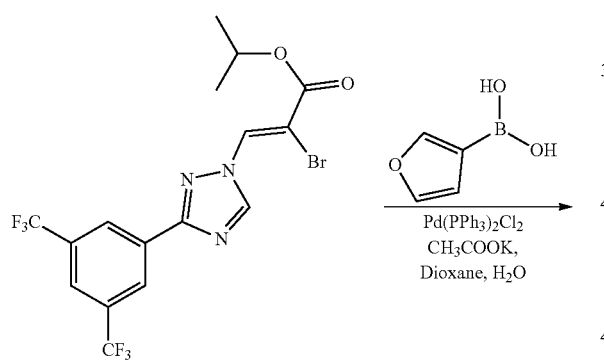

Isopropyl (E)-3-(3-(3, 5-bis (trifluoromethyl) phenyl)-1H-1, 2, 4-triazol-1-yl)-2-(furan-3-yl) acrylate (122) was synthesized using General Procedure 6. (Yield: 0.2 g, 21%). $^1$H NMR (400 MHz, DMSO-$d_6$) δ 8.93 (s, 1H), 8.42 (s, 2H), 8.26 (d, J=10 Hz, 2H), 7.86 (s, 1H), 7.73 (s, 1H), 6.41 (dd, $J_1$, $J_2$=0.8 Hz, 1H), 5.10-5.07 (m, 1H), 1.30 (d, J=6 Hz, 6H).

Synthesis of (E)-3-(3-(3,5-bis(trifluoromethyl)phenyl)-1H-1,2,4-triazol-1-yl)-2-(pyrimidin-5-yl) acrylic acid (123)

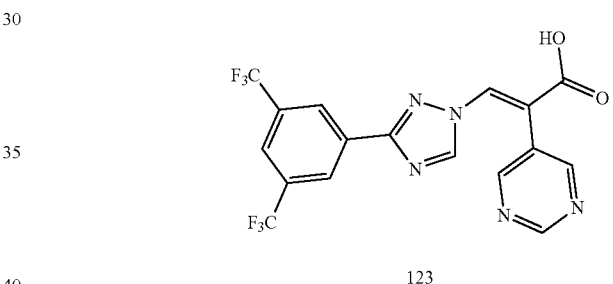

(E)-3-(3-(3,5-Bis(trifluoromethyl)phenyl)-1H-1,2,4-triazol-1-yl)-2-(pyrimidin-5-yl) acrylic acid (123) was synthesized using General Procedure 2. (Yield: 0.15 g, 19%). $^1$H NMR (400 MHz, DMSO-$d_6$) δ 13.52 (s, 1H), 9.23 (s, 1H), 9.18 (s, 1H), 8.77 (s, 2H), 8.69 (s, 1H), 8.26 (s, 1H), 8.07 (s, 2H). LCMS: m/z 430.0 [M+H]$^+$, $t_R$=2.21 min.

Synthesis of (E)-3-(3-(3,5-bis(trifluoromethyl)phenyl)-1H-1,2,4-triazol-1-yl)-2-(pyrimidin-5-yl)acrylamide (124)

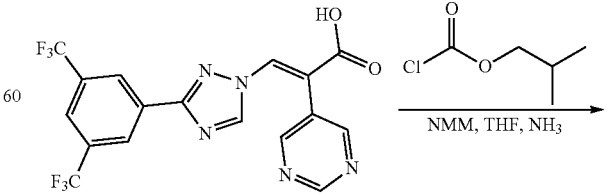

-continued

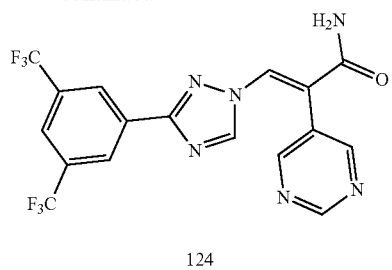

124

(E)-3-(3-(3,5-Bis(trifluoromethyl)phenyl)-1H-1,2,4-triazol-1-yl)-2-(pyrimidin-5-yl)acrylamide (124) was synthesized using General Procedure 3 (Yield: 0.03 g, 30%). $^1$H NMR (400 MHz, DMSO-$d_6$) δ 9.21 (s, 1H), 9.14 (s, 1H), 8.73 (s, 2H), 8.43 (s, 1H), 8.24 (s, 1H), 8.06 (s, 2H), 7.65 (s, 1H), 7.40 (s, 1H). LCMS: m/z 429.13 [M+H]$^+$, $t_R$=2.14 min.

Synthesis of (E)-3-(3-(3,5-bis(trifluoromethyl)phenyl)-1H-1,2,4-triazol-1-yl)-2-(5-fluoropyridin-3-yl)acrylic acid (125)

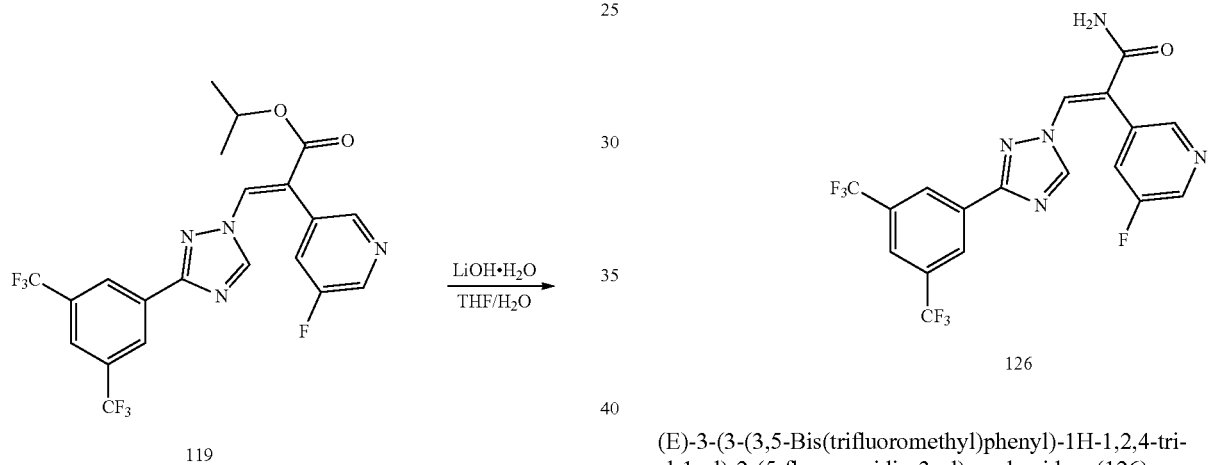

119

125

(E)-3-(3-(3,5-Bis(trifluoromethyl)phenyl)-1H-1,2,4-triazol-1-yl)-2-(5-fluoropyridin-3-yl)acrylic acid (125) was synthesized using General Procedure 2 (Yield: 0.07 g, 64%). $^1$H NMR (400 MHz, DMSO $d_6$) δ 13.46 (s, 1H), 9.18 (s, 1H), 8.63 (s, 1H), 8.58 (s, 1H), 8.35 (t, J=3.5 Hz, 1H), 8.25 (s, 1H), 8.07 (s, 2H), 7.81-7.77 (m, 1H). LCMS: m/z 447.3 [M+H]$^+$, $t_R$=2.43 min.

Synthesis of 3-(3-(3,5-bis(trifluoromethyl)phenyl)-1H-1,2,4-triazol-1-yl)-2-(5-fluoropyridin-3-yl)acrylamide (126)

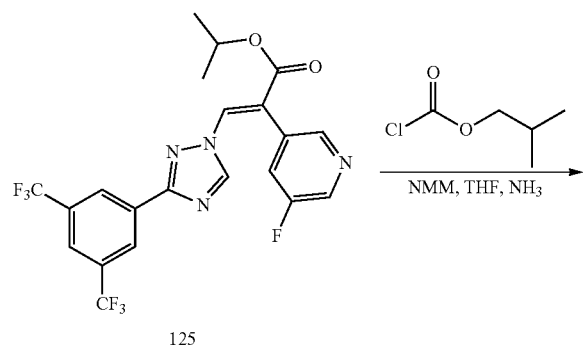

125

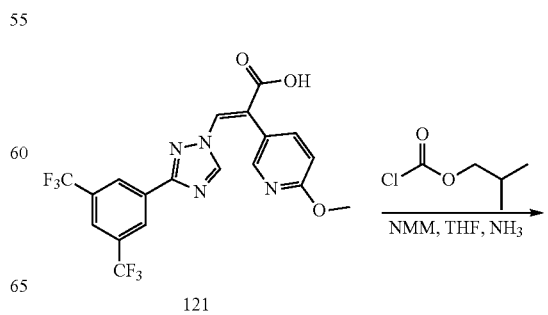

126

(E)-3-(3-(3,5-Bis(trifluoromethyl)phenyl)-1H-1,2,4-triazol-1-yl)-2-(5-fluoropyridin-3-yl)acrylamide (126) was synthesized using General Procedure 3 (Yield: 0.04 g, 66%). $^1$H NMR (400 MHz, DMSO $d_6$) δ 9.08 (s, 1H), 8.60 (d, J=2.8 Hz, 1H), 8.37 (s, 1H), 8.43 (t, J=1.6 Hz, 1H), 8.23 (s, 1H), 8.08 (s, 2H), 7.78-7.74 (m, 1H), 7.65 (s, 1H), 7.24 (s, 1H). LCMS: m/z 446.3 [M+H]$^-$, $t_R$=2.32 min.

Synthesis of (E)-3-(3-(3,5-bis(trifloromethyl)phenyl)-1H-1,2, 4-triazol-1-yl)-2-(6-methoxy pyridin-3-yl) acryl amide (127)

121

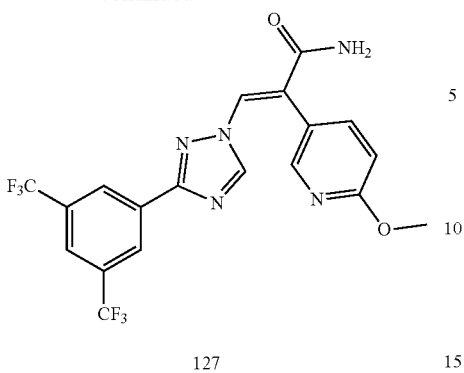

127

(E)-3-(3-(3, 5-bis (trifloromethyl) phenyl)-1H-1, 2, 4-triazol-1-yl)-2-(6-methoxy pyridin-3-yl) acryl amide (127) was synthesized using General Procedure 3 (Yield: 0.05 g, 36%). ¹H NMR (400 MHz, DMSO-d₆) δ 8.97 (s, 1H), 8.23 (d, J=10 Hz, 2H), 8.16 (s, 2H), 8.04 (d, J=0.8 Hz, 1H), 7.57 (dd, J₁=2.4 Hz, J₂=2.4 Hz, 2H), 7.17 (s, 1H), 6.88 (d, J=8 Hz, 1H), 3.90 (s, 3H). LCMS: m/z 458.36 [M+H]⁺. $t_R$=2.44 min.

Synthesis of (E)-3-(3-(3,5-bis(trifluoromethyl)phenyl)-1H-1,2,4-triazol-1-yl)-2-(furan-3-yl) acrylic acid (128)

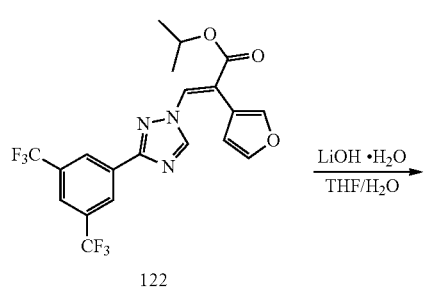

122

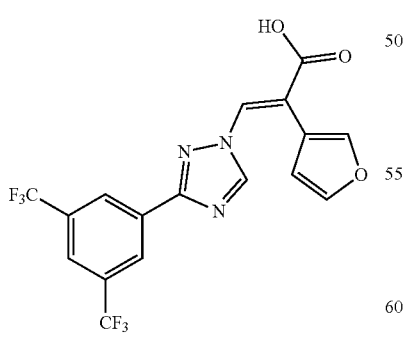

128

(E)-3-(3-(3,5-Bis (trifluoromethyl) phenyl)-1H-1, 2, 4-triazol-1-yl)-2-(furan-3-yl) acrylic acid (128) was synthesized using General Procedure 2 (Yield: 0.11 g, 81%). ¹H NMR (400 MHz, DMSO-d₆) δ 13.31 (s, 1H), 8.91 (s, 1H), 8.42 (s, 2H), 8.27 (d, J=3.2 Hz, 2H), 7.84 (s, 1H), 7.70 (s, 1H), 6.40 (s, 1H). LCMS: m/z 416.25 [M–H]⁻, $t_R$=2.57 min.

Synthesis of (E)-3-(3-(3,5-bis(trifluoromethyl)phenyl)-1H-1,2,4-triazol-1-yl)-2-(furan-3-yl) acrylamide (129)

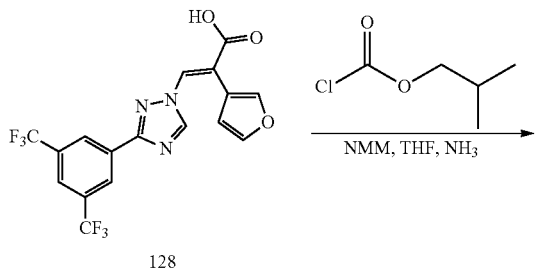

128

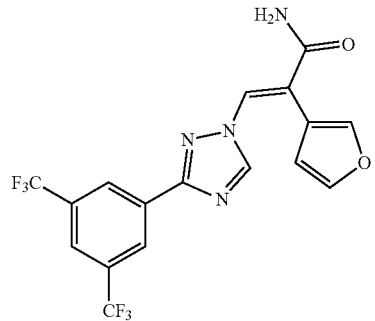

129

(E)-3-(3-(3,5-Bis (trifluoromethyl) phenyl)-1H-1, 2, 4-triazol-1-yl)-2-(furan-3-yl) acrylamide (129) was synthesized using General Procedure 3 (Yield: 0.05 g, 50%). ¹H NMR (400 MHz, DMSO-d₆) δ 8.77 (s, 1H), 8.43 (s, 2H), 8.27 (s, 1H), 7.91 (s, 1H), 7.83 (s, 1H), 7.74 (s, 1H), 7.60 (s, 1H), 7.46 (s, 1H). 6.29 (s, 1H).

Synthesis of isopropyl (E)-3-(3-(3,5-bis(trifluoromethyl)phenyl)-1H-1,2,4-triazol-1-yl)-2-(1-methyl-1H-pyrazol-4-yl)acrylate (130)

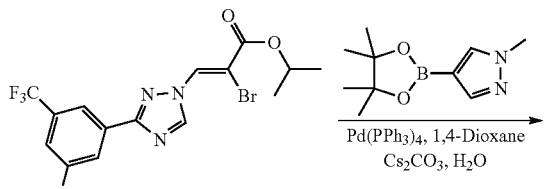

7

101
-continued

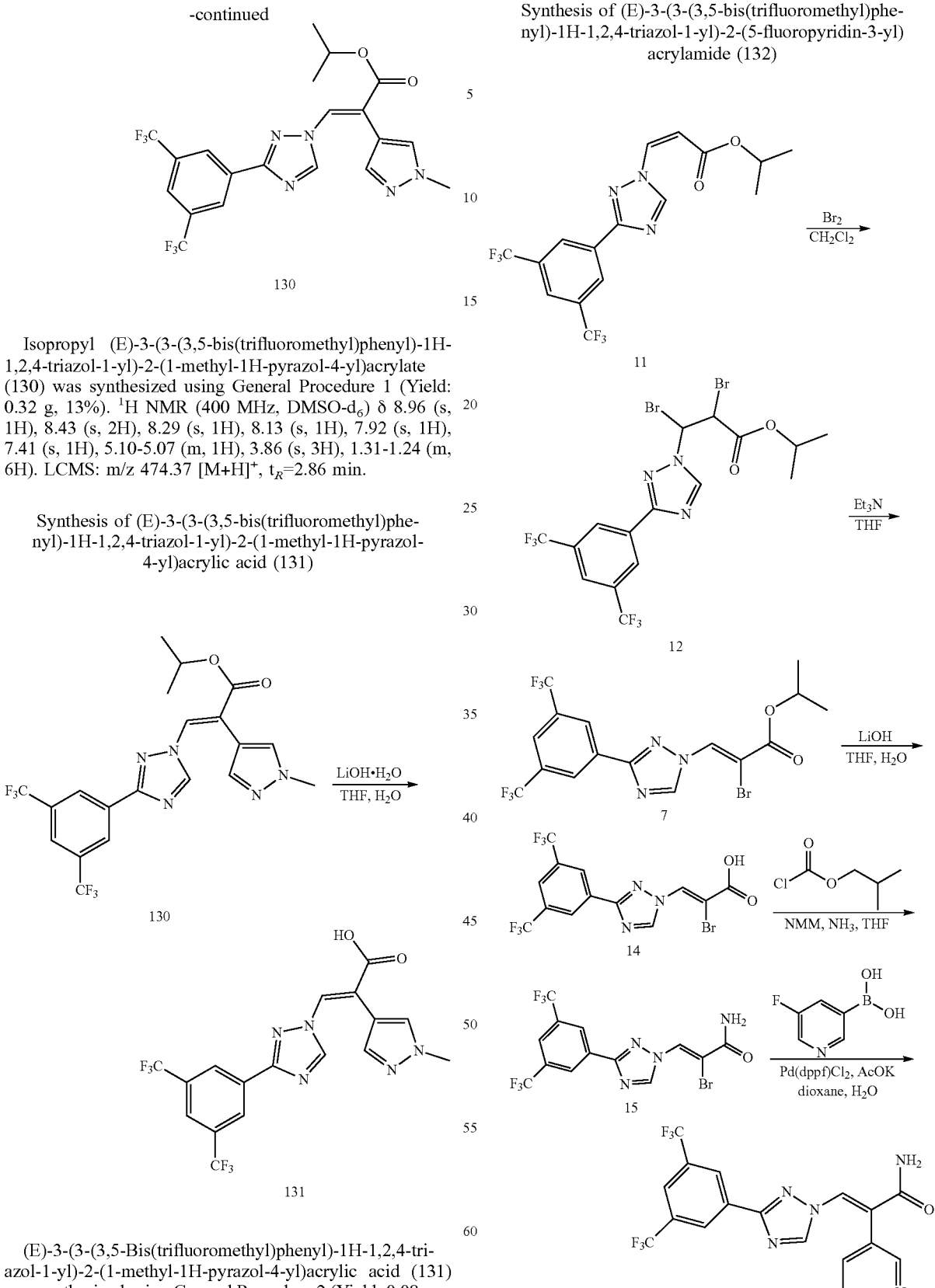

Isopropyl (E)-3-(3-(3,5-bis(trifluoromethyl)phenyl)-1H-1,2,4-triazol-1-yl)-2-(1-methyl-1H-pyrazol-4-yl)acrylate (130) was synthesized using General Procedure 1 (Yield: 0.32 g, 13%). $^1$H NMR (400 MHz, DMSO-$d_6$) δ 8.96 (s, 1H), 8.43 (s, 2H), 8.29 (s, 1H), 8.13 (s, 1H), 7.92 (s, 1H), 7.41 (s, 1H), 5.10-5.07 (m, 1H), 3.86 (s, 3H), 1.31-1.24 (m, 6H). LCMS: m/z 474.37 [M+H]$^+$, $t_R$=2.86 min.

Synthesis of (E)-3-(3-(3,5-bis(trifluoromethyl)phenyl)-1H-1,2,4-triazol-1-yl)-2-(1-methyl-1H-pyrazol-4-yl)acrylic acid (131)

(E)-3-(3-(3,5-Bis(trifluoromethyl)phenyl)-1H-1,2,4-triazol-1-yl)-2-(1-methyl-1H-pyrazol-4-yl)acrylic acid (131) was synthesized using General Procedure 2 (Yield: 0.08 mg, 88%). $^1$H NMR (400 MHz, DMSO-$d_6$) δ 13.25 (s, 1H), 8.93 (s, 1H), 8.43 (s, 2H), 8.28 (s, 1H), 8.16 (s, 1H), 7.90 (s, 1H), 7.38 (s, 1H), 3.86 (s, 3H). LCMS: m/z 432.29 [M+H]$^+$, $t_R$=2.32 min.

102

Synthesis of (E)-3-(3-(3,5-bis(trifluoromethyl)phenyl)-1H-1,2,4-triazol-1-yl)-2-(5-fluoropyridin-3-yl)acrylamide (132)

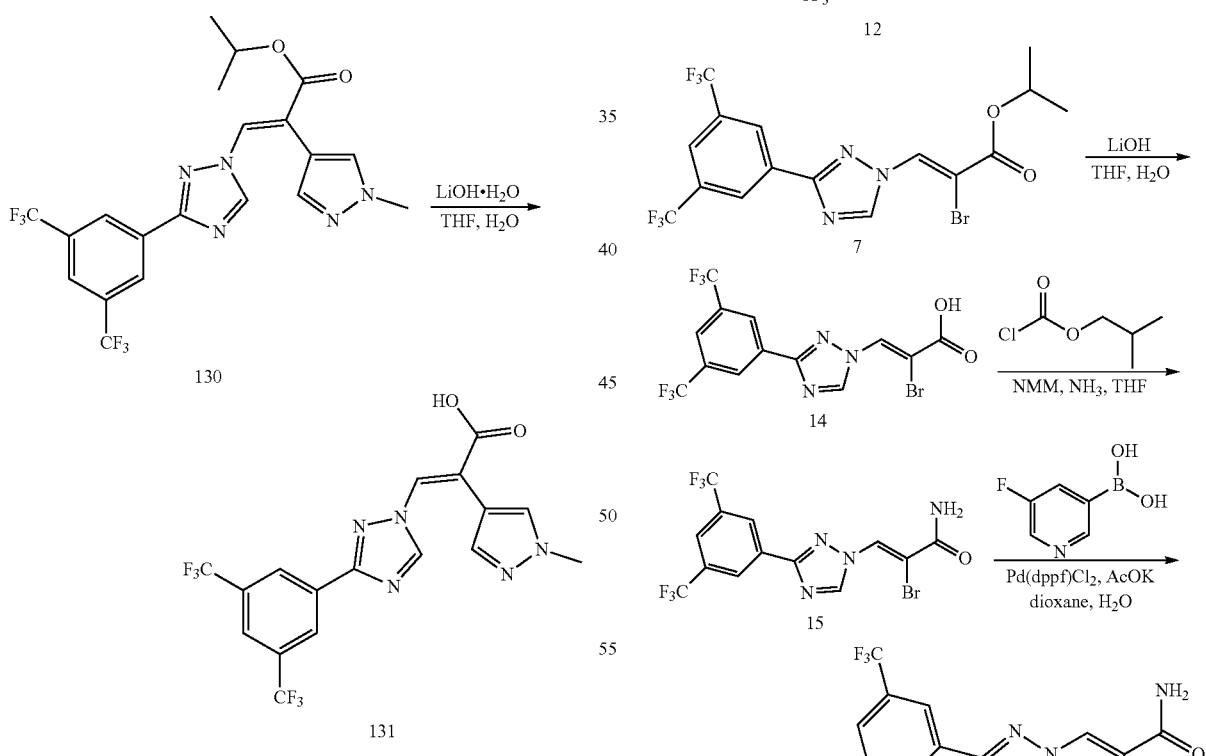

Synthesis of isopropyl 3-(3-(3,5-bis(trifluoromethyl) phenyl)-1H-1,2,4-triazol-1-yl)-2,3-dibromopropanoate (12)

(Z)-isopropyl 3-(3-(3,5-bis(trifluoromethyl)phenyl)-1H-1,2,4-triazol-1-yl)acrylate (11) (100 g, 254.4 mmol) was dissolved in dichloromethane (500 mL) at room temperature. Bromine (80 g, 500 mmol) was added dropwise over 40 min at 0° C. The reaction mixture was allowed to warm to room temperature and stirred for 6 h. The reaction mixture was transferred into iced water and extracted with $CH_2Cl_2$ (500 mL×3). The combined organic layers were washed with saturated sodium bisulphite aqueous solution (500 mL) followed by brine, dried over anhydrous $Na_2SO_4$ and concentrated under reduced pressure to give isopropyl 3-(3-(3,5-bis(trifluoromethyl)phenyl)-1H-1,2,4-triazol-1-yl)-2,3-dibromopropanoate (12), which was used in next step without further purification. (130 g, 93% yield). LCMS: m/z 554.09 $[M+H]^+$, $t_R$=1.95 min.

Synthesis of (Z)-isopropyl 3-(3-(3,5-bis(trifluoromethyl)phenyl)-1H-1,2,4-triazol-1-yl)-2-bromoacrylate (13)

Isopropyl 3-(3-(3,5-bis(trifluoromethyl)phenyl)-1H-1,2,4-triazol-1-yl)-2,3-dibromopropanoate (12) (120 g, 217 mmol) was dissolved in tetrahydrofuran (350 mL) and cooled down to 0° C. Triethylamine (44 g, 434 mmol) was added and the mixture was stirred at room temperature for 16 h. The reaction mixture was diluted with water (120 mL) and extracted with ethyl acetate (200 mL×3). The combined organic layers were washed with brine, dried over anhydrous $Na_2SO_4$ and concentrated under reduced pressure. The crude product was purified by recrystallization from 8% EtOAc in petroleum ether to get (Z)-isopropyl 3-(3-(3,5-bis(trifluoromethyl)phenyl)-1H-1,2,4-triazol-1-yl)-2-bromoacrylate (13) as white solid (90 g, 88% yield). $^1$H NMR (400 MHz, DMSO-$d_6$) δ 9.46 (s, 1H), 8.92 (s, 1H), 8.56 (s, 2H), 8.32 (s, 1H), 5.13-5.07 (m, 1H), 1.33 (d, J=6 Hz, 6H). LCMS: m/z 472.0 $[M+H]^+$, $t_R$=2.10 min.

Synthesis of (Z)-3-(3-(3,5-bis(trifluoromethyl)phenyl)-1H-1,2,4-triazol-1-yl)-2-bromoacrylic acid (14)

(Z)-isopropyl 3-(3-(3,5-bis(trifluoromethyl)phenyl)-1H-1,2,4-triazol-1-yl)-2-bromoacrylate (13) (40 g, 85 mmol) was dissolved in tetrahydrofuran (350 mL) and water (85 mL). Lithium hydroxide aqueous solution (20 mL, 254 mmol, 12.7 N) was added drop wise to the mixture at 0° C. The reaction mixture was stirred at 0° C. for 1 h, and poured into water (100 mL), acidified with HCl (3 N) until pH=3, extracted with ethyl acetate (200 mL×3). The combined organic layers were washed with brine, dried over anhydrous $Na_2SO_4$, concentrated under reduced pressure, and purified by recrystallization from 20% EtOAc in petroleum ether to afford (Z)-3-(3-(3,5-bis(trifluoromethyl)phenyl)-1H-1,2,4-triazol-1-yl)-2-bromoacrylic acid (14) as white solid (27 g, 75% yield). $^1$H NMR (400 MHz, DMSO-$d_6$) δ 9.43 (s, 1H), 8.89 (s, 1H), 8.56 (s, 2H), 8.31 (s, 1H). LCMS: m/z 431.9 $[M+H]^+$, $t_R$=1.85 min.

Synthesis of (Z)-3-(3-(3,5-bis(trifluoromethyl)phenyl)-1H-1,2,4-triazol-1-yl)-2-bromoacrylamide (15)

(Z)-3-(3-(3,5-bis(trifluoromethyl)phenyl)-1H-1,2,4-triazol-1-yl)-2-bromoacrylic acid (14) (50 g, 34.9 mmol) was dissolved in THF (400 mL) and isobutyl chloroformate (31.7 g, 224 mmol), N-methyl morpholine (17.8 g, 175.5 mmol) were added at 0° C. The reaction mixture was stirred at 0° C. for 1 h. Ammonia gas was purged for 40 min at 0° C. The reaction mixture was transferred into iced water and extracted with ethyl acetate (300 mL×3). The combined organic layers were washed with brine, dried over anhydrous $Na_2SO_4$ and concentrated under reduced pressure to give crude product, which was purified by recrystallization from EtOAc to give 42 g of (Z)-3-(3-(3,5-bis(trifluoromethyl)phenyl)-1H-1,2,4-triazol-1-yl)-2-bromoacrylamide (15). Yield: 85%. $^1$H NMR (400 MHz, DMSO-$d_6$) δ 9.40 (s, 1H), 8.70 (s, 1H), 8.54 (s, 2H), 8.29 (s, 1H), 8.0-7.95 (m, 2H). LCMS: m/z 429.0 $[M+H]^+$, $t_R$=1.78 min.

Synthesis of (E)-3-(3-(3,5-bis(trifluoromethyl)phenyl)-1H-1,2,4-triazol-1-yl)-2-(5-fluoropyridin-3-yl) acrylamide (132)

(E)-3-(3-(3,5-bis(trifluoromethyl)phenyl)-1H-1,2,4-triazol-1-yl)-2-(5-fluoropyridin-3-yl)acrylamide (132) was synthesized according to General Procedure 6. Yield: 6%. $^1$H NMR (400 MHz, DMSO-$d_6$) δ 9.08 (s, 1H), 8.60 (d, J=3 Hz, 1H), 8.37 (s, 1H), 8.32 (s, 1H), 8.22 (s, 1H), 8.08 (s, 2H), 7.76 (d, J=9 Hz, 1H), 7.63 (s, 1H), 7.24 (s, 1H). LCMS: m/z 446.1 $[M+H]^+$, $t_R$=1.70 min.

Synthesis of (E)-3-(3-(3,5-bis(trifluoromethyl)phenyl)-1H-1,2,4-triazol-1-yl)-2-(pyridazin-4-yl)acrylamide (133)

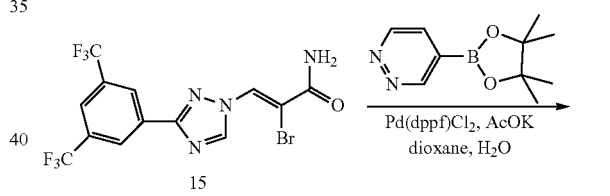

(E)-3-(3-(3,5-bis(trifluoromethyl)phenyl)-1H-1,2,4-triazol-1-yl)-2-(pyridazin-4-yl)acrylamide (133) was synthesized according to General Procedure 6. Yield: 2%. $^1$H NMR (400 MHz, DMSO-$d_6$) δ 9.28 (dd, $J_1$=5 Hz, $J_2$=1 Hz, 1H), 9.17-9.09 (m, 2H), 8.40 (s, 1H), 8.22 (s, 1H), 8.02 (s, 2H), 7.70-7.61 (m, 2H), 7.36 (s, 1H). LCMS: m/z 429.1 $[M+H]^+$, $t_R$=1.54 min.

Synthesis of (E)-3-(3-(3,5-bis(trifluoromethyl)phenyl)-1H-1,2,4-triazol-1-yl)-2-(6-fluoropyridin-2-yl)acrylamide (134)

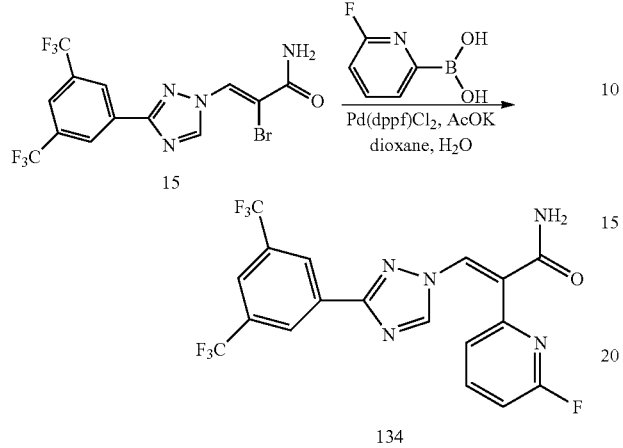

134

(E)-3-(3-(3,5-bis(trifluoromethyl)phenyl)-1H-1,2,4-triazol-1-yl)-2-(6-fluoropyridin-2-yl)acrylamide (134) was synthesized according to General Procedure 6. Yield: 40%. $^1$H NMR (400 MHz, DMSO-d$_6$) δ 9.17 (s, 1H), 8.54 (s, 2H), 8.32-8.23 (m, 2H), 8.14-8.00 (m, 2H), 7.91 (s, 1H), 7.47-7.39 (m, 1H), 7.24-7.17 (m, 1H). LCMS: m/z 446.1 [M+H]$^+$, t$_R$=1.84 min.

Synthesis of (E)-3-(3-(3,5-bis(trifluoromethyl)phenyl)-1H-1,2,4-triazol-1-yl)-2-(2-fluoropyridin-3-yl)acrylamide (135)

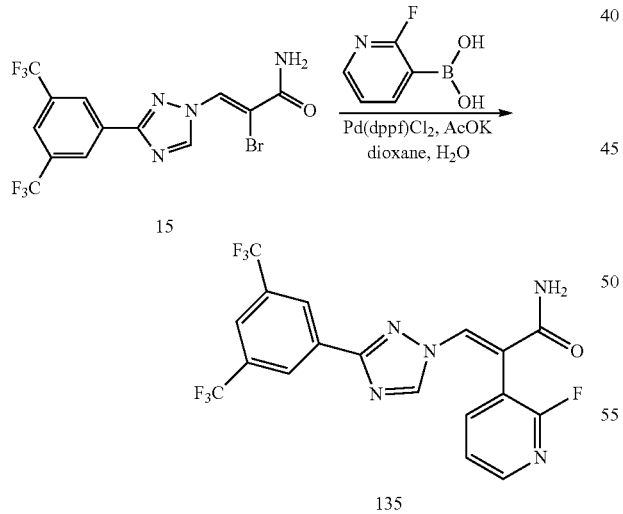

135

(E)-3-(3-(3,5-bis(trifluoromethyl)phenyl)-1H-1,2,4-triazol-1-yl)-2-(2-fluoropyridin-3-yl)acrylamide (135) was synthesized according to General Procedure 6. Yield: 14%. $^1$H NMR (400 MHz, CD$_3$OD) δ 8.90 (s, 1H), 8.42 (s, 1H), 8.34 (d, J=4 Hz, 1H), 8.19 (s, 2H), 8.02 (s, 1H), 7.97-7.88 (m, 1H), 7.52-7.42 (m, 1H). LCMS: m/z 446.1 [M+H]$^+$, t$_R$=1.82 min.

Synthesis of (E)-2-(2-aminopyrimidin-5-yl)-3-(3-(3,5-bis(trifluoromethyl)phenyl)-1H-1,2,4-triazol-1-yl)acrylamide (136)

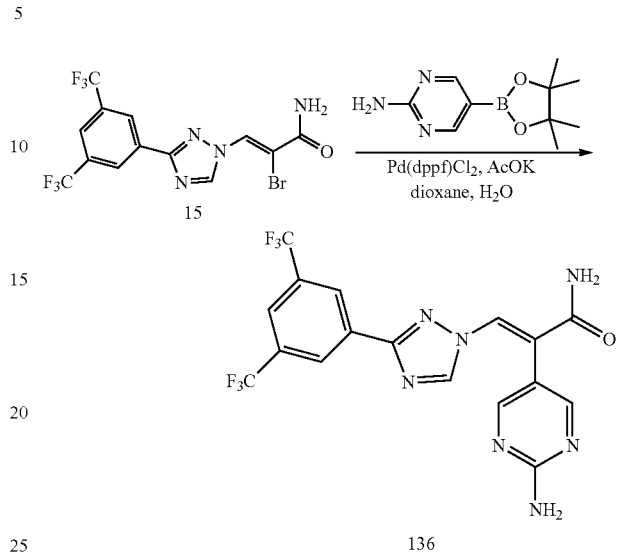

136

(E)-2-(2-aminopyrimidin-5-yl)-3-(3-(3,5-bis(trifluoromethyl)phenyl)-1H-1,2,4-triazol-1-yl)acrylamide (136). Yield: 25%. $^1$H NMR (400 MHz, DMSO-d$_6$) δ 9.01 (s, 1H), 8.30 (s, 2H), 8.25 (s, 1H), 8.14 (s, 1H), 8.07 (s, 2H), 7.52 (s, 1H), 7.40 (s, 1H), 6.79 (s, 2H). LCMS: m/z 444.1 [M+H]$^+$, t$_R$=1.64 min.

Synthesis of (E)-3-(3-(3,5-bis(trifluoromethyl)phenyl)-1H-1,2,4-triazol-1-yl)-2-(2-fluoropyrimidin-5-yl)acrylamide (137)

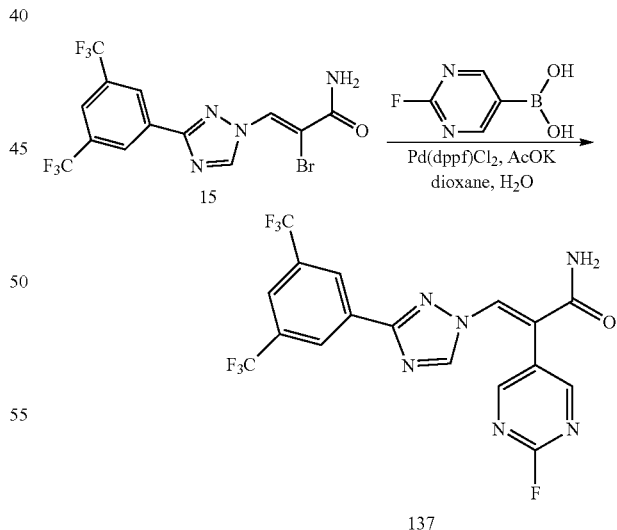

137

(E)-3-(3-(3,5-Bis(trifluoromethyl)phenyl)-1H-1,2,4-triazol-1-yl)-2-(2-fluoropyrimidin-5-yl)acrylamide (137) was synthesized according to General Procedure 6. Yield: 18%. $^1$H NMR (400 MHz, DMSO-d$_6$) δ 9.19 (s, 1H), 8.75 (s, 2H), 8.48 (s, 1H), 8.25 (s, 1H), 8.09 (s, 2H), 7.67 (s, 1H), 7.36 (s, 1H). LCMS: m/z 447.1 [M+H]$^+$, t$_R$=1.81 min.

107

Synthesis of (E)-3-(3-(3,5-bis(trifluoromethyl)phenyl)-1H-1,2,4-triazol-1-yl)-2-(3-fluoropyridin-4-yl)acrylamide (138)

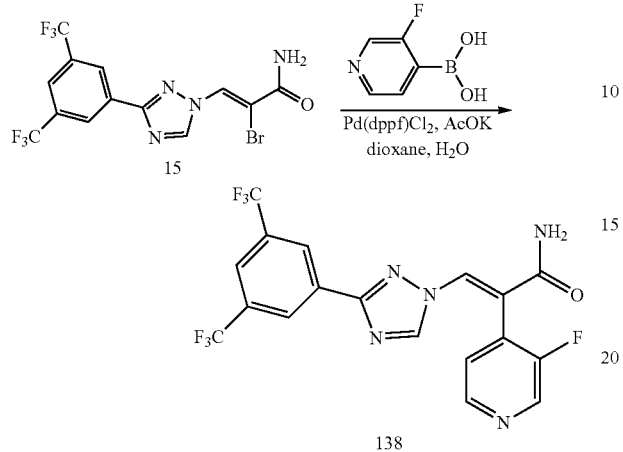

138

(E)-3-(3-(3,5-bis(trifluoromethyl)phenyl)-1H-1,2,4-triazol-1-yl)-2-(3-fluoropyridin-4-yl)acrylamide (138) was synthesized according to general procedure 6. Yield: 3%.
$^1$H NMR (400 MHz, CD$_3$OD) δ 8.78 (s, 1H), 8.48 (s, 1H), 8.41 (d, J=5 Hz, 1H), 8.34 (s, 1H), 8.06 (s, 2H), 7.92 (s, 1H), 7.43-7.37 (m, 1H). LCMS: m/z 446.0 [M+H]$^+$, t$_R$=1.69 min.

Synthesis of (E)-3-(3-(3,5-bis(trifluoromethyl)phenyl)-1H-1,2,4-triazol-1-yl)-2-(6-fluoropyridin-3-yl)acrylamide (139)

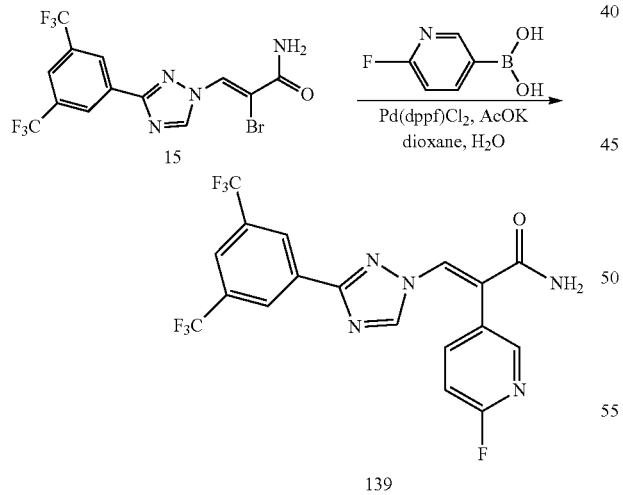

139

(E)-3-(3-(3,5-bis(trifluoromethyl)phenyl)-1H-1,2,4-triazol-1-yl)-2-(6-fluoropyridin-3-yl)acrylamide (139) was synthesized according to General Procedure 6. Yield: 15%.
$^1$H NMR (400 MHz, CD$_3$OD) δ 8.80 (s, 1H), 8.37 (s, 1H), 8.24 (s, 2H), 8.19 (d, J=2 Hz, 1H), 8.03 (s, 1H), 7.98-7.90 (m, 1H), 7.27-7.19 (m, 1H). LCMS: m/z 446.1 [M+H]$^+$, t$_R$=1.84 min.

108

Synthesis of (E)-3-(3-(3,5-bis(trifluoromethyl)phenyl)-1H-1,2,4-triazol-1-yl)-2-(2-fluoropyridin-4-yl)acrylamide (140)

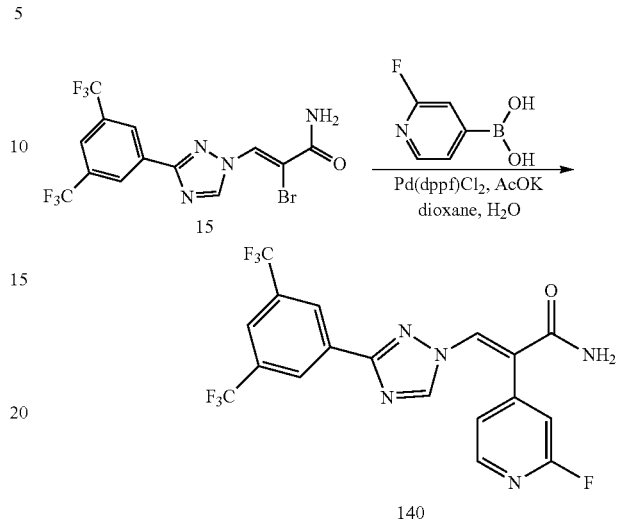

140

(E)-3-(3-(3,5-bis(trifluoromethyl)phenyl)-1H-1,2,4-triazol-1-yl)-2-(2-fluoropyridin-4-yl)acrylamide (140) was synthesized according to General Procedure 6. Yield: 29%.
$^1$H NMR (400 MHz, CD$_3$OD) δ 8.79 (s, 1H), 8.36-8.30 (m, 2H), 8.23 (s, 2H), 8.03 (s, 1H), 7.33 (d, J=5 Hz, 1H), 7.17 (s, 1H). LCMS: m/z 446.1[M+H]$^+$, t$_R$=1.84 min.

Synthesis of (E)-3-(3-(3,5-bis(trifluoromethyl)phenyl)-1H-1,2,4-triazol-1-yl)-2-(5-chloropyridin-3-yl)acrylamide (141)

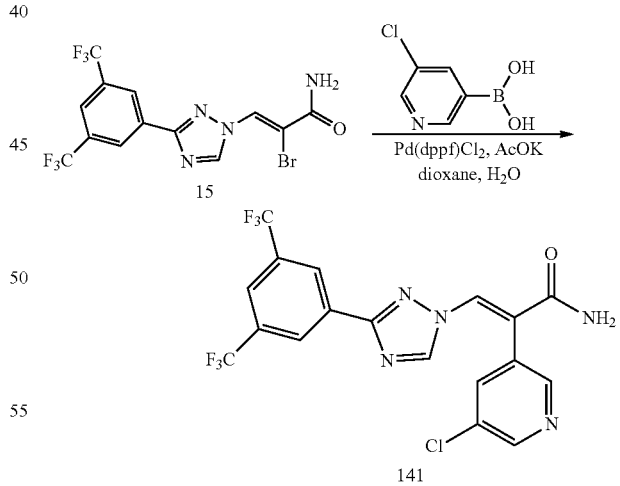

141

(E)-3-(3-(3,5-bis(trifluoromethyl)phenyl)-1H-1,2,4-triazol-1-yl)-2-(5-chloropyridin-3-yl)acrylamide (141) was synthesized according to General Procedure 6. Yield: 31%.
$^1$H NMR (400 MHz, DMSO-d$_6$) δ 9.10 (s, 1H), 8.65 (d, J=2 Hz, 1H), 8.40 (d, J=2 Hz, 1H), 8.37 (s, 1H), 8.22 (s, 1H), 8.08 (s, 2H), 7.98-91 (m, 1H), 7.62 (s, 1H), 7.27 (s, 1H). LCMS: m/z 462.0 [M+H]$^+$, t$_R$=1.76 min.

Synthesis of (E)-3-(3-(3,5-bis(trifluoromethyl)phenyl)-1H-1,2,4-triazol-1-yl)-2-(6-chloropyridin-3-yl)acrylamide (143)

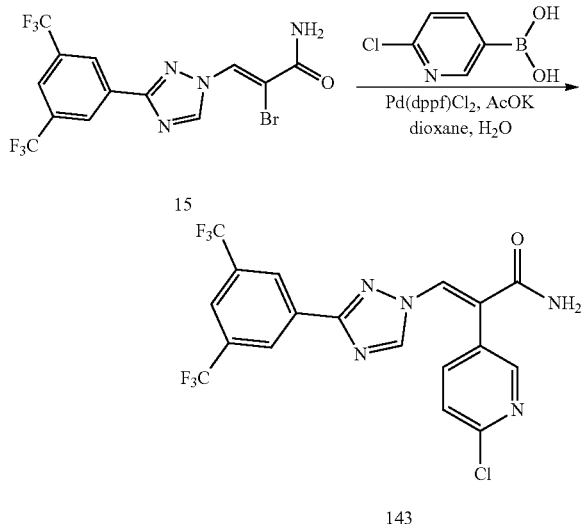

143

(E)-3-(3-(3,5-bis(trifluoromethyl)phenyl)-1H-1,2,4-triazol-1-yl)-2-(6-chloropyridin-3-yl)acrylamide (143) was synthesized according to General Procedure 6. Yield: 24%. $^1$H NMR (400 MHz, DMSO-d$_6$) δ 9.09 (s, 1H), 8.35 (s, 1H), 8.30 (d, J=2.0 Hz, 1H), 8.22 (s, 1H), 8.10 (s, 2H), 7.80-7.74 (m, 1H), 7.65-7.55 (m, 2H), 7.24 (s, 1H). LCMS: m/z 462.0 [M+H]$^+$, t$_R$=1.77 min.

Synthesis of (E)-3-(3-(3,5-bis(trifluoromethyl)phenyl)-1H-1,2,4-triazol-1-yl)-2-(2-chloropyridin-3-yl)acrylamide (144)

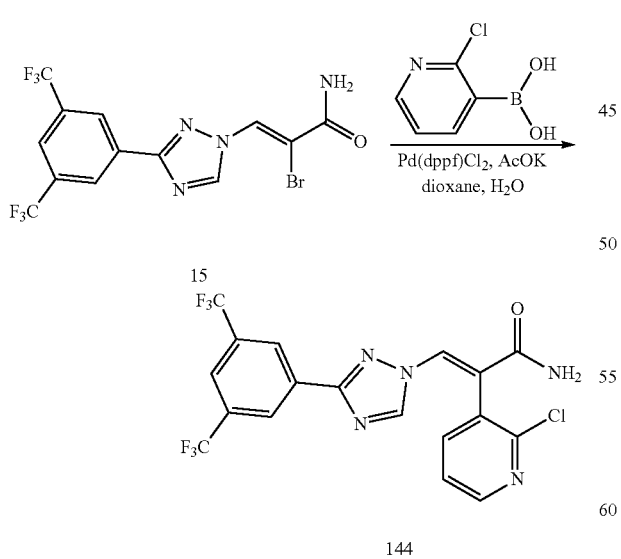

144

(E)-3-(3-(3,5-bis(trifluoromethyl)phenyl)-1H-1,2,4-triazol-1-yl)-2-(2-chloropyridin-3-yl)acrylamide (144) was synthesized according to General Procedure 6. Yield: 4%. $^1$H NMR (400 MHz, CD$_3$OD) δ 8.89 (s, 1H), 8.54-8.49 (m, 1H), 8.42 (s, 1H), 8.17 (s, 2H), 8.03 (s, 1H), 7.88-7.83 (m, 1H), 7.57-7.52 (m, 1H). LCMS: m/z 462.0 [M+H]$^+$, t$_R$=1.70 min.

Synthesis of (E)-3-(3-(3,5-bis(trifluoromethyl)phenyl)-1H-1,2,4-triazol-1-yl)-2-(2,6-difluoropyridin-3-yl)acrylamide (145)

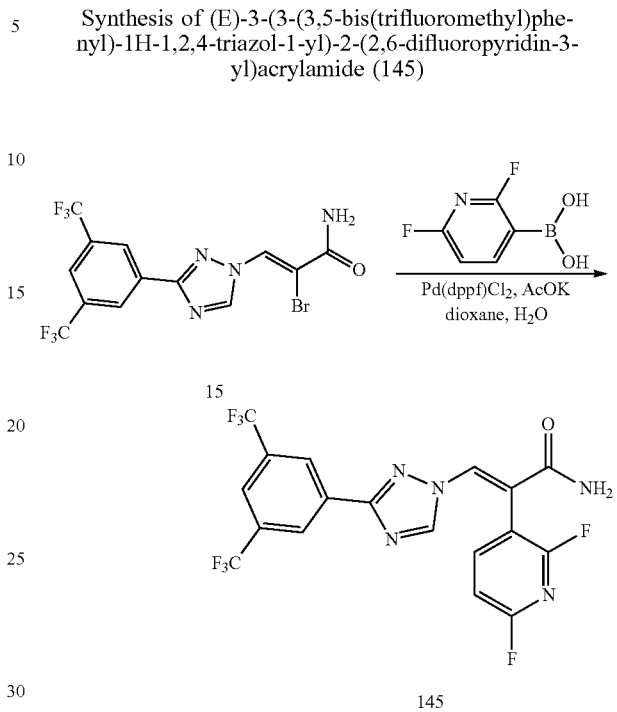

145

(E)-3-(3-(3,5-bis(trifluoromethyl)phenyl)-1H-1,2,4-triazol-1-yl)-2-(2,6-difluoropyridin-3-yl)acrylamide (145) was synthesized according to General Procedure 6. Yield: 5%. $^1$H NMR (400 MHz, CD$_3$OD) δ 8.80 (s, 1H), 8.32 (s, 1H), 8.12 (s, 2H), 7.95-7.86 (m, 2H), 7.01 (dd, J$_1$=8 Hz, J$_2$=2 Hz, 1H). LCMS: m/z 464.0 [M+H]$^+$, t$_R$=1.74 min.

Synthesis of (E)-3-(3-(3,5-bis(trifluoromethyl)phenyl)-1H-1,2,4-triazol-1-yl)-2-phenylacrylamide (146)

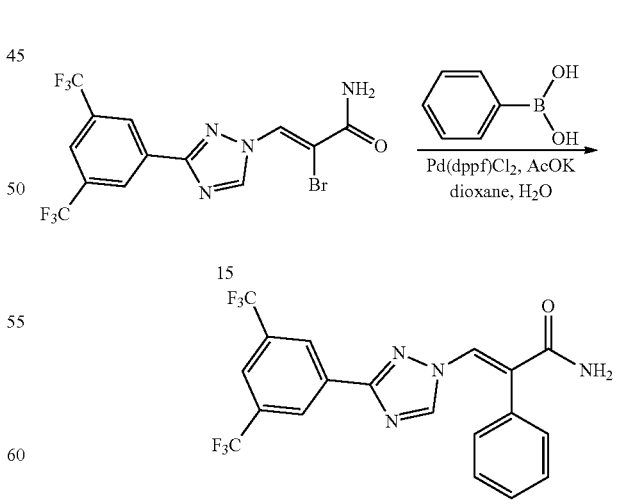

146

(E)-3-(3-(3,5-bis(trifluoromethyl)phenyl)-1H-1,2,4-triazol-1-yl)-2-phenylacrylamide (146) was synthesized according to General Procedure 6. Yield: 32%. ¹H NMR (400 MHz, CD₃OD) δ 8.24 (s, 2H), 8.11 (s, 1H), 8.04 (s, 1H), 7.90 (s, 1H), 7.49-7.40 (m, 3H), 7.30-7.21 (m, 2H). LCMS: m/z 427.1 [M+H]⁺, t$_R$=2.10 min.

Synthesis of (E)-3-(3-(3,5-bis(trifluoromethyl)phenyl)-1H-1,2,4-triazol-1-yl)-2-(2-(trifluoromethyl)pyridin-4-yl)acrylamide (147)

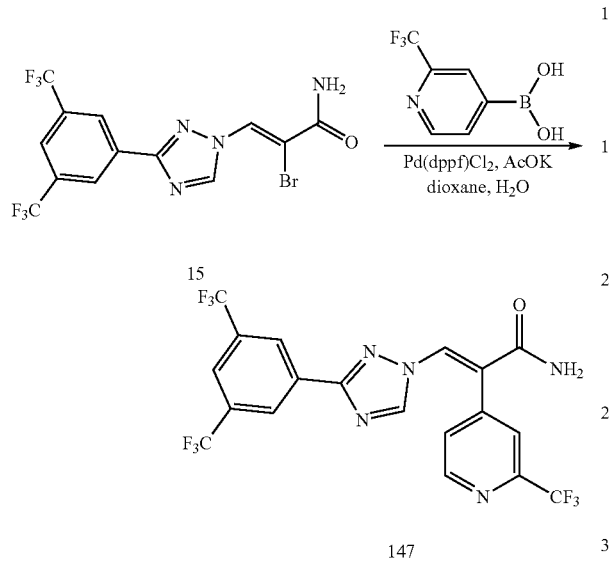

147

(E)-3-(3-(3,5-bis(trifluoromethyl)phenyl)-1H-1,2,4-triazol-1-yl)-2-(2-(trifluoromethyl)pyridin-4-yl)acrylamide (147) was synthesized according to General procedure 6. Yield: 11%. ¹H NMR (400 MHz, DMSO-d₆) δ 9.13 (s, 1H), 8.81 (d, J=5 Hz, 1H), 8.36 (s, 1H), 8.20 (s, 1H), 8.00 (s, 2H), 7.88 (s, 1H), 7.66 (s, 1H), 7.61 (d, J=5 Hz, 1H), 7.25 (s, 1H). LCMS: m/z 496.0 [M+H]⁺, t$_R$=1.79 min.

Synthesis of (E)-3-(3-(3,5-bis(trifluoromethyl)phenyl)-1H-1,2,4-triazol-1-yl)-2-(5-cyanopyridin-3-yl)acrylamide (148)

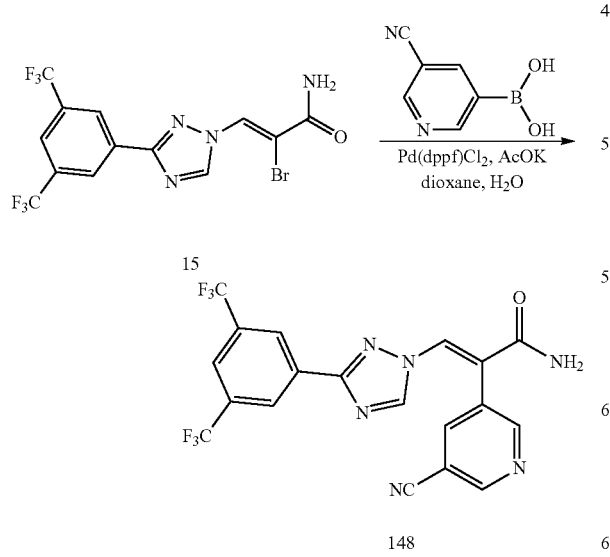

148

(E)-3-(3-(3,5-bis(trifluoromethyl)phenyl)-1H-1,2,4-triazol-1-yl)-2-(5-cyanopyridin-3-yl)acrylamide (148) was synthesized according to General Procedure 6. Yield: 20%. ¹H NMR (400 MHz, DMSO-d₆) δ 9.14 (s, 1H), 9.06 (d, J=2 Hz, 1H), 8.75 (d, J=2 Hz, 1H), 8.43 (s, 1H), 8.37-8.32 (m, 1H), 8.23 (s, 1H), 8.03 (s, 2H), 7.66 (s, 1H), 7.27 (s, 1H). LCMS: m/z 453.1 [M+H]⁺, t$_R$=1.79 min.

Synthesis of (E)-3-(3-(3,5-bis(trifluoromethyl)phenyl)-1H-1,2,4-triazol-1-yl)-2-(quinolin-3-yl)acrylamide (149)

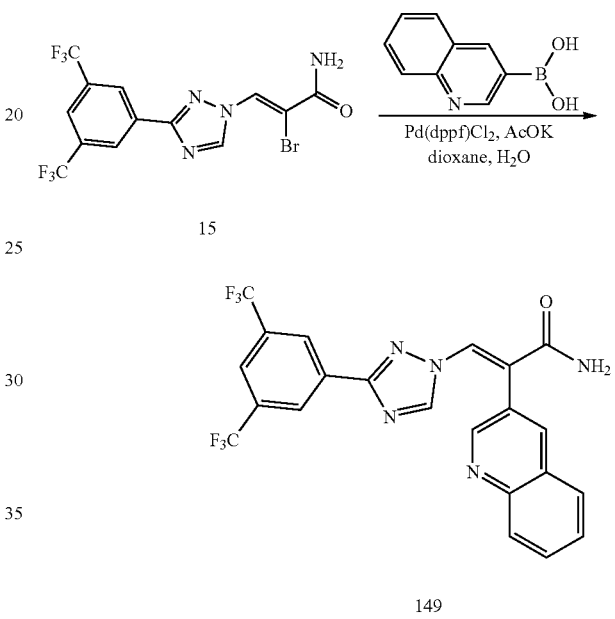

149

(E)-3-(3-(3,5-bis(trifluoromethyl)phenyl)-1H-1,2,4-triazol-1-yl)-2-(quinolin-3-yl)acrylamide (149) was synthesized according to General Procedure 6. Yield: 80%. ¹H NMR (400 MHz, DMSO-d₆) δ 9.09 (s, 1H), 8.75 (d, J=2 Hz, 1H), 8.42 (s, 1H), 8.29 (d, J=2 Hz, 1H), 8.12-7.97 (m, 3H), 7.88 (s, 2H), 7.82 (t, J=7 Hz, 1H), 7.63 (t, J=7 Hz, 2H), 7.31 (s, 1H). LCMS: m/z 478.1 [M+H]⁺, t$_R$=1.64 min.

Synthesis of (E)-3-(3-(3,5-bis(trifluoromethyl)phenyl)-1H-1,2,4-triazol-1-yl)-2-(2-fluorobiphenyl-4-yl)acrylamide (150)

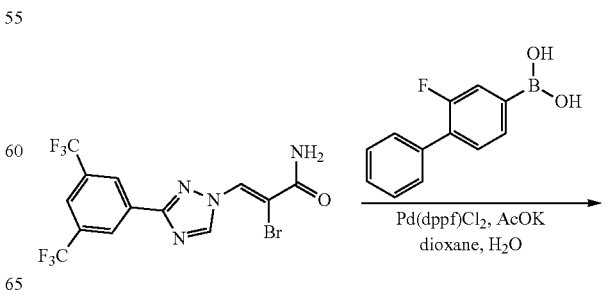

114

Synthesis of (E)-3-(3-(3,5-bis(trifluoromethyl)phenyl)-1H-1,2,4-triazol-1-yl)-2-(1H-indazol-6-yl)acrylamide (152)

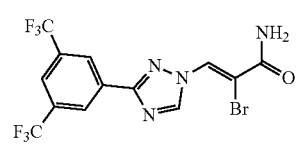
15

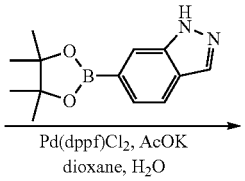

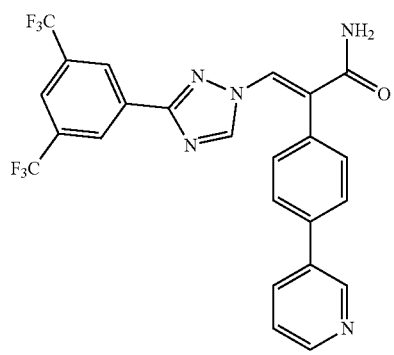

152

(E)-3-(3-(3,5-bis(trifluoromethyl)phenyl)-1H-1,2,4-triazol-1-yl)-2-(1H-indazol-6-yl)acrylamide (152) was synthesized according to General Procedure 6. Yield: 46%. $^1$H NMR (400 MHz, DMSO-d$_6$) δ 8.54 (s, 1H), 8.20-8.10 (m, 3H), 8.06 (s, 2H), 7.85 (d, J=8 Hz, 1H), 7.47 (s, 1H), 6.98 (d, J=8 Hz, 1H). LCMS: m/z 467.1 [M+H]$^+$, t$_R$=1.67 min.

Synthesis of (Z)-3-(3-(3,5-bis(trifluoromethyl)phenyl)-1H-1,2,4-triazol-1-yl)-2-(pyrimidin-5-yl)acrylamide (153)

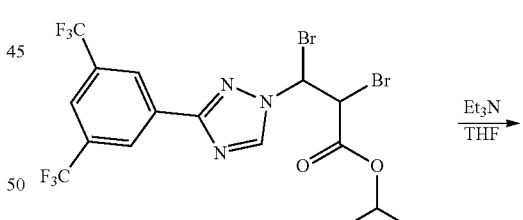

12

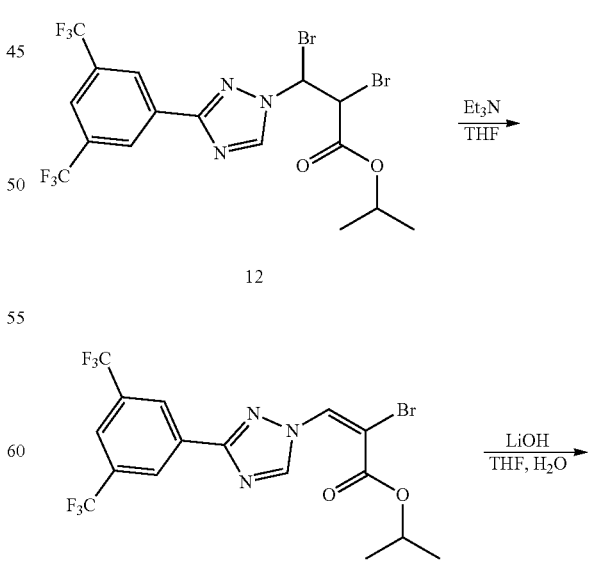

16

113

-continued

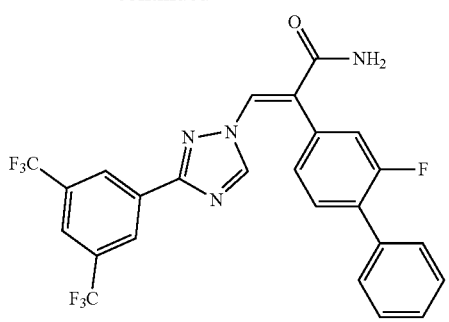

150

(E)-3-(3-(3,5-bis(trifluoromethyl)phenyl)-1H-1,2,4-triazol-1-yl)-2-(2-fluorobiphenyl-4-yl)acrylamide (150) was synthesized according to General Procedure 6. Yield: 30%. $^1$H NMR (400 MHz, DMSO-d$_6$) δ 8.89 (s, 1H), 8.23-8.18 (m, 4H), 7.63-7.56 (m, 4H), 7.54-7.48 (m, 2H), 7.47-7.40 (m, 1H), 7.31-7.25 (m, 1H), 7.20-7.14 (m, 2H). LCMS: m/z 521.1 [M+H]$^+$, t$_R$=2.06 min.

Synthesis of (E)-3-(3-(3,5-bis(trifluoromethyl)phenyl)-1H-1,2,4-triazol-1-yl)-2-(4-(pyridin-3-yl)phenyl)acrylamide (151)

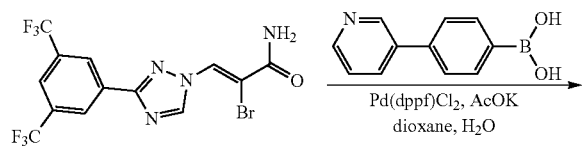

15

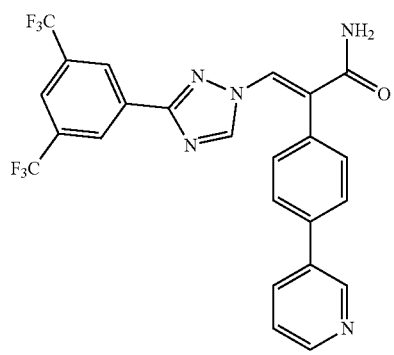

151

(E)-3-(3-(3,5-bis(trifluoromethyl)phenyl)-1H-1,2,4-triazol-1-yl)-2-(4-(pyridin-3-yl)phenyl)acrylamide (151) was synthesized according to General Procedure 6. Yield: 11%. $^1$H NMR (400 MHz, CD$_3$OD) δ 9.19 (s, 1H), 8.84-8.74 (m, 2H), 8.52 (s, 1H), 8.31-8.26 (m, 3H), 8.07-7.95 (m, 4H), 7.59 (d, J=8 Hz, 2H). LCMS: m/z 504.1 [M+H]$^+$, t$_R$=1.55 min.

115

-continued

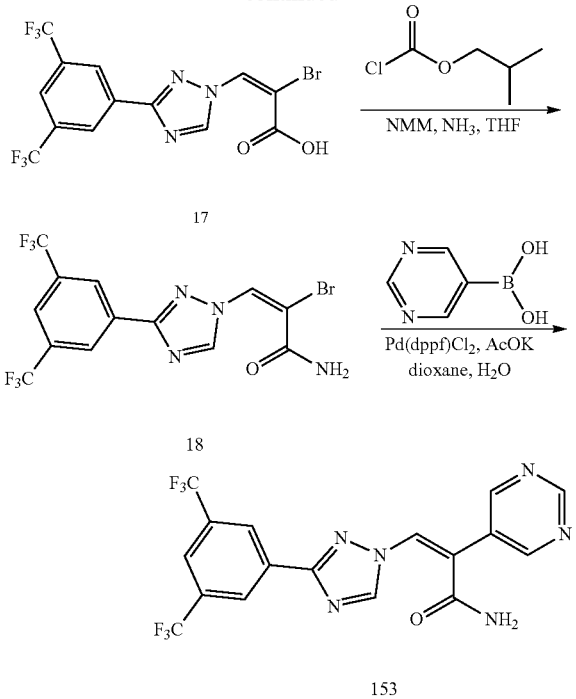

Synthesis of (E)-isopropyl 3-(3-(3,5-bis(trifluoromethyl)phenyl)-1H-1,2,4-triazol-1-yl)-2-bromoacrylate (16)

Isopropyl 3-(3-(3,5-bis(trifluoromethyl)phenyl)-1H-1,2,4-triazol-1-yl)-2,3-dibromopropanoate (12) (6.2 g, 11.3 mmol) was dissolved in tetrahydrofuran (40 mL) and cooled down to 0° C. Triethylamine (2.3 g, 22.5 mmol) was added and the mixture was stirred at room temperature for 16 h. The reaction mixture was diluted with water (20 mL) and extracted with ethyl acetate (30 mL×3). The combined organic layers were washed with brine, dried over anhydrous Na₂SO₄ and concentrated under reduced pressure. The crude product was purified by silica gel chromatography to afford (E)-isopropyl 3-(3-(3,5-bis(trifluoromethyl)phenyl)-1H-1,2,4-triazol-1-yl)-2-bromoacrylate (16) as white solid (3.1 g, 59% yield). ¹H NMR (400 MHz, DMSO-d₆) δ 8.95 (s, 1H), 8.46 (s, 1H), 8.29 (s, 2H), 8.09 (s, 1H), 5.13-5.07 (m, 1H), 1.26 (d, J=6 Hz, 6H). LCMS: m/z 472.0 [M+H]⁺, $t_R$=2.02 min.

Synthesis of (E)-3-(3-(3,5-bis(trifluoromethyl)phenyl)-1H-1,2,4-triazol-1-yl)-2-bromoacrylic acid (17)

(E)-isopropyl 3-(3-(3,5-bis(trifluoromethyl)phenyl)-1H-1,2,4-triazol-1-yl)-2-bromoacrylate (16) (2.36 g, 5 mmol) was dissolved in tetrahydrofuran (25 mL). A solution of lithium hydroxide (1.05 g, 25 mmol) in water (25 mL) was added drop wise at 0° C. The reaction mixture was stirred at 0° C. for 3 h, and poured into water (30 mL), acidified with HCl (3 N) until pH=5, extracted with ethyl acetate (200 mL×3). The combined organic layers were washed with brine, dried over anhydrous Na₂SO₄, concentrated under reduced pressure, and purified by recrystallization from 20% EtOAc in petroleum ether to afford (E)-3-(3-(3,5-bis(trifluoromethyl)phenyl)-1H-1,2,4-triazol-1-yl)-2-bromoacrylic acid (17) as white solid (1.2 g, 56% yield). ¹H NMR (400

116

MHz, DMSO-d₆) δ 8.98 (s, 1H), 8.49 (s, 1H), 8.29 (s, 2H), 8.00 (s, 1H). LCMS: m/z 433.0 [M+H]⁺, $t_R$=1.81 min.

Synthesis of (E)-3-(3-(3,5-bis(trifluoromethyl)phenyl)-1H-1,2,4-triazol-1-yl)-2-bromoacrylamide (18)

(E)-3-(3-(3,5-bis(trifluoromethyl)phenyl)-1H-1,2,4-triazol-1-yl)-2-bromoacrylic acid (17) (0.9 g, 2.1 mmol) was dissolved in THF (20 mL) and isobutyl chloroformate (0.57 g, 4.2 mmol), N-methyl morpholine (0.32 g, 3.1 mmol) were added at 0° C. The reaction mixture was stirred at 0° C. for 1 h. Ammonia gas was purged for 40 min at 0° C. The reaction mixture was transferred into iced water and extracted with ethyl acetate (20 mL×3). The combined organic layers were washed with brine, dried over anhydrous Na₂SO₄ and concentrated under reduced pressure to give crude product, which was purified by recrystallization from EtOAc to give 0.8 g of (E)-3-(3-(3,5-bis(trifluoromethyl)phenyl)-1H-1,2,4-triazol-1-yl)-2-bromoacrylamide (18). Yield: 90%. ¹H NMR (400 MHz, DMSO-d₆) δ 8.88 (s, 1H), 8.49 (s, 1H), 8.29 (s, 2H), 8.01 (s, 1H), 7.87 (s, 1H), 7.81 (s, 1H). LCMS: m/z 429.0 [M+H]⁺, $t_R$=1.80 min.

Synthesis of (Z)-3-(3-(3,5-bis(trifluoromethyl)phenyl)-1H-1,2,4-triazol-1-yl)-2-(pyrimidin-5-yl)acrylamide (153)

A mixture of (E)-3-(3-(3,5-bis(trifluoromethyl)phenyl)-1H-1,2,4-triazol-1-yl)-2-bromoacrylamide (18) (600 mg, 1.4 mmol), pyrimidin-5-ylboronic acid (261 mg, 2.1 mmol), potassium acetate (277 mg, 2.8 mmol), [1,1'-bis(diphenlphosphiino)ferrocene]palladium-(II) chloride (91 mg, 0.11 mmol) in dioxane (60 mL) and water (5 mL) was heated at 80° C. for 45 minutes under nitrogen atmosphere. The mixture was poured into 30 mL of water and extracted with ethyl acetate (10 mL×3). The combined organic layers were washed with brine, dried over anhydrous Na₂SO₄, concentrated under reduced pressure and purified by Prep-HPLC to afford (Z)-3-(3-(3,5-bis(trifluoromethyl)phenyl)-1H-1,2,4-triazol-1-yl)-2-(pyrimidin-5-yl)acrylamide (153) (130 mg, 22% yield). ¹H NMR (400 MHz, DMSO-d₆) δ 9.22 (s, 1H), 8.96 (s, 3H), 8.54 (s, 2H), 8.31 (s, 1H), 8.10 (s, 1H), 8.01 (s, 1H), 7.94 (s, 1H). LCMS: m/z 429.1 [M+H]⁺, $t_R$=1.67 min.

Synthesis of (Z)-3-(3-(3,5-bis(trifluoromethyl)phenyl)-1H-1,2,4-triazol-1-yl)-2-(6-fluoropyridin-3-yl)acrylamide (154)

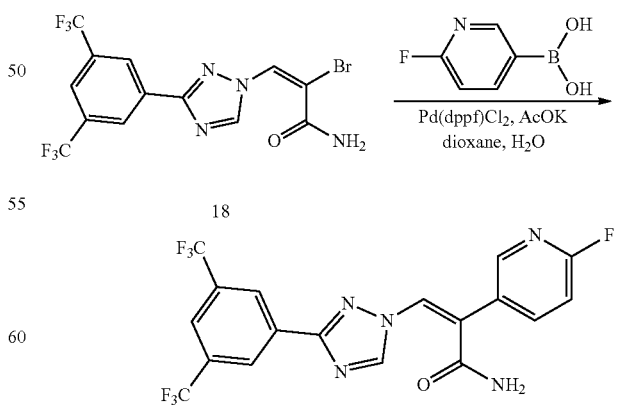

(Z)-3-(3-(3,5-bis(trifluoromethyl)phenyl)-1H-1,2,4-triazol-1-yl)-2-(6-fluoropyridin-3-yl)acrylamide (154) was synthesized according to General Procedure 6. Yield: 7%.

¹H NMR (400 MHz, CD₃OD) δ 8.70 (s, 1H), 8.56 (s, 2H), 8.34 (d, J=3 Hz, 1H), 8.11-8.03 (m, 1H), 7.97 (s, 1H), 7.64 (s, 1H), 7.11-7.05 (m, 1H). LCMS: m/z 446.1 [M+H]⁺, t$_R$=1.68 min.

Synthesis of (Z)-3-(3-(3,5-bis(trifluoromethyl)phenyl)-1H-1,2,4-triazol-1-yl)-2-(2-fluoropyridin-4-yl)acrylamide (155)

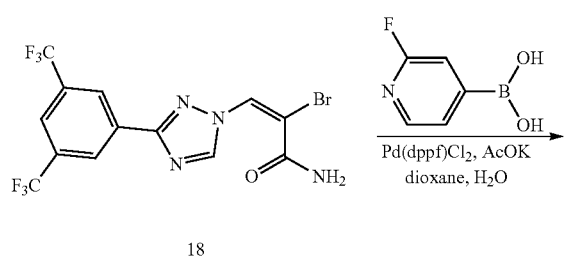

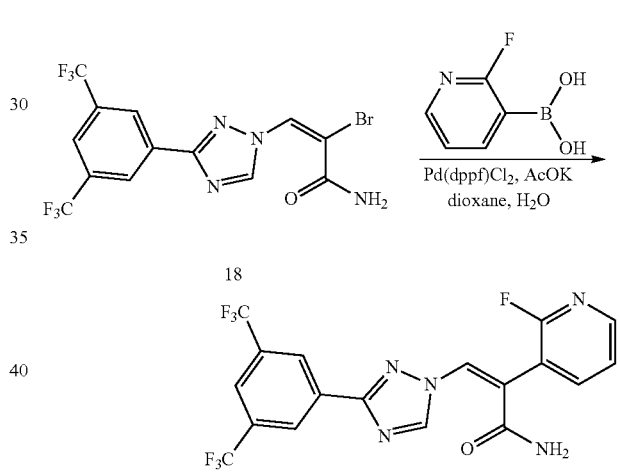

(Z)-3-(3-(3,5-bis(trifluoromethyl)phenyl)-1H-1,2,4-triazol-1-yl)-2-(2-fluoropyridin-4-yl)acrylamide (155) was synthesized according to General Procedure 6. Yield: 30%.
¹H NMR (400 MHz, CD₃OD) δ 8.75 (s, 1H), 8.57 (s, 2H), 8.18 (d, J=5 Hz, 1H), 7.99 (s, 1H), 7.93 (s, 1H), 7.47-7.40 (m, 1H), 7.19 (s, 1H). LCMS: m/z 446.1 [M+H]⁺, t$_R$=1.79 min.

Synthesis of (Z)-3-(3-(3,5-bis(trifluoromethyl)phenyl)-1H-1,2,4-triazol-1-yl)-2-(6-chloropyridin-3-yl)acrylamide (156)

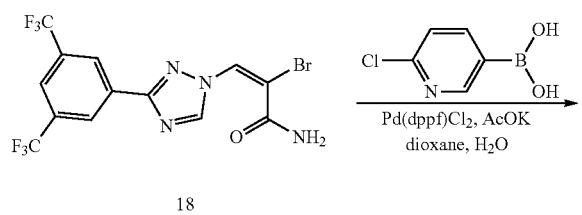

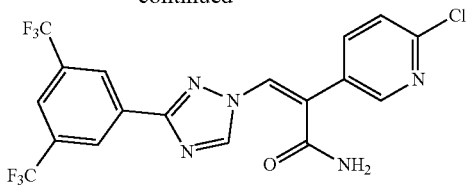

(Z)-3-(3-(3,5-bis(trifluoromethyl)phenyl)-1H-1,2,4-triazol-1-yl)-2-(6-chloropyridin-3-yl)acrylamide (156) was synthesized according to General procedure 6. Yield: 7%. ¹H NMR (400 MHz, DMSO-d₆) δ 8.94 (s, 1H), 8.60 (d, J=2 Hz, 1H), 8.54 (s, 2H), 8.30 (s, 1H), 8.06 (s, 1H), 8.02-7.97 (m, 1H), 7.93 (s, 1H), 7.89 (s, 1H), 7.65 (d, J=8 Hz, 1H). LCMS: m/z 462.1 [M+H]⁺, t$_R$=1.82 min.

Synthesis of (Z)-3-(3-(3,5-bis(trifluoromethyl)phenyl)-1H-1,2,4-triazol-1-yl)-2-(2-fluoropyridin-3-yl)acrylamide (157)

(Z)-3-(3-(3,5-bis(trifluoromethyl)phenyl)-1H-1,2,4-triazol-1-yl)-2-(2-fluoropyridin-3-yl)acrylamide (157) was synthesized according to General Procedure 6. Yield: 29%.
¹H NMR (400 MHz, DMSO-d₆) δ 9.06 (s, 1H), 8.60 (s, 2H), 8.38-8.33 (m, 2H), 8.20-8.11 (m, 1H), 8.03 (s, 1H), 7.86-7.81 (m, 2H), 7.60-7.51 (m, 1H). LCMS: m/z 446.1 [M+H]⁺, t$_R$=1.69 min.

Example 2. Assays

Certain compounds of the invention were tested in various assays.

Inhibition of Nuclear Export—Rev-GFP Assay

The inhibition of CRM1 mediated nuclear export by compounds of the invention was determined in a RevGFP assay. Rev is a protein from human immunodeficiency virus type 1 (HIV-1) and contains a nuclear export signal (NES) in its C-terminal domain and a nuclear localization signal (NLS) in its N-terminal domain. Nuclear export of Rev protein is dependent on the classical NES/CRM1 pathway (Neville et al, 1997, Kau et al, 2003). Nuclear and nucleolar accumulation of Rev is observed in cells treated with specific inhibitors of CRM1, such as LMB (Kau et al, 2003).

In this assay, U2OS-RevGFP cells were seeded onto clear-bottom, black, 384-well plates the day before the experiment. Compounds were serially diluted 1:2 starting from 40 µM in a separate 384-well plate in DMEM, and then transferred onto cells. Cells were incubated with compound for approximately 1 hour before fixation with 3.7% formaldehyde and nuclei staining with Hoechst 33258. The amount of GFP in cell nuclei was measured and compound $IC_{50}$s were determined (Kau et al, 2003). The results of this assay are shown in Table 1.

In a separate experiment, U2OS Rev-GFP cells were treated with Compound 124 (that was serially diluted 1:3 starting from 10 µM) or DMSO for 4 hours. After 4 hours, the cells were fixed with paraformaldehyde (PFA) and counterstained with the nuclear dye DAPI. Using dose-response curves, the $IC_{50}$ for Compound 124 was determined to be about 40 nM in the U2OS Rev-GFP assay. Thus, Compound 124 recapitulates the CRM1 inhibition observed using LMB, and treatment with Compound 124 results in nuclear Rev-GFP.

MTT Cell Proliferation Assay

The MTT cell proliferation assay was used to study the cytotoxic properties of the compounds. The assay was performed according to the method described by Roche Molecular Biochemicals, with minor modifications. The assay is based on the cleavage of the tetrazolium salt, MTT, in the presence of an electron-coupling reagent. The water-insoluble formazan salt produced must be solubilized in an additional step. Cells grown in a 96-well tissue culture plate were incubated with the MTT solution for approximately 4 hours. After this incubation period, a water-insoluble formazan dye formed. After solubilization, the formazan dye was quantitated using a scanning multi-well spectrophotometer (ELISA reader). The absorbance revealed directly correlates to the cell number. The cells were seeded at 5,000-10,000 cells in each well of 96-well plate in 100 µL of fresh culture medium and were allowed to attach overnight. The stock solutions of the compounds were diluted in 100 µL cell culture medium to obtain eight concentrations of each test compound, ranging from 1 nM to 30 µM. After incubation for approximately 64-72 hours, 20 µL of CellTiter 96 Aqueous One Solution Reagent (Promega, G358B) was added to each well and the plate was returned to the incubator (37° C.; 5% $CO_2$) until an absolute OD of 1.5 was reached for the control cells. All optical densities were measured at 490 nm using a Vmax Kinetic Microplate Reader (Molecular Devices). In most cases, the assay was performed in duplicate and the results were presented as a mean percent inhibition to the negative control±SE. The following formula was used to calculate the percent of inhibition: Inhibition (%)=(1−($OD_o$/OD))×100.

The compounds were tested against Z138, MM1S and 3T3 cells. The Z138 cell line is a mature B-cell acute lymphoblastic leukemia cell line derived from a patient with chronic lumphocytic leukemia. The MM1S cell line was established from the peripheral blood of a human multiple myeloma patient. 3T3 cells are standard fibroblast cells; they were originally isolated from Swiss mouse embryo tissue.

The results of the MTT assay are reported in Table 1.

TABLE 1

Assay Results for Exemplary Compounds (A = <100 nM; B = 100 nM to <5 µM; C = 5 µM to 30 µM; D = >30 µM; NT = Not tested).

| Cmpd. No. | Structure | RevGFP | MTT (Z138) | MTT (MM1S) | MTT (3T3) | Name |
|---|---|---|---|---|---|---|
| 100 | 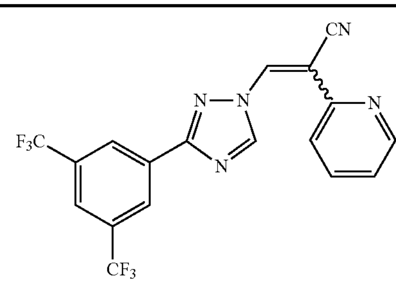 | D | D | D | D | 3-(3-(3,5-bis-(trifluoromethyl)-phenyl)-1H-1,2,4-triazol-1-yl)-2-(pyridin-2-yl)-acrylonitrile |
| 101 | 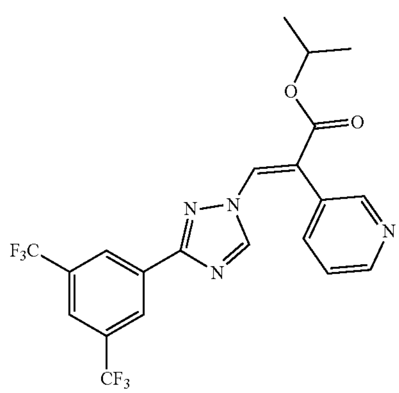 [SMILES: CC(C)OC(=O)/C(=C/n1cnc(-c2cc(C(F)(F)F)cc(C(F)(F)F)c2)n1)c1cccnc1] | C | B | A | C | isopropyl (E)-3-(3-(3,5-bis(trifluoro-methyl)phenyl)-1H-1,2,4-triazol-1-yl)-2-(pyridin-3-yl)acrylate |

TABLE 1-continued

Assay Results for Exemplary Compounds (A = <100 nM; B = 100 nM to <5 µM; C = 5 µM to 30 µM; D = >30 µM; NT = Not tested).

| Cmpd. No. | Structure | RevGFP | MTT (Z138) | MTT (MM1S) | MTT (3T3) | Name |
|---|---|---|---|---|---|---|
| 102 | 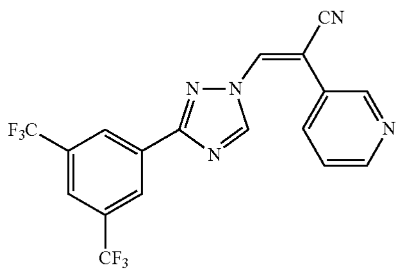 [SMILES: N#C/C(=C/n1cnc(-c2cc(C(F)(F)F)cc(C(F)(F)F)c2)n1)c1cccnc1] | B | B | B | C | (E)-3-(3-(3,5-bis-(trifluoromethyl)-phenyl)-1H-1,2,4-triazol-1-yl)-2-(pyridin-3-yl)-acrylonitrile |
| 103 | 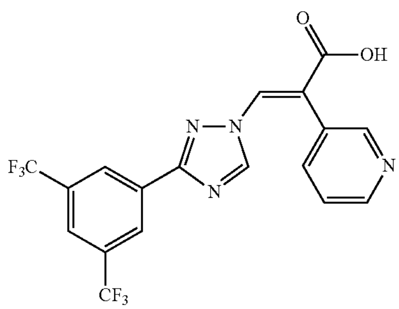 [SMILES: O=C(O)/C(=C/n1cnc(-c2cc(C(F)(F)F)cc(C(F)(F)F)c2)n1)c1cccnc1] | NT | D | D | D | (E)-3-(3-(3,5-bis-(trifluoromethyl)-phenyl)-1H-1,2,4-triazol-1-yl)-2-(pyridin-3-yl)-acrylic acid |
| 104 | 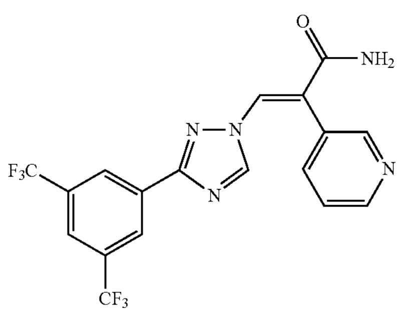 [SMILES: NC(=O)/C(=C/n1cnc(-c2cc(C(F)(F)F)cc(C(F)(F)F)c2)n1)c1cccnc1] | B | A | A | B | (E)-3-(3-(3,5-bis-(trifluoromethyl)-phenyl)-1H-1,2,4-triazol-1-yl)-2-(pyridin-3-yl)-acrylamide |
| 105 | 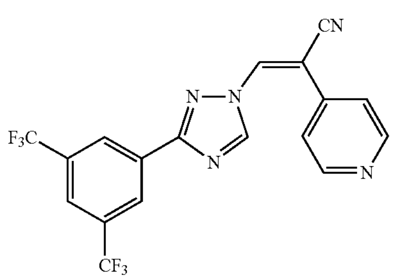 [SMILES: N#C/C(=C/n1cnc(-c2cc(C(F)(F)F)cc(C(F)(F)F)c2)n1)c1ccncc1] | B | NT | B | D | (E)-3-(3-(3,5-bis-(trifluoromethyl)-phenyl)-1H-1,2,4-triazol-1-yl)-2-(pyridin-4-yl)-acrylonitrile |
| 106 | 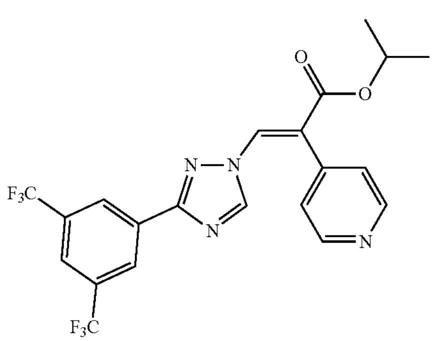 [SMILES: CC(C)OC(=O)/C(=C/n1cnc(-c2cc(C(F)(F)F)cc(C(F)(F)F)c2)n1)c1ccncc1] | NT | NT | B | NT | isopropyl (E)-3-(3-(3,5-bis(trifluoro-methyl)phenyl)-1H-1,2,4-triazol-1-yl)-2-(pyridin-4-yl)acrylate |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 107 | 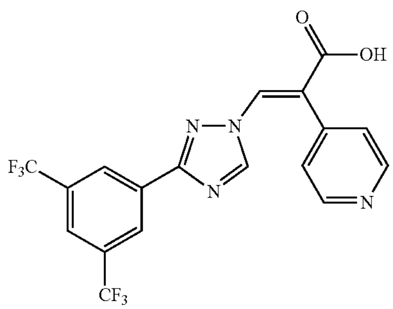 [SMILES: O=C(O)/C(=C/n1cnc(-c2cc(C(F)(F)F)cc(C(F)(F)F)c2)n1)c1ccncc1] | NT | NT | C | NT | (E)-3-(3-(3,5-bis-(trifluoromethyl)-phenyl)-1H-1,2,4-triazol-1-yl)-2-(pyridin-4-yl)-acrylic acid |
| 108 | 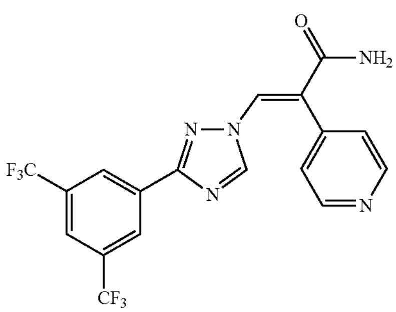 [SMILES: NC(=O)/C(=C/n1cnc(-c2cc(C(F)(F)F)cc(C(F)(F)F)c2)n1)c1ccncc1] | A | B | A | D | (E)-3-(3-(3,5-bis-(trifluoromethyl)-phenyl)-1H-1,2,4-triazol-1-yl)-2-(pyridin-4-yl)-acrylamide |
| 109 | 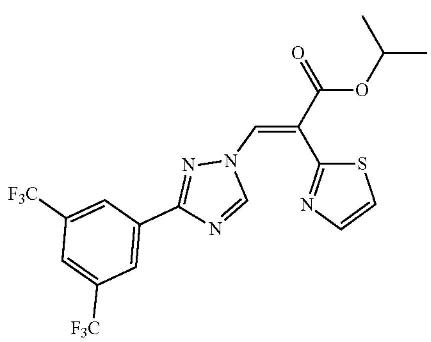 [SMILES: CC(C)OC(=O)/C(=C/n1cnc(-c2cc(C(F)(F)F)cc(C(F)(F)F)c2)n1)c1nccs1] | NT | NT | B | NT | isopropyl (Z)-3-(3-(3,5-bis(trifluoromethyl)phenyl)-1H-1,2,4-triazol-1-yl)-2-(thiazol-2-yl)acrylate |
| 110 | 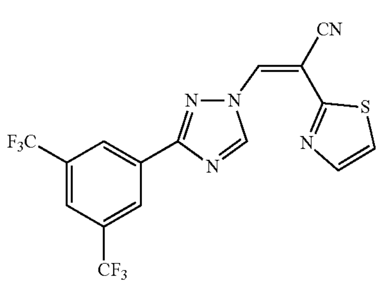 [SMILES: N#C/C(=C/n1cnc(-c2cc(C(F)(F)F)cc(C(F)(F)F)c2)n1)c1nccs1] | NT | NT | B | NT | (Z)-3-(3-(3,5-bis-(trifluoromethyl)-phenyl)-1H-1,2,4-triazol-1-yl)-2-(thiazol-2-yl)-acrylonitrile |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 111 | 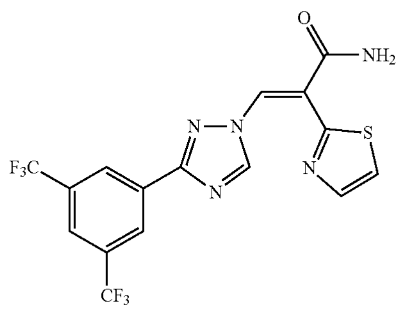 [SMILES: NC(=O)/C(=C/n1cnc(-c2cc(C(F)(F)F)cc(C(F)(F)F)c2)n1)c1nccs1] | A | NT | A | D | (Z)-3-(3-(3,5-bis-(trifluoromethyl)-phenyl)-1H-1,2,4-triazol-1-yl)-2-(thiazol-2-yl)-acrylamide |
| 112 | 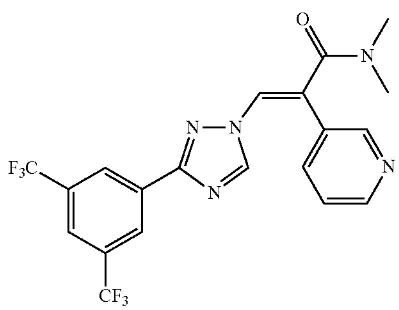 [SMILES: CN(C)C(=O)/C(=C/n1cnc(-c2cc(C(F)(F)F)cc(C(F)(F)F)c2)n1)c1cccnc1] | NT | NT | D | NT | (E)-3-(3-(3,5-bis-(trifluoromethyl)-phenyl)-1H-1,2,4-triazol-1-yl)-N,N-dimethyl-2-(pyridin-3-yl)-acrylamide |
| 113 | 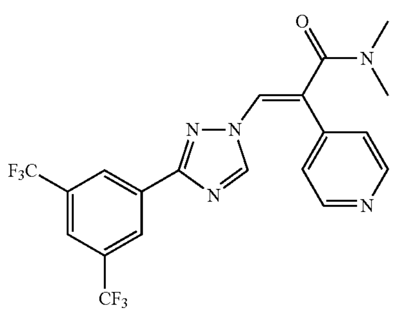 [SMILES: CN(C)C(=O)/C(=C/n1cnc(-c2cc(C(F)(F)F)cc(C(F)(F)F)c2)n1)c1ccncc1] | C | NT | B | NT | (E)-3-(3-(3,5-bis-(trifluoromethyl)-phenyl)-1H-1,2,4-triazol-1-yl)-N,N-dimethyl-2-(pyridin-4-yl)-acrylamide |
| 114 | 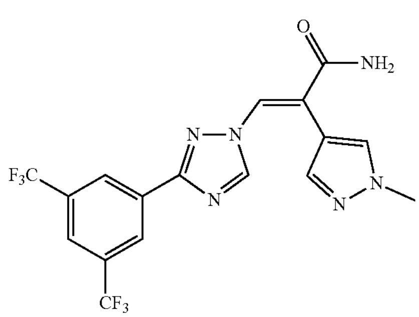 [SMILES: Cn1cc(/C(=C\n2cnc(-c3cc(C(F)(F)F)cc(C(F)(F)F)c3)n2)C(N)=O)cn1] | B | NT | A | NT | (E)-3-(3-(3,5-bis-(trifluoromethyl)-phenyl)-1H-1,2,4-triazol-1-yl)-2-(1-methyl-1H-pyrazol-4-yl)-acrylamide |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 115 | 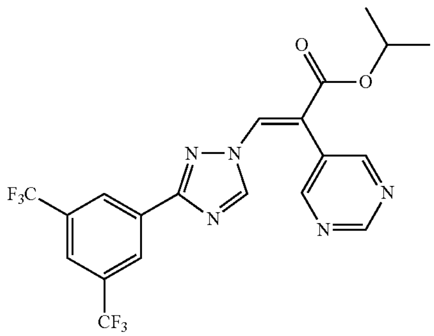 [SMILES: CC(C)OC(=O)/C(=C/n1cnc(-c2cc(C(F)(F)F)cc(C(F)(F)F)c2)n1)c1cncnc1] | B | NT | B | NT | isopropyl (E)-3-(3-(3,5-bis(trifluoromethyl)phenyl)-1H-1,2,4-triazol-1-yl)-2-(pyrimidin-5-yl)acrylate |
| 116 | 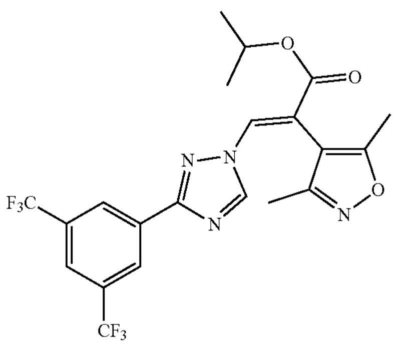 [SMILES: Cc1noc(C)c1/C(=C\n1cnc(-c2cc(C(F)(F)F)cc(C(F)(F)F)c2)n1)C(=O)OC(C)C] | B | NT | B | NT | isopropyl (E)-3-(3-(3,5-bis(trifluoromethyl)phenyl)-1H-1,2,4-triazol-1-yl)-2-(3,5-dimethylisoxazol-4-yl)acrylate |
| 117 | 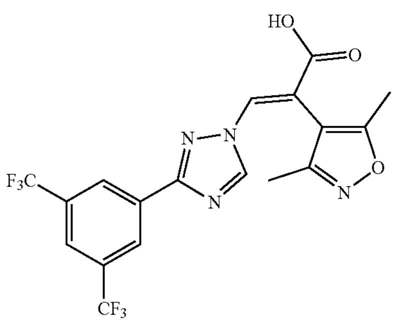 [SMILES: Cc1noc(C)c1/C(=C\n1cnc(-c2cc(C(F)(F)F)cc(C(F)(F)F)c2)n1)C(=O)O] | NT | NT | D | NT | (E)-3-(3-(3,5-bis-(trifluoromethyl)-phenyl)-1H-1,2,4-triazol-1-yl)-2-(3,5-dimethylisoxazol-4-yl)acrylic acid |
| 118 | 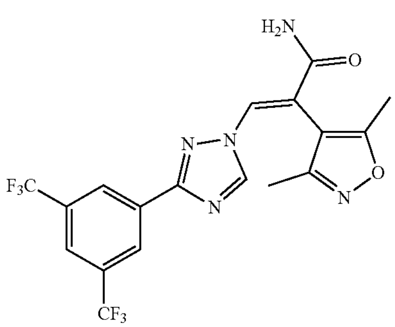 [SMILES: Cc1noc(C)c1/C(=C\n1cnc(-c2cc(C(F)(F)F)cc(C(F)(F)F)c2)n1)C(N)=O] | B | B | B | D | (E)-3-(3-(3,5-bis-(trifluoromethyl)-phenyl)-1H-1,2,4-triazol-1-yl)-2-(3,5-dimethylisoxazol-4-yl)acrylamide |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 119 | 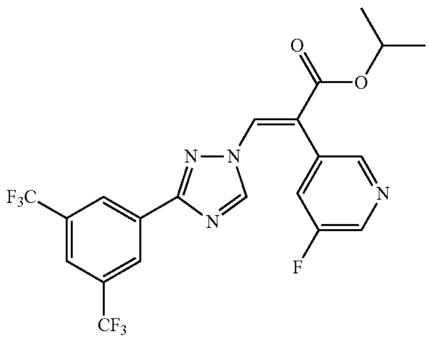 [SMILES: CC(C)OC(=O)/C(=C/n1cnc(-c2cc(C(F)(F)F)cc(C(F)(F)F)c2)n1)c1cncc(F)c1] | B | B | B | D | isopropyl (E)-3-(3-(3,5-bis(trifluoromethyl)phenyl)-1H-1,2,4-triazol-1-yl)-2-(5-fluoropyridin-3-yl)acrylate |
| 120 | 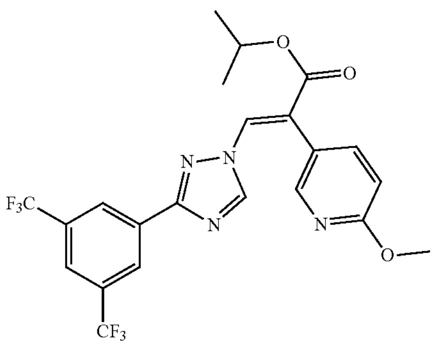 [SMILES: COc1ccc(/C(=C\n2cnc(-c3cc(C(F)(F)F)cc(C(F)(F)F)c3)n2)C(=O)OC(C)C)cn1] | B | B | B | D | isopropyl (E)-3-(3-(3,5-bis(trifluoromethyl)phenyl)-1H-1,2,4-triazol-1-yl)-2-(6-methoxypyridin-3-yl)-acrylate |
| 121 | 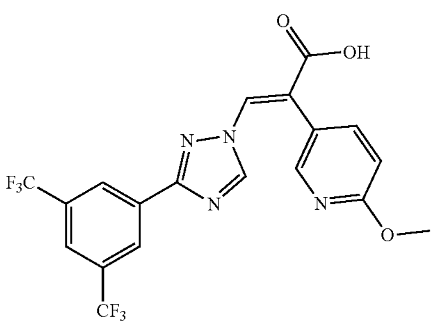 [SMILES: COc1ccc(/C(=C\n2cnc(-c3cc(C(F)(F)F)cc(C(F)(F)F)c3)n2)C(=O)O)cn1] | NT | NT | D | NT | (E)-3-(3-(3,5-bis-(trifluoromethyl)-phenyl)-1H-1,2,4-triazol-1-yl)-2-(6-methoxypyridin-3-yl)acrylic acid |
| 122 | 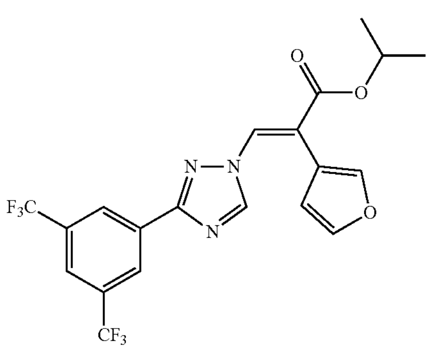 [SMILES: CC(C)OC(=O)/C(=C/n1cnc(-c2cc(C(F)(F)F)cc(C(F)(F)F)c2)n1)c1ccoc1] | NT | NT | B | NT | isopropyl (E)-3-(3-(3,5-bis-(trifluoromethyl)phenyl)-1H-1,2,4-triazol-1-yl)-2-(furan-3-yl)-acrylate |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 123 | 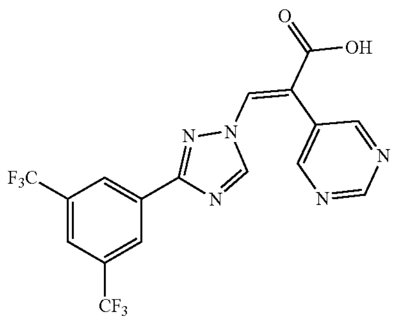 [SMILES: O=C(O)/C(=C/n1cnc(-c2cc(C(F)(F)F)cc(C(F)(F)F)c2)n1)c1cncnc1] | NT | NT | D | NT | (E)-3-(3-(3,5-bis-(trifluoromethyl)-phenyl)-1H-1,2,4-triazol-1-yl)-2-(pyrimidin-5-yl)-acrylic acid |
| 124 | 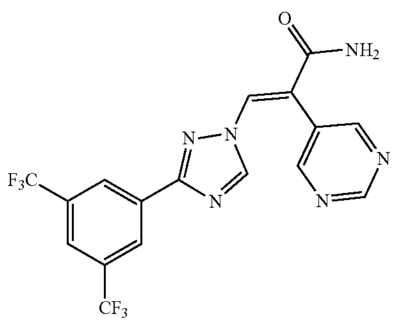 [SMILES: NC(=O)/C(=C/n1cnc(-c2cc(C(F)(F)F)cc(C(F)(F)F)c2)n1)c1cncnc1] | A | A | A | C | (E)-3-(3-(3,5-bis-(trifluoromethyl)-phenyl)-1H-1,2,4-triazol-1-yl)-2-(pyrimidin-5-yl)-acrylamide |
| 125 | 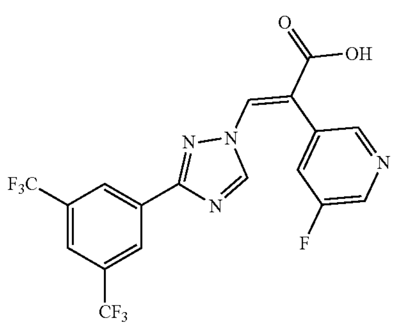 [SMILES: O=C(O)/C(=C/n1cnc(-c2cc(C(F)(F)F)cc(C(F)(F)F)c2)n1)c1cncc(F)c1] | NT | NT | D | NT | (E)-3-(3-(3,5-bis-(trifluoromethyl)-phenyl)-1H-1,2,4-triazol-1-yl)-2-(5-fluoropyridin-3-yl)acrylic acid |
| 126 | 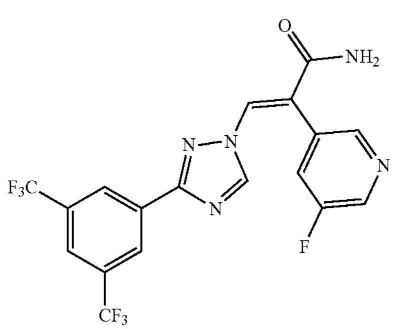 [SMILES: NC(=O)/C(=C/n1cnc(-c2cc(C(F)(F)F)cc(C(F)(F)F)c2)n1)c1cncc(F)c1] | NT | A | A | D | (E)-3-(3-(3,5-bis-(trifluoromethyl)-phenyl)-1H-1,2,4-triazol-1-yl)-2-(5-fluoropyridin-3-yl)acrylamide |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 127 | 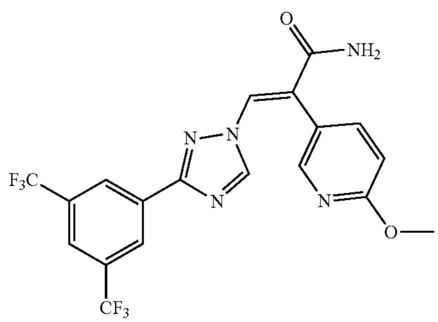 [SMILES: COc1ccc(/C(=C\n2cnc(-c3cc(C(F)(F)F)cc(C(F)(F)F)c3)n2)C(N)=O)cn1] | NT | NT | B | NT | (E)-3-(3-(3,5-bis-(trifluoromethyl)-phenyl)-1H-1,2,4-triazol-1-yl)-2-(6-methoxypyridin-3-yl)acrylamide |
| 128 | 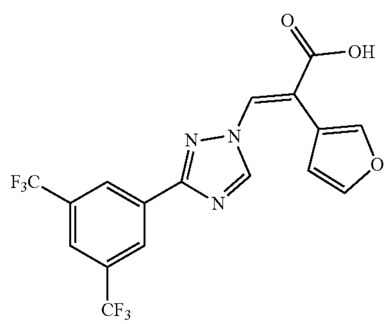 [SMILES: O=C(O)/C(=C/n1cnc(-c2cc(C(F)(F)F)cc(C(F)(F)F)c2)n1)c1ccoc1] | NT | NT | D | NT | (E)-3-(B-(3,5-bis-(trifluoromethyl)-phenyl)-1H-1,2,4-triazol-1-yl)-2-(furan-3-yl)acrylic acid |
| 129 | 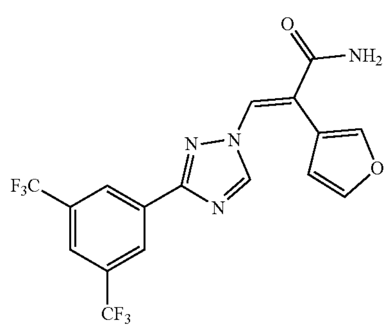 [SMILES: NC(=O)/C(=C/n1cnc(-c2cc(C(F)(F)F)cc(C(F)(F)F)c2)n1)c1ccoc1] | NT | NT | B | NT | (E)-3-(3-(3,5-bis-(trifluoromethyl)-phenyl)-1H-1,2,4-triazol-1-yl)-2-(furan-3-yl)acrylamide |
| 130 | 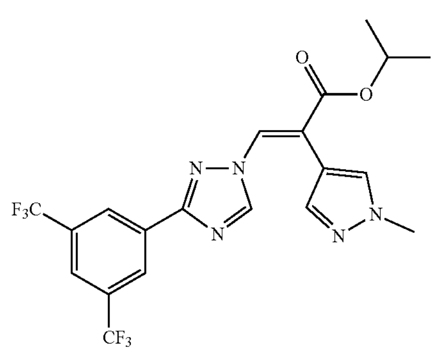 [SMILES: CC(C)OC(=O)/C(=C/n1cnc(-c2cc(C(F)(F)F)cc(C(F)(F)F)c2)n1)c1cnn(C)c1] | B | NT | A | NT | isopropyl (E)-3-(3-(3,5-bis(trifluoromethyl)phenyl)-1H-1,2,4-triazol-1-yl)-2-(1-methyl-1H-pyrazol-4-yl)-acrylate |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 131 | 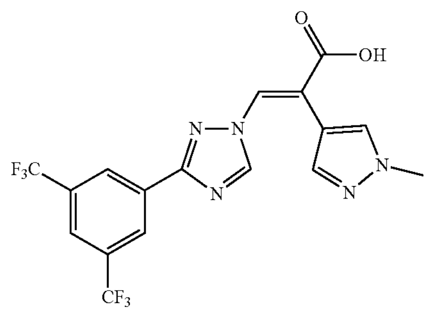 [SMILES: Cn1cc(/C(=C\n2cnc(-c3cc(C(F)(F)F)cc(C(F)(F)F)c3)n2)C(=O)O)cn1] | NT | NT | B | NT | (E)-3-(3-(3,5-bis-(trifluoromethyl)-phenyl)-1H-1,2,4-triazol-1-yl)-2-(1-methyl-1H-pyrazol-4-yl)-acrylic acid |
| 132 | 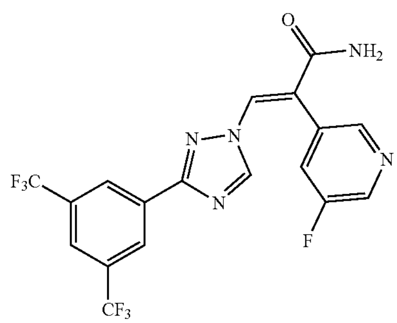 [SMILES: NC(=O)/C(=C/n1cnc(-c2cc(C(F)(F)F)cc(C(F)(F)F)c2)n1)c1cncc(F)c1] | A | A | A | D | (E)-3-(3-(3,5-bis-(trifluoromethyl)-phenyl)-1H-1,2,4-triazol-1-yl)-2-(5-fluoropyridin-3-yl)acrylamide |
| 133 | 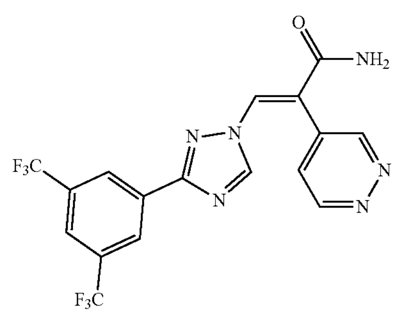 | NT | A | A | C | (E)-3-(3-(3,5-bis-(trifluoromethyl)-phenyl)-1H-1,2,4-triazol-1-yl)-2-(pyridazin-4-yl)-acrylamide |
| 134 | 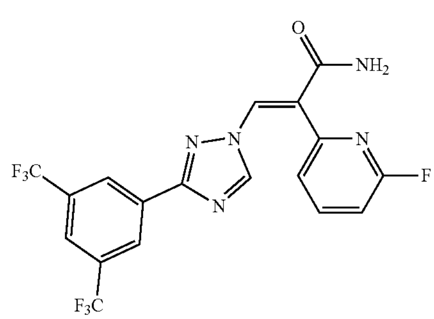 [SMILES: NC(=O)/C(=C/n1cnc(-c2cc(C(F)(F)F)cc(C(F)(F)F)c2)n1)c1cccc(F)n1] | NT | B | A | B | (E)-3-(3-(3,5-bis-(trifluoromethyl)-phenyl)-1H-1,2,4-triazol-1-yl)-2-(6-fluoropyridin-2-yl)acrylamide |

TABLE 1-continued

Assay Results for Exemplary Compounds (A = <100 nM; B = 100 nM to <5 µM; C = 5 µM to 30 µM; D = >30 µM; NT = Not tested).

| Cmpd. No. | Structure | RevGFP | MTT (Z138) | MTT (MM1S) | MTT (3T3) | Name |
|---|---|---|---|---|---|---|
| 135 | 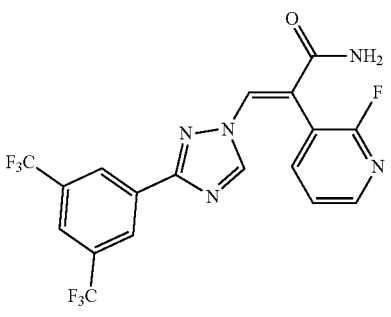 [SMILES: NC(=O)/C(=C/n1cnc(-c2cc(C(F)(F)F)cc(C(F)(F)F)c2)n1)c1cccnc1F] | NT | B | A | D | (E)-3-(3-(3,5-bis-(trifluoromethyl)-phenyl)-1H-1,2,4-triazol-1-yl)-2-(2-fluoropyridin-3-yl)acrylamide |
| 136 | 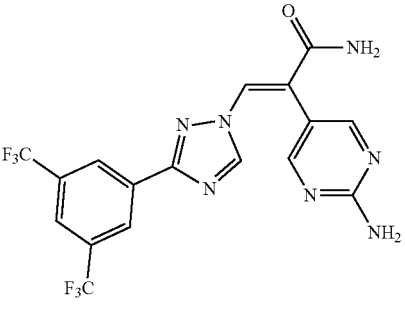 [SMILES: NC(=O)/C(=C/n1cnc(-c2cc(C(F)(F)F)cc(C(F)(F)F)c2)n1)c1cnc(N)nc1] | B | B | A | D | (E)-2-(2-amino-pyrimidin-5-yl)-3-(3-(3,5-bis-(trifluoromethyl)-phenyl)-1H-1,2,4-triazol-1-yl)acryl-amide |
| 137 | 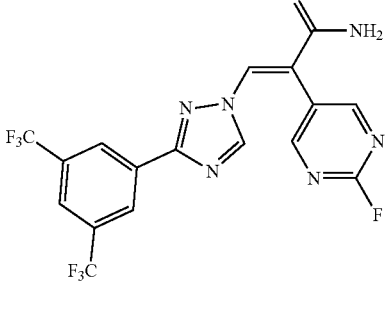 | A | B | A | D | (E)-3-(3-(3,5-bis-(trifluoromethyl)-phenyl)-1H-1,2,4-triazol-1-yl)-2-(2-fluoropyrimidin-5-yl)acrylamide |
| 138 | 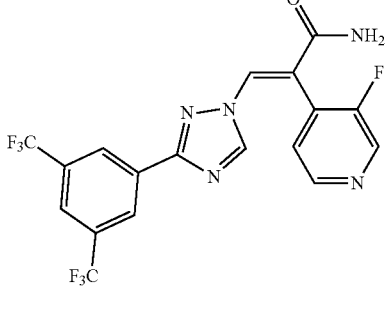 | A | A | A | B | (E)-3-(3-(3,5-bis-(trifluoromethyl)-phenyl)-1H-1,2,4-triazol-1-yl)-2-(3-fluoropyridin-4-yl)acrylamide |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 139 | 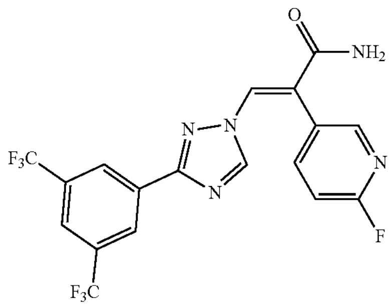 [SMILES: NC(=O)/C(=C/n1cnc(-c2cc(C(F)(F)F)cc(C(F)(F)F)c2)n1)c1ccc(F)nc1] | NT | B | B | D | (E)-3-(3-(3,5-bis-(trifluoromethyl)-phenyl)-1H-1,2,4-triazol-1-yl)-2-(6-fluoropyridin-3-yl)acrylamide |
| 140 | 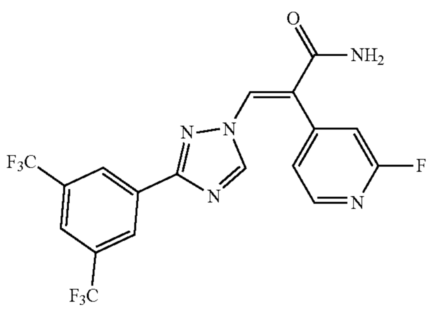 [SMILES: NC(=O)/C(=C/n1cnc(-c2cc(C(F)(F)F)cc(C(F)(F)F)c2)n1)c1ccnc(F)c1] | A | A | A | D | (E)-3-(3-(3,5-bis-(trifluoromethyl)-phenyl)-1H-1,2,4-triazol-1-yl)-2-(2-fluoropyridin-4-yl)acrylamide |
| 141 | 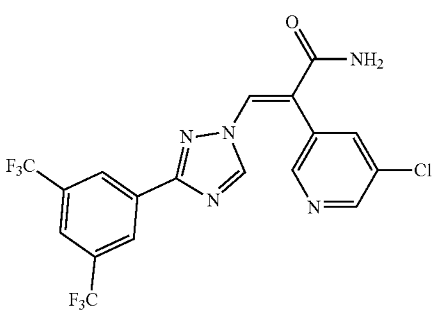 [SMILES: NC(=O)/C(=C/n1cnc(-c2cc(C(F)(F)F)cc(C(F)(F)F)c2)n1)c1cncc(Cl)c1] | B | B | A | D | (E)-3-(3-(3,5-bis-(trifluoromethyl)-phenyl)-1H-1,2,4-triazol-1-yl)-2-(5-chloropyridin-3-yl)acrylamide |
| 143 | 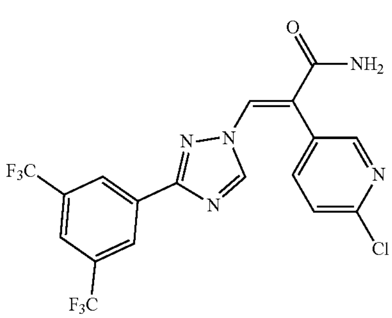 [SMILES: NC(=O)/C(=C/n1cnc(-c2cc(C(F)(F)F)cc(C(F)(F)F)c2)n1)c1ccc(Cl)nc1] | B | B | A | D | (E)-3-(3-(3,5-bis-(trifluoromethyl)-phenyl)-1H-1,2,4-triazol-1-yl)-2-(6-chloropyridin-3-yl)acrylamide |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 144 | 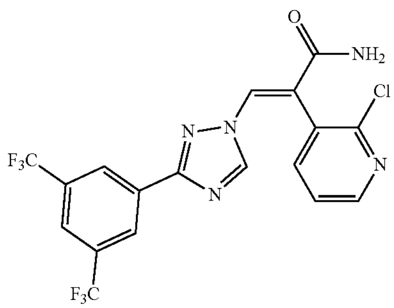 [SMILES: NC(=O)/C(=C/n1cnc(-c2cc(C(F)(F)F)cc(C(F)(F)F)c2)n1)c1cccnc1Cl] | NT | B | B | D | (E)-3-(3-(3,5-bis-(trifluoromethyl)-phenyl)-1H-1,2,4-triazol-1-yl)-2-(2-chloropyridin-3-yl)acrylamide |
| 145 | 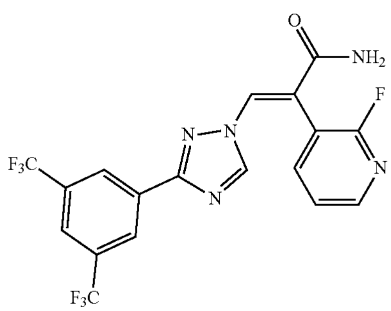 | NT | B | A | D | (E)-3-(3-(3,5-bis-(trifluoromethyl)-phenyl)-1H-1,2,4-triazol-1-yl)-2-(2,6-difluoro-pyridin-3-yl)-acrylamide |
| 146 | 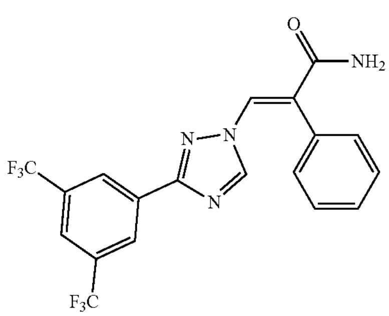 [SMILES: NC(=O)/C(=C/n1cnc(-c2cc(C(F)(F)F)cc(C(F)(F)F)c2)n1)c1ccccc1] | NT | B | B | D | (E)-3-(3-(3,5-bis-(trifluoromethyl)-phenyl)-1H-1,2,4-triazol-1-yl)-2-phenylacrylamide |
| 147 | 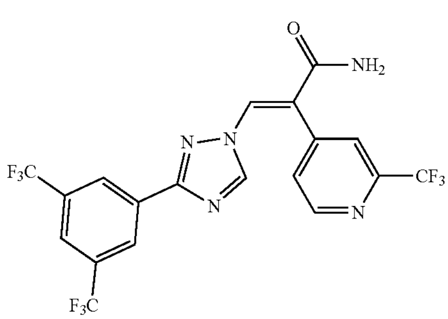 [SMILES: NC(=O)/C(=C/n1cnc(-c2cc(C(F)(F)F)cc(C(F)(F)F)c2)n1)c1ccnc(C(F)(F)F)c1] | A | B | A | B | (E)-3-(3-(3,5-bis-(trifluoromethyl)-phenyl)-1H-1,2,4-triazol-1-yl)-2-(2-(trifluoromethyl)-pyridin-4-yl)-acrylamide |

TABLE 1-continued

Assay Results for Exemplary Compounds (A = <100 nM; B = 100 nM to <5 μM; C = 5 μM to 30 μM; D = >30 μM; NT = Not tested).

| Cmpd. No. | Structure | RevGFP | MTT (Z138) | MTT (MM1S) | MTT (3T3) | Name |
|---|---|---|---|---|---|---|
| 148 | 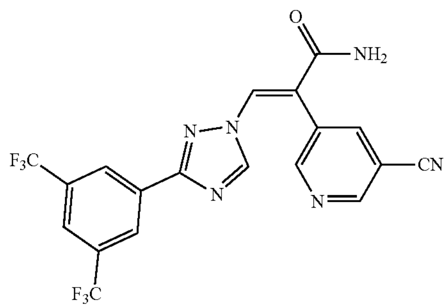 [SMILES: N#Cc1cncc(/C(=C\n2cnc(-c3cc(C(F)(F)F)cc(C(F)(F)F)c3)n2)C(N)=O)c1] | A | A | A | D | (E)-3-(3-(3,5-bis-(trifluoromethyl)-phenyl)-1H-1,2,4-triazol-1-yl)-2-(5-cyanopyridin-3-yl)acrylamide |
| 149 | 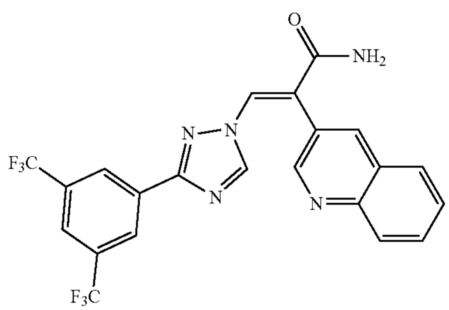 [SMILES: NC(=O)/C(=C/n1cnc(-c2cc(C(F)(F)F)cc(C(F)(F)F)c2)n1)c1cnc2ccccc2c1] | A | A | A | D | (E)-3-(3-(3,5-bis-(trifluoromethyl)-phenyl)-1H-1,2,4-triazol-1-yl)-2-(quinolin-3-yl)-acrylamide |
| 150 | 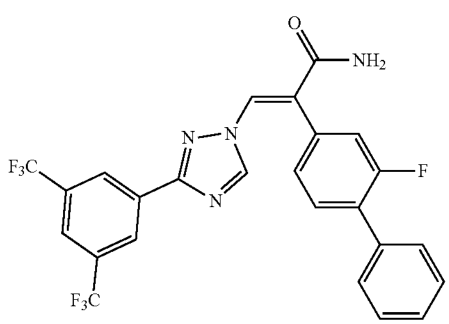 [SMILES: NC(=O)/C(=C/n1cnc(-c2cc(C(F)(F)F)cc(C(F)(F)F)c2)n1)c1ccc(-c2ccccc2)c(F)c1] | NT | C | C | D | (E)-3-(3-(3,5-bis-(trifluoromethyl)-phenyl)-1H-1,2,4-triazol-1-yl)-2-(2-fluorobiphenyl-4-yl)acrylamide |
| 151 | 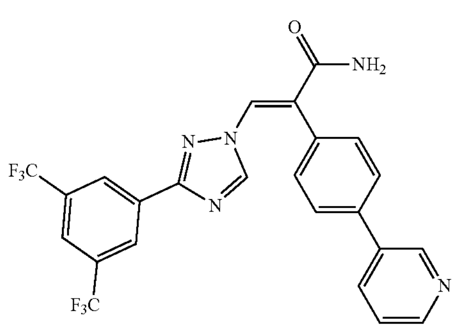 [SMILES: NC(=O)/C(=C/n1cnc(-c2cc(C(F)(F)F)cc(C(F)(F)F)c2)n1)c1ccc(-c2cccnc2)cc1] | NT | C | B | D | (E)-3-(3-(3,5-bis-(trifluoromethyl)-phenyl)-1H-1,2,4-triazol-1-yl)-2-(4-(pyridin-3-yl)-phenyl)acrylamide |

TABLE 1-continued

Assay Results for Exemplary Compounds (A = <100 nM; B = 100 nM to <5 µM; C = 5 µM to 30 µM; D = >30 µM; NT = Not tested).

| Cmpd. No. | Structure | RevGFP | MTT (Z138) | MTT (MM1S) | MTT (3T3) | Name |
|---|---|---|---|---|---|---|
| 152 | 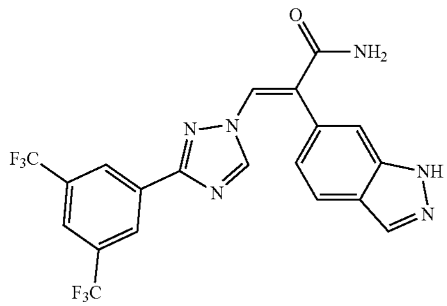 [SMILES: NC(=O)/C(=C/n1cnc(-c2cc(C(F)(F)F)cc(C(F)(F)F)c2)n1)c1ccc2cn[nH]c2c1] | NT | B | B | D | (E)-3-(3-(3,5-bis-(trifluoromethyl)-phenyl)-1H-1,2,4-triazol-1-yl)-2-(1H-indazol-6-yl)acryl-amide |
| 153 | 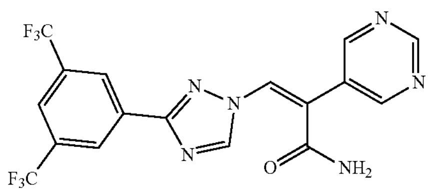 [SMILES: NC(=O)/C(=C\n1cnc(-c2cc(C(F)(F)F)cc(C(F)(F)F)c2)n1)c1cncnc1] | NT | B | A | D | (Z)-3-(3-(3,5-bis-(trifluoromethyl)-phenyl)-1H-1,2,4-triazol-1-yl)-2-(pyrimidin-5-yl)-acrylamide |
| 154 | 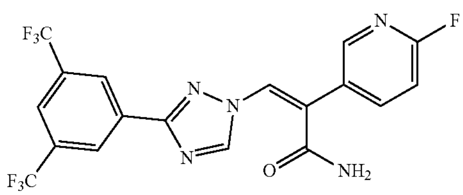 [SMILES: NC(=O)/C(=C\n1cnc(-c2cc(C(F)(F)F)cc(C(F)(F)F)c2)n1)c1ccc(F)nc1] | NT | NT | B | NT | (Z)-3-(3-(3,5-bis-(trifluoromethyl)-phenyl)-1H-1,2,4-triazol-1-yl)-2-(6-fluoropyridin-3-yl)acrylamide |
| 155 | 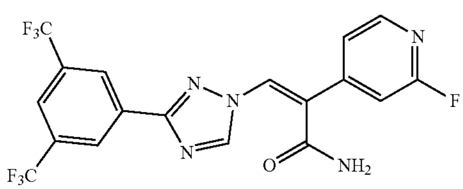 [SMILES: NC(=O)/C(=C\n1cnc(-c2cc(C(F)(F)F)cc(C(F)(F)F)c2)n1)c1ccnc(F)c1] | A | A | A | B | (Z)-3-(3-(3,5-bis-(trifluoromethyl)-phenyl)-1H-1,2,4-triazol-1-yl)-2-(2-fluoropyridin-4-yl)acrylamide |
| 156 | 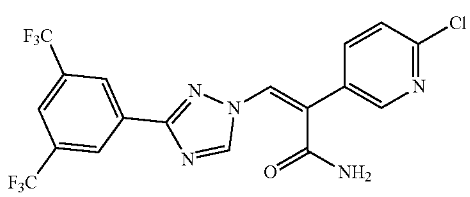 [SMILES: NC(=O)/C(=C\n1cnc(-c2cc(C(F)(F)F)cc(C(F)(F)F)c2)n1)c1ccc(Cl)nc1] | B | B | B | D | (Z)-3-(3-(3,5-bis-(trifluoromethyl)-phenyl)-1H-1,2,4-triazol-1-yl)-2-(6-chloropyridin-3-yl)acrylamide |
| 157 | 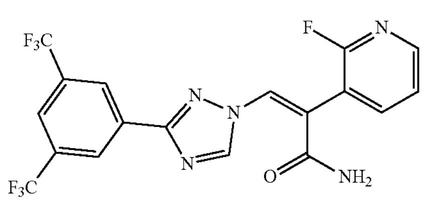 [SMILES: NC(=O)/C(=C\n1cnc(-c2cc(C(F)(F)F)cc(C(F)(F)F)c2)n1)c1cccnc1F] | NT | B | B | B | (Z)-3-(3-(3,5-bis-(trifluoromethyl)-phenyl)-1H-1,2,4-triazol-1-yl)-2-(2-fluoropyridin-3-yl)acrylamide |

Compound 124 was further tested against a panel of selected solid and hematological cancer cell lines and selected normal cell lines in an MTT assay. Briefly, the various cell lines above were plated at different densities on day 1. After 24 hours of growth, cells were treated with dose curves (10 µM start with 1:3 dilutions) of Compound 124 in duplicate rows. Cells and Compound 124 were incubated in a 37° C. incubator for 72 hours. Cell Titer AQueous One was added to each well, and the plates were read in a plate reader at OD 495.

Hematological cancer cell lines tested included MOLT-4, Z-138, THP1, MO7E, OCIAML-5, AML-193, Daudi, Toledo, TF-1, Farage, Pfieffer, MV-4-11, MINO, HEL.92.1.7, KG-1, BL-2, MM1R, HS-Sultan, RL, U-937, DB, BL-40, U-266 and ANBL-6. Solid cancer cell lines tested included PATU-8902, SK-CO-1, NCI-H2170, PL-45, NCI-H1650, TFK-1, NCI-H520, RKO, U118 MG, HeLa, HuCCT-1, CAPAN-1, NCI-H889, NCI-H187, L3.6p1, HEP 3B, MS751, NCI-H69, AU-565, SHSY5Y, Tera-1, SW-620, PC3, LS-180, SW-48, NCI-H1299, Colo-205, NCI-H28, HT1080, SHP-77, MSTO-211H, LoVo, HCT-15, NCI-H2030, Calu-6, Calu-3, SW-403, HPAC, NCI-H1563, PATU-8988T, PATU-8988S, HPAF-II, Colo-201, NCI-H747, SW-837, HCC-4006, NCI-H358, HCC-827, PANC-10.05, SW-948, SW-480, SW-1417, DLD-1, SW-1116, MDA-MB-231, NCI-H508, MCF7, LN-18, NCI-H820, HCC-2935, SNU-398, NCI-H2122, NCI-H226, LS-174T, HCT116, MDA-MB-361, SW-900, NCI-H1993, HCT116.1, C6, MHCC97H and SKOV3. Normal cell lines tested included IMR-90 and 3T3. The results of further testing of Compound 124 are reported in Table 2.

TABLE 2

| Cell line | Cmpd 124 (uM) |
|---|---|
| Z-138MTT | 0.006 |
| MM1RMTT | 0.008 |
| DaudiMTT | 0.008 |
| MOLT4MTT | 0.01 |
| HCC-4006MTT | 0.02 |
| MINOMTT | 0.02 |
| MO7eMTT | 0.02 |
| RLMTT | 0.02 |
| CAPAN-1MTT | 0.02 |
| NCI-H226MTT | 0.03 |
| BL-2MTT | 0.03 |
| OCIAML5MTT | 0.04 |
| SHSY5YMTT | 0.05 |
| NCI-H1299MTT | 0.05 |
| HuCCT-1MTT | 0.05 |
| DBMTT | 0.06 |
| HS-SultanMTT | 0.06 |
| MSTO-211HMTT | 0.07 |
| ToledoMTT | 0.07 |
| NCI-H747MTT | 0.07 |
| KG-1MTT | 0.09 |
| MV-4-11MTT | 0.1 |
| HCT116MTT | 0.11 |
| TF-1MTT | 0.11 |
| MDA-MB-231MTT | 0.12 |
| Colo-205MTT | 0.12 |
| SW-48MTT | 0.12 |
| PfiefferMTT | 0.14 |
| Tera-1MTT | 0.15 |
| C6MTT | 0.15 |
| HCT116.1MTT | 0.2 |
| ANBL-6MTT | 0.22 |
| U-266MTT | 0.23 |
| HEL.92.1.7MTT | 0.23 |
| U-937MTT | 0.25 |
| HEP3BMTT | 0.3 |
| HT1080MTT | 0.31 |
| NCI-H28MTT | 0.34 |
| U118MGMTT | 0.37 |
| MS751MTT | 0.4 |
| BL-40MTT | 0.4 |
| SHP-77MTT | 0.41 |
| SW-1116MTT | 0.41 |
| PATU-8902MTT | 0.41 |
| NCI-H358MTT | 0.42 |
| SW-620MTT | 0.42 |
| SK-CO-1MTT | 0.43 |
| RKOMTT | 0.45 |
| HCC-827MTT | 0.46 |
| FarageMTT | 0.46 |
| HCT-15MTT | 0.46 |
| L3.6p1MTT | 0.47 |
| AU-565MTT | 0.49 |
| SW-837MTT | 0.5 |
| NCI-H187MTT | 0.53 |

TABLE 2-continued

| Cell line | Cmpd 124 (uM) |
|---|---|
| MCF7MTT | 0.68 |
| LoVoMTT | 0.68 |
| DLD-1MTT | 0.8 |
| NCI-H2122MTT | 0.84 |
| NCI-H508MTT | 0.86 |
| SW-403MTT | 0.91 |
| SNU-398MTT | 0.97 |
| PANC-10.05MTT | 0.99 |
| NCI-H889MTT | 1.02 |
| HeLaMTT | 1.05 |
| 3T3MTT | 1.1 |
| Calu-6MTT | 1.27 |
| NCI-H520MTT | 1.3 |
| Calu-3MTT | 1.38 |
| NCI-H69MTT | 1.64 |
| SW-900MTT | 1.85 |
| AML-193MTT | 1.93 |
| NCI-H2030MTT | 2.05 |
| LN18MTT | 2.06 |
| NCI-H2170MTT | 2.14 |
| THP1MTT | 3.38 |
| NCI-H820MTT | 3.4 |
| HCC-2935MTT | 6.7 |
| PL-45MTT | 6.94 |
| PATU-8988TMTT | 7.17 |
| NCI-H1563MTT | 7.82 |
| SW-480MTT | 10 |
| LS-174TMTT | 10 |
| PATU-8988SMTT | 10 |
| HPACMTT | 10 |
| NCI-H1650MTT | >10 |
| NCI-H1993MTT | >10 |
| IMR-90MTT | >10 |
| MDA-MB-361MTT | >10 |
| MHCC97HMTT | >10 |
| TFK-1MTT | >10 |
| SKOV3MTT | >10 |
| Colo-201MTT | >10 |
| SW-948MTT | >10 |
| SW-1417MTT | >10 |
| HTB-38MTT | >10 |
| LS-180MTT | >10 |
| HPAF-IIMTT | >10 |

Cys 528 Mutation Assay

U2OS (osteosarcoma) cells stably expressing GFP-tagged HIV-Rev fused to the cAMP-dependent protein kinase inhibitor (PM) nuclear export signal (Rev-GFP) were transiently transfected with constructs expressing wild-type CRM1 or mutant CRM1-Cys528Ser for 36 hours. The transient transfection efficiency in the experiment was estimated to be 50%. When Rev-GFP and wild-type CRM1 were co-expressed in the cells and the cells were treated with 30 μM Compound 124 for 4 hours, Rev-GFP was localized to the cell nucleus and nucleolus. However, when Rev-GFP and mutant CRM-Cys528Ser were co-expressed in cells, treatment of the cells with 30 μM Compound 124 did not induce nuclear localization of Rev-GFP. The 30 μM Compound 124 treatment was chosen to maximize drug exposure on the transfected cells. These results demonstrate the importance of Cys528 for CRM1 inhibition by Compound 124.

Washout Assay

U2OS cells stably expressing a green fluorescent protein-tagged HIV-Rev fused to the cAMP-dependent PM nuclear export signal (Rev-GFP) were used to evaluate the level of CRM1 inhibition and the resulting IC50 of Compound 124 with or without washing the compound out after treatment. Three 96-well plates of U2OS Rev-GFP cells were treated with Compound 124 (that had been serially diluted 1:3 starting at 10 μM) or DMSO for 4 hours. After 4 hours, one of the plates was fixed with PFA (no washout, condition A). Media was removed from the other two plates, and the cells were washed twice with fresh media and incubated further in media that did not contain Compound 124. A second plate was fixed with PFA after a 4 hour washout (4 hr washout, condition B) and a third plate was fixed with PFA after a 24 hour washout (24 h washout, condition C). Cells were counterstained with the nuclear dye DAPI. The $IC_{50}$s of Compound 124 under condition A, condition B and condition C were determined, and are reported in Table 3. Table 3 shows that Compound 124 is still very effective following a 4 hour washout, and decreases only 6-fold after a 24 hour washout. These results confirm that Compound 124 covalently binds to XPO1.

TABLE 3

| | Condition A 4 h treatment + no washout | Condition B 4 h treatment + 4 h washout | Condition C 4 h treatment + 24 h washout |
|---|---|---|---|
| Compound 124 $IC_{50}$ | 51 nM | 57 nM | 310 nM |

XPO1 Cargo Localization Assay

U2OS cells were treated with 500 nM Compound 124 for 4 to 24 hours and either fixed with 100% ice-cold methanol (MeOH) and permeabilized/blocked with 0.1% Tween 20, 0.3 M glycine, and 1% BSA in PBS or fixed with PFA (3% paraformaldehyde and 2% sucrose in PBS) and permeabilized/blocked with 0.1% Triton-X100 and 1% BSA in PBS. The fixed cells were analyzed by immunofluorescence (IF) for the nuclear localization of the following XPO1 cargo proteins: p53, IκB, Foxo1A, PP2A, p21 and p27. Nuclei were stained with DAPI. Images were taken at 20× magnification. The images of cells treated with Compound 124 showed increased or complete nuclear localization of XPO1 cargoes.

XPO1 Degradation Assay

HT1080 (fibrosarcoma) cells were treated with five different concentrations of Compound 124 for 24 hours. Western blot analysis of cellular lysates of the treated cells was used to determine the protein expression of XPO1. Beta-actin was used as a loading control. FIG. 1 is an image of a Western blot obtained from this experiment, and shows that Compound 124 degraded XPO1 in a dose-dependent manner.

Example 3. Collagen Antibody-Induced Arthritis (CAIA) Mouse Model

Compound 124 was evaluated in an anti-collagen antibody-induced mouse model of rheumatoid arthritis. Specifically, twenty-four (24) male Balb/c mice, aged 6 to 7 weeks, were randomly assigned to 3 groups that would receive vehicle, Compound 124 at 20 mg/kg or Compound 124 at 40 mg/kg. On study Day 0 (study commencement), all mice were subjected to a 4 mg intravenous injection of ArthritoMAb™ antibody cocktail (MD Biosciences #51306001), followed by an intraperitoneal injection of LPS (50 μg/mouse) on study Day 3. The mice began treatment on Day 6, when the average clinical scores reached 2. Treatment with Compound 124 was given PO, twice a week (Mondays and Wednesdays) up until Day 17.

The animals were examined for signs of arthritis on study Day 0 in all paws (front left and right paws, hind left and right paws). The signs of arthritis on study Day 0 served as a baseline for the arthritis clinical score parameter. Arthritic responses were examined daily from Day 3 until Day 8, and on Days 10, 12, 15 and 18 (study termination). Arthritis reactions were reported for each paw according to a 0-4 scale in ascending order of severity as shown in Table 4.

TABLE 4

Arthritis clinical score

| Arthritis Score | Grade |
|---|---|
| No reaction, normal | 0 |
| Mild, but definite redness and swelling of the ankle/ wrist or apparent redness and swelling limited to individual digits, regardless of the number of affected digits | 1 |
| Moderate to severe redness and swelling of the ankle/wrist | 2 |
| Redness and swelling of the entire paw including digits | 3 |
| Maximally inflamed limb with involvement of multiple joints | 4 |

Clinical signs data are presented as means±SEM (standard error of the mean). Treatment groups 2-3 were compared to vehicle group 1 using one-way ANOVA test followed by Tukey post-test. A p value of <0.05 is considered to represent a significant difference.

On study Day 6, 88% of the animals treated with vehicle showed clinical signs of arthritis. At the end of the study, this value decreased to 75%. The percentage of animals that showed clinical signs of arthritis and were treated with Compound 124 at a dose of 20 mg/kg was reduced from 78% on study Day 6 to 22% on study Day 18. The percentage of animals that showed clinical signs of arthritis and were treated with Compound 124 at a dose of 40 mg/kg was reduced from 88% on study Day 6 to 13% on study Day 18.

Figure 2:
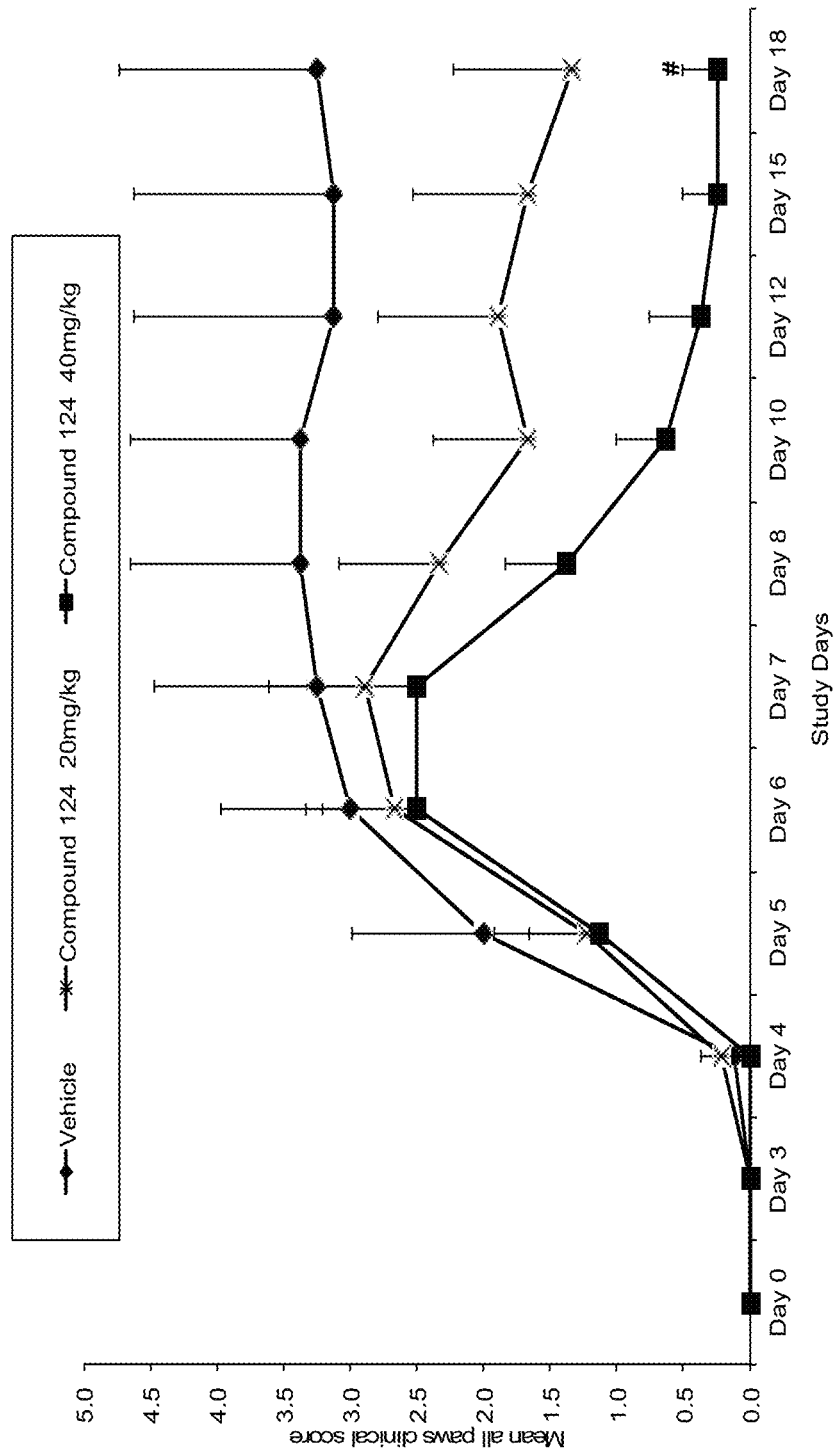
FIG. 2 is a graph of mean clinical score for all paws in the CAIA mouse model of rheumatoid arthritis described in Example 3 as a function of study day, and shows the effect of treatment with vehicle only and Compound 124 on mean clinical scores for all paws of mice in the study.

FIG. 2 is a graph of mean clinical score for all paws in the CAIA mouse model of rheumatoid arthritis as a function of study day. FIG. 1 shows that treatment with Compound 124 reduced arthritis scores of mice in the study compared to vehicle treatment.

In conclusion, treatment with 20 mg/kg or 40 mg/kg Compound 124 reduced the number of animals expressing disease, as well as the arthritis scores of the animals in this study.

Example 4. Xenograft Models

Compound 124 and Compound 149 were evaluated in several xenograft models in mice.

The oncological impact of Compound 124 and Compound 149 was evaluated using an MDA-MB-468 (triple negative breast cancer) xenograft model in CB-17 SCID mice. MDA-MB-468 (ATCC #HTB-102) breast adenocarcinoma cells were obtained from ATCC. These cells were grown in high glucose DMEM medium supplemented with 10% fetal bovine serum, 1% penicillin and streptomycin, and 2 mM L-Glutamine. Cells were sub-cultured by dilution at a ratio of 1:4. MDA-MB-468 cells were harvested by trypsinization and counted using a hemocytometer. Cells were resuspended in PBS at a concentration of $4 \times 10^8$ cells per mL. Cells were placed on ice and mixed with an equal volume of Matrigel (BD Biosciences CB-40234). Twenty-two (22) CB-17 SCID mice were inoculated sub-cutaneously in the left flank with $4 \times 10^7$ MDA-MB-468 cells. Treatment was initiated when the tumors reached a mean volume of ~100 mm³. Mice were allocated to three (3)

groups of eight (8) mice for the vehicle and seven (7) mice for each treatment group—Compound 124 and Compound 149—such that mean tumor volume was ~100 mm$^3$ in each group. Mice were treated with vehicle, Compound 124 or Compound 149. Compound 124 (10 mg/kg) and Compound 149 (10 mg/kg) were given orally (PO) once daily every day of the week. Animals' weights and condition were recorded daily, and tumors were measured on Mondays, Wednesdays, and Fridays.

Figure 3A:
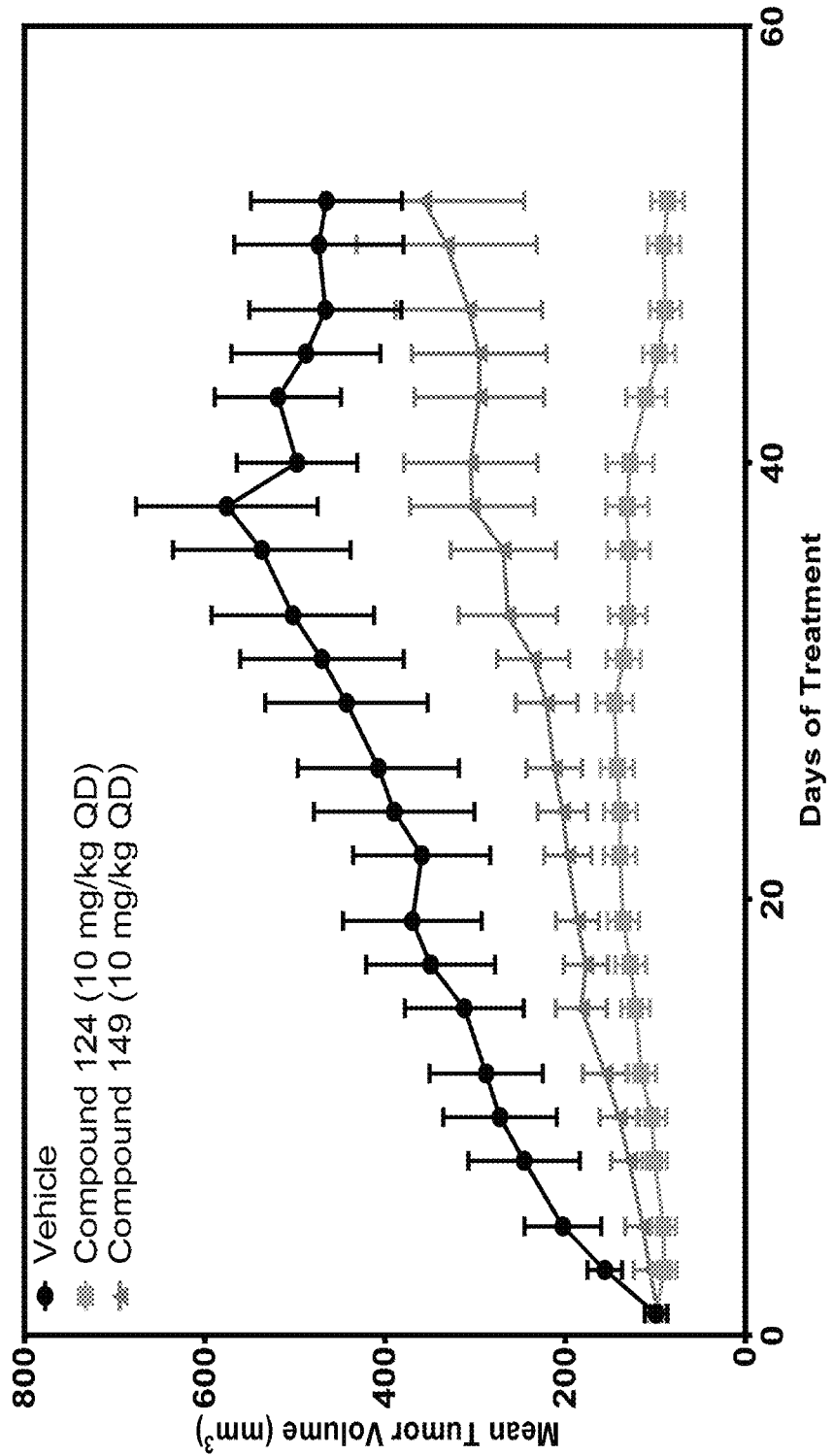
FIG. 3A is a graph of mean tumor volume as a function of time, and shows the effects of treatment with Compound 124 or Compound 149 on mean tumor volume in mice bearing MDA-MB-468 xenografts.

FIG. 3A is a graph of mean tumor volume as a function of time, and shows that mean tumor volume was reduced in mice bearing an MDA-MB-468 xenograft and treated with Compound 124 or Compound 149 compared to mice bearing an MDA-MB-468 xenograft and treated with vehicle.

In another study, the impact of Compound 124 on tumor growth was tested using a Z-138 mantle cell lymphoma cancer xenograft model in SCID mice. Z-138 (ATCC #CRL-3001) mantle cell lymphoma cells were obtained from ATCC. These cells were grown in IMEM medium supplemented with 10% horse serum, 1% penicillin and streptomycin, and 2 mM L-glutamine. Cells were sub-cultured by dilution at a ratio of 1:5 to 1:10. Z-138 cells were harvested by centrifugation and counted using a hemocytometer. Cells were resuspended in PBS at a concentration of 2×10$^8$ cells per mL. Cells were placed on ice and mixed with an equal volume of Matrigel (BD Biosciences CB-40234). This mixture was kept on ice and injected into the left flank of mice in a volume of 0.2 mL, equivalent to 2×10$^7$ cells per mouse. Thirty-two (32) CB-17 SCID mice were inoculated subcutaneously in the left flank with 2×10$^7$ Z-138 cells. Treatment was initiated when the tumors reached a mean volume of 125.2 mm$^3$. Mice were allocated to four (4) groups of eight (8) mice such that mean tumor volume in each group was within the range of 106.5 to 138.8 mm$^3$. Mice were treated with vehicle, standard of care/positive control drug (cyclophosphamide) or Compound 124 (5 mg/kg or 15 mg/kg). Compound 124 (5 or 15 mg/kg) was given orally (PO) daily beginning on Day 1. Animal weights and conditions were recorded daily, and tumors were measured on Mondays, Wednesdays and Fridays.

Figure 3B:
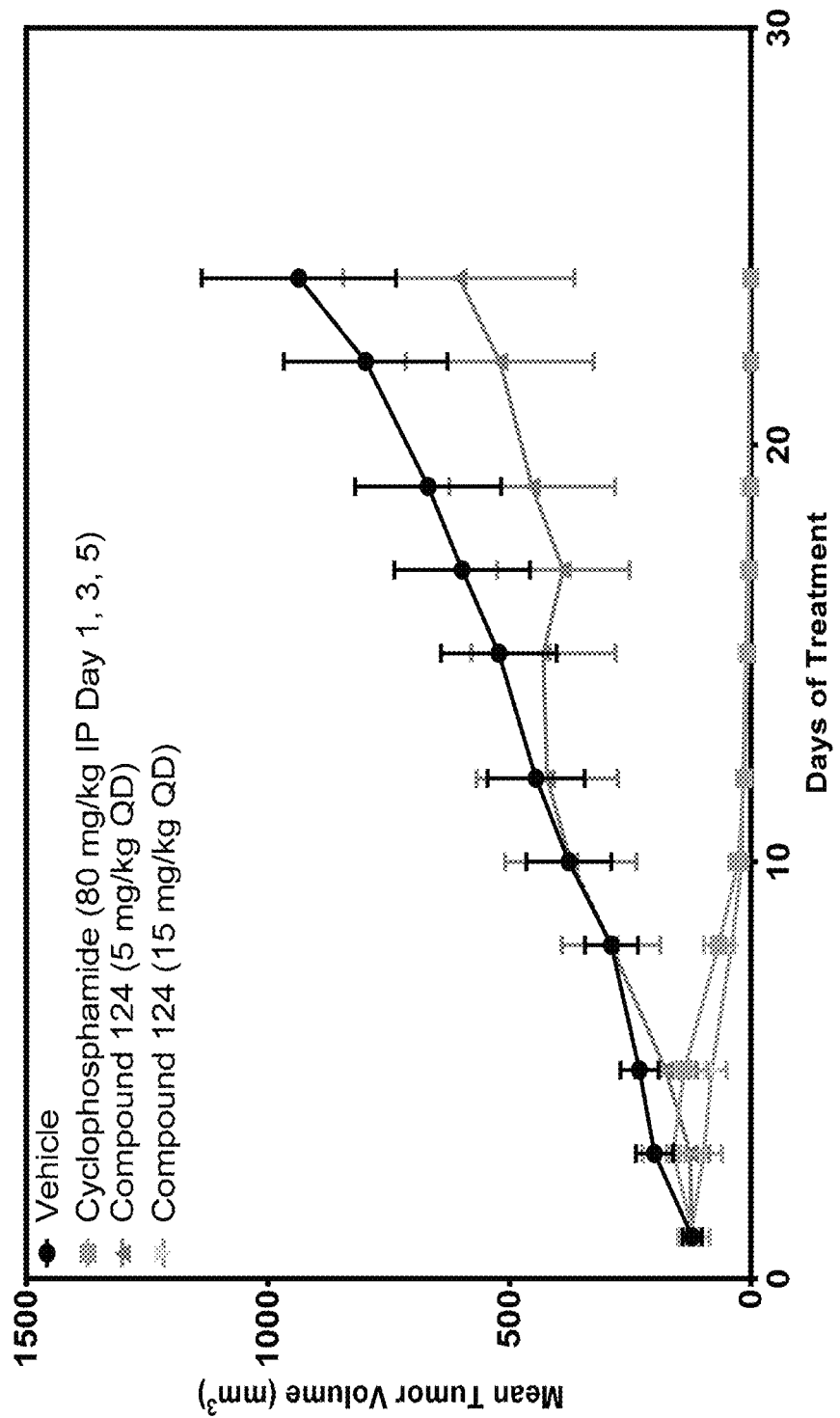
FIG. 3B is a graph of mean tumor volume as a function of time, and shows the effects of treatment with Compound 124 (5 mg/kg or 15 mg/kg) or cyclophosphamide on mean tumor volume in mice bearing Z-138 xenografts.

FIG. 3B is a graph of mean tumor volume as a function of time, and shows that mean tumor volume was reduced in mice bearing a Z-138 xenograft and treated with Compound 124 compared to mice bearing a Z-138 xenograft and treated with vehicle. Results obtained from the 15 mg/kg dose of Compound 124, in particular, compared favorably with the results obtained using cyclophosphamide.

In yet another study, the effects of Compound 124 on tumor growth were evaluated using a Hep3B hepatocellular carcinoma xenograft model in SCID mice. Hep 3B cells (ATCC #HTB-8064) hepatocellular carcinoma cells were obtained from ATCC. These cells were grown in DMEM medium supplemented with 10% fetal bovine serum, 1% penicillin and streptomycin. Cells were sub-cultured by dilution at a ratio of 1:4. Hep3B cells were harvested by centrifugation and counted using a hemocytometer. Cells were resuspended in PBS at a concentration of 5×10$^7$ cells per mL. Cells were placed on ice, and then mixed with an equal volume of Matrigel™ (BD Biosciences CB-40234). This mixture was kept on ice and injected into the left flank of mice in a volume of 0.2 mL, equivalent to 5×10$^6$ cells per mouse. Thirty-two (32) SCID mice were inoculated subcutaneously in the left flank with 5×10$^6$ Hep 3B cells. Treatment was initiated when the tumors reached a mean volume of 103.7 mm$^3$ (standard deviation±30 mm$^3$, range 17-183 mm$^3$). Mice were allocated to four (4) groups of eight (8) mice such that mean tumor volume in each group was within the range of 95 to 104 mm$^3$. Mice were treated with vehicle, standard of care control (doxorubicin), or Compound 124 (5 mg/kg or 15 mg/kg). With the exception of doxorubicin (which was given IP), all compounds were given by oral gavage. Compound 124 (5 or 15 mg/kg) was given orally (PO) daily. Animal weights and conditions were recorded daily, and tumors were measured on Mondays, Wednesdays and Fridays.

Figure 3C:
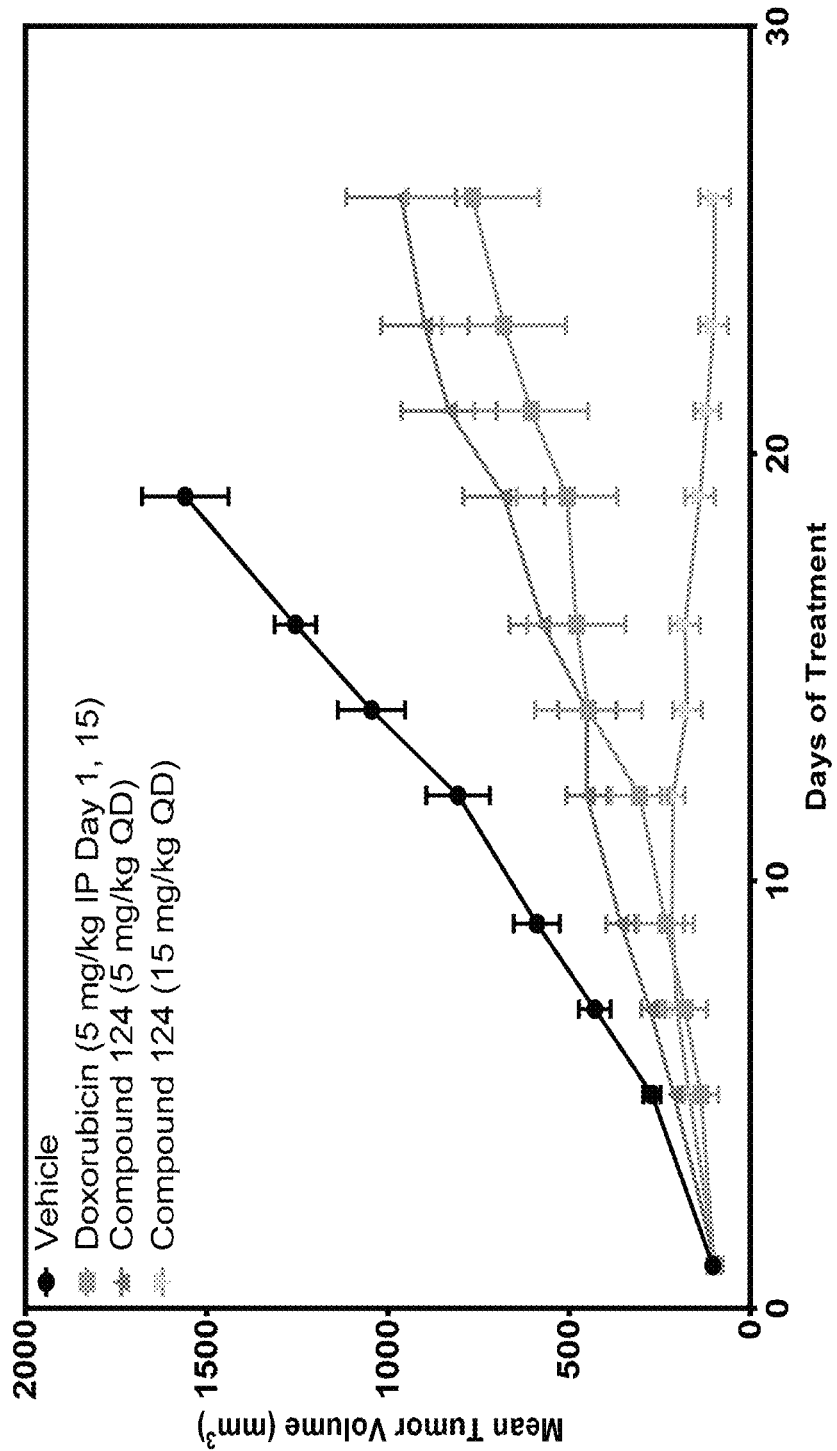
FIG. 3C is a graph of mean tumor volume as a function of time, and shows the effects of treatment with Compound 124 (5 mg/kg or 15 mg/kg) or doxorubicin on mean tumor volume in mice bearing Hep 3B xenografts.

FIG. 3C is a graph of mean tumor volume as a function of time, and shows that mean tumor volume was reduced in mice bearing a Hep 3B xenograft and treated with Compound 124 compared to mice bearing a Hep 3B xenograft and treated with vehicle. The results obtained from treatment with Compound 124, particularly the 15 mg/kg dose of Compound 124, compared favorably with the results obtained using doxorubicin.

In another study, the effects of Compound 124 on tumor growth were evaluated using a COLO 205 colorectal carcinoma xenograft model in SCID mice. COLO 205 (CCL-222) colorectal cancer cells were obtained from ATCC. These cells were grown in RPMI-1640 medium supplemented with 10% fetal bovine serum, 1% penicillin and streptomycin. Cells were sub-cultured by transferring floating cells to a new flask and trypsinizing adherent cells before sub-culturing at a ratio of 1:4. COLO 205 cells were harvested by centrifugation and counted using a hemocytometer. Cells were resuspended in PBS at a concentration of 5×10$^7$ cells per mL. Cells were placed on ice, and then mixed with an equal volume of Matrigel™ (BD Biosciences CB-40234). This mixture was kept on ice and injected into the left flank of mice in a volume of 0.2 mL, equivalent to 5×10$^6$ cells per mouse. Thirty-two (32) SCID mice were inoculated subcutaneously in the left flank with 5×10$^6$ COLO 205 cells. Treatment was initiated when the tumors reached a mean volume of 103.7 mm$^3$ (standard deviation±30 mm$^3$, range 17-183 mm$^3$). Mice were allocated to four (4) groups of eight (8) mice such that mean tumor volume in each group was within the range of 95 to 104 mm$^3$. Mice were treated with vehicle, standard of care control (5-FU, 5-fluorouracil) and Compound 124 (5 mg/kg or 15 mg/kg). With the exception of 5-FU (which was given IP on days 1 and 3), all compounds were given by oral gavage. Compound 124 (5 or 15 mg/kg) was given orally (PO) daily. Animal weights and conditions were recorded daily, and tumors were measured on Mondays, Wednesdays and Fridays.

Figure 3D:
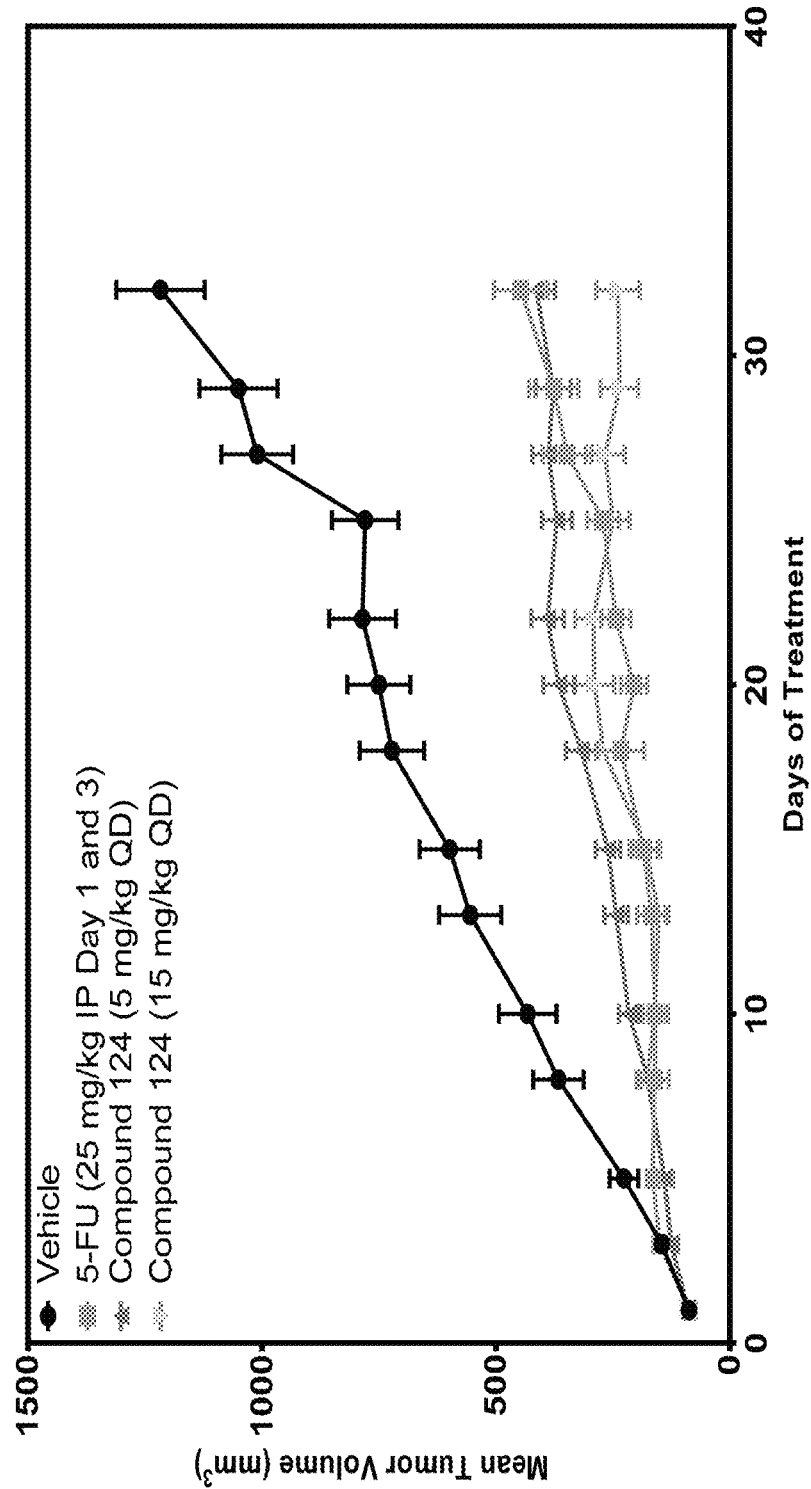
FIG. 3D is a graph of mean tumor volume as a function of time, and shows the effects of treatment with Compound 124 (5 mg/kg or 15 mg/kg) or 5-FU on mean tumor volume in mice bearing COLO 205 xenografts.

FIG. 3D is a graph of mean tumor volume as a function of time, and shows that mean tumor volume was reduced in mice bearing a COLO 205 xenograft and treated with Compound 124 compared to mice bearing a COLO 205 xenograft and treated with vehicle. The results obtained from treatment with Compound 124, particularly the 15 mg/kg dose of Compound 124, compared favorably with the results obtained using 5-FU.

In another study, the effects of Compound 124 on tumor growth were evaluated using a MOLT 4 acute lymphoblastic leukemia xenograft model in SCID mice. MOLT 4 (CRL-1582) acute lymphoblastic leukemia cells were obtained from ATCC. These cells were grown in RPMI-1640 medium supplemented with 10% fetal bovine serum, 1% penicillin and streptomycin. Cells were sub-cultured by transferring floating cells to a new flask and trypsinizing adherent cells before subculturing at a ratio of 1:4. MOLT 4 cells were harvested by centrifugation and counted using a hemocytometer. Cells were resuspended in PBS at a concentration of 5×10$^7$ cells per mL. Cells were placed on ice, and then mixed with an equal volume of Matrigel™ (BD Biosciences CB-40234). This mixture was kept on ice and injected into the left flank of mice in a volume of 0.2 mL, equivalent to 5×10$^6$ cells per mouse. Thirty-two (32) SCID mice were inoculated subcutaneously in the left flank with 5×10$^6$ MOLT 4 cells. Treatment was initiated when the tumors reached a mean volume of 106.5 mm$^3$ (standard deviation±33.9 mm$^3$, CV 31.9%, range 43-181 mm$^3$). Mice were allocated to four (4) groups of eight (8) mice, one group of 5 mice and one group of four mice, such that mean tumor volume in each group was within the range of 102 to 111 mm$^3$. Mice were treated with vehicle, standard of care control (doxorubicin 5 mg/kg IP Days 1 and 15) or Compound 124 (5 mg/kg or 15 mg/kg). With the exception of doxorubicin (which was given IP), all compounds were given by oral gavage. Compound 124 (5 or 15 mg/kg) was given orally (PO) daily. Animal weights and conditions were recorded daily, and tumors were measured on Mondays, Wednesdays and Fridays.

Figure 3E:
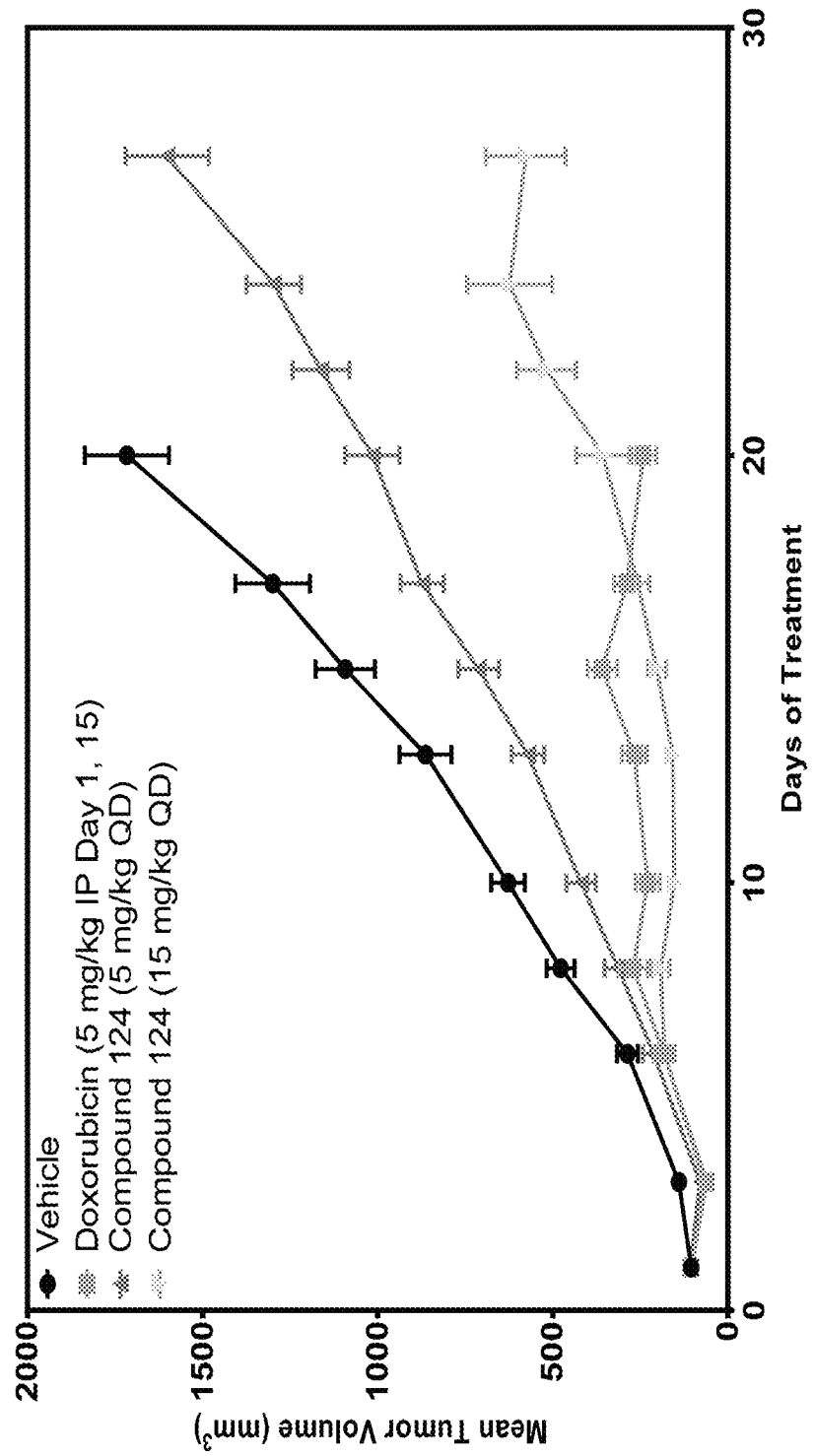
FIG. 3E is a graph of mean tumor volume as a function of time, and shows the effects of treatment with Compound 124 (5 mg/kg or 15 mg/kg) or doxorubicin on mean tumor volume in mice bearing MOLT 4 xenografts.

FIG. 3E is a graph of mean tumor volume as a function of time, and shows that mean tumor volume was reduced in mice bearing a MOLT 4 xenograft and treated with Compound 124 compared to mice bearing a MOLT 4 xenograft and treated with vehicle.

Example 5. Glioblastoma

Cells (U87MG and U251MG) were detached and re-suspended at 1×10$^5$ cells/mL. 5,000 cells were loaded into a hanging drop plate (3D Biomatrix Cat. No.: HDP1096) and incubated for 5 days (37° C.; 5% CO$_2$) to form spheroids. 300 μL of Matrix Gel (Corning Matrigel Cat #354234; Lot #3330622) were plated per well in a 24-well plate and incubated for 30 minutes. Spheroids were removed from the hanging drop plate and seeded into the MATRIGEL™ (1 spheroid per well). Spheroids were incubated for 15 minutes and then 460 μL media was added. After overnight incubation of the spheroids, 1 μM Compound 124 was added to a final volume of 1 mL/well. The plates were analyzed at several time points using 40× and 20× phase microscopes, and photos of the spheroids were taken.

Figure 4:
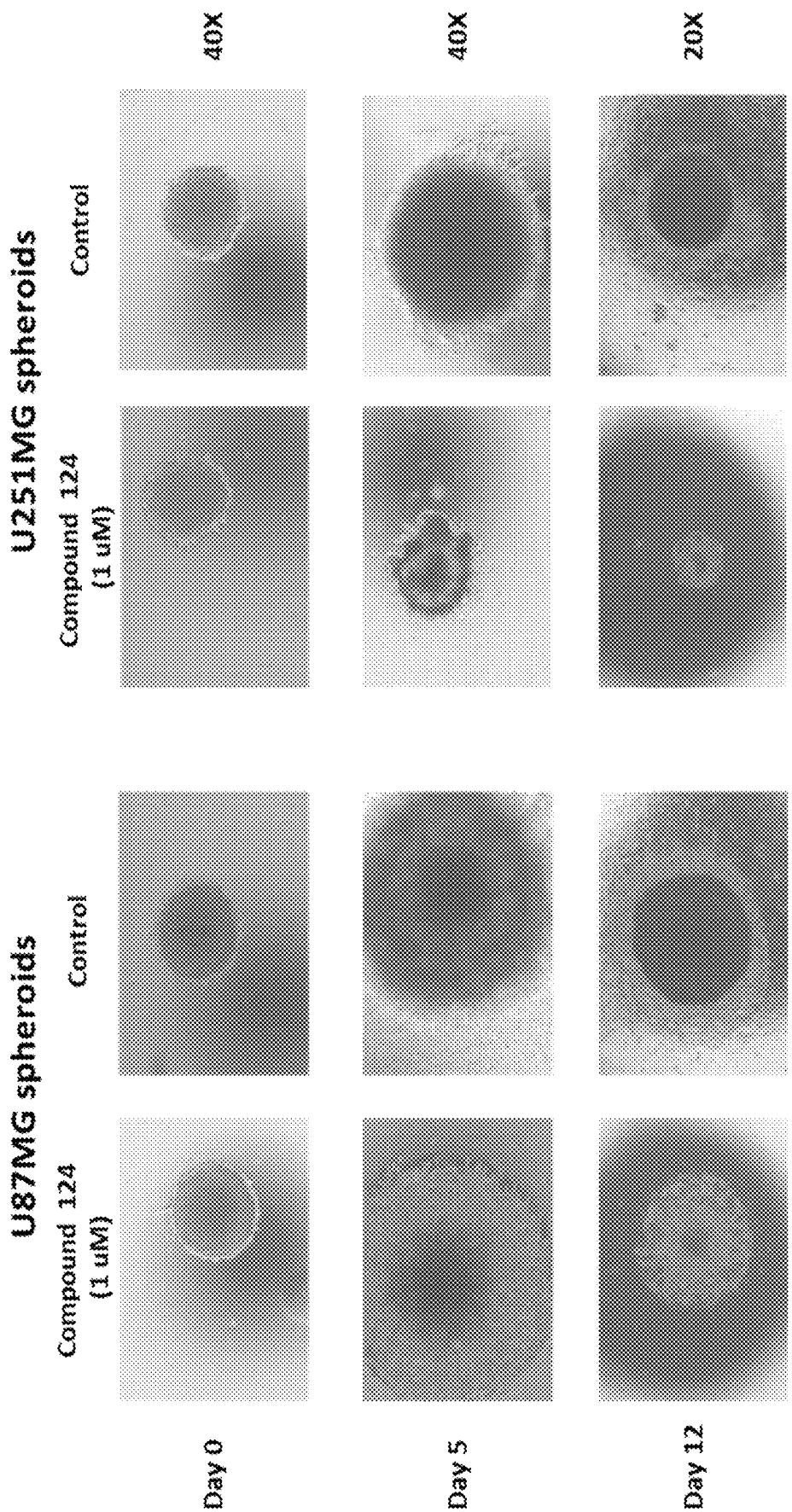
FIG. 4 are images of U87MG and U251MG control spheroids and U87MG and U251MG spheroids treated with 1 μM Compound 124, and shows the effects of treatment with Compound 124 on two glioblastoma cell lines.

FIG. 4 are images of U87MG and U251MG control spheroids and U87MG and U251MG spheroids treated with 1 μM Compound 124, and shows the effects of treatment with Compound 124 on two glioblastoma cell lines. The U87MG spheroids treated with Compound 124 (1 μM) demonstrated a significant reduction in cell growth as compared with the control, without showing any spreading or growth of the cells out of the sphere. In the U251 spheroids treated with Compound 124, however, in addition to the significant reduction in cell growth as compared with the control, shrinking of the spheroid with complete elimination of any cell growth out of the sphere was noted. Based on microscopic analysis, complete destruction of these cells was observed.

BIBLIOGRAPHY

Cronshaw J M and Matunis M J. 2004. The nuclear pore complex: disease associations and functional correlations TRENDS Endocrin Metab. 15:34-39

Falini B et al. 2006. Both carboxy-terminus NES motif and mutated tryptophan(s) are crucial for aberrant nuclear export of nucleophosmin leukemic mutants in NPMc+ AML Blood. 107:4514-4523.

Cai X and Liu X. 2008. Inhibition of Thr-55 phosphorylation restores p53 nuclear localization and sensitizes cancer cells to DNA damage. PNAS. 105:16958-16963.

Daelemans D, Afonina E, Nilsson J 2002 A synthetic HIV-1 Rev inhibitor interfering with the CRM1-mediated nuclear export. Proc Natl Acad Sci USA 99(22):14440-5.98052-2517.

Davis J R et al. 2007. Controlling protein compartmentalization to overcome disease Pharmaceut Res. 24:17-27.

Freundt E, Yu L, Park E, et al 2009 Molecular determinants for subcellular localization of the severe acute respiratory syndrome coronavirus open reading frame 3b protein. J Virol 83(13):6631-40.

Ghildyal R, Ho A, Dias M, et al 2009 The respiratory syncytial virus matrix protein possesses a Crm1-mediated nuclear export mechanism. J Virol 83(11):5353-62.

Ghosh C C et al 2008 Analysis of nucleocytoplasmic shuttling of NF kappa B proteins in human leukocytes. Methods Mol Biol. 457:279-92.

Gupta N et al 2008 Retinal tau pathology in human glaucomas. Can J Ophthalmol. 2008 February; 43(1):53-60.

Hoshino L et al. 2008. Combined effects of p53 gene therapy and leptomycin B in human esophageal squamous cell carcinoma. Oncology. 75:113-119.

Lain S et al. 1999a An inhibitor of nuclear export activates the p53 response and induces the localization of HDM2 and p53 to U1A-positive nuclear bodies associated with the PODs Exp Cell Res. 248:457-472.

Lain S et al. 1999b. Accumulating active p53 in the nucleus by inhibition of nuclear export: a novel strategy to promote the p53 tumor suppressor function Exp Cell Res. 253:315.

Muller P A et al. 2009 Nuclear-cytosolic transport of COMMD1 regulates NF-kappaB and HIF-1 activity. Traffic 10(5):514-27.

Mutka S 2007 Nuclear Export Inhibitors (NEIs) as novel cancer therapies AACR Annual Meeting. Poster 5609.

Mutka S, Yang W, Dong S, et al. 2009. Identification of nuclear export inhibitors with potent anticancer activity in vivo. Cancer Res. 69: 510-7.

Nakahara J et al. 2009. Abnormal expression of TIP30 and arrested nucleocytoplasmic transport within oligodendrocyte precursor cells in multiple sclerosis J Clin Invest. 119:169-181.

Noske A et al. 2008. Expression of the nuclear export protein chromosomal region maintenance/exportin 1/Xpo1 is a prognostic factor in human ovarian cancer. Cancer. 112: 1733-1743.

Pollard V & Malim M. 1998 The HIV-1 Rev protein Annu Rev Microbiol 52:491-532.

Rawlinson S, Pryor M, Wright P, Jans D 2009 CRM1-mediated nuclear export of dengue virus RNA polymerase NS5 modulates interleukin-8 induction and virus production. J Biol Chem 284(23):15589-97.

Sanchez V, Mahr J, Orazio N, et al 2007 Nuclear export of the human cytomegalovirus tegument protein pp65 requires cyclin-dependent kinase activity and the Crm1 exporter. J Virol 81(21):11730-6.

Sorokin A V et al. 2007. Nucleocytoplasmic transport of proteins. Biochemistry 72:1439-1457.

Terry L J et al. 2007. Crossing the nuclear envelope: hierarchical regulation of nucleocytoplasmic transport. Science 318:1412-1416.

Van der Watt P J et al. 2008. The Karyopherin proteins, Crm1 and Karyopherin betal, are overexpressed in cervical cancer and are critical for cancer cell survival and proliferation. Int J Canc. 124:1829-1840.

Walsh M D et al. 2008 Exportin 1 inhibition attenuates nuclear factor-kappaB-dependent gene expression. Shock 29:160-166.

Williams P, Verhagen J, Elliott G 2008 Characterization of a CRM1-dependent nuclear export signal in the C terminus of herpes simplex virus type 1 tegument protein UL47. J Virol 82(21):10946-52.

Yang W 2007 Anti-tumor activity of novel nuclear export inhibitors (NEIs) in multiple murine leukemia models. AACR Annual Meeting. Poster 5597.

Yao Y et al. 2009. The expression of CRM1 is associated with prognosis in human osteosarcoma. Oncol Rep. 21:229-35.

Zimmerman T L et al 2006 Nuclear export of retinoid X receptor alpha in response to interleukin-1beta-mediated cell signaling: roles for JNK and SER260. J Biol Chem281:15434-15440.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

We claim:

1. A compound, represented by structural formula IV:

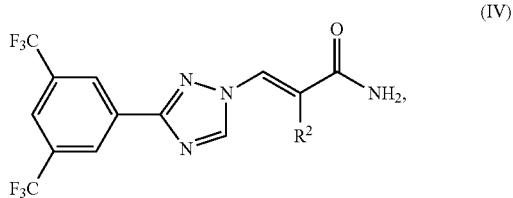

or a pharmaceutically acceptable salt thereof, wherein:
$R^2$ is selected from optionally substituted heteroaryl and optionally substituted aryl.

2. The compound of claim 1, wherein $R^2$ is an optionally substituted $C_5$-$C_{15}$ heteroaryl.

3. The compound of claim 1, wherein $R^2$ is an optionally substituted 5-6-membered heteroaryl having 1, 2 or 3 heteroatoms independently selected from the group consisting of nitrogen, oxygen and sulfur.

4. The compound of claim 3, wherein $R^2$ is an optionally substituted 5-membered heteroaryl having 1, 2 or 3 heteroatoms independently selected from the group consisting of nitrogen, oxygen and sulfur.

5. The compound of claim 4, wherein $R^2$ is an optionally substituted pyrrolyl, furanyl, thiophenyl, pyrazolyl, imidazolyl, thiazolyl, isothiazolyl, oxazolyl, isoxazolyl, triazolyl, thiadiazolyl, or oxadiazolyl.

6. The compound of claim 3, wherein $R^2$ is an optionally substituted 6-membered heteroaryl having 1, 2 or 3 heteroatoms independently selected from the group consisting of nitrogen, oxygen and sulfur.

7. The compound of claim 6, wherein $R^2$ is an optionally substituted pyridinyl, pyrimidinyl, pyrazinyl, pyridazinyl or triazinyl.

8. The compound of claim 1, wherein $R^2$ is optionally substituted with 1, 2 or 3 substituents independently selected from halogen, $C_1$-$C_4$ alkyl, halo-$C_1$-$C_4$ alkyl, $C_1$-$C_4$ alkoxy, $C_1$-$C_4$ thioalkoxy, hydroxyl, amino, $C_1$-$C_4$ alkylamino, $C_1$-$C_4$ dialkylamino, sulfhydryl, cyano, $C_6$ aryl and $C_5$-$C_6$ heteroaryl.

9. The compound of claim 8, wherein $R^2$ is optionally substituted with 1, 2 or 3 substituents independently selected from fluoro, chloro, $C_1$-$C_4$ alkyl, —$CF_3$, amino and cyano.

10. A compound of structural formula III:

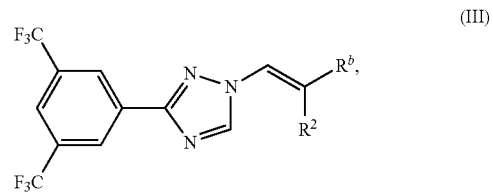

or a pharmaceutically acceptable salt thereof, wherein:
$R^b$ is selected from —
C(O)OH, —C(O)NH$_2$, —C(O)—N(R$^7$)—N(R$^5$)(R$^6$), —C(O)—N(R$^7$)—N(R$^7$)—C(O)—R$^4$ and —C(O)—N(R$^7$)—N(R$^7$)—S(O)$_{1-2}$—R$^4$; wherein:
$R^4$ is selected from —N(H)(C$_3$-C$_6$ cycloalkyl), —N(C$_1$-C$_4$ alkyl)(C$_3$-C$_6$ cycloalkyl), —C$_1$-C$_6$ alkyl, —(C$_0$-C$_4$ alkylene)-carbocyclyl, —(C$_0$-C$_4$ alkylene)-heterocyclyl, -(C$_0$-C$_4$ alkylene)-aryl, and —(C$_0$-C$_4$ alkylene)-heteroaryl;
$R^5$ and $R^6$ are each independently selected from hydrogen, $C_1$-$C_4$ alkyl, $C_2$-$C_4$ alkenyl, $C_2$-$C_4$ alkynyl, carbocyclyl, aryl, heterocyclyl and heteroaryl; or
$R^5$ and $R^6$ are taken together with the nitrogen atom to which they are commonly attached to form a heterocyclyl or heteroaryl; and
each $R^7$ is independently hydrogen or $C_1$-$C_4$ alkyl; and
$R^2$ is an optionally substituted $C_5$-$C_{15}$ heteroaryl, wherein:
unless otherwise designated, each alkyl, alkenyl, alkynyl, alkylene, carbocyclyl, aryl, cycloalkyl, heterocyclyl and heteroaryl is optionally and independently substituted.

11. The compound of claim 10, wherein:
$R^b$ is selected from:
—C(O)—OH; or
—C(O)—NH$_2$; or
—C(O)—NH—NH(R$^6$), and $R^6$ is an optionally substituted heteroaryl; or
—C(O)—NH—NH—C(O)—R$^4$ or —C(O)—NH—NH-S(O)$_{1-2}$—R$^4$, and $R^4$ is selected from optionally substituted —N(H)(C$_3$-C$_6$ cycloalkyl), —N(C$_1$-C$_4$ alkyl)(C$_3$-C$_6$ cycloalkyl), —C$_1$-C$_6$ alkyl, —(C$_0$-C$_4$ alkylene)-heterocyclyl and —(C$_0$-C$_4$ alkylene)-heteroaryl.

12. The compound of claim 10, wherein $R^2$ is an optionally substituted 5-6-membered heteroaryl having 1, 2 or 3 heteroatoms independently selected from the group consisting of nitrogen, oxygen and sulfur.

13. The compound of claim 12, wherein $R^2$ is an optionally substituted 5-membered heteroaryl having 1, 2 or 3 heteroatoms independently selected from the group consisting of nitrogen, oxygen and sulfur.

14. The compound of claim 12, wherein $R^2$ is an optionally substituted 6-membered heteroaryl having 1, 2 or 3 heteroatoms independently selected from the group consisting of nitrogen, oxygen and sulfur.

15. The compound of claim 10, wherein $R^2$ is optionally substituted with 1, 2 or 3 substituents independently selected from halogen, $C_1$-$C_4$ alkyl, halo-$C_1$-$C_4$ alkyl, $C_1$-$C_4$ alkoxy, $C_1$-$C_4$ thioalkoxy, hydroxyl, amino, $C_1$-$C_4$ alkylamino, $C_1$-$C_4$ dialkylamino, sulfhydryl, cyano, $C_6$ aryl and $C_5$-$C_6$ heteroaryl.

16. A compound represented by any one of the following structural formulas:
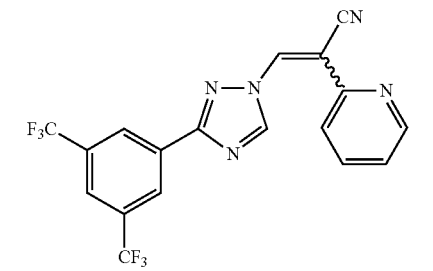
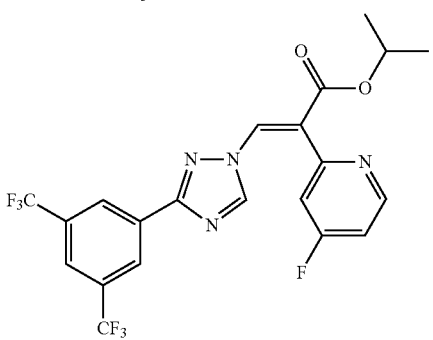
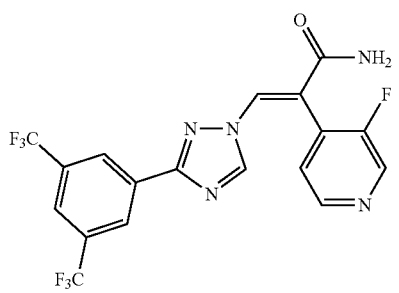
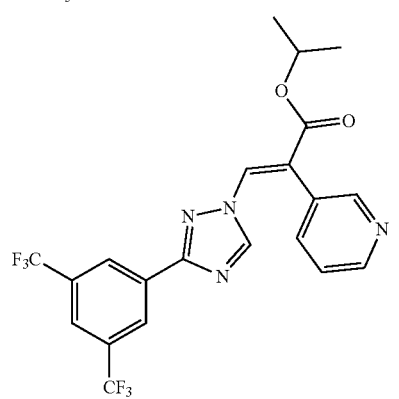
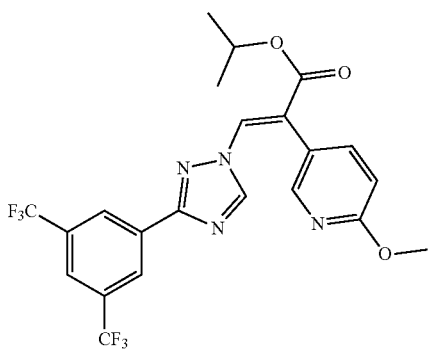
-continued
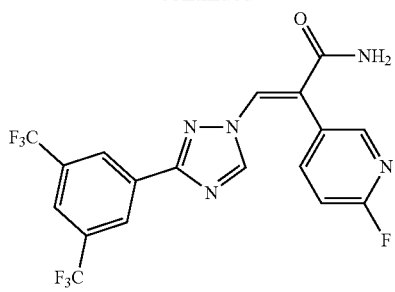
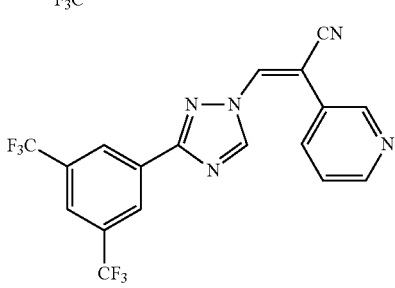
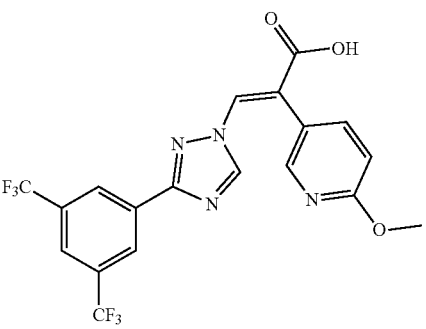
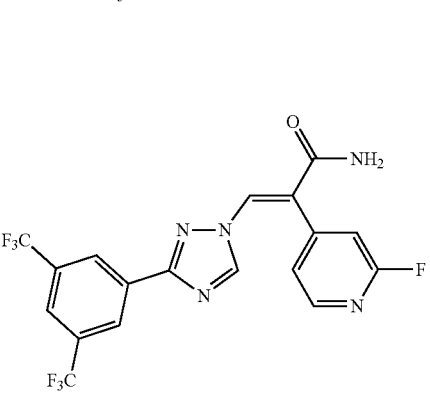
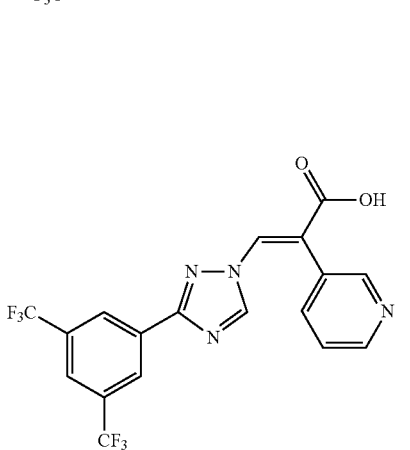

159
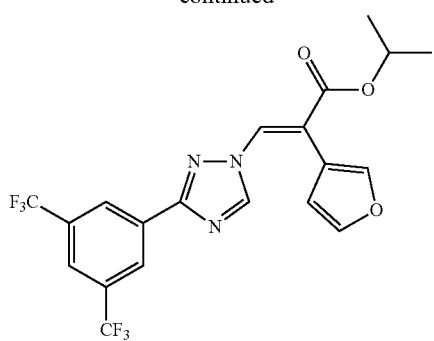
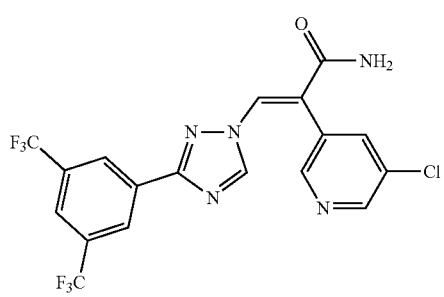
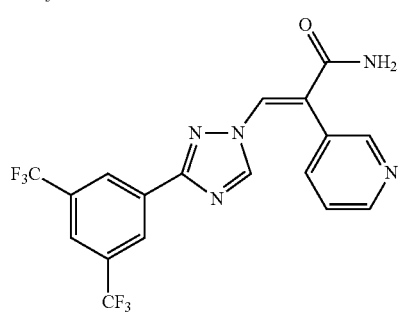
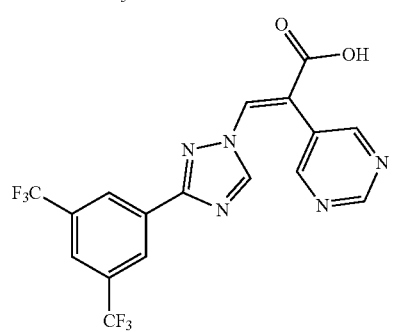
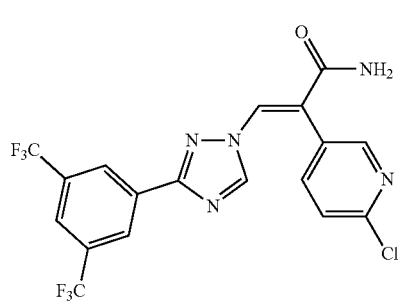
160
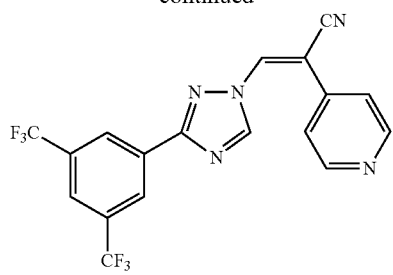
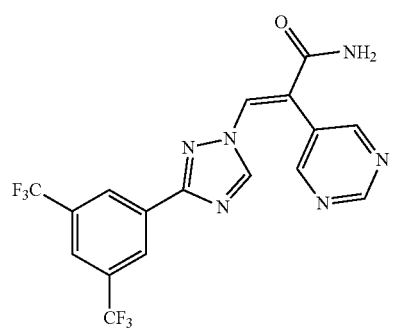
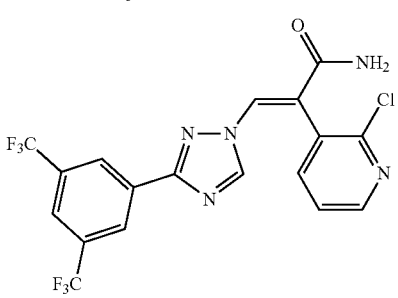
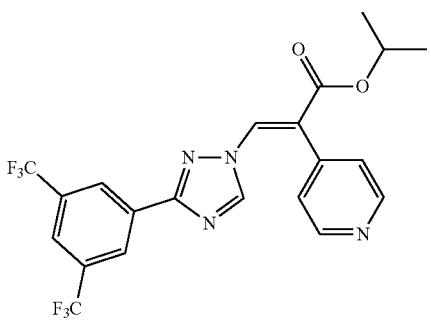
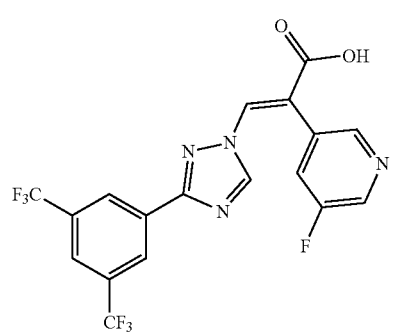

-continued
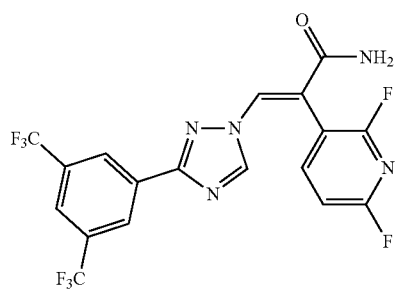
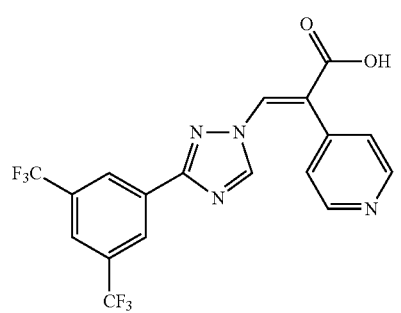
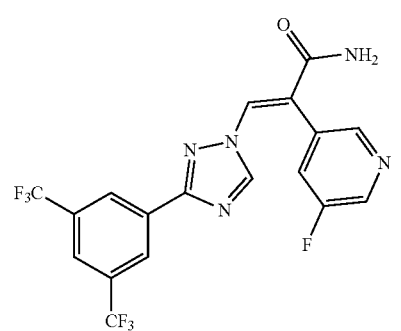
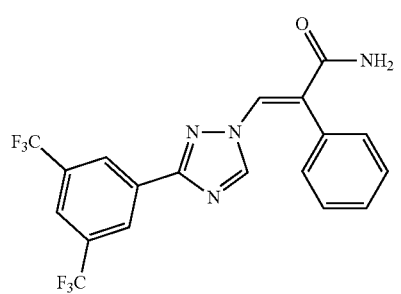
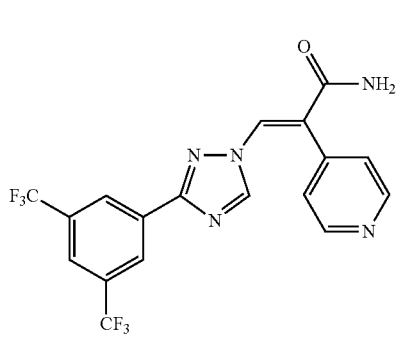
-continued
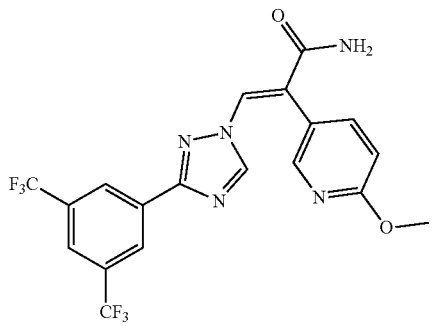
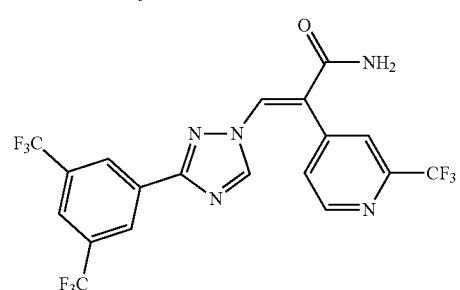
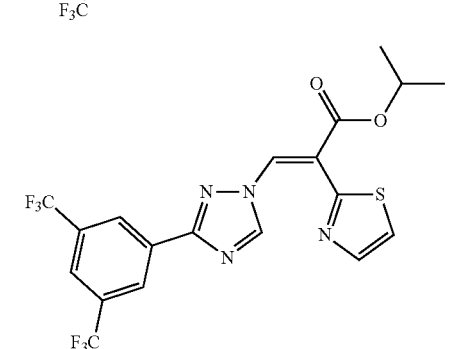
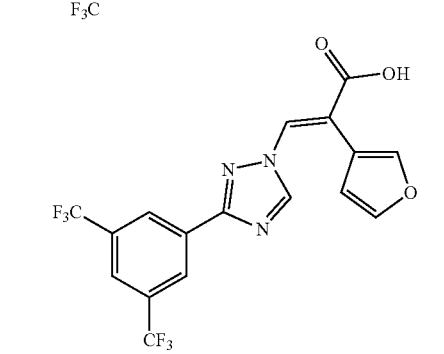
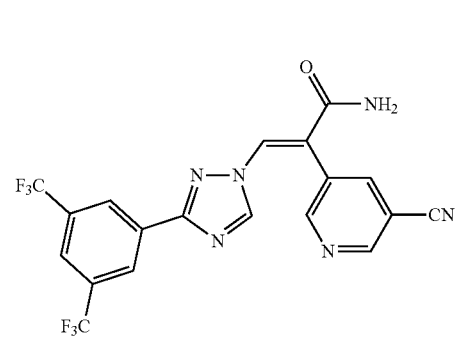

163
-continued
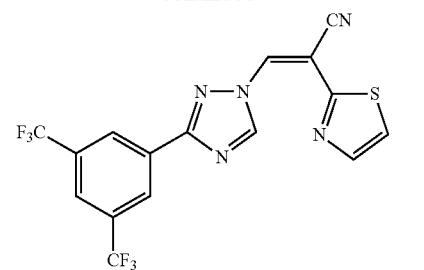
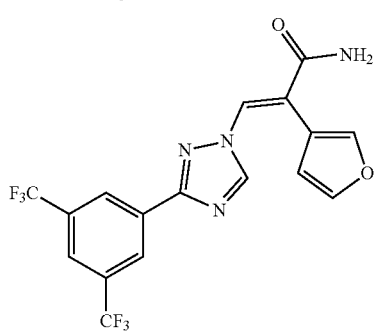
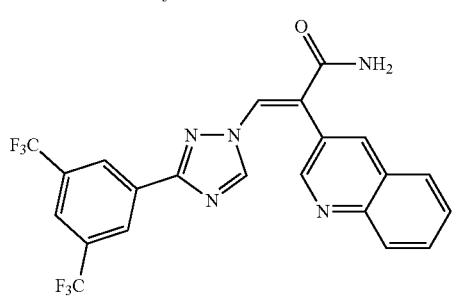
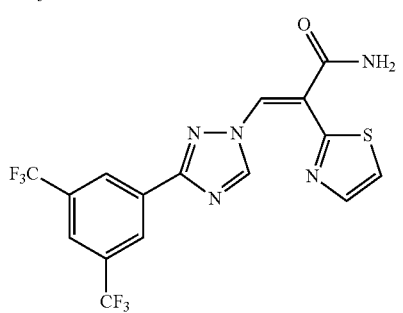
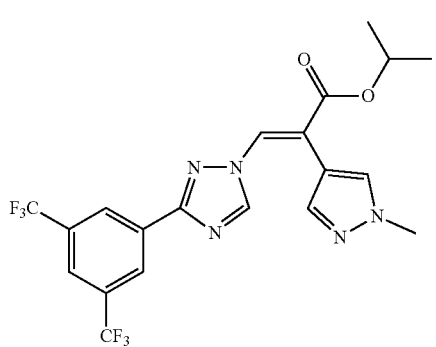
164
-continued
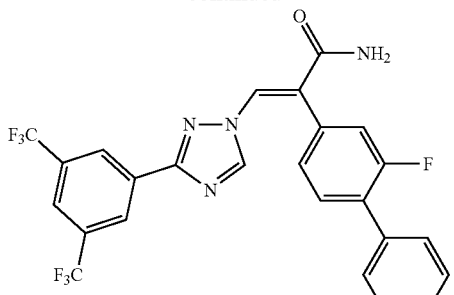
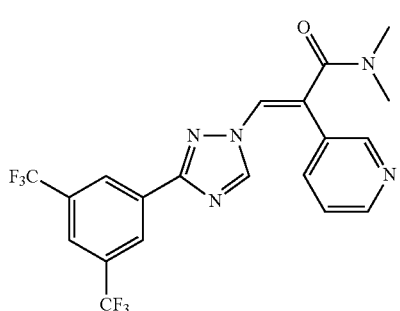
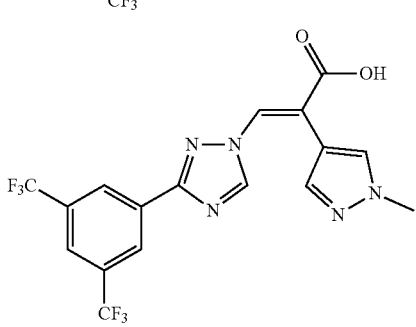
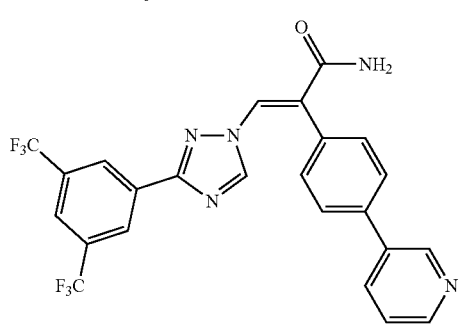
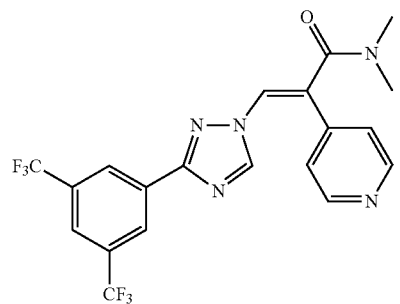

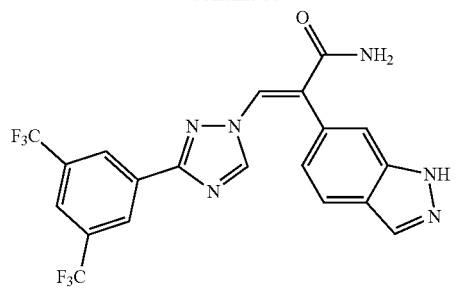
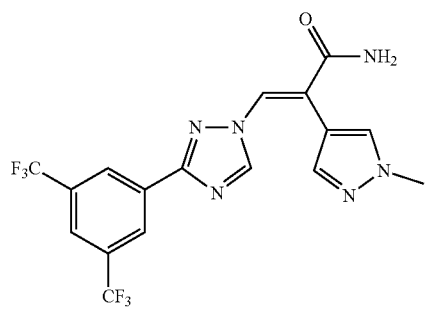
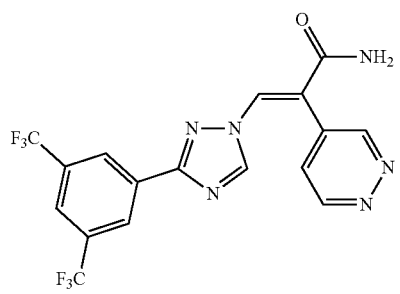
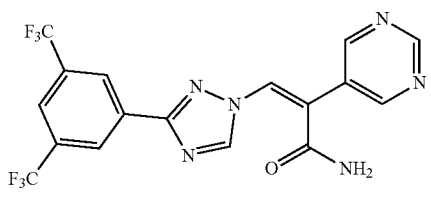
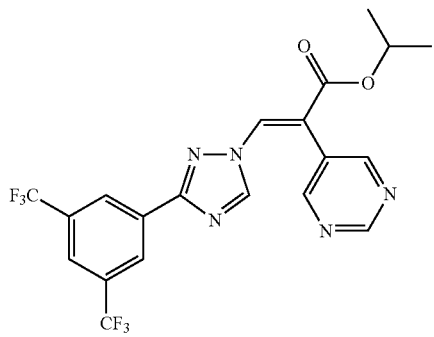
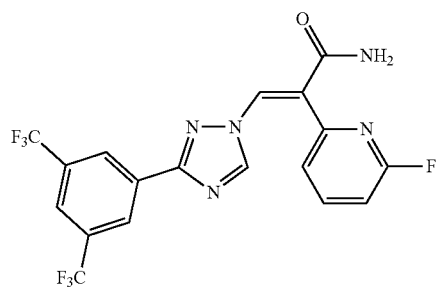
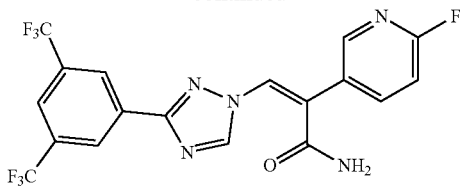
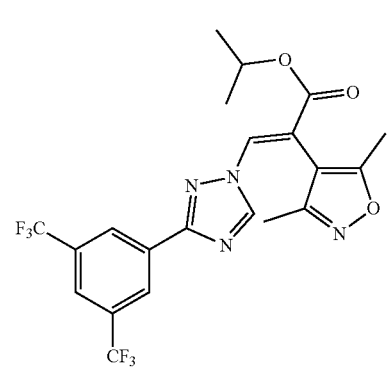
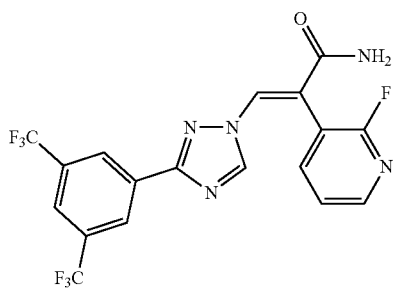
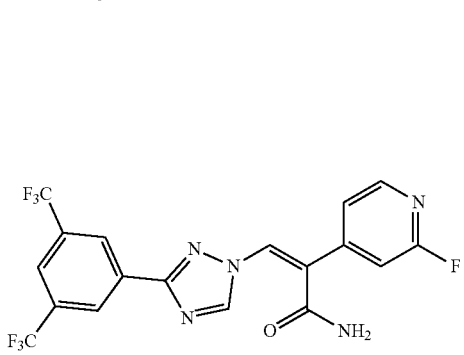
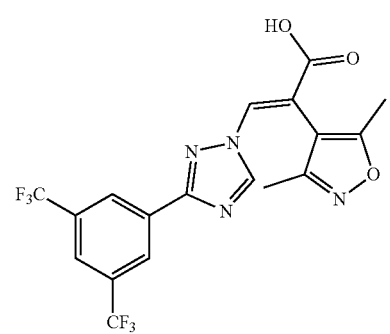

-continued

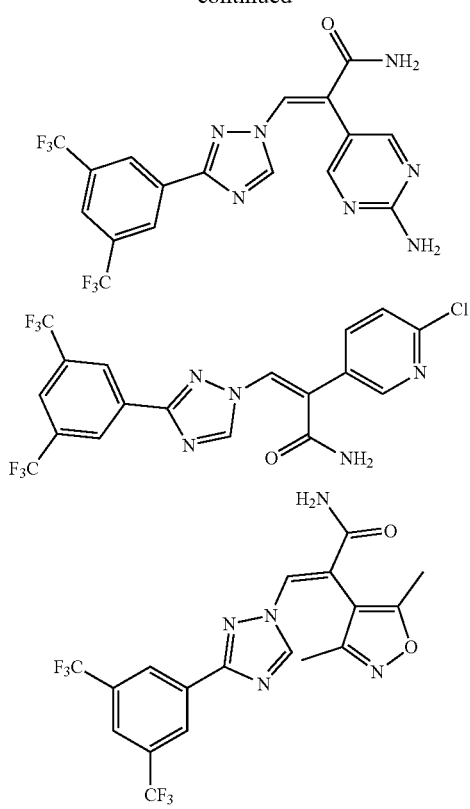

-continued

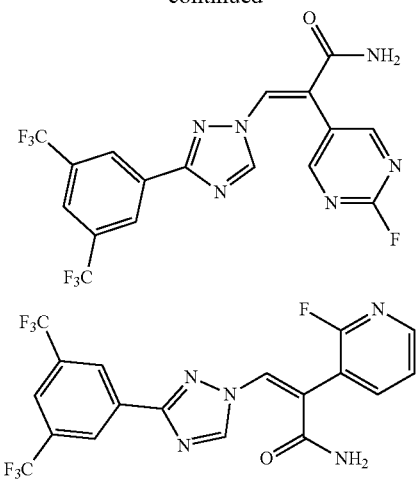

or a pharmaceutically acceptable salt of any of the foregoing.

17. A pharmaceutically acceptable composition comprising a compound of claim 1, or a pharmaceutically acceptable salt thereof, and a pharmaceutically acceptable carrier.

18. A method for promoting wound healing in a subject in need thereof, comprising administering to the subject in need thereof a therapeutically effective amount of a compound of claim 1.

* * * * *